United States Patent
Kozak et al.

(10) Patent No.: US 11,970,481 B1
(45) Date of Patent: Apr. 30, 2024

(54) SUBSTITUTED PYRIDINE DERIVATIVES AS SARM1 INHIBITORS

(71) Applicant: Nura Bio, Inc., South San Francisco, CA (US)

(72) Inventors: Jennifer Aiden Kozak, Pacifica, CA (US); Sean Pomeroy Brown, Half Moon Bay, CA (US); Christopher Michael Tegley, San Carlos, CA (US); Alexander Wayne Schammel, San Francisco, CA (US); Liusheng Zhu, Foster City, CA (US); Maximiliano De La Higuera Macias, San Francisco, CA (US); Shilpa Sambashivan, Los Altos, CA (US)

(73) Assignee: NURA BIO, INC., South San Francisco, CA (US)

( * ) Notice: Subject to any disclaimer, the term of this patent is extended or adjusted under 35 U.S.C. 154(b) by 0 days.

(21) Appl. No.: 18/481,173

(22) Filed: Oct. 4, 2023

Related U.S. Application Data

(63) Continuation of application No. 18/019,452, filed as application No. PCT/US2021/044389 on Aug. 3, 2021.

(60) Provisional application No. 63/060,790, filed on Aug. 4, 2020.

(51) Int. Cl.
*C07D 403/14* (2006.01)
*A61P 25/28* (2006.01)
*C07D 403/04* (2006.01)

(52) U.S. Cl.
CPC ............ *C07D 403/14* (2013.01); *A61P 25/28* (2018.01); *C07D 403/04* (2013.01)

(58) Field of Classification Search
CPC ...... C07D 403/14; C07D 403/04; A61P 25/28
See application file for complete search history.

(56) References Cited

U.S. PATENT DOCUMENTS

| | | | |
|---|---|---|---|
| 11,629,136 B1 | 4/2023 | Kolluri et al. | |
| 2004/0186129 A1 | 9/2004 | Koya et al. | |
| 2006/0252778 A1 | 11/2006 | Guo et al. | |
| 2017/0197981 A1 | 7/2017 | Shaw et al. | |
| 2017/0355708 A1 | 12/2017 | Jefson et al. | |
| 2022/0056013 A1* | 2/2022 | Bosanac | C07D 401/14 |
| 2022/0081417 A1 | 3/2022 | Brown et al. | |
| 2023/0286941 A1 | 9/2023 | Kolluri et al. | |
| 2023/0286978 A1* | 9/2023 | Bentley | C07D 471/04 |
| 2023/0339913 A1 | 10/2023 | Kozak et al. | |

FOREIGN PATENT DOCUMENTS

| WO | WO-9918096 A1 | 4/1999 |
|---|---|---|
| WO | WO-2005085220 A1 | 9/2005 |
| WO | WO-2005105780 A2 | 11/2005 |
| WO | WO-2009046802 A1 | 4/2009 |
| WO | WO-2009114552 A1 | 9/2009 |
| WO | WO-2010093849 A2 | 8/2010 |
| WO | WO-2012049161 A1 | 4/2012 |
| WO | WO-2012050141 A1 | 4/2012 |
| WO | WO-2014158998 A1 | 10/2014 |
| WO | WO-2014187928 A1 | 11/2014 |
| WO | WO-2015140130 A1 | 9/2015 |
| WO | WO-2016012474 A1 | 1/2016 |
| WO | WO-2016187324 A1 | 11/2016 |
| WO | WO-2018094362 A1 | 5/2018 |
| WO | WO-2019236890 A1 | 12/2019 |
| WO | WO-2020176863 A1 | 9/2020 |
| WO | WO-2020247701 A2 | 12/2020 |
| WO | WO-2020252229 A2 | 12/2020 |
| WO | WO-2021142006 A1 | 7/2021 |
| WO | WO-2022031736 A1 | 2/2022 |
| WO | WO-2022046606 A1 | 3/2022 |
| WO | WO-2022060812 A1 | 3/2022 |
| WO | WO-2023009663 A1 | 2/2023 |

OTHER PUBLICATIONS

U.S. Appl. No. 62/958,178, published by WIPO in International Application No. PCT/US2021/012333 on Jul. 15, 2021. (Year: 2021).*
Chemical Abstracts STN Registry Database, Record for RN 2224489-34-1, Entered STN: May 21, 2018. (Year: 2018).*
Berge et al. Pharmaceutical Salts. Journal of Pharmaceutical Sciences 66(1):1-19 (Jan. 1977).
Bosanac et al., Pharmacological SARM1 inhibition protects axon structure and function in paclitaxel-induced peripheral neuropathy. Brain 144(10):3226-3238 (2021).
Bratkowski et al., Structural and mechanistic regulation of the pro-degenerative NAD hydrolase SARM1. Cell Rep. 32(5):107999 (2020).
Cavaletti et al., Chemotherapy-induced peripheral neurotoxicity: a multifaceted, still unsolved issue. J Peripher Nerv Syst. 24(Suppl 2):S6-S12 (2019).
Cecil Textbook of Medicine, 20th edition (1996), vol. 2, pp. 1992-1996.
Cecil Textbook of Medicine, 20th edition (1996), vol. 2, pp. 2050-2057.
Coleman et al. An 85-kb tandem triplication in the slow Wallerian degeneration (Wlds) mouse. PNAS USA 95(17):9985-90 (1998).
Essuman et al. The SARM1 Toll/Interleukin-1 Receptor Domain Possesses Intrinsic NAD + Cleavage Activity that Promotes Pathological Axonal Degeneration. Neuron 93(6):1334-43 (2017).
Essuman et al., TIR domain proteins are an ancient family of NAD+-consuming enzymes. Curr Biol. 28(3):421-430.e4 (2018).
FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html.

(Continued)

*Primary Examiner* — Daniel R Carcanague
(74) *Attorney, Agent, or Firm* — WILSON SONSINI GOODRICH & ROSATI

(57) ABSTRACT

This disclosure is drawn to substituted pyridine compounds and compositions, and associated methods, useful for inhibition of SARM1 activity and/or for treating or preventing a neurological diseases.

18 Claims, No Drawings

(56) References Cited

OTHER PUBLICATIONS

Figley et al., SARM1 is a metabolic sensor activated by an increased NMN/NAD+ ratio to trigger axon degeneration. Neuron 109(7):1118-1136.e11 (2021).
Fischer et al. Amyotrophic lateral sclerosis is a distal axonopathy: evidence in mice and man. Exp Neurol 185:232-240 (2004).
Flierl et al. Mouse closed head injury model induced by a weight-drop device. Na Protoc 4(9):1328-1337 (2009).
Fukuda et al., A mechanistic understanding of axon degeneration in chemotherapy-induced peripheral neuropathy. Front Neurosci. 11:481 (2017).
Gaetani et al., Neurofilament light chain as a biomarker in neurological disorders. J Neurol Neurosurg Psychiatry 90(8):870-881 (2019).
Gagliardi et al., Diagnostic and prognostic value of CSF neurofilaments in a cohort of patients with motor neuron disease: A cross-sectional study. J Cell Mol Med. 25(8):3765-3771 (2021).
Geisler et al. Prevention of vincristine-induced peripheral neuropathy by genetic deletion of SARM1 in mice. Brain 139(Pt 12):3092-3108 (2016).
Gerdts et al. Axon Self-Destruction: New Links among SARM1, MAPKs, and NAD+ Metabolism. Neuron 89:449-60 (2016).
Gerdts et al., Image-based screening identifies novel roles for IkappaB kinase and glycogen synthase kinase 3 in axonal degeneration. J Biol Chem. 286(32):28011-28018 (2011).
Gerdts et al. SARM1 activation triggers axon degeneration locally via NAD+ destruction. Science 348(6233):453-57 (2015).
Gerdts et al., Sarm1-mediated axon degeneration requires both SAM and TIR interactions. J Neurosci. 33(33):13569-13580 (2013).
Gordon BA, Neurofilaments in disease: what do we know? Curr Opin Neurobiol. 61:105-115 (2020).
Graham et al., Diffuse axonal injury predicts neurodegeneration after moderate-severe traumatic brain injury. Brain 143(12):3685-3698 (2020).
Haffner et al., Discovery, synthesis, and biological evaluation of thiazoloquin(az)olin(on)es as potent CD38 inhibitors. J Med Chem. 58(8):3548-3571 (2015).
Henninger et al. Attenuated traumatic axonal injury and improved functional outcome after traumatic brain injury in mice lacking Sarm1. Brain 139(Pt 4):1094 (2016).
Horsefield et al., NAD+ cleavage activity by animal and plant TIR domains in cell death pathways. Science 365(6455):793-799 (2019).
Huang et al., Longitudinal biomarkers in amyotrophic lateral sclerosis. Ann Clin Transl Neurol. 7(7):1103-1116 (2020).
Hughes et al., Small molecule SARM1 inhibitors recapitulate the SARM1-/- phenotype and allow recovery of a metastable pool of axons fated to degenerate. Cell Rep. 34(1):108588 (2021).
Ishita et al. Synthesis and biological evaluation of aminothiazoles against Histoplasma capsula-tum and Cryptococcus neoformans. Bioorg Med Chem 26:2251-2261 (2018).
Jiang et al., The NAD+-mediated self-inhibition mechanism of pro-neurodegenerative SARM1. Nature 588(7839):658-663 (2020).
Kanamori et al. Retrograde and Wallerian axonal degeneration occur synchronously after retinal ganglion cell axotomy. Am. J. Pathol. 181(1):62-73 (2012).
Kaneko et al., Protecting axonal degeneration by increasing nicotinamide adenine dinucleotide levels in experimental autoimmune encephalomyelitis models. J Neurosci. 26(38):9794-9804 (2006).
Kim et al., MyD88-5 links mitochondria, microtubules, and JNK3 in neurons and regulates neuronal survival. J Exp Med. 204(9):2063-2074 (2007).
Koliatsos et al., Wallerian degeneration as a therapeutic target in traumatic brain injury. Curr Opin Neurol. 32(6):786-795 (2019).
Kurowska et al. Is Axonal Degeneration a Key Early Event in Parkinson's Disease? J. Parkinson's Dis. 6:703-07 (2016).
Lipinski. Bioisosteric Design of Conformationally Restricted Pyridyltriazole Histamine H2 Receptor Antagonists. J Med Chem 26(1):1-6 (1983).
Loring et al. Identification of the First Noncompetitive SARM1 Inhibitors. Bioorg Med Chem 28(18):115644 (2020).
Lyons et al. B cells are critical to induction of experimental allergic encephalomyelitis by protein but not by a short encephalitogenic peptide. Eur J of Immunology 29(11):3432-9 (1999).
Ma et al., Direct pathogen-induced assembly of an NLR immune receptor complex to form a holoenzyme. Science 370(6521):eabe3069 (2020).
Maglemose et al., Potassium channel abnormalities are consistent with early axon degeneration of motor axons in the G127X SOD1 mouse model of amyotrophic lateral sclerosis. Exp Neurol. 292:154-167 (2017).
Martin et al., Structure of the activated ROQ1 resistosome directly recognizing the pathogen effector XopQ. Science 370(6521):eabd9993 (2020).
Osterloh et al., dSarm/Sarm1 is required for activation of an injury-induced axon death pathway. Science 337(6093):481-484 (2012).
PCT/US2021/044389 International Invitation to Pay Additional Fees dated Nov. 12, 2021.
PCT/US2021/044389 International Search Report and Written Opinion dated Jan. 10, 2022.
PCT/US2021/050426 International Search Report and Written Opinion dated Dec. 20, 2021.
PCT/US2022/038577 International Search Report and Written Opinion dated Nov. 17, 2022.
Perry et al., Evidence that very slow wallerian degeneration in C57BL/Ola mice is an intrinsic property of the peripheral nerve. Eur J Neurosci. 2(9):802-808 (1990).
Ravin. Chapter 76: Preformulation. Remington's Pharmaceutical Sciences, 17th ed., Mack Publishing Company, Easton, Pa. (pp. 1409-1423) (1985).
RCSB Protein Data Bank, 7NAI Crystal structure of the TIR domain from human SARM1 in complex with 3AD. https://www.rcsb.org/structure/7NAI (2021).
Registry No. 1372613-10-9, File Registry on STN, entered STN May 3, 2012.
Registry No. 1372613-27-8, File Registry on STN, entered STN May 3, 2012.
Salvadores et al. Axonal Degeneration during Aging and Its Functional Role in Neurodegenerative Disorders. Front. Neurosci. 11:451 (2017).
Sasaki et al., Nicotinamide mononucleotide adenylyl transferase-mediated axonal protection requires enzymatic activity but not increased levels of neuronal nicotinamide adenine dinucleotide. J Neurosci. 29(17):5525-5535 (2009).
Schlaepfer. Calcium-induced degeneration of axoplasm in isolated segments of rat peripheral nerve. Brain Res. 69(2):203-215 (1974).
Scully et al., Synthesis and evaluation of thiazoloquinolinones with linkers to enable targeting of CD38. ACS Med Chem Lett. 8(2):196-200 (2017).
Segapelo et al. Pyrazolylmethyl)amino-pyridine platinum (II) and gold (II) complexes. Syn-theses, structures and evaluation as anti-cancer agents. Inorganic Chimica Acta 362(9):3314-3324 (2009).
Shen et al., Multiple domain interfaces mediate SARM1 autoinhibition. Proc Natl Acad Sci USA. 118(4):e2023151118 (2021).
Shi et al. Structural basis of SARM1 activation, substrate recognition, and inhibition by small molecules. Mol Cell 82(9):1643-1659 (2022).
Sporny et al., Structural basis for SARM1 inhibition and activation under energetic stress. Elife 9:e62021 (2020).
Sprowl et al. Oxaliplatin-induced neurotoxicity is dependent on the organic cation transporter OCT2. PNAS USA 110(27):11199-11204 (2013).
Summers et al. Mitochondrial dysfunction induces Sarm1-dependent cell death in sensory neurons. J Neurosci. 34(28):9338-50 (2014).
Summers et al. SARM1-specific motifs in the TIR domain enable NAD+ loss and regulate injury-induced SARM1 activation. PNAS USA 113(41):E6271-E6280 (2016).
Tarrago et al., A Potent and Specific CD38 Inhibitor Ameliorates Age-Related Metabolic Dysfunction by Reversing Tissue NAD+ Decline. Cell Metab. 27(5):1081-1095.e10 (2018).

(56) References Cited

OTHER PUBLICATIONS

Uccellini et al., Passenger mutations confound phenotypes of SARM1-deficient mice. BioRxiv. Oct. 18, 2019; Cell Reports 31(1):107498 (2020).
U.S. Appl. No. 17/475,896 Office Action dated Aug. 7, 2023.
U.S. Appl. No. 17/475,896 Office Action dated Jan. 17, 2023.
U.S. Appl. No. 17/875,301 Office Action dated Nov. 8, 2022.
Viar et al., Sarm1 knockout protects against early but not late axonal degeneration in experimental allergic encephalomyelitis. PLoS One 15(6):e0235110 (2020).
Waller A. Experiments on the section of the glossopharyngeal and hypoglossal nerves of the frog, and observations of the alterations produced thereby in the structure of their primitive fibres. Philosophical Transactions of the Royal Society of London 140(0):423-429 (1850).
Wang et al. WldS mice are resistant to paclitaxel (taxol) neuropathy. Ann. Neurol. 52(4)442-7 (2002).
Weber et al., CLARITY reveals a more protracted temporal course of axon swelling and disconnection than previously described following traumatic brain injury. Brain Pathol. 29(3):437-450 (2019).
Williams et al., Neurofilaments in progressive multiple sclerosis: a systematic review. J Neurol. 268(9):3212-3222 (2021).
Yang et al. Pathological axonal death through a MAPK cascade that triggers a local energy deficit. Cell 160(1-2):161-76 (2015).
Zhao et al., A cell-permeant mimetic of NMN activates SARM1 to produce cyclic ADP-ribose and induce non-apoptotic cell death. iScience 15:452-466 (2019).
Chemical Abstracts STN Registry Database, Record for RN 2224489-34-1, Entered STN: May 21, 2018.
PCT/US2023/071058 International Search Report and Written Opinion dated Oct. 10, 2023.
U.S. Appl. No. 18/178,325 Office Action dated Nov. 21, 2023.

\* cited by examiner

SUBSTITUTED PYRIDINE DERIVATIVES AS SARM1 INHIBITORS

FIELD OF THE INVENTION

This disclosure is drawn to compounds and compositions, and associated methods, useful for inhibition of SARM1 activity and/or for treating or preventing a neurological disorder.

BACKGROUND OF THE INVENTION

Aging constitutes the main risk factor for the development of neurodegenerative diseases. Axonal degeneration is an important pathological event in many neurodegenerative and neurological disorders, including peripheral neuropathy and traumatic brain injury (Gerdts, J. et al., Neuron, 2016, 89, 449-60). Axonal degeneration has also been implicated in, for example, Alzheimer's disease, Parkinson's disease and Amyotrophic Lateral Sclerosis, where degeneration precedes symptom onset and widespread neuronal loss (Kurowska, Z. et al., J. Parkinson's Dis., 2016, 6, 703-07). While these neurological conditions have unique underlying etiologies, inhibition of axonal degeneration in the conditions' early stages may slow or prevent their progression by preventing the loss of functional synapses and maintaining neuronal connectivity (Essuman, K. et al., Neuron, 2017 Mar. 22, 93(6), 1334-43).

Axonal degeneration after injury occurs both toward the proximal cell body (termed retrograde degeneration) and toward the distal axon terminal (termed Wallerian or orthograde degeneration) (Kanamori A. et al., Am. J. Pathol. 2012 July; 181(1):62-73). Wallerian degeneration, which occurs in that section of the axon that is distal to the site of injury, occurs after axonal injury in both the peripheral nervous system (PNS) and the central nervous system (CNS). Wallerian degeneration usually begins within 24-36 hours of a lesion. Prior to degeneration, the distal section of the axon tends to remain electrically excitable, while after injury, the axonal skeleton disintegrates and the axonal membrane breaks apart.

The processes of death of the cell body and degeneration of the axon are independent events. As alluded to above, evidence exists indicating that the degeneration of axons precedes clinical symptoms in neurodegenerative diseases and occurs before cell body loss. Thus, axonal degeneration constitutes an early event in pathological processes and provides a potential therapeutic target to treat neurodegeneration prior to neuronal cell death (Salvadores, N. et al., Front. Neurosci., 2017, 11, 451).

In view of the above, new modalities are needed for the treatment of neurological disorders such as neurodegenerative disease by the prevention of axonal degeneration.

SUMMARY OF THE INVENTION

The present invention is directed to inhibitors of SARM1 such as a compound of Formula Ia, Ib, Ic, or Id:

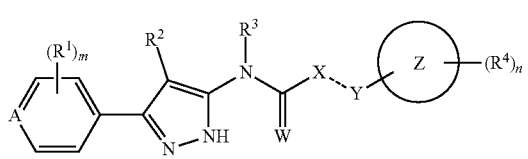

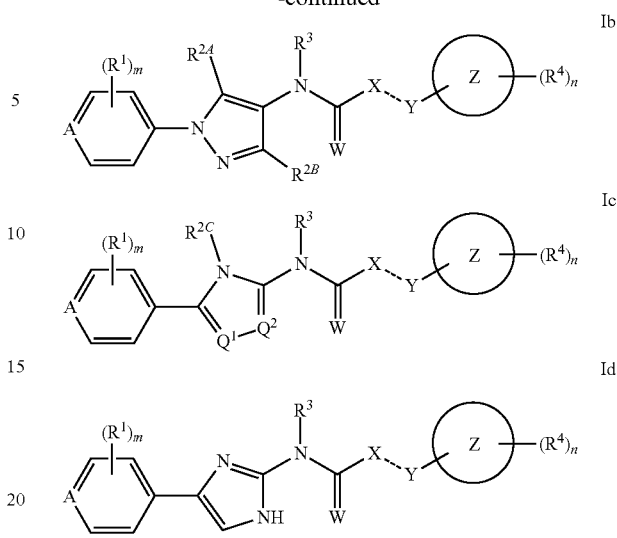

or a pharmaceutically acceptable salt thereof, wherein constituent members are defined herein.

The present invention is further directed to a pharmaceutical composition comprising a compound of Formula Ia, Ib, Ic, or Id, or a pharmaceutically acceptable salt thereof, and at least one pharmaceutically acceptable carrier.

The present invention is further directed to a method of inhibiting SARM1 comprising contacting the SARM1 with a compound of Formula Ia, Ib, Ic, or Id, or a pharmaceutically acceptable salt thereof.

The present invention is further directed to a method of inhibiting axonal degeneration in a patient in need thereof comprising administering to the patient an inhibiting amount of a compound of Formula Ia, Ib, Ic, or Id, or a pharmaceutically acceptable salt thereof.

The present invention is further directed to a method of treating or preventing a neurological disorder in a patient in need thereof comprising administering to the patient a therapeutically effective amount of a compound of Formula Ia, Ib, Ic, or Id, or a pharmaceutically acceptable salt thereof.

The present invention is further directed to use of a compound of Formula Ia, Ib, Ic, or Id, or a pharmaceutically acceptable salt thereof, in treating or preventing a neurological disorder in a patient in need thereof.

The present invention is further directed to a compound of Formula Ia, Ib, Ic, or Id, or a pharmaceutically acceptable salt thereof, for use in the preparation of a medicament for treating or preventing a neurological disorder in a patient in need thereof.

DETAILED DESCRIPTION

Similar to programmed cell death pathways (e.g., apoptosis), axonal degeneration in response to injury or disease stimulates a local signaling cascade that causes destruction of the injured axon segment (Summers D. W., et al., PNAS USA, 2016 Oct. 11, 113(41):E6271-E6280). Following injury, the axonal skeleton disintegrates, and the axonal membrane breaks apart. Subsequent to axonal degeneration, the myelin sheath degrades and infiltration by macrophages follows; the macrophages, along with Schwann cells, clear the cellular debris resulting from the degeneration (Coleman M. P., et al., PNAS USA, 1998 August, 95(17):9985-90).

SARM1 (sterile alpha and TIR motif-containing 1) protein (NP_055892) is a 724 amino acid protein involved in axon degeneration. It has also been implicated in infectious and inflammatory disorders. The SARM1 protein, also known as FLJ36296, KIAA0524, MyD88-5, SAM domain-containing protein 2, and SAMD2, comprises four domains, i) a mitochondrial localization signal, ii) an auto-inhibitory N-terminus region consisting of armadillo/HEAT motifs, iii) two sterile alpha motifs responsible for multimerization, and iv) a C-terminus Toll/Interleukin-1 receptor that possesses enzymatic activity (Essuman K., et al., Neuron 2017 March, 93(6):1334-43.e5).

SARM1 protein plays a critical role in the Wallerian degeneration pathway. Activation of SARM1 triggers a rapid collapse of $NAD^+$ levels in the distal section of the injured axon, which then undergoes degeneration (Gerdts J. et al., Science 2015 April 348(6233):453-57). Promoting dimerization of the Toll/interleukin receptor (TIR) domain of SARM1 has been shown to be sufficient to promote $NAD^+$ loss and axon degeneration.

SARM1's activity is responsible for, at least in part, the protective nature of the survival factor NMNAT2, as NMKNAT enzymes have found to prevent SARM1-mediated depletion of $NAD^+$. Other pro-degeneration signaling pathways, including the MAP kinase pathway, have been linked to SARM1 activation. MAPK signaling has been shown to promote the loss of NMNAT2, which promotes SARM1 activation (See, e.g., Yang J. et al., Cell 2015 January 160(1-2):161-76).

SARM1 is involved in the innate immune response. It promotes neuronal cell death in response to stress and other stimuli. SARM1 acts as a negative regulator of TICAM1/TRIF-dependent Toll-like receptor signaling by inhibiting induction of TLR3- and TLR4-dependent genes, which play a pivotal role in activating axonal degeneration following injury. In addition, SARM1 specifically blocks TICAM1/TRIF-dependent transcription factor activation and gene induction, without affecting the MYD88-dependent pathway or non-TLR signaling. It is also a negative regulator of NF-kappa-B and IRF activation. (See, e.g., Summers, D. W. et al., J Neurosci., 2014 Jul. 9, 34(28):9338-50).

In some embodiments, the present invention provides inhibitors (e.g., small molecules) of SARM1. SARM1 activation is known to cause a rapid reduction in $NAD^+$ levels in injured axons, which then undergo degeneration. In particular embodiments, the compounds inhibit axonal degeneration, including axonal degeneration that results from reduction or depletion of $NAD^1$ (e.g., inhibition of SARM1 NADase).

The present invention is directed to inhibitors of SARM1 such as a compound of Formula Ia, Ib, Ic, or Id:

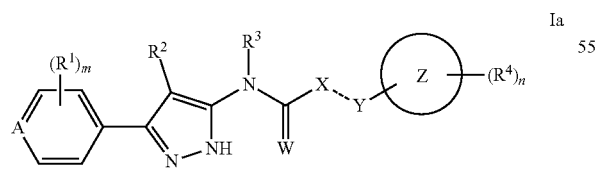

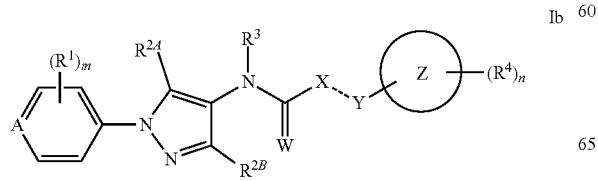

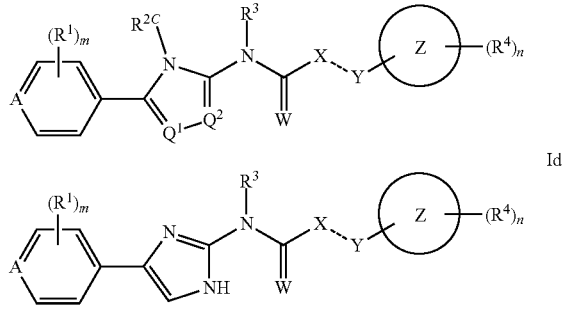

or a pharmaceutically acceptable salt thereof, wherein:
A is N or $N^+$—O—;
$Q^1$ and $Q^2$ are each independently selected from CH and N;
W is O, S, or $NR^N$;
---- is a single, double, or triple bond;
wherein when the ---- bond between X and Y is a single bond, then:
X is $CR^5R^6$, $NR^7$, or O and Y is $CR^8R^9$, $NR^{10}$, O, S, SO, or $SO_2$,
wherein when X is $NR^7$ or O, then Y is $CR^8R^9$;
wherein when the ---- bond between X and Y is a double bond, then:
X is $CR^5$ and Y is $CR^8$; and
wherein when the ---- bond between X and Y is a triple bond, then:
X is C and Y is C;
Ring Z is $C_{6-10}$ aryl, $C_{3-7}$ cycloalkyl, 5-10 membered heteroaryl, or 4-10 membered heterocycloalkyl;
$R^N$ is H, $C_{1-4}$ alkyl, or CN;
$R^1$ is halo, $C_{1-4}$ alkyl, $C_{1-4}$ haloalkyl, $C_{1-4}$ alkoxy, or $C_{1-4}$ haloalkoxy;
$R^2$, $R^{2A}$, and $R^{2B}$ are each independently selected from H, halo, CN, $C_{1-4}$ alkyl, $C_{1-4}$ haloalkyl, $C_{1-4}$ hydroxyalkyl, $C_{1-4}$ cyanoalkyl, $C_{1-4}$ alkoxy, $C_{1-4}$ alkoxy-$C_{1-4}$ alkyl, $C_{1-4}$ haloalkoxy, and $C_{3-7}$ cycloalkyl;
$R^{2C}$ is selected from H, $C_{1-4}$ alkyl, $C_{1-4}$ hydroxyalkyl, $C_{1-4}$ cyanoalkyl, and $C_{3-7}$ cycloalkyl;
$R^3$ is H, $C_{1-4}$ alkyl, —C(=O)—($C_{1-6}$ alkyl), —S(=O)$_2$—($C_{1-6}$ alkyl), or a group of Formula (ii):

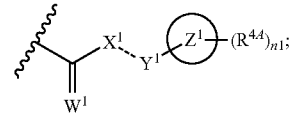

or
$R^3$ and $R^5$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy; or
$R^3$ and $R^7$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy; or $R^3$ and $R^8$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy; or $R^3$ and $R^{10}$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy;

each $R^4$ is independently halo, nitro, cyano, $C_{1-4}$ alkyl, $C_{2-4}$ alkenyl, $C_{2-4}$ alkynyl, $C_{1-4}$ haloalkyl, $C_{1-4}$ alkoxy, or $C_{1-4}$ haloalkoxy;

or two adjacent $R^4$ together with the atoms to which they are attached form a fused phenyl ring, $C_{3-7}$ cycloalkyl ring, 5-7 membered heteroaryl ring, or 4-7 membered heterocycloalkyl ring, each optionally substituted with 1, 2, or 3 substituents independently selected from oxo, halo, nitro, cyano, $C_{1-4}$ alkyl, $C_{2-4}$ alkenyl, $C_{2-4}$ alkynyl, $C_{1-4}$ haloalkyl, $C_{1-4}$ alkoxy, and $C_{1-4}$ haloalkoxy; or $R^4$ and $R^9$, together with the atoms to which they are attached and together with any intervening atoms, form a $C_{5-7}$ membered cycloalkyl ring fused with ring Z or a 5-7 membered heterocycloalkyl ring fused with ring Z, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy;

$R^5$, $R^6$, $R^7$, $R^8$, $R^9$, and $R^{10}$ are each independently selected from H, halo, $NH_2$, OH, $C_{1-4}$ alkyl, $C_{1-4}$ haloalkyl, $C_{1-4}$ cyanoalkyl, $C_{1-4}$ alkoxy, and $C_{1-4}$ haloalkoxy; or $R^5$ and $R^9$ together with the atoms to which they are attached form a $C_{3-7}$ cycloalkyl ring or a 5-7 membered heterocycloalkyl ring, each optionally substituted with 1, 2 or 3 substituents independently selected from oxo, halo, $NH_2$, OH, CN, $C_{1-4}$ alkyl, $C_{1-4}$ haloalkyl, $C_{1-4}$ alkoxy, and $C_{1-4}$ haloalkoxy; or $R^5$ and $R^{10}$ together with the atoms to which they are attached form a 5-7 membered heterocycloalkyl ring optionally substituted with 1, 2 or 3 substituents independently selected from oxo, halo, $NH_2$, OH, CN, $C_{1-4}$ alkyl, $C_{1-4}$ haloalkyl, $C_{1-4}$ alkoxy, and $C_{1-4}$ haloalkoxy;

$W^1$ is O, S, or $NR^N$;

wherein when the ---- bond between $X^1$ and $Y^1$ is a single bond, then:
$X^1$ is $CR^5R^6$, $NR^7$, or O and $Y^1$ is $CR^8R^9$, $NR^{10}$, O, S, SO, or $SO_2$,
wherein when $X^1$ is $NR^7$ or O, then $Y^1$ is $CR^8R^9$;

wherein when the ---- bond between $X^1$ and $Y^1$ is a double bond, then:
$X^1$ is $CR^5$ and $Y^1$ is $CR^8$; and wherein when the ---- bond between $X^1$ and $Y^1$ is a triple bond, then:
$X^1$ is C and $Y^1$ is C;

Ring $Z^1$ is $C_{6-10}$ aryl, $C_{3-7}$ cycloalkyl, 5-10 membered heteroaryl, or 4-10 membered heterocycloalkyl;

$R^{4A}$ is halo, nitro, cyano, $C_{1-4}$ alkyl, $C_{2-4}$ alkenyl, $C_{2-4}$ alkynyl, $C_{1-4}$ haloalkyl, $C_{1-4}$ alkoxy, or $C_{1-4}$ haloalkoxy;

or two adjacent $R^{4A}$ together with the atoms to which they are attached form a fused phenyl ring, fused $C_{3-7}$ cycloalkyl ring, fused 5-7 membered heteroaryl ring, or fused 4-7 membered heterocycloalkyl ring, each optionally substituted with 1, 2, or 3 substituents independently selected from halo, nitro, cyano, $C_{1-4}$ alkyl, $C_{2-4}$ alkenyl, $C_{2-4}$ alkynyl, $C_{1-4}$ haloalkyl, $C_{1-4}$ alkoxy, and $C_{1-4}$ haloalkoxy;

m is 0, 1, or 2;
n is 0, 1, 2, 3, 4, or 5; and
n1 is 0, 1, 2, 3, 4, or 5.

In some embodiments, the compound of Formula Ia, Ib, Ic, or Id is other than

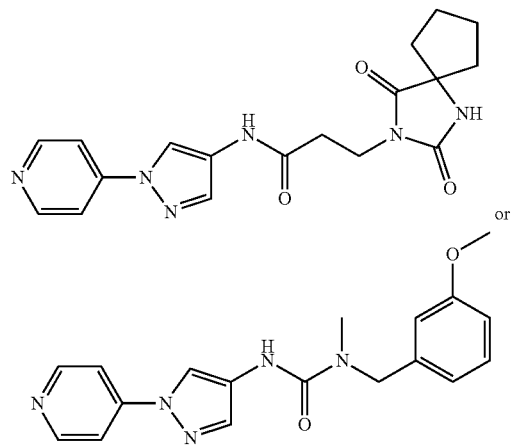

In some embodiments, the compound has a structure according to Formula Ia.

In some embodiments, the compound has a structure according to Formula Ib.

In some embodiments, the compound has a structure according to Formula Ic.

In some embodiments, the compound has a structure according to Formula Id.

In some embodiments, A is N.
In some embodiments, A is $N^+$—O—.
In some embodiments, one of $Q^1$ and $Q^2$ is CH and the other is N.
In some embodiments, $Q^1$ is CH and $Q^2$ is N.
In some embodiments, $Q^1$ is N and $Q^2$ is CH.
In some embodiments, $Q^1$ is CH and $Q^2$ is N.
In some embodiments, both $Q^1$ and $Q^2$ are CH.
In some embodiments, both $Q^1$ and $Q^2$ are N.
In some embodiments, W is O or S.
In some embodiments, W is O.
In some embodiments, W is S.
In some embodiments, ---- is a single bond.
In some embodiments, ---- is a double bond.
In some embodiments, ---- is a triple bond.
In some embodiments, X is $CR^5R^6$.
In some embodiments, X is $NR^7$.
In some embodiments, X is O.
In some embodiments, Y is $CR^8R^9$.
In some embodiments, Y is $NR^{10}$.
In some embodiments, Y is O.
In some embodiments, Y is S, SO, or $SO_2$.

In some embodiments, Ring Z is $C_{6-10}$ aryl or 5-10 membered heteroaryl.

In some embodiments, Ring Z is $C_{6-10}$ aryl.

In some embodiments, Ring Z is phenyl.

In some embodiments, Ring Z is 5-10 membered heteroaryl.

In some embodiments, Ring Z is 5-6 membered heteroaryl.

In some embodiments, Ring Z is pyridyl, pyrimidinyl, thienyl, thiazolyl, isoxazolyl, or pyrrazolyl.

In some embodiments, Ring Z is $C_{3-7}$ cycloalkyl.

In some embodiments, Ring Z is cyclohexyl or cyclopentyl.

In some embodiments, Ring Z is selected from the following (a)-(k):

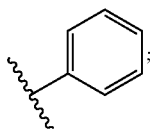
(a)

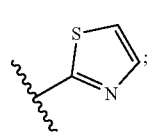
(b)

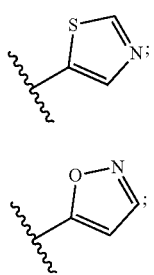
(c), (d), (e), (f), (g), (h)

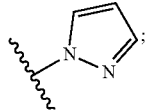
(i)

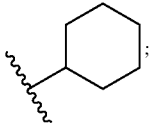
(j)

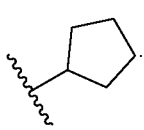
(k)

In some embodiments, m is 0 or 1.
In some embodiments, m is 0.
In some embodiments, m is 1.
In some embodiments, $R^1$ is halo, $C_{1-4}$ alkyl, or $C_{1-4}$ alkoxy.
In some embodiments, $R^1$ is halo, $C_{1-4}$ alkyl, or $C_{1-4}$ alkoxy.
In some embodiments, $R^1$ is F, methyl, or methoxy.
In some embodiments, $R^2$, $R^{2A}$, and $R^{2B}$ are each independently selected from H, halo, $C_{1-4}$ alkyl, $C_{1-4}$ haloalkyl, $C_{1-4}$ hydroxyalkyl, $C_{1-4}$ alkoxy, and $C_{3-7}$ cycloalkyl.
In some embodiments, $R^2$ and $R^{2A}$ are each independently selected from halo, $C_{1-4}$ alkyl, $C_{1-4}$ haloalkyl, $C_{1-4}$ hydroxyalkyl, $C_{1-4}$ alkoxy, and $C_{3-7}$ cycloalkyl.
In some embodiments, $R^2$, $R^{2A}$, and $R^{2B}$ are each independently selected from H, Cl, Br, methyl, ethyl, trifluoromethyl, methoxy, cyclopropyl, and hydroxymethyl.
In some embodiments, $R^2$, $R^{2A}$, and $R^{2B}$ are each independently selected from Cl, Br, methyl, ethyl, trifluoromethyl, methoxy, cyclopropyl, and hydroxymethyl.
In some embodiments, $R^2$ and $R^{2A}$ are each independently selected from H, Cl, Br, methyl, ethyl, trifluoromethyl, methoxy, cyclopropyl, and hydroxymethyl.
In some embodiments, $R^{2B}$ is H.
In some embodiments, $R^3$ is H, $C_{1-4}$ alkyl, —C(=O)—($C_{1-6}$ alkyl), or —S(=O)$_2$—($C_{1-6}$ alkyl).
In some embodiments, $R^3$ is H or $C_{1-4}$ alkyl.
In some embodiments, $R^3$ is H.
In some embodiments, $R^3$ is a group of Formula (ii):

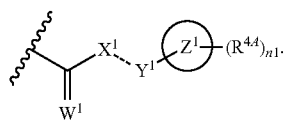
(ii)

In some embodiments, n is 1, 2, 3, 4, or 5.
In some embodiments, n is 1, 2, 3, or 4.
In some embodiments, n is 1, 2, or 3.
In some embodiments, n is 1 or 2.
In some embodiments, n is 1.
In some embodiments, n is 0, 1, 2, 3, or 4.
In some embodiments, n is 0, 1, 2, or 3.
In some embodiments, n is 0, 1, or 2.
In some embodiments, n is 0 or 1.
In some embodiments, n is 0.

In some embodiments, each $R^4$ is independently halo, nitro, cyano, $C_{1-4}$ alkyl, $C_{2-4}$ alkenyl, $C_{2-4}$ alkynyl, $C_{1-4}$ haloalkyl, $C_{1-4}$ alkoxy, or $C_{1-4}$ haloalkoxy.

In some embodiments, each $R^4$ is independently F, Cl, Br, I, CN, $NO_2$, methyl, ethyl, $CF_3$, $CHF_2$, $OCF_3$, or $OCHF_2$.

In some embodiments, each $R^4$ is independently halo.

In some embodiments, each $R^4$ is independently F or Cl.

In some embodiments, two adjacent $R^4$ together with the atoms to which they are attached form a fused phenyl ring, $C_{3-7}$ cycloalkyl ring, 5-7 membered heteroaryl ring, or 4-7 membered heterocycloalkyl ring, each optionally substituted with 1, 2, or 3 substituents independently selected from oxo, halo, nitro, cyano, $C_{1-4}$ alkyl, $C_{2-4}$ alkenyl, $C_{2-4}$ alkynyl, $C_{1-4}$ haloalkyl, $C_{1-4}$ alkoxy, and $C_{1-4}$ haloalkoxy.

In some embodiments, two adjacent $R^4$ together with the atoms to which they are attached form a fused phenyl ring or 4-7 membered heterocycloalkyl ring.

In some embodiments, two adjacent $R^4$ together with the atoms to which they are attached form a fused phenyl ring or 5-6 membered heterocycloalkyl ring.

In some embodiments, two adjacent $R^4$ together with the atoms to which they are attached form a fused phenyl ring.

In some embodiments, two adjacent $R^4$ together with the atoms to which they are attached form a fused 4-7 membered heterocycloalkyl ring.

In some embodiments, two adjacent $R^4$ together with the atoms to which they are attached form a fused phenyl ring or 5-6 membered heterocycloalkyl ring.

In some embodiments, $R^5$ and $R^6$ are each independently selected from H, F, $NH_2$, and OH.

In some embodiments, one of $R^5$ and $R^6$ is H and the other is selected from H, F, $NH_2$, and OH.

In some embodiments, $R^5$ and $R^6$ are both H.

In some embodiments, each $R^7$ is independently selected from H and $C_{1-4}$ alkyl.

In some embodiments, each $R^7$ is independently selected from H and methyl.

In some embodiments, $R^7$ is H.

In some embodiments, $R^8$ and $R^9$ are each independently selected from H and methyl.

In some embodiments, $R^8$ and $R^9$ are both H.

In some embodiments, $R^3$ and $R^5$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$haloalkyl, $C_{1-4}$ alkoxy, and $C_{1-4}$ haloalkoxy.

In some embodiments, $R^3$ and $R^7$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy.

In some embodiments, $R^3$ and $R^8$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy.

In some embodiments, $R^3$ and $R^{10}$, together with the atoms to which they are attached and together with any intervening atoms, form a $C_{5-7}$ membered cycloalkyl ring or a 5-7 membered heterocycloalkyl ring, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy.

In some embodiments, $R^4$ and $R^9$, together with the atoms to which they are attached and together with any intervening atoms, form a $C_{5-7}$ membered cycloalkyl ring fused with ring Z or a 5-7 membered heterocycloalkyl ring fused with ring Z, each optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy.

In some embodiments, $R^5$ and $R^9$ together with the atoms to which they are attached form a $C_{3-7}$ cycloalkyl ring or a 5-7 membered heterocycloalkyl ring, each optionally substituted with 1, 2 or 3 substituents independently selected from oxo, halo, $NH_2$, OH, CN, $C_{1-4}$ alkyl, $C_{1-4}$ haloalkyl, $C_{1-4}$ alkoxy, and $C_{1-4}$ haloalkoxy.

In some embodiments, $R^5$ and $R^{10}$ together with the atoms to which they are attached form a 5-7 membered heterocycloalkyl ring optionally substituted with 1, 2 or 3 substituents independently selected from oxo, halo, $NH_2$, OH, CN, $C_{1-4}$ alkyl, $C_{1-4}$ haloalkyl, $C_{1-4}$ alkoxy, and $C_{1-4}$ haloalkoxy.

In some embodiments, $R^8$, $R^9$, and $R^{10}$ are each independently selected from H and $C_{1-4}$ alkyl.

In some embodiments, $R^{10}$ is selected from H and $C_{1-4}$ alkyl.

In some embodiments, $R^{10}$ is H.

In some embodiments, the compound has Formula IIa:

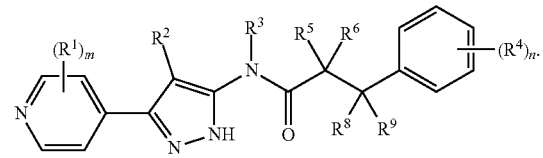

IIa

In some embodiments, the compound has Formula IIb:

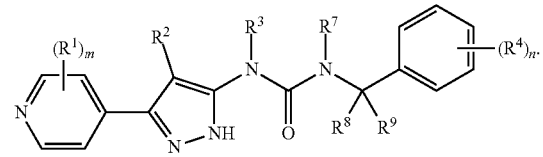

IIb

In some embodiments, the compound has Formula IIIa:

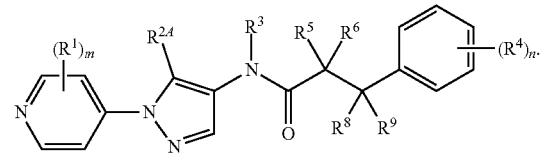

IIIa

In some embodiments, the compound has Formula IIIb:

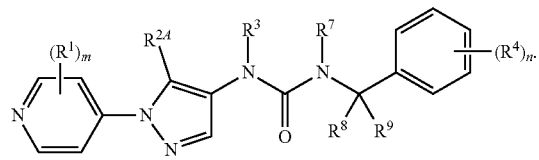

IIIb

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

At various places in the present specification a di-valent or linking group may be present. Each linking group is understood as linking in either direction. That is, if a linking group is described as -A-B-, then it is understood, unless otherwise specified, that the linking group is not directionally limited and can also be -B-A-.

For example, when a linking group is written as —C(=O)—O—, it also means —O—C(=O)—.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency. In some embodiments, an atom substituted by oxo (=O) has two hydrogen atoms replaced by the oxo substituent.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched.

In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the alkyl group has 1 to 6 or 1 to 4 carbon atoms. An example haloalkoxy group is —OCF$_3$.

As used herein, "amino," employed alone or in combination with other terms, refers to NH$_2$.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems.

In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahydropyridine, azetidine ring, or tetrahydrofuran ring.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl. In some embodiments, the aryl group is phenyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole.

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric isomers, tautomers, and isotopes of the structures depicted, unless otherwise specified. The term "compound" is also not limited by the way in which it was made. Thus, a compound of the invention includes molecules that were made by a synthetic process or by a biological process (such as through enzyme conversion or metabolism), or combinations thereof.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of a compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Methods of Use

Compounds of the invention can inhibit the activity of SARM1. For example, the compounds of the invention can be used to inhibit activity or a function of SARM1 in a cell or in an individual or patient in need of inhibition of the enzyme by administering an inhibiting amount of a compound of the invention to the cell, individual, or patient. As used herein, the term "in a cell" includes both inside the cell membrane and on the surface of the cell membrane.

Compounds of the invention, as SARM1 inhibitors, can increase levels of NAD+ in a cell. Accordingly, the present invention is further directed to a method of increasing the level of NAD+ in a sample or in a patient, comprising contacting the sample or administering to the patient a compound of Formula I, or a pharmaceutically acceptable salt thereof, wherein the increased level of NAD+ is relative to the level of NAD+ prior to the contacting or administering.

Compounds of the invention, as SARM1 inhibitors, can inhibit axonal degeneration. Accordingly, the present invention is further directed to a method of inhibiting axonal degeneration in a sample or in a patient, comprising contacting the sample or administering to the patient an inhibiting amount of a compound of Formula I, or a pharmaceutically acceptable salt thereof.

The compounds of the invention are useful in the treatment and prevention of various diseases associated with abnormal expression or activity of SARM1. For example, the compounds of the invention are useful in the treatment and prevention of neurological disorders. The term "neurological disorder" generally refers to a disorder affecting the nervous system, including the central nervous system or the peripheral nervous system. The term "neurological disorder" also includes ocular indications having a nexus to the nervous system.

In some embodiments, the neurological disorder treatable or preventable by administration of a compound of the invention includes neurodegenerative diseases.

Neurodegenerative diseases are characterized by damage to the central nervous system and can be identified by progressive dysfunction, degeneration and death of specific populations of neurons which are often synaptically interconnected.

Examples of neurodegenerative diseases include Parkinson's disease (PD), Alzheimer's disease (AD), Huntington's disease (HD), prion disease, motor neuron diseases (MND), spinocerebellar ataxia (SCA), spinal muscular atrophy (SMA), amyotrophic lateral sclerosis (ALS), and epilepsy.

Examples of neurological disorders treatable or preventable according to the methods of the invention include spinal muscular atrophy (SMA), Chemotherapy Induced Peripheral Neuropathy (representative chemotherapeutic agents include vinca-alkaloids, taxols and platins), multiple sclerosis (MS), traumatic brain injury (TBI), spinal cord injury, stroke, Parkinson' disease, glaucoma, Huntington's disease, Alzheimer's disease, Charcot-Marie-Tooth disease (CMT), retinitis pigmentosa (RP), age-related macular degeneration (AMD), small fiber neuropathies, peripheral neuropathy (e.g., viral neuropathy), spinocerebellar ataxias, cystic fibrosis, familial amyloidotic polyneuropathy, spongiform encephalopathies, spinal and bulbar muscular atrophy, hereditary dentatorubral-pallidoluysian atrophy, adrenoleukodystrophy, adrenomyeloneuropathy, Alexander's disease, amyotrophic lateral sclerosis (ALS), Bassen-Kornzweig syndrome, Bell's palsy, progressive supra nuclear palsy (PSP), central pontine myelolysis, cluster headache, congenital hypomyelination, corticobasal degeneration, Creutzfeldt-Jakob disease, epilepsy, dementia (e.g., frontotemporal dementia and Lewy body dementia), demyelination disorders (e.g., ischemic demyelination), encephalomyelitis, Friedrich's ataxia, Gaucher's disease, hereditary sensory and autonomic neuropathy (HSAN), Hurler syndrome, Krabbe's disease, metachromatic leukodystrophy, migraine and tension headaches, mild cognitive impairment, motor spinoneuron disease, neuromyelitis optica, Niemann-Pick disease, optic neuritis, Pelizaeus Merzbacher disease, peripheral neuropathy, periventricular leukomalacia, postherpetic neuralgia, prion disease, progressive supranuclear palsy, progressive multifocal leukoencephalopathy, Tay-Sacks disease, thoracic disc herniation, traverse myelitis, trigeminal neuralgia, wallerian degeneration, cerebellar degeneration, chiari malformation, dystonia, encephalitis (e.g., pediatric viral encephalitis and La Crosse virus encephalitis), hyperekplexia, multifocal motor neuropathy, muscular dystrophy, myasthenia gravis, myopathy, neurofibromatosis, neuronal ceroid lipofuscinosis, neuropathies (e.g., peripheral neuropathy), pseudobulbar affect, restless legs syndrome, spina bifida, syringomyelia, thoracic outlet syndrome, and transverse myelitis.

In other embodiments, the neurological disorder treatable or preventable by administration of a compound of the invention is a neuropathy. As used herein, the term "neuropathy" refers broadly to diseased conditions of the nervous system, including polyneuropathy; neuropathy, ataxia, and retinosa pigmentosa (NARP); familial amyloid neuropathies; diabetic neuropathy (peripheral neuropathy due to diabetes mellitus); peripheral neuropathy (e.g., chemotherapy-induced peripheral neuropathy (CIPN), including CIPN caused by vinca alkaloids, bortezomib, lxabepilone, thalidomide and its analogs, taxanes, and platinum-based agents); and cranial neuropathy (e.g., auditory neuropathy and optic neuropathy). The term also includes other neuropathies associated with genetic disorders (e.g., NMNAT2 genetic mutation disorders).

In still other embodiments, the neurological disorder treatable or preventable by administration of a compound of the invention is an ocular neuropathy (e.g., optic neuropathy). The term "optic neuropathy" refers to damage to the optic nerve from a number of causes. Types of optic neuropathy include ischemic optic neuropathy (e.g., anterior and posterior ischemic optic neuropathy); optic neuritis (e.g., chronic relapsing inflammatory optic neuropathy (CRION), single isolated optic neuritis (SION), and relapsing isolated optic neuritis); compressive optic neuropathy; infiltrative optic neuropathy; traumatic optic neuropathy; mitochondrial optic neuropathies; and hereditary optic neuropathies (e.g., Leber's hereditary optic neuropathy (LHON), hereditary neuropathy with liability to pressure palsy (HNPP), and dominant optic atrophy).

In still other embodiments, the neurological disorder treatable or preventable by administration of a compound of the invention is multiple sclerosis (MS), chemotherapy-induced peripheral neuropathy (CIPN), amyotrophic lateral sclerosis (ALS), glaucoma, traumatic brain injury (TBI), or stroke.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" SARM1 or "contacting" a cell with a compound of the invention includes the administration of a compound of the present invention to an individual or patient, such as a human, having SARM1, as well as, for example, introducing a compound of the invention into a sample containing a cellular or purified preparation containing SARM1.

As used herein, the term "individual" or "patient," used interchangeably, refers to mammals, and particularly humans. The individual or patient can be in need of treatment.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the phrase "inhibiting amount" refers to the amount of active compound or pharmaceutical agent that elicits a measurable SARM1 inhibition or axonal degeneration in a tissue, system, animal, individual or human.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease. In some embodiments, the invention is directed to a method of preventing a disease in a patient, by administering to the patient a therapeutically effective amount of a compound of the invention, or a pharmaceutically acceptable salt thereof.

Combination Therapy

One or more additional pharmaceutical agents or treatment methods can be used in combination with the compounds of the present invention. The agents can be combined with the present compounds in a single dosage form, or the agents can be administered simultaneously or sequentially as separate dosage forms. Examples of additional agents include acamprosate, agomelatine, almotriptan, amantadine, amisulpride, amitriptyline, apomorphine, aripiprazole, asenapine, atomoxetine, baclofen, botulinum toxin type A, bromocriptine, buccal midazolam, buprenorphine, buspirone, cabergoline, carbamazepine, chlordiazepoxide, chlorpromazine, citalopram, clobazam, clomethiazole, clomipramine, clonazepam, clozapine, denzapine, co-beneldopa, co-careldopa, dantrolene, dexamfetamine, diazepam, divalproex sodium, donepezil, doxepin, duloxetine, eletriptan, entacapone, epinephrine, escitalopram, eslicarbazepine, ethosuximide, fingolimod, fluoxetine, flupentixol, flupentixol, fluphenazine long-acting injection (modecate), fluvoxamine (Faverin), frovatriptan, gabapentin, galantamine, haloperidol, imipramine, lacosamide, lamotrigine, levetiracetam, levomepromazine, lisdexamfetamine, lithium, lofepramine, loprazolam, lorazepam, lormetazepam, lurasidone, melatonin, memantine, methylphenidate, mianserin, mirtazapine, moclobemide, modafinil, naratriptan, neostigmine, nitrazepam, nortriptyline, olanzapine, orlistat, orphenadrine, oxazepam, oxcarbazepine, paliperidone, paliperidone, paroxetine, perampanel, pergolide, pericyazine, phenobarbital, phenytoin, piracetam, pizotifen, pramipexole, pregabalin, primidone, prochlorperazine, procyclidine, pyridostigmine, quetiapine, rasagiline, reboxetine, risperidone, rivastigmine, rizatriptan, ropinirole, rotigotine, rufinamide, selegiline, sertraline, sodium oxybate, sodium valproate, sulpiride, sumatriptan, temazepam, tetrabenazine, tiagabine, tizanidine, tolcapone, topiramate, trazodone, trihexyphenidyl, trimipramine, valproate semisodium, venlafaxine, vigabatrin, vortioxetine, zolmitriptan, zolpidem, zonisamide, zopiclone, and zuclopenthixol.

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of SARM1 according to one or more of the assays provided herein.

EXAMPLES

General Experimental:

All reactions sensitive to air or moisture were carried out in flame-dried glassware under an atmosphere of nitrogen. All commercially available reagents were purchased from suppliers such as Sigma-Aldrich (MilliporeSigma), Combi-Blocks, Enamine, Sinopharm Chemical Reagent Co. (SCRC), or Alfa Aesar and were used without purification unless otherwise noted. Proton nuclear magnetic resonance ($^1$H NMR) spectra were recorded on Bruker AVIII 400 or Bruker AVIII 500 spectrometers. Samples were dissolved in deuterated chloroform (CDCl$_3$), dimethyl sulfoxide (DMSO-d$_6$) or methanol (CD$_3$OD). Chemical shifts are recorded in parts per million (ppm) and are referenced to the centerline of deuterochloroform (δ 7.26 ppm), of DMSO-d$_6$ (δ 2.50 ppm), or of CD$_3$OD (δ 3.31 ppm). Data were recorded as follows: chemical shift, multiplicity (s=singlet, d=doublet, t=triplet, q=quartet, qt=quintet, m=multiplet, br=broad). Coupling constants (J values) are given in Hertz (Hz). Low resolution ESI mass spectra were recorded on a either an Agilent 1200 HPLC/6100 SQ system or an Agilent 1260 Infinity II HPLC/6125 SQ system.

| List of Abbreviations: |
| --- |
| MeCN acetonitrile |
| Boc tert-butyloxycarbonyl |
| Boc$_2$O Boc anhydride or di-tert-butyl dicarbonate |
| CDI 1,1'-carbonyl-diimidazole |
| d day(s) |
| D $^2$H (deuterium) |
| DABCO 1,4-diazabicyclo[2.2.2]octane |
| DCM dichloromethane |
| DIAD diisopropyl azodicarboxylate |
| DIPEA N,N-diisopropylethylamine |
| DMAP 4-(dimethylamino)pyridine |
| DMF dimethylformamide |
| DMSO dimethylsulfoxide |
| DPPA diphenyl phosphoryl azide |
| ESI-MS electrospray ionization-mass spectrometry |
| EtOAc ethyl acetate |
| EtOH ethanol |
| equiv equivalent(s) |
| FA formic acid |
| h hour(s) |
| HATU 1-[bis(dimethylamino)methylene]-1H-1,2,3-triazolo[4,5-b]pyridinium 3-oxide hexafluorophosphate |
| IPA isopropyl alcohol, 2-propanol |
| LAH lithium aluminum hydride |
| LCMS liquid chromatography mass spectrometry |
| LiHMDS lithium bis(trimethylsilyl)amide |
| MS mass spectrometry |
| MeOH methanol |
| MHz megahertz |
| min minute(s) |
| mg milligram(s) |
| mL milliliter(s) |
| mmol millimolar |
| M molar |
| mol mole(s) |
| Ms methanesulfonyl |
| N normal |
| NBS N-bromosuccinimide |
| NCS N-chlorosuccinimide |
| Oxone ® Potassium peroxymonosulfate |

| List of Abbreviations: |
| --- |
| Pd/C palladium on carbon |
| Pd(dppf)Cl$_2$ [1,1'-bis(diphenylphosphino)ferrocene]dichloropalladium(II) |
| PE petroleum ether |
| Ph phenyl |
| $^1$H NMR proton nuclear magnetic resonance |
| RP-HPLC reverse-phase high performance liquid chromatography |
| rt room temperature |
| SEM 2-(trimethylsilyl)ethoxymethyl |
| SFC supercritical fluid chromatography |
| T3P propylphosphonic anhydride |
| TBAF letrabuty lammonium fluoride |
| TBPH tert-butyl hydroperoxide solution (Luperox ®, TBH70X) |
| THF tetrahydrofuran |
| TFA trifluoroacetic acid |
| TLC thin layer chromatography |
| Tol toluene |
| wt % weight percent |
| v/v % volume by volume percent |
| w/v % weight by volume percent |

Reverse-Phase HPLC Purification:

Compounds purified by RP-HPLC were run on one of the following four types of columns:
  Method A: RediSep® C18 prep column, 20×150 mm (100 Å/5 micron)
  Method B: Phenomenex® C18 prep column, 21.2×250 mm (100 Å/Luna 10 micron)
  Method C: Xtimate® C18 prep column, 21.2×250 mm (10 micron)
  Method D: Boston Prep® C18 prep column 21.2×250 mm (10 micron)

Intermediates:
Intermediate #1

4-Methyl-3-(pyridin-4-yl)-1H-pyrazol-5-amine

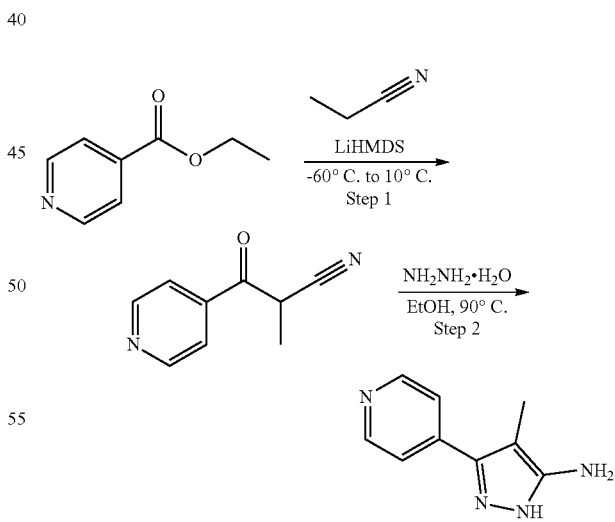

Step 1: 2-Methyl-3-oxo-3-(pyridin-4-yl)propanenitrile. A solution of propiononitrile (2.0 g, 36 mmol, 1.0 equiv) in anhydrous THF (150 mL, 0.24 M) under at atmosphere of nitrogen was cooled to −60° C. To the cold solution was then added LiHMDS (1.0 M in THF, 75 mL, 75 mmol, 2.1 equiv) dropwise. The resulting mixture was warmed to 10° C. and stirred for 30 min. The reaction mixture was cooled again to −60° C., and ethyl isonicotinate (10 g, 73 mmol, 2.0 equiv) was added. After the addition, the resulting mixture was warmed to rt and stirred for 3 h. The suspension was then filtered, and the solid was collected and triturated with DCM (200 mL) to obtain crude 2-methyl-3-oxo-3-(pyridin-4-yl) propanenitrile (9.0 g, 34 mmol, 60% purity) as an off-white solid. The crude material was used on the next step without further purification. LCMS: ESI-MS m/z: 161.1 [M+H]$^+$.

Step 2: 4-Methyl-3-(pyridin-4-yl)-1H-pyrazol-5-amine. To a solution of crude 2-methyl-3-oxo-3-(pyridin-4-yl)propanenitrile (9.0 g, 34 mmol, 1.0 equiv) in ethanol (100 mL, 0.34 M) was added hydrazine hydrate (10 mL, 170 mmol, 5.0 equiv). The resulting mixture was heated to 90° C. and stirred for 12 h. The solution was then concentrated in vacuo, and the residue was purified directly by silica gel column chromatography (10% MeOH in DCM) to give 4-methyl-3-(pyridin-4-yl)-1H-pyrazol-5-amine (3.0 g, 17 mmol, 47% yield over 2 steps) as a light yellow solid. $^1$H NMR (400 MHz, DMSO-d$_6$) δ 11.9 (s, 1H), 8.57 (d, J=4.1 Hz, 2H), 7.55 (d, J=2.8 Hz, 2H), 4.67 (s, 2H), 2.04 (s, 3H). LCMS: ESI-MS m/z: 175.2 [M+H]$^+$.

Intermediate #2

4-Methyl-3-(pyridin-4-yl)-1-((2-(trimethylsilyl) ethoxy)methyl)-1H-pyrazol-5-amine

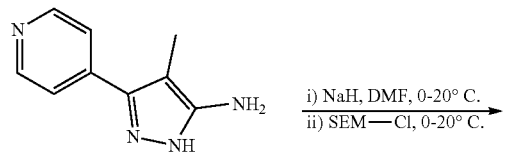

To a solution of 4-methyl-3-(pyridin-4-yl)-1H-pyrazol-5-amine (10 g, 57 mmol, 1.0 equiv) in anhydrous DMF (100 mL, 0.57 M) was added NaH (60 wt % in mineral oil, 2.8 g, 69 mmol, 1.2 equiv) under nitrogen at 0° C. After the addition, the mixture was stirred at 0° C. for 30 min, then 2-(trimethylsilyl)ethoxymethyl chloride (11 g, 63 mmol, 1.1 equiv) was slowly added. The resulting solution was maintained at 0° C. for 30 min, then was slowly quenched with water (200 mL) and extracted with ethyl acetate (3×300 mL). The combined organic extracts were washed with brine (300 mL) and dried over Na$_2$SO$_4$, filtered, and concentrated in vacuo. The resulting residue was purified by silica gel column chromatography (0-5% MeOH in DCM) to afford 4-methyl-3-(pyridin-4-yl)-1-((2-(trimethylsilyl)ethoxy) methyl)-1H-pyrazol-5-amine (11 g, 37 mmol, 64% yield) as a light-yellow solid. LCMS: ESI-MS m/z: 305.3 [M+H]$^+$.

Intermediate #3

3-(4-Chlorophenyl)-N-(4-methyl-3-(pyridin-4-yl)-1-((2-(trimethylsilyl)ethoxy)methyl)-1H-pyrazol-5-yl) propenamide

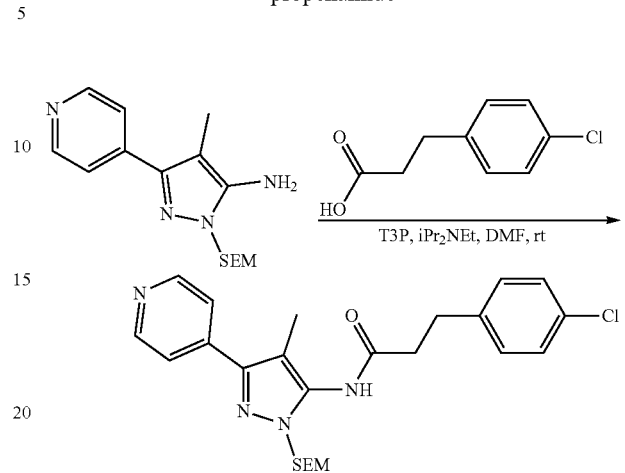

To a solution of 3-(4-chlorophenyl)propanoic acid (10 g, 33 mmol, 1.0 equiv) in DMF (100 mL, 0.33 M), was added DIPEA (8.5 g, 66 mmol, 2.0 equiv) and the resulting solution was stirred at rt for 5 min. The solution was then cooled to 0° C. and T3P (50% w/w in EtOAc, 14 g, 43 mmol, 1.3 equiv) was added. The resulting reaction mixture was stirred for 5 min, followed by the addition of 4-methyl-3-(pyridin-4-yl)-1-((2-(trimethylsilyl)ethoxy)methyl)-1H-pyrazol-5-amine (10 g, 33 mmol, 1.0 equiv). The mixture was stirred at rt for 20 hours. Upon completion, the reaction mixture was extracted with EtOAc (3×100 mL). The combined organic fractions were washed with brine, dried over Na$_2$SO$_4$, filtered, and concentrated in vacuo. The crude product was purified by silica gel column chromatography (0-12% MeOH in DCM) to afford 3-(4-chlorophenyl)-N-(4-methyl-3-(pyridin-4-yl)-1-((2-(trimethylsilyl)ethoxy) methyl)-1H-pyrazol-5-yl)propenamide (11 g, 23 mmol, 70% yield) as a light yellow solid. LCMS: ESI-MS m/z: 471.3 [M+H]$^+$.

Intermediate #4

4-Ethyl-3-(Pyridin-4-yl)-1H-pyrazol-1-amine

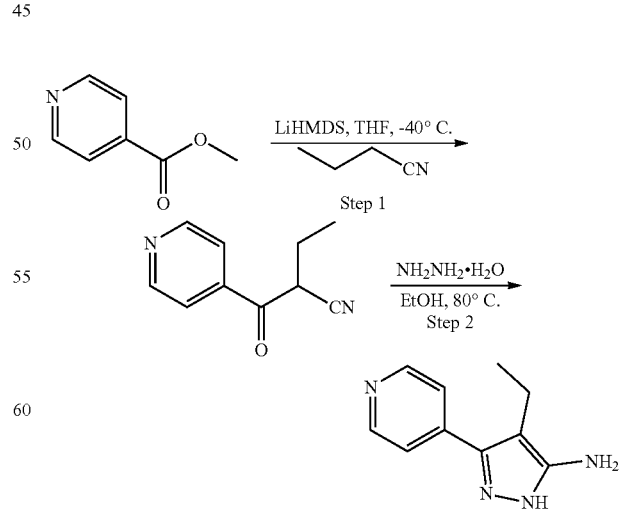

Step 1: 2-Isonicotinoylbutanenitrile. To a solution of butyronitrile (2.2 g, 32 mmol, 1.7 equiv) in anhydrous THF (20 mL, 1.6 M) was cooled to −40° C. and LiHMDS (1.0 M in THF, 40 mL, 40 mmol, 2.2 equiv) was added by dropwise addition. The resulting mixture was warmed to 0° C. and stirred for 1 h. The mixture was cooled again to −40° C. and methyl isonicotinate (2.5 g, 18 mmol, 1.0 equiv) was added. The reaction mixture was warmed to rt and stirred for 0.5 h. The organic material was then filtered and concentrated in vacuo to afford 2-isonicotinoylbutanenitrile (3.4 g, 18 mmol, >95% crude yield) as a white solid. The crude material was carried forward without further purification. LCMS: ESI-MS m/z: 175.1 [M+H]$^+$.

Step 2: 4-Ethyl-3-(pyridin-4-yl)-1H-pyrazol-5-amine. A mixture of crude 2-isonicotinoylbutanenitrile (3.4 g, 18 mmol, 1.0 equiv) and hydrazine hydrate (85% w/w in water, 8.1 g, 140 mmol, 7.6 equiv) in EtOH (20 mL, 0.90 M) was heated to 80° C. and stirred for 20 h. The mixture was cooled to rt and concentrated in vacuo. The crude product was purified by silica gel column chromatography (0-5% MeOH in DCM) to afford 4-ethyl-3-(pyridin-4-yl)-1H-pyrazol-5-amine (1.5 g, 8.2 mmol, 45% yield over 2 steps) as a light yellow solid. LCMS: ESI-MS m/z: 189.2 [M+H]$^+$.
Intermediate #5

3-(4-Chlorophenyl)-2-fluoropropanoic acid

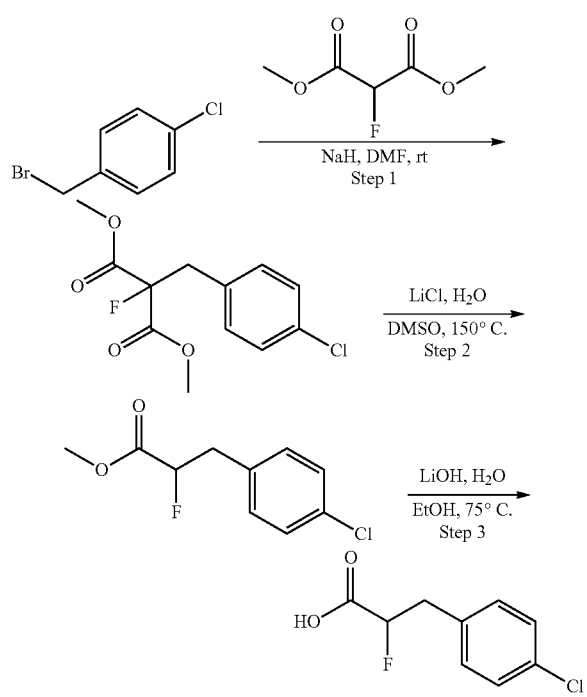

Step 1: Dimethyl 2-(4-chlorobenzyl)-2-fluoromalonate. A solution of dimethyl 2-fluoromalonate (2.0 g, 9.7 mmol, 1.2 equiv) in anhydrous DMF (12 mL, 0.68 M) was cooled to 0° C. and was treated with sodium hydride (60 wt % dispersion in mineral oil, 320 mg, 8.1 mmol, 1.0 equiv). The resulting suspension was stirred at 0° C. for 1 h. Subsequently, 1-(bromomethyl)-4-chlorobenzene (1.2 g, 8.1 mmol, 1.0 equiv) was added to the mixture, and the solution was warmed to rt and stirred for 1 h. The mixture was then cooled to 0° C. and quenched by the slow addition of water (30 mL). After warming again to rt, the solution was extracted with EtOAc (3×30 mL).

The organic material was washed with a saturated aqueous solution of NH$_4$Cl, filtered over Na$_2$SO$_4$ and concentrated in vacuo to afford dimethyl 2-(4-chlorobenzyl)-2-fluoromalonate (3.0 g, 11 mmol, >95% crude yield) as an oil. The crude material was carried forward to the next step without further purification.
LCMS: ESI-MS m/z: 275.1 [M+H]$^+$.

Step 2: Methyl 3-(4-chlorophenyl)-2-fluoropropanoate. A mixture of dimethyl 2-(4-chlorobenzyl)-2-fluoromalonate (3.0 g, 11 mmol, 1.0 equiv) and lithium chloride (630 mg, 15 mmol, 1.3 equiv) in a 10:1 solution of DMSO:water (22 mL, 0.50 M) was heated to 150° C. and stirred for 4 h. After cooling to rt, the solution was diluted with water (20 mL) and extracted with EtOAc (3×30 mL). The organic material was dried over Na$_2$SO$_4$, filtered, and concentrated in vacuo. The crude product was purified by silica gel column chromatography (0-25% EtOAc in PE) to afford methyl 3-(4-chlorophenyl)-2-fluoropropanoate (700 mg, 3.3 mmol, 30% yield) as a light yellow oil. LCMS: ESI-MS m/z: 217.1 [M+H]$^+$.

Step 3: 3-(4-Chlorophenyl)-2-fluoropropanoic acid. A mixture of methyl 3-(4-chlorophenyl)-2-fluoropropanoate (700 mg, 3.2 mmol, 1.0 equiv) and lithium hydroxide (160 mg, 6.5 mmol, 2.0 equiv) in a 4:1 solution of EtOH:water (25 mL, 0.13 M) was heated to 75° C. and stirred for 2 h. After cooling to rt, the solution was brought to pH ~5 by the addition of 2 M HCl and extracted with EtOAc (3×30 mL). The organic material was dried over Na$_2$SO$_4$, filtered, and concentrated in vacuo to afford 3-(4-chlorophenyl)-2-fluoropropanoic acid (500 mg, 2.5 mmol, 76% crude yield) as a white solid. The crude material was carried forward to the next step without further purification. LCMS: ESI-MS m/z: 203.1 [M+H]$^+$.
Intermediate #6

5-Methyl-1-(pyridin-4-yl)-1H-pyrazol-4-amine

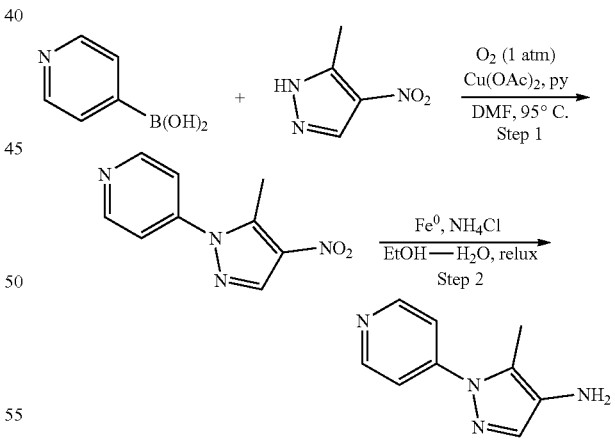

Step 1: 4-(5-Methyl-4-nitro-1H-pyrazol-1-yl)pyridine: A solution of 5-methyl-4-nitro-1H-pyrazole (200 mg, 1.6 mmol, 1.0 equiv), pyridin-4-ylboronic acid (290 mg, 2.4 mmol, 1.5 equiv), copper(II) acetate (940 mg, 5.2 mmol, 3.3 equiv), and pyridine (250 mg, 3.2 mmol, 2.0 equiv) in DMF (5.0 mL, 0.31 M) was stirred at 95° C. under an oxygen balloon for 16 h. The mixture was diluted with ethyl acetate (15 mL) and sequentially washed with water (10 mL) and brine (10 mL). The organic phase was separated and concentrated in vacuo. The resulting residue was purified by silica gel chromatography (0-10% MeOH in DCM) to give 4-(5-methyl-4-nitro-1H-pyrazol-1-yl)pyridine (170 mg, 53%) as a white solid. LCMS: ESI-MS m/z: 250.0 [M+H]⁺.

Step 2: 5-Methyl-1-(pyridin-4-yl)-1H-pyrazol-4-amine: A mixture of 4-(5-methyl-4-nitro-1H-pyrazol-1-yl)pyridine (170 mg, 0.83 mmol), iron powder (70 mg, 1.3 mmol, 1.5 equiv), and ammonium chloride (130 mg, 2.5 mmol, 3.0 equiv) in ethanol-water (5:1, 6.0 mL, 0.14 M) was stirred at reflux for 3 h. The mixture was cooled to rt and then filtered. The filtrate was concentrated in vacuo and then purified by silica gel column chromatography (10% MeOH in DCM) to afford 5-methyl-1-(pyridin-4-yl)-1H-pyrazol-4-amine (120 mg, 83% yield) as a white solid. $^1$H NMR (400 MHz, DMSO-$d_6$) δ 8.58 (dd, J=4.8, 1.6 Hz, 2H), 7.57 (dd, J=4.8, 1.6 Hz, 2H), 7.32 (s, 1H), 4.07 (br s, 2H), 2.34 (s, 3H). LCMS: ESI-MS m/z: 175.0 [M+H]⁺.

Intermediate #7

5-Chloro-1-(pyridin-4-yl)-1H-pyrazol-4-amine

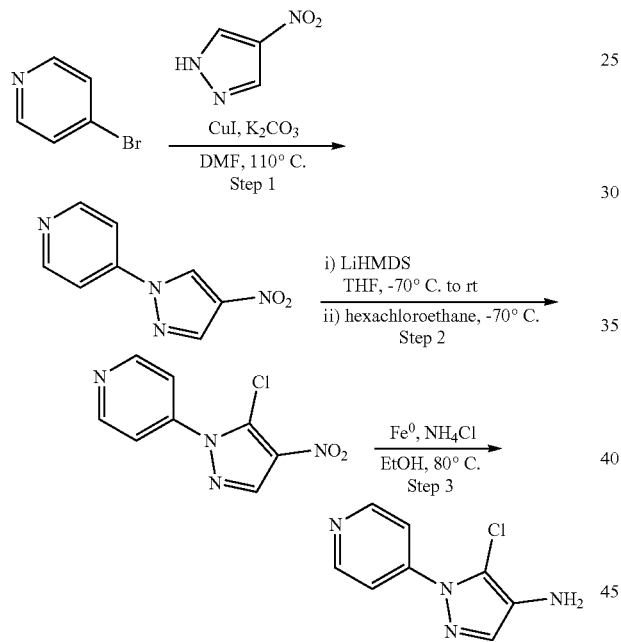

Step 1: 4-(4-Nitro-1H-pyrazol-1-yl)pyridine: A mixture of 4-bromopyridine (1.0 g, 6.4 mmol, 1.0 equiv), 4-nitro-1H-pyrazole (720 mg, 6.4 mmol, 1.0 equiv), copper(I) iodide (120 mg, 0.64 mmol, 1.0 equiv), and potassium carbonate (1.8 g, 13 mmol, 2.0 equiv) in DMF (20 mL, 0.32 M) was stirred at 110° C. for 16 h. The reaction mixture was cooled to rt and filtered. The filtrate was treated with water (100 mL) and extracted with EtOAc (3×30 mL). The combined organic extracts were washed with a saturated aqueous solution of ammonium chloride (2×50 mL), then dried over anhydrous sodium sulfate, filtered, and concentrated in vacuo. The resulting residue was purified by silica gel column chromatography (5% MeOH in DCM) to give 4-(4-nitro-1H-pyrazol-1-yl)pyridine (600 mg, 50% yield) as a yellow solid. LCMS: ESI-MS m/z: 191.0 [M+H]⁺.

Step 2: 4-(5-Chloro-4-nitro-1H-pyrazol-1-yl)pyridine: To a stirred solution of 4-(4-nitro-1N-pyrazol-1-yl)pyridine (500 mg, 2.6 mmol, 1.0 equiv) in anhydrous THF (10 mL, 0.26 M) was added LiHMDS (1 M in THF, 3.0 mL, 3.0 mmol, 1.1 equiv) at −70° C. After the addition, the mixture stirred at rt for 30 min, then hexachloroethane (450 µL, 4.0 mmol, 1.5 equiv) was added dropwise at −70° C. After the addition, the mixture was maintained at −70° C. for 1 h, then quenched with a saturated aqueous solution of ammonium chloride (10 mL). The mixture was extracted with EtOAc (3×10 mL). The combined organic extracts were dried over anhydrous sodium sulfate, filtered and concentrated in vacuo to afford crude 4-(5-chloro-4-nitro-1H-pyrazol-1-yl)pyridine (290 mg, 49% yield) that was carried forward in the next step without purification. LCMS: ESI-MS m/z: 225.0 [M+H]⁺.

Step 3: 5-Chloro-1-(pyridin-4-yl)-1H-pyrazol-4-amine: A mixture of 4-(5-chloro-4-nitro-1H-pyrazol-1-yl)pyridine (290 mg, 1.3 mmol, 1.0 equiv), iron powder (360 mg, 6.5 mmol, 5.0 equiv), and ammonium chloride (700 mg, 13 mmol, 10 equiv) in EtOH (20 mL, 0.065 M) was heated at 80° C. for 5 h. The reaction mixture was cooled to rt and filtered. The filtrate was concentrated in vacuo and then purified by silica gel column chromatography (5% MeOH in DCM) to afford 5-chloro-1-(pyridin-4-yl)-1H-pyrazol-4-amine (50 mg, 20% yield) as a light-yellow solid. $^1$H NMR (400 MHz, DMSO-$d_6$) δ 8.66 (dd, J=4.7, 1.6 Hz, 2H), 7.69 (dd, J=4.7, 1.6 Hz, 2H), 7.51 (s, 1H), 4.54 (s, 2H). LCMS: ESI-MS m/z: 195.1 [M+H]⁺.

Intermediate #8

3-(4-Cyano-3,5-difluorophenyl)propanoic acid

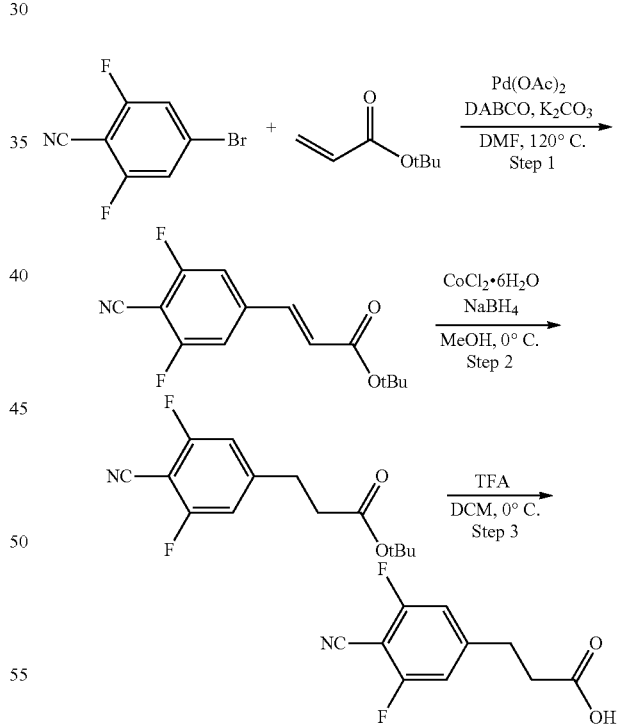

Step 1: tert-Butyl (E)-3-(4-cyano-3,5-difluorophenyl) acrylate: A mixture of 4-bromo-2,6-difluorobenzonitrile (10 g, 46 mmol, 1.0 equiv), tert-butyl acrylate (8.8 g, 69 mmol, 1.5 equiv), K₂CO₃ (5.7 g, 41 mmol, 0.89 equiv), palladium (II) acetate (170 mg, 0.70 mmol, 15 mol %), and DABCO (170 mg, 1.5 mmol, 3.3 mol %) in anhydrous DMF (100 mL, 0.46 M) was stirred at 120° C. for 1 h. The reaction mixture was concentrated in vacuo and purified by silica gel column chromatography (5-35% EtOAc in petroleum ether) to give tert-butyl (E)-3-(4-cyano-3,5-difluorophenyl)acrylate (3.0 g, 11 mmol, 25% yield) as a light-yellow solid. LCMS: ESI-MS m/z: 266.1 [M+H]$^+$.

Step 2: tert-Butyl 3-(4-cyano-3,5-difluorophenyl)propanoate: To a mixture of tert-butyl (E)-3-(4-cyano-3,5-difluorophenyl)acrylate (3.2 g, 12 mmol) and cobalt(II) chloride hexahydrate (300 mg, 1.3 mmol, 10 mol %) in methanol (50 mL, 0.24 M) was added sodium borohydride (2.3 g, 60 mmol, 5.0 equiv) slowly at 0° C. After the addition, the suspension stirred at 0° C. for 2 h. The mixture was diluted with EtOAc (150 mL) and washed with brine (2×50 mL). The organic phase was dried over anhydrous sodium sulfate, filtered, and concentrated in vacuo to give tert-butyl 3-(4-cyano-3,5-difluorophenyl)propanoate (1.9 g, 7.1 mmol, 59% yield) as a light-yellow liquid. This material was used with no further purification. LCMS: ESI-MS m/z: 268.1 [M+H]$^+$.

Step 3: 3-(4-Cyano-3,5-difluorophenyl)propanoic Acid: To a solution of tert-butyl 3-(4-cyano-3,5-difluorophenyl) propanoate (1.9 g, 7.1 mmol) in DCM (20 mL) was added TFA (4.2 g, 37 mmol, 5.2 equiv) dropwise at 0° C. After the addition, the solution was stirred for 2 h at 0° C. The mixture was concentrated in vacuo and the resulting residue was treated with ammonia in methanol (7 M) to adjust to pH 8, then concentrated in vacuo. The crude product was purified by silica gel column chromatography (5-25% MeOH in DCM) to give 3-(4-cyano-3,5-difluorophenyl)propanoic acid (1.5 g, 7.1 mmol, >95% yield) as an off-white solid. LCMS: ESI-MS m/z: 212.1 [M+H]$^+$.

Intermediate #9

3-(4-Chloro-3,5-difluorophenyl)propanoic acid

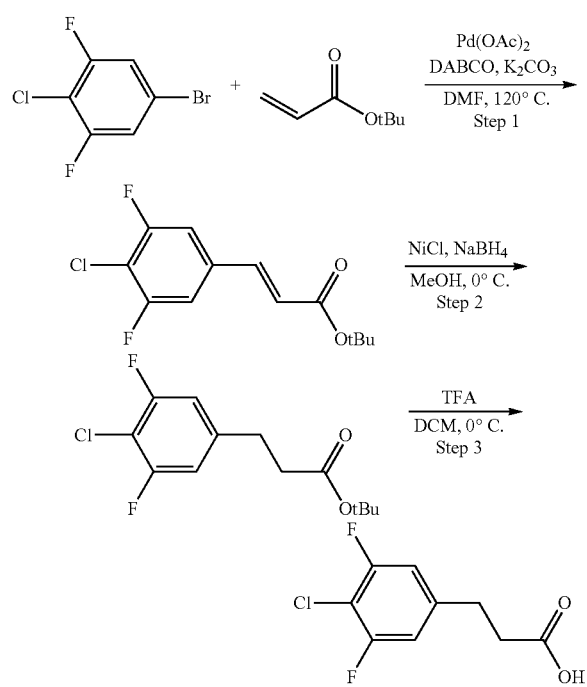

Step 1: tert-Butyl (E)-3-(4-chloro-3,5-difluorophenyl) acrylate. A mixture of 5-bromo-2-chloro-1,3-difluorobenzene (2.0 g, 8.9 mmol, 1.0 equiv), tert-butyl acrylate (1.1 g, 8.9 mmol, 1.0 equiv), potassium carbonate (1.2 g, 8.9 mmol, 1.0 equiv), palladium(II) acetate (18 mg, 0.080 mmol), DABCO (50 mg, 0.44 mmol, 0.050 equiv) in anhydrous DMF (15 mL, 0.59 M) was stirred at 120° C. for 1 h. The reaction mixture was concentrated and purified directly by silica gel column chromatography (5-35% EtOAc in petroleum ether) to give tert-butyl (E)-3-(4-chloro-3,5-difluorophenyl)acrylate (800 mg, 2.9 mmol, 33% yield) as a light yellow solid. LCMS: ESI-MS m/z: 219.0 [M-tBu]$^+$.

Step 2: tert-Butyl 3-(4-chloro-3,5-difluorophenyl)propanoate. To a mixture of tert-butyl (E)-3-(4-chloro-3,5-difluorophenyl)acrylate (800 mg, 2.9 mmol, 1.0 equiv) and NiCl (380 mg, 2.9 mmol, 1.0 equiv) in methanol (20 mL, 0.15 M) was added sodium borohydride (330 mg, 8.8 mmol, 3.0 equiv) slowly at 0° C. After the addition, the suspension was stirred at 0° C. for 1 h. The mixture was diluted with ethyl acetate (100 mL), washed with brine (2×50 mL). The combined organic fractions were dried over anhydrous sodium sulfate, filtered, and concentrated in vacuo, and purified by silica gel column chromatography (10-30% EtOAc in petroleum ether) to give tert-butyl 3-(4-chloro-3,5-difluorophenyl)propanoate (600 mg, 2.2 mmol, 74% yield) as a light yellow liquid. LCMS: ESI-MS m/z: 203.1 [M-Boc]$^+$.

Step 3: 3-(4-Chloro-3,5-difluorophenyl)propanoic acid. To a solution of tert-butyl 3-(4-chloro-3,5-difluorophenyl) propanoate (600 mg, 2.2 mmol, 1.0 equiv) in DCM (20 mL, 0.11 M) was added TFA (2.5 g, 22 mmol, 10 equiv) dropwise at 0° C. After the addition, the solution was stirred for 2 h at 0° C. The mixture was concentrated in vacuo to remove solvent, and the resulting residue was treated with ammonia in methanol (7 M) to adjust to pH 6, then concentrated in vacuo and purified by silica gel column chromatography (5-25% MeOH in DCM) to afford 3-(4-chloro-3,5-difluorophenyl)propanoic acid (470 mg, 2.1 mmol, 98% yield) as an off-white solid. $^1$H NMR (400 MHz, CDCl$_3$) δ 10.3 (br s, 1H), 6.35 (d, J=8.4 Hz, 2H), 2.93 (t, J=7.2 Hz, 2H), 2.68 (t, J=7.2 Hz, 2H). LCMS: ESI-MS m/z: 219.1 [M-H]$^+$.

Intermediate #10

3-(4-Cyano-3-fluorophenyl)propanoic acid

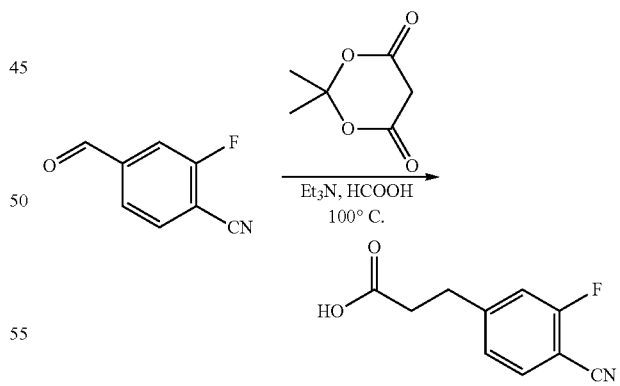

Formic acid (3.0 g, 66 mmol, 1.0 equiv) was treated with triethylamine (6.7 g, 66 mmol, 1.0 equiv) for 30 min at 0° C. Subsequently, 2-fluoro-4-formylbenzonitrile (10 g, 67 mmol, 1.0 equiv) and 2,2-dimethyl-1,3-dioxane-4,6-dione (9.5 g, 66 mmol, 1.0 equiv) were added to the mixture. The reaction mixture was heated to 100° C. for 5 h, then cooled to rt. The mixture was then diluted with water (100 mL) and extracted with EtOAc (4×50 mL). The organic material was washed with brine, filtered over anhydrous sodium sulfate and concentrated in vacuo. The crude product was purified by silica gel column chromatography (5-20% MeOH in DCM) to afford 3-(4-cyano-3-fluorophenyl)propanoic acid (2.8 g, 15 mmol, 22% yield) as a white solid. LCMS: ESI-MS m/z: 194.1 [M+H]+.

Intermediate #11

2-(5-Chloro-2,3-dihydro-1H-inden-1-yl)acetic acid

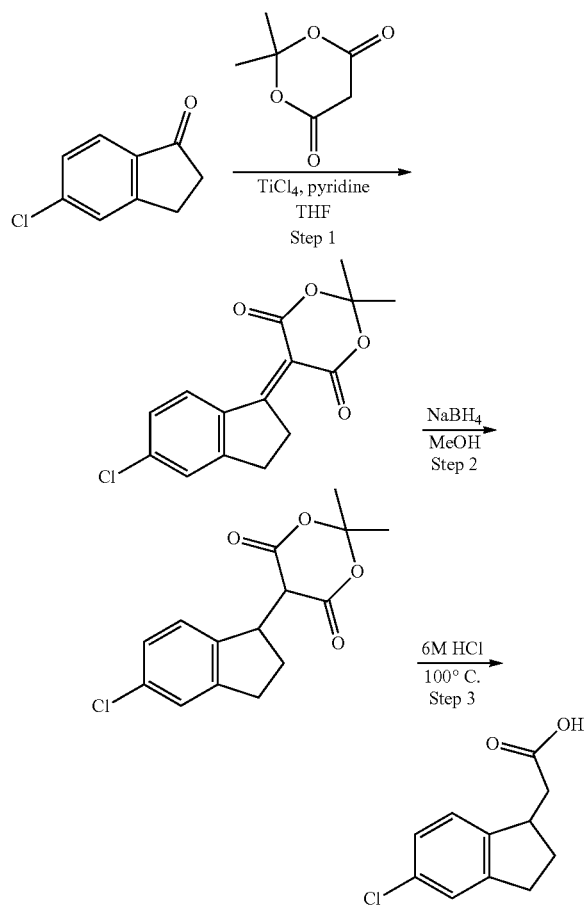

Step 1: 5-(5-Chloro-2,3-dihydro-1H-inden-1-ylidene)-2,2-dimethyl-1,3-dioxane-4,6-dione. An oven-dried flask was charged with titanium(IV) tetrachloride (230 mg, 1.2 mmol 2.0 equiv) and was dissolved in THF (3.0 mL, 0.20 M). The solution was cooled to 0° C. and 5-chloro-2,3-dihydro-1H-inden-1-one (100 mg, 0.60 mmol, 1.0 equiv) and 2,2-dimethyl-1,3-dioxane-4,6-dione (86 mg, 0.60 mmol, 1.0 equiv) were added. Pyridine (240 µL, 3.0 mmol, 5.0 equiv) was then added and the reaction mixture was warmed to rt over 2 h. The reaction mixture was suspended in EtOAc (50 mL) and water (50 mL) and was vigorously stirred for 30 min. The layers were separated and the aqueous layer was extracted with EtOAc (3×30 mL). The combined organic layers were washed with brine (50 mL), dried over anhydrous sodium sulfate, filtered, and concentrated in vacuo to afford the crude product. The crude material was purified by silica gel column chromatography (40% EtOAc in hexanes) to afford 5-(5-chloro-2,3-dihydro-1H-inden-1-ylidene)-2,2-dimethyl-1,3-dioxane-4,6-dione (10 mg, 0.030 mmol, 5.0% yield) as a white solid. LCMS: ESI-MS m/z: 291.1 [M−H]t.

Step 2. 5-(5-Chloro-2,3-dihydro-1H-inden-1-yl)-2,2-dimethyl-1,3-dioxane-4,6-dione. 5-(5-Chloro-2,3-dihydro-1H-inden-1-ylidene)-2,2-dimethyl-1,3-dioxane-4,6-dione (10 mg, 0.030 mmol, 1.0 equiv) was dissolved in methanol (300 µL, 0.10 M). Sodium borohydride (6.5 mg, 0.17 mmol, 5.0 equiv) was then added and the reaction mixture was stirred at rt for 12 h. The reaction mixture was slowly quenched with 1 M HCl (5 mL). The aqueous layer was extracted with EtOAc (3×20 mL). The combined organic fractions were washed with brine (30 mL), dried over anhydrous sodium sulfate, and concentrated in vacuo to afford 5-(5-chloro-2,3-dihydro-1H-inden-1-yl)-2,2-dimethyl-1,3-dioxane-4,6-dione (9.0 mg, 0.030 mmol, 89% yield) which was used without further purification. LCMS: ESI-MS m/z: 293.1 [M−H]+.

Step 3. 2-(5-Chloro-2,3-dihydro-1H-inden-1-yl)acetic acid. A solution of 5-(5-chloro-2,3-dihydro-1H-inden-1-yl)-2,2-dimethyl-1,3-dioxane-4,6-dione (7.0 mg, 0.020 mmol, 1.0 equiv) in 1,4-dioxane (250 µL, 0.080 M) was treated with 6 M HCl (60 µL) and the resulting mixture was heated to 100° C. for 12 h. The reaction mixture was then cooled to rt and extracted with EtOAc (3×10 mL). The combined organic fractions were dried over anhydrous sodium sulfate, concentrated in vacuo, and used without further purification. LCMS: ESI-MS m/z: 209.1 [M−H]+.

Intermediate #12

2-(6-Chloro-1,2,3,4-tetrahydronaphthalen-1-yl)acetic acid

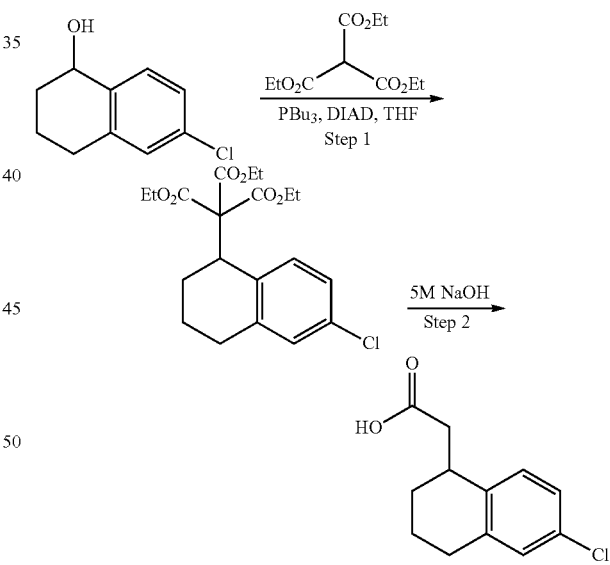

Step 1: Triethyl (6-chloro-1,2,3,4-tetrahydronaphthalen-1-yl)methanetricarboxylate. To a solution of 6-chloro-1,2,3,4-tetrahydronaphthalen-1-ol (160 mg, 0.87 mmol, 1.0 equiv) in toluene (8.6 mL, 0.10 M) was added triethyl methanetricarboxylate (370 L, 1.7 mmol, 2.0 equiv), followed by tributylphosphane (430 µL, 1.7 mmol, 2.0 equiv). The solution was cooled to −50° C., and DIAD (340 µL, 1.7 mmol, 2.0 equiv) was added slowly. The reaction mixture was warmed to rt and stirred for 3 h. After 3 h, the reaction mixture was concentrated in vacuo and purified directly by silica gel column chromatography (15% EtOAc in hexanes)

to afford triethyl (6-chloro-1,2,3,4-tetrahydronaphthalen-1-yl)methanetricarboxylate (260 mg, 0.65 mmol, 76% yield) as a white solid.

Step 2: 2-(6-Chloro-1,2,3,4-tetrahydronaphthalen-1-yl)acetic acid. To a solution of triethyl (6-chloro-1,2,3,4-tetrahydronaphthalen-1-yl)methanetricarboxylate (260 mg, 0.65 mmol, 1.0 equiv) in methanol (0.54 mL, 1.2 M), was added water (1.4 mL), and 5 M NaOH (0.70 mL). The reaction mixture was heated to 80° C. for 3 h. The reaction mixture was cooled to rt and concentrated in vacuo. Acetic acid (5 mL) was then added and the reaction was heated to 100° C. for 2 h. After 2 h, the reaction mixture was cooled to rt and concentrated in vacuo to afford a crude residue. The residue was dissolved in EtOAc (50 mL) and washed with water (50 mL). The layers were separated and the aqueous layer was extracted with EtOAc (3×30 mL). The combined organic fractions were washed with brine (50 mL), dried over anhydrous sodium sulfate, filtered, and purified by silica gel column chromatography (40% EtOAc in hexanes) to afford 2-(6-chloro-1,2,3,4-tetrahydronaphthalen-1-yl)acetic acid (62 mg, 0.28 mmol, 42% yield) as a white solid. $^1$H NMR (400 MHz, CDCl$_3$) δ 7.13 (d, J=1.4 Hz, 1H), 7.10 (s, OH), 3.35 (dq, J=9.9, 5.0 Hz, 1H), 2.88-2.68 (m, 2H), 2.60 (dd, J=15.7, 9.6 Hz, 1H), 2.04-1.92 (m, 1H), 1.91-1.69 (m, 1H).

Intermediate #13

3-(Pyridin-4-yl)-1H-pyrazol-5-amine

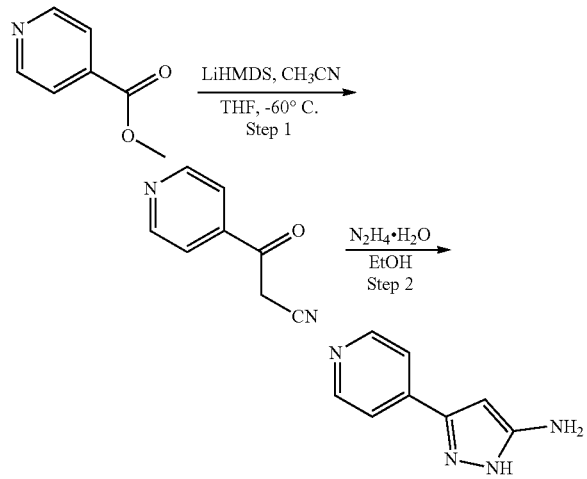

Step 1: 3-Oxo-3-(pyridin-4-yl)propanenitrile. To a 2 L three-neck round bottomed flask was added a solution of methyl isonicotinate (4.0 g, 29 mmol, 1.0 equiv) in anhydrous THF (40 mL, 0.73 M) under an atmosphere of nitrogen gas. The solution was cooled to −60° C., and LiHMDS (1.0 M in THF, 43 mL, 1.0 M, 43 mmol, 1.5 equiv) was then added dropwise. After stirring at −60° C. for 1.5 h, anhydrous acetonitrile (2.2 mL, 43 mmol, 1.5 equiv) was slowly added, forming a thick slurry. The reaction was stirred for 1.5 h at −60° C., and then warmed to rt. The reaction mixture was concentrated to a minimum amount of slurry and diluted with DCM (20 mL). After stirring for 5 min at −10° C., the slurry was filtered and the solid was washed with 10 mL of cold DCM. The solid collected was dried in vacuo to afford 3-oxo-3-(pyridin-4-yl)propanenitrile (6.2 g, 29 mmol, >95% yield) as a light yellow solid which was directly used for the next step without further purification. LCMS: ESI-MS m/z: 147.0 [M+H]$^+$.

Step 2: 3-(Pyridin-4-yl)-1H-pyrazol-5-amine. A solution of 3-oxo-3-(pyridin-4-yl)propanenitrile (100 mg, 0.68 mmol, 1.0 equiv) and hydrazine hydrate (85% solution in H$_2$O, 1.0 g, 17 mmol, 25 equiv) in EtOH (5 mL, 0.14 M) was stirred at 100° C. for 2 h. The solution was filtered, and the filtrate was concentrated in vacuo and directly purified by silica gel column chromatography (5% MeOH in DCM) to afford 3-(pyridin-4-yl)-1H-pyrazol-5-amine (50 mg, 46% yield) as a light yellow solid. $^1$H NMR (400 MHz DMSO-d$_6$) δ 11.7 (br s, 1H), 8.53 (dd, J=1.6 Hz, 4.8 Hz, 2H), 7.62 (dd, J=1.6 Hz, 4.4 Hz, 2H), 5.89 (s, 1H), 5.04 (s, 2H). LCMS: ESI-MS m/z: 161.1 [M+H]t.

Intermediate #14

3-(4-Cyano-3-fluorophenyl)-2-fluoropropanoic acid

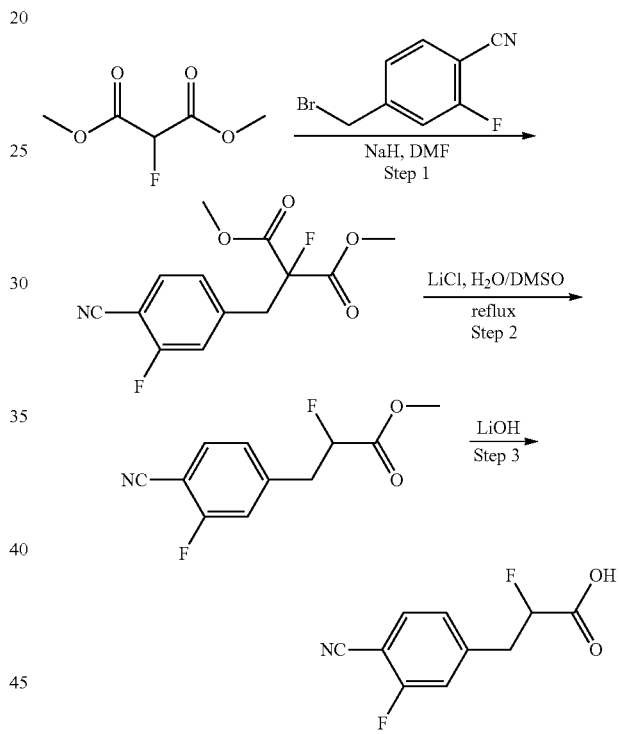

Step 1: Dimethyl 2-(4-cyano-3-fluorobenzyl)-2-fluoromalonate. To a solution of dimethyl 2-fluoromalonate (370 mg, 2.5 mmol, 1.1 equiv) in anhydrous DMF (10 mL, 0.23 M) was added NaH (60 wt % in mineral oil, 120 mg, 3.0 mmol, 1.3 equiv) at 0° C. under an atmosphere of nitrogen. After the addition, the mixture was stirred for 1 h at 0° C., followed by the addition of 4-(bromomethyl)-2-fluorobenzonitrile (500 mg, 2.3 mmol, 1.0 equiv). The mixture was stirred for 1 h at 0° C., and then was diluted with water (30 mL) and extracted with EtOAc (3×20 mL). The combined extracts were washed with brine, dried over anhydrous sodium sulfate, filtered, and concentrated in vacuo. The crude material was purified by silica gel column chromatography (5-60% EtOAc in hexanes) to afford dimethyl 2-(4-cyano-3-fluorobenzyl)-2-fluoromalonate (520 mg, 74% yield) as a light yellow solid. LCMS: ESI-MS m/z: 284.1 [M+H]$^+$.

Step 2: Methyl 3-(4-cyano-3-fluorophenyl)-2-fluoropropanoate. To a solution of dimethyl 2-(4-cyano-3-fluorobenzyl)-2-fluoromalonate (520 mg, 1.7 mmol, 1.0 equiv) in DMSO (5 mL, 0.34 M) was added LiCl (370 mg, 8.7 mmol, 5.1 equiv) and water (5 mL). The mixture was stirred at 150° C. for 3 h, and then cooled to rt. The mixture was then diluted with water (15 mL) and extracted with EtOAc (3×15 mL). The combined extracts were washed with brine, dried over anhydrous sodium sulfate, filtered, and concentrated in vacuo. The crude product was purified by silica gel column chromatography (5-80% EtOAc in hexanes) to afford methyl 3-(4-cyano-3-fluorophenyl)-2-fluoropropanoate (140 mg, 35% yield) as a light yellow solid. LCMS: ESI-MS m/z: 226.1 $[M+H]^+$.

Step 3: 3-(4-Cyano-3-fluorophenyl)-2-fluoropropanoic acid. To a solution of methyl 3-(4-cyano-3-fluorophenyl)-2-fluoropropanoate (140 mg, 0.62 mmol, 1.0 equiv) in methanol (5 mL, 0.12 M) was added a solution of LiOH (15 mg, 0.62 mmol, 1.0 equiv) in water (5 mL). The mixture was stirred at 50° C. for 3 h, then cooled to rt and treated with an aqueous solution of HCl (0.5 M) until it reached pH 6. The mixture was then extracted with EtOAc (4×10 mL). The combined organic fractions were washed with brine, dried over anhydrous sodium sulfate, filtered, and concentrated in vacuo to afford crude 3-(4-cyano-3-fluorophenyl)-2-fluoropropanoic acid (110 mg, 81% yield) as a light yellow solid. LCMS: ESI-MS m/z: 212.1 $[M+H]^+$.
Intermediate #15

1-Methyl-2-(pyridin-4-yl)-1H-imidazol-5-amine

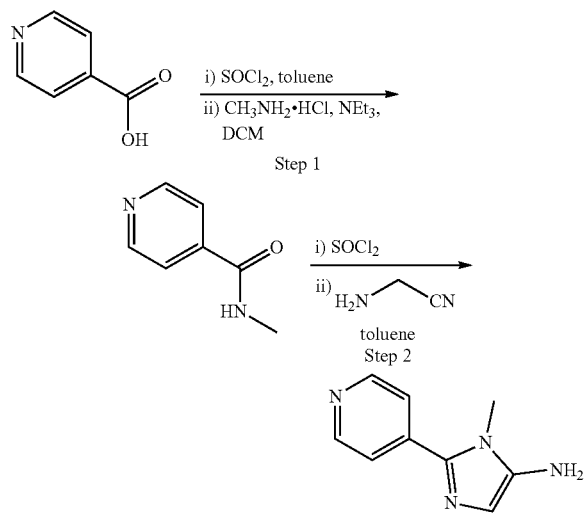

Step 1: N-Methylisonicotinamide. To a solution of isonicotinic acid (500 mg, 4.1 mmol, 1.0 equiv) in anhydrous toluene (5 mL, 0.82 M) was added SOCl$_2$ (2 mL, 27 mmol, 6.6 equiv) at rt. The mixture was stirred at rt for 2 h and then concentrated in vacuo. The residue was dissolved in anhydrous DCM (5 mL), and then methylamine hydrochloride (540 mg, 8.2 mmol, 2.0 equiv) was added, followed by the addition of triethylamine (840 mg, 8.1 mmol, 2.0 equiv). The resulting mixture was then stirred at rt for another 2 h. The mixture was treated with water (10 mL) and extracted with ethyl acetate (3×10 mL). The combined organic fractions were washed with a saturated solution of NH$_4$Cl (10 mL×2), dried over anhydrous sodium sulfate, filtered, and concentrated in vacuo to afford N-methylisonicotinamide (300 mg, 54% yield) as a light yellow solid, which was used without further purification. LCMS: ESI-MS m/z: 137.1 $[M+H]^1$.

Step 2: 1-Methyl-2-(pyridin-4-yl)-1H-imidazol-5-amine. A mixture of crude N-methylisonicotinamide (300 mg, 2.2 mmol, 1.0 equiv) in SOCl$_2$ (5 mL) was stirred at rt for 4 h. The reaction was monitored by TLC, and after complete consumption of the starting material, the reaction mixture was concentrated in vacuo. To the resulting residue was added 2-aminoacetonitrile (630 mg 11 mmol, 5.0 equiv) and toluene (5 mL) and the mixture was stirred at 100° C. for 2 h. It was then cooled to rt and concentrated in vacuo, and the resulting crude material was purified by silica gel column chromatography (5% MeOH in DCM) to afford 1-methyl-2-(pyridin-4-yl)-1H-imidazol-5-amine (50 mg, 13% yield) as a light yellow solid. LCMS: ESI-MS m/z: 175.1 $[M+H]^+$.
Intermediate #16

3-(3-Methylpyridin-4-yl)-1H-pyrazol-5-amine

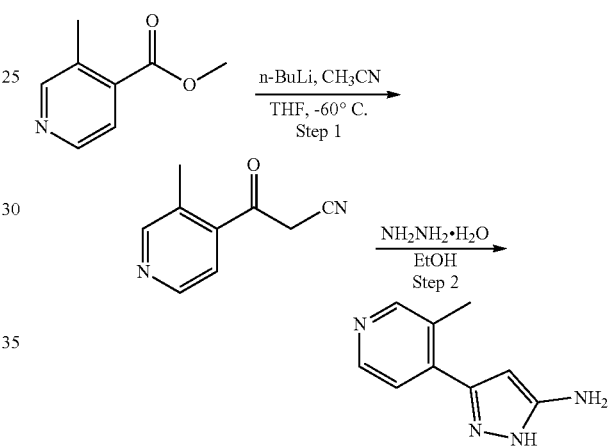

Step 1: 3-(3-Methylpyridin-4-yl)-3-oxopropanenitrile. To a three-necked round bottomed flask under an atmosphere of nitrogen was added a solution of methyl 3-methylisonicotinate (500 mg, 3.3 mmol, 1.0 equiv) in anhydrous THF (40 mL, 0.083 M), and the solution was cooled to −60° C. To this solution was added n-butyllithium (2.5 M in hexanes, 2.0 mL, 5.0 mmol, 1.5 equiv) dropwise, maintaining the temperature below −55° C. After stirring at −60° C. for 1.5 h, anhydrous acetonitrile (210 mg, 5.0 mmol, 1.5 equiv) was slowly added, maintaining the temperature below −55° C., resulting in a thick slurry. The reaction was stirred for another 1.5 h at −60° C. and then warmed to rt. The mixture was concentrated in vacuo and to the resulting slurry was added 2 mL of DCM. After stirring for 5 min at −10° C., the slurry was filtered and the solid was collected was dried in vacuo to give crude 3-(3-methylpyridin-4-yl)-3-oxopropanenitrile (400 mg, 76% yield) as a light yellow solid which was used without further purification. LCMS: ESI-MS m/z: 161 $[M+H]^+$.

Step 2: 3-(3-Methylpyridin-4-yl)-1H-pyrazol-5-amine. To a stirred mixture of 3-(3-methylpyridin-4-yl)-3-oxopropanenitrile (400 mg, 2.5 mmol, 1.0 equiv) in ethanol (5.0 mL, 0.50 M) under an atmosphere of nitrogen was added hydrazine hydrate (0.40 mL, 8.0 mmol, 3.2 equiv), and the mixture was stirred at reflux for 3 h. The solvent was concentrated in vacuo and the residue was purified by silica gel column chromatography (0-10% MeOH in DCM) to afford 3-(3-methylpyridin-4-yl)-1H-pyrazol-5-amine (400 mg, 92% yield) as a light yellow solid. LCMS: ESI-MS m/z: 175.2 [M+H]⁺.

Intermediate #17

3-(2-Chlorothiazol-5-yl)propanoic acid

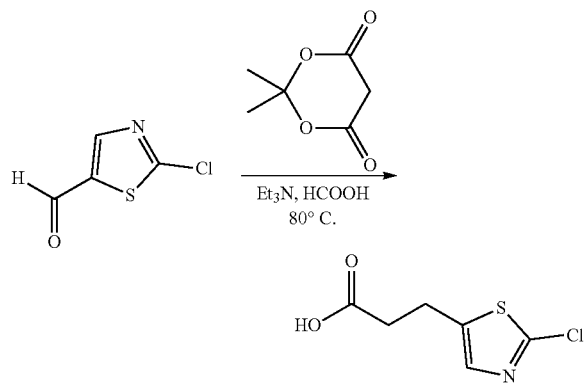

Formic acid (470 mg, 10 mmol, 3.0 equiv) was treated with triethylamine (410 mg, 4.1 mmol, 1.2 equiv) for 30 min at rt. Subsequently, 2-chlorothiazole-5-carbaldehyde (500 mg, 3.4 mmol, 1.0 equiv) and 2,2-dimethyl-1,3-dioxane-4,6-dione (490 mg, 3.4 mmol, 1.0 equiv) were added to the mixture. The reaction mixture was heated to 80° C. for 20 h, then cooled to rt. The mixture was then diluted with water (100 mL) and extracted with EtOAc (4×50 mL). The organic material was washed with brine, filtered over anhydrous sodium sulfate and concentrated in vacuo. The crude product was purified by silica gel column chromatography (15-30% EtOAc in DCM) to afford 3-(2-chlorothiazol-5-yl)propanoic acid (310 mg, 15 mmol, 22% yield) as a white solid. LCMS: ESI-MS m/z: 194.1 [M+H]⁺.

Intermediate #18

3-(5-Chlorothiazol-2-yl)propanoic acid

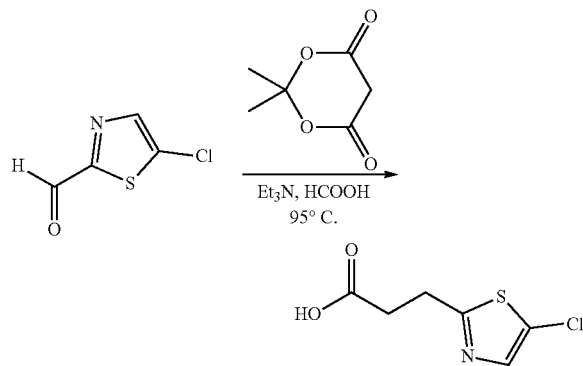

Formic acid (280 mg, 6.0 mmol, 3.0 equiv) was treated with triethylamine (247 mg, 2.4 mmol, 1.2 equiv) for 30 min at rt. Subsequently, 5-chlorothiazole-2-carbaldehyde (300 mg, 2.0 mmol, 1.0 equiv) and 2,2-dimethyl-1,3-dioxane-4,6-dione (293 mg, 2.0 mmol, 1.0 equiv) were added to the mixture. The reaction mixture was heated to 95° C. for 20 h, then cooled to rt. The mixture was then diluted with water (100 mL) and extracted with EtOAc (4×50 mL). The organic material was washed with brine, filtered over anhydrous sodium sulfate and concentrated in vacuo. The crude product was purified by silica gel column chromatography (15-30% EtOAC in DCM) to afford 3-(5-chlorothiazol-2-yl)propanoic acid (320 mg, 83% yield) as a white solid. LCMS: ESI-MS m/z: 192.0 [M+H]⁺.

Intermediate #19

1-(3-Methylpyridin-4-yl)-1H-pyrazol-4-amine

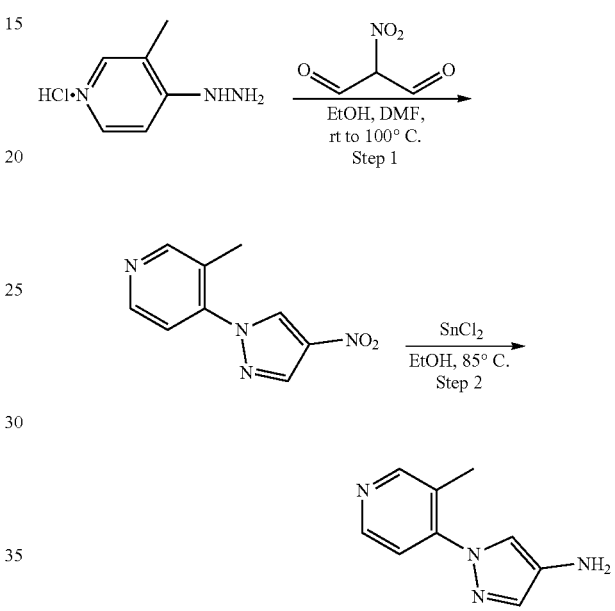

Step 1: 3-Methyl-4-(4-nitro-1H-pyrazol-1-yl)pyridine. A mixture of 4-hydrazineyl-3-methylpyridine hydrochloride (130 mg, 0.81 mmol, 1.0 equiv) and 2-nitromalonaldehyde (110 mg, 0.90 mmol, 1.1 equiv) in EtOH (2.5 mL, 0.32 M) and DMF (2.5 mL, 0.32 M, 0.16 M overall) was stirred at rt for 35 min, and then heated to 100° C. for 4 h. The reaction mixture was diluted with EtOAc (150 mL), then washed with a saturated solution of NaHCO₃, water, and brine. The organic fraction was dried over anhydrous sodium sulfate, filtered, and concentrated in vacuo to afford the crude product. The crude material was purified by silica gel column chromatography (5-55% EtOAc in DCM) to afford 3-methyl-4-(4-nitro-1H-pyrazol-1-yl)pyridine (67 mg, 40% yield) as a white solid. LCMS: ESI-MS m/z: 205.1 [M+H]⁺.

Step 2: 1-(3-Methylpyridin-4-yl)-1H-pyrazol-4-amine. A mixture of 3-methyl-4-(4-nitro-1H-pyrazol-1-yl)pyridine (67 mg, 0.33 mmol, 1.0 equiv) and SnCl₂ (380 mg, 2.0 mmol, 6.1 equiv) in EtOH (8 mL, 0.041M) was stirred at 85° C. for 5 h. The mixture was then concentrated in vacuo and the residue was neutralized with a saturated solution of NaHCO₃. The resulting solution was extracted with EtOAc (2×80 mL). The combined organic fractions were dried over anhydrous sodium sulfate, filtered, and the filtrate was concentrated in vacuo and purified by silica gel column chromatography (5-25% EtOAc in hexanes) to afford 1-(3-methylpyridin-4-yl)-1H-pyrazol-4-amine (5.0 mg, 9.0% yield) as a white solid. LCMS: ESI-MS m/z: 175.1 [M+H]⁺.

Intermediate #20

4-Methyl-3-(3-methylpyridin-4-yl)-1H-pyrazol-5-amine

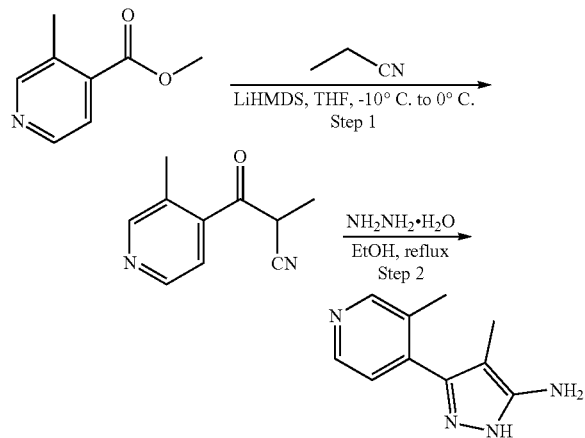

Step 1: 2-Methyl-3-(3-methylpyridin-4-yl)-3-oxopropanenitrile A solution of propionitrile (1.2 g, 22 mmol, 2.2 equiv) in THF (20 mL, 0.50 M) was cooled to −40° C., and LiHMDS in THF (1.0 M solution in THF, 22 mL, 22 mmol, 2.2 equiv) was added dropwise. After the addition, the mixture was stirred at 0° C. for 1 h. Then the mixture was cooled to −40° C. again and methyl 3-methylisonicotinate (1.5 g, 9.9 mmol, 1.0 equiv) was added. After the addition, the mixture was stirred at rt for 30 min. The mixture was filtered and the white solid was collected and dried in vacuo to give crude 2-methyl-3-(3-methylpyridin-4-yl)-3-oxopropanenitrile (1.9 g, >95% yield) which was used directly in the next step without further purification. LCMS: ESI-MS: m/z: 175.1 [M+H]+.

Step 2: 4-Methyl-3-(3-methylpyridin-4-yl)-1H-pyrazol-5-amine A mixture of crude 2-methyl-3-(3-methylpyridin-4-yl)-3-oxopropanenitrile (1.9 g, 11 mmol, 1.0 equiv) and hydrazine hydrate (85% w/w in water, 3.7 g, 63 mmol, 5.7 equiv) in ethanol (20 mL, 0.55 M) was stirred at 80° C. overnight. The mixture was concentrated, and purified by silica gel column chromatography (5% MeOH in DCM) to give 4-methyl-3-(3-methylpyridin-4-yl)-1H-pyrazol-5-amine (0.55 g, 27% over 2 steps) as a light yellow solid. LCMS: ESI-MS m/z: 189.1 [M+H]+.

Intermediate #21

1-(Pyridin-4-yl)-1H-pyrazol-4-amine

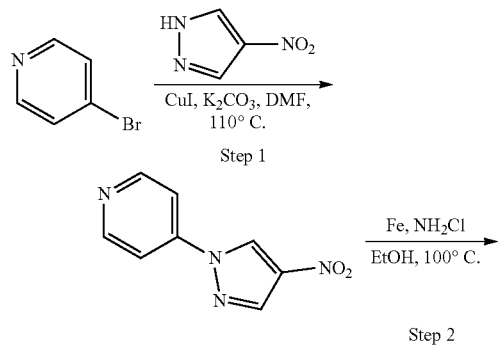

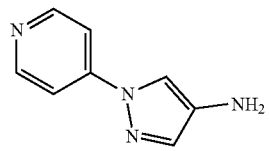

Step 1: 4-(4-Nitro-1H-pyrazol-1-yl)pyridine: A mixture of 4-bromopyridine (1.0 g, 6.4 mmol, 1.0 equiv), 4-nitro-1H-pyrazole (0.72 g, 6.4 mmol, 1.0 equiv), CuI (120 mg, 0.64 mmol, 0.10 equiv), and potassium carbonate (1.8 g, 13 mmol, 2.0 equiv) in anhydrous DMF (20 mL, 0.30 M) was stirred at 110° C. under nitrogen gas for 16 h. The reaction was then cooled to rt and filtered. The filtrate was treated with water (100 mL) and extracted with ethyl acetate (3×30 mL). The combined organic layers were washed with saturated aqueous NH4Cl (2×50 mL), dried over anhydrous sodium sulfate, filtered, and concentrated in vacuo. Purification by silica gel column chromatography (5% MeOH in DCM) gave 4-(4-nitro-1H-pyrazol-1-yl)pyridine (600 mg, 49% yield) as a yellow solid. LCMS: ESI-MS m/z: 191.0 [M+H]+.

Step 2: 1-(Pyridin-4-yl)-1H-pyrazol-4-amine: A mixture of 4-(4-nitro-1H-pyrazol-1-yl)pyridine (600 mg, 3.1 mmol, 1.0 equiv), iron powder (960 mg, 17 mmol, 5.4 equiv), and ammonium chloride (930 mg, 17 mmol, 5.4 equiv) in ethanol (10 mL, 0.30 M) was stirred at 100° C. After 2 h, the mixture was filtered and the filtrated was concentrated in vacuo to give 1-(pyridin-4-yl)-1H-pyrazol-4-amine (500 mg, 99% yield) as a yellow solid. LCMS: ESI-MS m/z: 161.0 [M+H]+.

Intermediate #22

(5-Amino-3-(pyridin-4-yl)-1H-pyrazol-4-yl)methanol

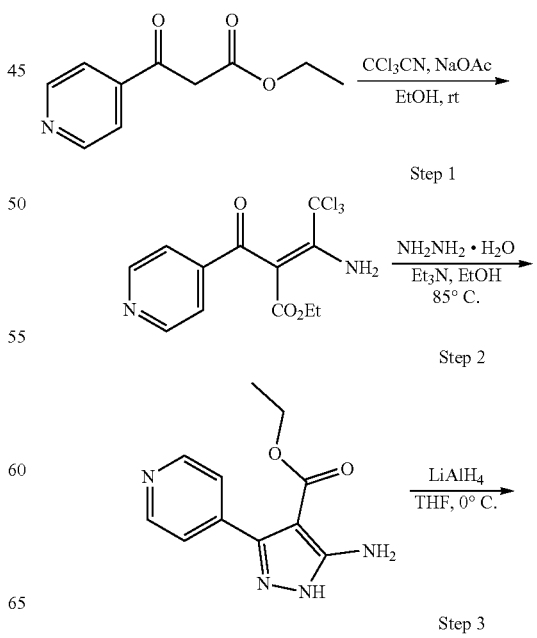

-continued

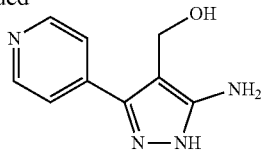

Step 1: Ethyl (Z)-3-amino-4,4,4-trichloro-2-isonicotinoylbut-2-enoate. To a solution of ethyl 3-oxo-3-(pyridin-4-yl)propanoate (20 g, 100 mmol, 1.0 equiv) in ethanol (500 mL, 0.20 M) was added 2,2,2-trichloroacetonitrile (15 g, 100 mmol, 1.0 equiv) and sodium acetate (8.5 g, 100 mmol, 1.0 equiv). The mixture was stirred at rt for 30 min. The mixture was then filtered, the filtrate was collected and dried in vacuo then used directly in the next step without further manipulation. LCMS: ESI-MS m/z: 337.0 [M+H]$^+$.

Step 2: Ethyl 5-amino-3-(pyridin-4-yl)-1H-pyrazole-4-carboxylate. To a solution of crude ethyl (Z)-3-amino-4,4,4-trichloro-2-isonicotinoylbut-2-enoate (100 mmol, 1.0 equiv) in ethanol (500 mL, 0.20 M) was added hydrazine hydrate (5.7 g, 110 mmol, 1.1 equiv) and triethylamine (11 g, 100 mmol, 1.0 equiv) at 0° C. After the addition, the mixture was heated to 85° C. and stirred for 1 h. The mixture was cooled to rt, the suspension was filtered, the solid was collected and purified by silica gel column chromatography (105 DCM in MeOH) to afford ethyl 5-amino-3-(pyridin-4-yl)-1H-pyrazole-4-carboxylate (14 g, 56% over 2 steps) as a yellow solid. LCMS: ESI-MS m/z: 233.0 [M+H]$^+$.

Step 3: (5-Amino-3-(pyridin-4-yl)-1H-pyrazol-4-yl)methanol. To a solution of ethyl 5-amino-3-(pyridin-4-yl)-1H-pyrazole-4-carboxylate (1.0 g, 4.3 mmol, 1.0 equiv) in anhydrous THF (100 mL, 0.043 M) was added LiAlH$_4$ (1.0 M solution in THF, 26 mL, 26 mmol, 6.0 equiv) dropwise at −40° C. under an atmosphere of nitrogen. After the addition, the reaction mixture was warmed to 0° C. and stirred for 4 h. At 0° C., the reaction mixture was quenched carefully by adding 1.0 mL of water dropwise, followed by 3.0 M aqueous NaOH (1.0 mL), and another 1.0 mL of water. The mixture was filtered and the solid was washed a 1:5 solution of MeOH:DCM (3×60 mL). The filtrate was collected and concentrated in vacuo, then purified directly by silica gel column chromatography (10% MeOH in DCM+5% ammonia) to obtain (5-amino-3-(pyridin-4-yl)-1H-pyrazol-4-yl)methanol (300 mg, 61% yield) as a light yellow solid. LCMS: ESI-MS m/z: 191.1 [M+H]$^+$.

Intermediate #23

4-Chloro-3-(pyridin-4-yl)-1H-pyrazol-5-amine

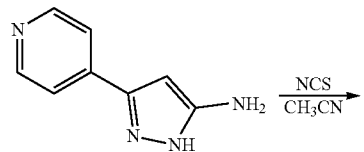

A mixture of 3-(pyridin-4-yl)-1H-pyrazol-5-amine (Intermediate 13, 100 mg, 0.63 mmol, 1.0 equiv) and N-chlorosuccinimide (36 mg, 0.63 mmol, 1.0 equiv) in acetonitrile (2 mL, 0.32 M) was stirred at rt for 2 h. The reaction mixture was then concentrated in vacuo and purified by silica gel column chromatography (5% MeOH in DCM). The desired fractions were concentrated in vacuo to afford 4-chloro-3-(pyridin-4-yl)-1H-pyrazol-5-amine (50 mg, 0.31 mmol, 50% yield) as a light yellow solid. LCMS: ESI-MS m/z: 195.1 [M+H]$^+$.

Intermediate #24

3-(4-Chloro-3,5-difluorophenyl)-N-(4-methyl-3-(pyridin-4-yl)-1-((2-(trimethylsilyl)ethoxy)methyl)-1H-pyrazol-5-yl)propanamide

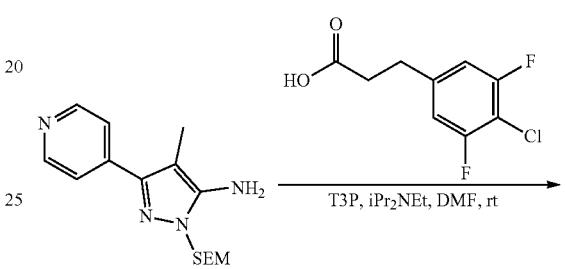

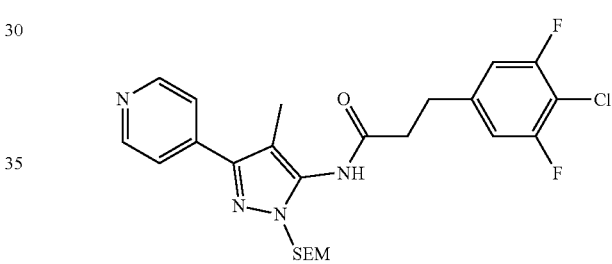

The product was prepared according to General Procedure #1 using Intermediate 2 and Intermediate 9 to afford the desired product 3-(4-chloro-3,5-difluorophenyl)-N-(4-methyl-3-(pyridin-4-yl)-1-((2-(trimethylsilyl)ethoxy)methyl)-1H-pyrazol-5-yl)propanamide (910 mg, 1.8 mmol, 55% yield) as a light yellow solid. LCMS: ESI-MS m/z: 507.2 [M+H]$^+$.

Intermediate #25

N-(4-Methyl-3-(pyridin-4-yl)-1-((2-(trimethylsilyl)ethoxy)methyl)-1H-pyrazol-5-yl)-3-(3,4,5-trifluorophenyl)propanamide

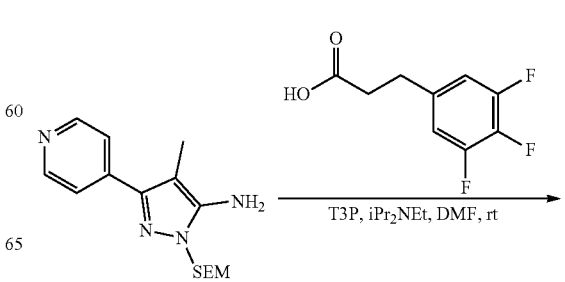

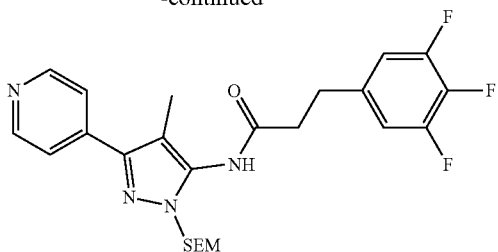

The product was prepared according to General Procedure #1 using Intermediate 2 and 3-(3,4,5-trifluorophenyl)propanoic acid to afford the desired product N-(4-methyl-3-(pyridin-4-yl)-1-((2-(trimethylsilyl)ethoxy)methyl)-1H-pyrazol-5-yl)-3-(3,4,5-trifluorophenyl)propanamide in 60% yield. LCMS: ESI-MS m/z: 491.1 [M+H]$^+$.

Intermediate #26

3-(4-Chlorophenyl)-2,2-difluoropropanoic acid

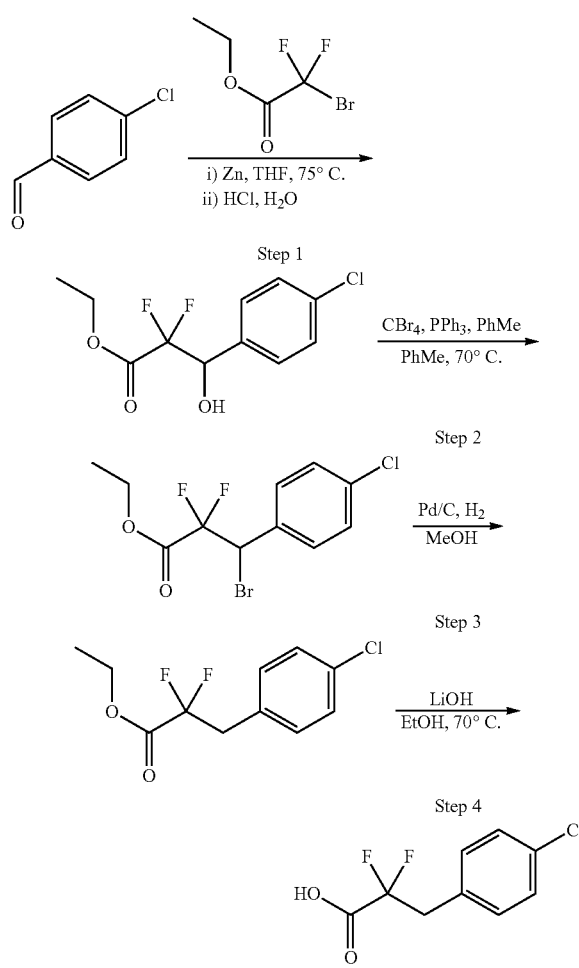

Step 1: Ethyl 3-(4-chlorophenyl)-2,2-difluoro-3-hydroxypropanoate. A mixture of 4-chlorobenzaldehyde (1.5 g, 11 mmol, 1.0 equiv), ethyl 2-bromo-2,2-difluoroacetate (2.4 g, 12 mmol, 1.1 equiv) and Zn dust (840 mg, 13 mmol, 1.2 equiv) in THF (30 mL, 0.37 M) was heated to 75° C. for 16 h. The reaction mixture was then cooled to rt, and an aqueous solution of HCl (2.0 M, 4.0 mL, 2.0 equiv) was added. The mixture was washed with water (20 mL) and extracted with EtOAc (3×30 mL). The combined organic fractions were dried over anhydrous sodium sulfate, filtered, and concentrated in vacuo, and the resulting residue was purified by silica gel column chromatography (10-60% EtOAc in hexanes). The desired fractions were concentrated in vacuo to afford ethyl 3-(4-chlorophenyl)-2,2-difluoro-3-hydroxypropanoate (1.8 g, 6.8 mmol, 64% yield) as a light-yellow oil. $^1$H NMR (400 MHz, DMSO-d$_6$) δ 7.46 (s, 4H), 6.75 (d, J=8.0 Hz, 1H), 5.16-5.08 (m, 1H), 4.32-4.27 (m, 2H), 1.25 (t, J=7.2 Hz, 2H). LCMS: ESI-MS m/z: 287.1 [M+Na]$^+$.

Step 2: Ethyl 3-bromo-3-(4-chlorophenyl)-2,2-difluoropropanoate. To a solution of ethyl 3-(4-chlorophenyl)-2,2-difluoro-3-hydroxypropanoate (1.8 g, 6.8 mmol, 1.0 equiv) in toluene (30 mL, 0.23 M) was added carbon tetrabromide (2.50 g, 7.5 mmol, 1.1 equiv) followed by triphenylphosphine (2.10 g, 8.1 mmol, 1.2 equiv). The reaction mixture was heated to 70° C. for 4 h. It was then cooled to rt and diluted with water (20 mL), and extracted with ethyl acetate (3×30 mL). The combined organic fractions were dried over anhydrous sodium sulfate, filtered, and concentrated in vacuo. The resulting residue was purified by silica gel column chromatography (0-50% EtOAc in petroleum ether). Fractions containing desired product were concentrated in vacuo to afford ethyl 3-bromo-3-(4-chlorophenyl)-2,2-difluoropropanoate (1.9 g, 5.8 mmol, 85% yield) as a light-yellow oil. No ionization was observed for the product using LCMS so the material was moved forward to the next reaction without further characterization.

Step 3: Ethyl 3-(4-chlorophenyl)-2,2-difluoropropanoate. To a solution of ethyl 3-bromo-3-(4-chlorophenyl)-2,2-difluoropropanoate (600 mg, 1.8 mmol, 1.0 equiv) in methanol (20 mL, 0.090 M) was added Pd/C (10 wt. %, 200 mg). The atmosphere was exchanged with hydrogen gas, and a hydrogen gas balloon was attached. The reaction mixture was stirred at rt for 16 h. The mixture was then filtered, and the filtrate was concentrated and purified by RP-HPLC (Method C, 5-25% MeCN in H$_2$O+10 mM NH$_4$HCO$_3$+0.025% NH$_3$·H$_2$O) to afford ethyl 3-(4-chlorophenyl)-2,2-difluoropropanoate (30 mg, 0.12 mmol, 6.5% yield) as a white solid. LCMS: ESI-MS m/z: 249.1 [M+H]$^+$.

Step 4: 3-(4-Chlorophenyl)-2,2-difluoropropanoic acid. Ethyl 3-(4-chlorophenyl)-2,2-difluoropropanoate (30 mg, 0.12 mmol, 1.0 equiv) was dissolved in a 2:1 solution of EtOH:H$_2$O (6 mL, 0.020 M) and LiOH·H$_2$O (5.1 mg, 0.12 mmol, 1.0 equiv) was added. The reaction mixture was stirred at 70° C. for 1 h. The mixture was cooled to rt, then treated with an aqueous solution of HCl (0.50 M) until pH 5~6. The solid that was precipitated was collected by filtration and dried in vacuo to afford 3-(4-chlorophenyl)-2,2-difluoropropanoic acid (22 mg, 0.10 mmol, 83% yield) as a white solid. LCMS: ESI-MS m/z: 203.0 [M-OH]$^+$. This material was used with no further purification.

Intermediate #27

(rac)-3-(4-Chloro-3,5-difluorophenyl)-2-fluoropropanoic acid

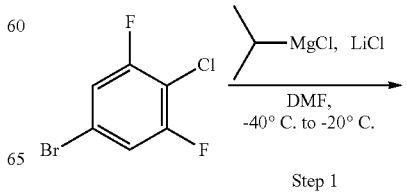

Step 1

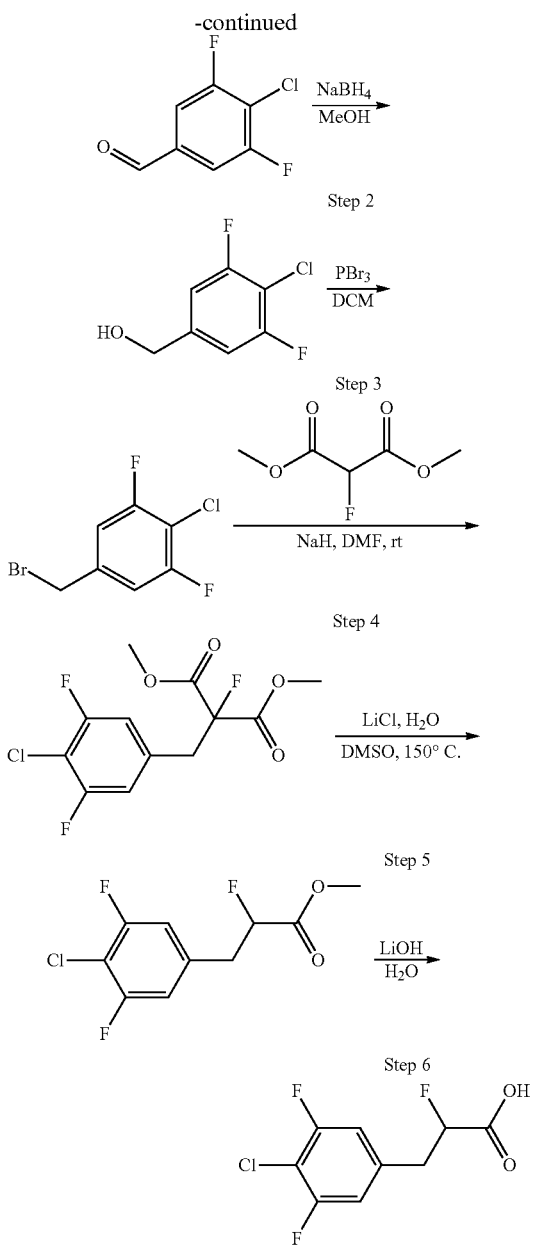

Step 1: 4-Chloro-3,5-difluorobenzaldehyde. To a stirred mixture of 5-bromo-2-chloro-1,3-difluorobenzene (4.5 g, 20 mmol, 1.0 equiv) and LiCl (850 mg, 20 mmol, 1.0 equiv) in anhydrous THF (50 mL, 0.40 M) was added isopropylmagnesium chloride (1.0 M solution in THF, 22 mL, 22 mmol, 1.1 equiv) at −40° C. under an atmosphere of nitrogen gas. After the addition, the mixture was stirred at −40° C. for 1 h, and then anhydrous DMF (1.83 g, 25 mmol, 1.3 equiv) was added dropwise. After the addition, the mixture was warmed to −20° C. for another 1 h. The mixture was quenched with water (20 mL), extracted with ethyl acetate (3×20 mL). The organic fractions were combined, washed with brine (30 mL), dried over anhydrous sodium sulfate, filtered, and concentrated in vacuo to afford crude 4-chloro-3,5-difluorobenzaldehyde (3.4 g, 13 mmol, 68% yield) as a light yellow liquid. $^1$H NMR (400 MHz, CDCl$_3$) δ 9.85 (s, 1H), 7.45 (d, J=6.4 Hz, 2H). LCMS: ESI-MS m/z: 191.1 [M+H]$^+$.

Step 2: (4-Chloro-3,5-difluorophenyl)methanol. To a stirred solution of 4-chloro-3,5-difluorobenzaldehyde (3.4 g, 13 mmol, 1.0 equiv) in methanol (40 mL, 0.33 M) was added sodium borohydride (1.1 g, 30 mmol, 2.3 equiv) portionwise at rt. After the addition, the mixture was stirred at rt for another 1 h. The mixture was concentrated in vacuo to remove methanol. The resulting residue was diluted with EtOAc (50 mL), washed with water (20 mL), brine (30 mL), dried over anhydrous sodium sulfate, filtered, and concentrated in vacuo to afford crude (4-chloro-3,5-difluorophenyl)methanol (3.3 g, 12 mmol, 89% yield) as a light yellow liquid. LCMS: ESI-MS m/z: 161.1 [M−17]$^1$.

Step 3: 5-(Bromomethyl)-2-chloro-1,3-difluorobenzene. To a stirred solution of (4-chloro-3,5-difluorophenyl)methanol (1.1 g, 4.0 mmol, 1.0 equiv) in DCM (10 mL, 0.40 M) was added phosphorus tribromide (1.4 g, 5.0 mmol, 1.3 equiv) at 0° C. After the addition, the mixture was stirred at rt for another 2 h. The mixture was poured into ice water (15 mL), stirred for 3 min, and then extracted with DCM (3×15 mL). The organic fractions were combined, washed with brine (30 mL), dried over anhydrous sodium sulfate, filtered, and concentrated in vacuo to afford the crude product. The crude material was purified by silica gel column chromatography (5-10% EtOAc in petroleum ether) to afford 5-(bromomethyl)-2-chloro-1,3-difluorobenzene (800 mg, 3.3 mmol, 83% yield) as a light yellow liquid. $^1$H NMR (400 MHz, CDCl$_3$) δ 7.03 (d, J=6.8 Hz, 2H), 4.39 (s, 2H).

Step 4: Dimethyl 2-(4-chloro-3,5-difluorobenzyl)-2-fluoromalonate. To a solution of dimethyl 2-fluoromalonate (530 mg, 3.5 mmol, 1.1 equiv) in anhydrous DMF (15 mL, 0.22 M) was added sodium hydride (60 wt % dispersion in mineral oil, 160 mg, 4.0 mmol, 1.1 equiv) at 0° C. under an atmosphere of nitrogen gas. After the addition, the mixture was stirred for 1 h at 0° C. Then 5-(bromomethyl)-2-chloro-1,3-difluorobenzene (800 mg, 3.3 mmol, 1.0 equiv) was added at 0° C. The mixture was stirred for 1 h at 0° C., then was diluted with water (30 mL) and extracted with EtOAc (3×20 mL). The combined organic fractions were washed with brine, dried over anhydrous sodium sulfate, filtered, and purified by silica gel column chromatography (10-50% EtOAc in petroleum ether) to afford dimethyl 2-(4-chloro-3,5-difluorobenzyl)-2-fluoromalonate (950 mg, 3.2 mmol, 88% yield) as a light yellow solid. LCMS: ESI-MS m/z: 311.0 [M+H]$^+$.

Step 5: (rac)-Methyl 3-(4-chloro-3,5-difluorophenyl)-2-fluoropropanoate. To a solution of dimethyl 2-(4-chloro-3,5-difluorobenzyl)-2-fluoromalonate (950 mg, 3.1 mmol, 1.0 equiv) in DMSO (10 mL, 0.31 M) was added LiCl (650 mg, 15 mmol, 4.8 equiv) and water (10 mL). The mixture was stirred at 150° C. for 3 h, then cooled to rt. The mixture was diluted with water (30 mL) and extracted with EtOAc (3×30 mL). The combined organic fractions were washed with brine (30 mL), dried over anhydrous sodium sulfate, filtered, concentrated in vacuo, and purified by silica gel column chromatography (15-80% EtOAc in petroleum ether) to give (rac)-methyl 3-(4-chloro-3,5-difluorophenyl)-2-fluoropropanoate (250 mg, 0.99 mmol, 32% yield) as a light yellow solid. LCMS: ESI-MS m/z: 253.1 [M+H]$^+$.

Step 6: (rac)-3-(4-Chloro-3,5-difluorophenyl)-2-fluoropropanoic acid. To a solution of (rac)-methyl 3-(4-chloro-3,5-difluorophenyl)-2-fluoropropanoate (250 mg, 0.99 mmol, 1.0 equiv) in methanol (10 mL, 0.099 M) was added a solution of LiOH (72 mg, 3.0 mmol, 3.0 equiv) in water (10 mL). The mixture was stirred at rt for 4 h, and then treated with an aqueous solution of HCl (0.50 M) until pH~6, extracted with EtOAc (4×15 mL). The combined organic fractions were washed with brine, dried over anhydrous sodium sulfate, filtered, and concentrated in vacuo to give crude (rac)-3-(4-chloro-3,5-difluorophenyl)-2-fluoropropanoic acid (200 mg, 0.84 mmol, 84% yield) as a light yellow solid. This material was used with no further purification. LCMS: ESI-MS m/z: 219.1 [M−19][1].

Intermediate #28 tert-Butyl 5-amino-4-methyl-3-(pyridin-4-yl)-1H-pyrazole-1-carboxylate

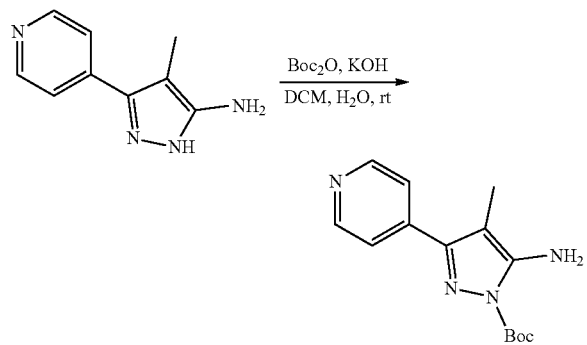

To a mixture of 4-methyl-3-(pyridin-4-yl)-1H-pyrazol-5-amine (Intermediate 1, 8.9 g, 51 mmol, 1.0 equiv) in DCM (100 mL, 0.51 M) and an aqueous solution of potassium hydroxide (2.0 M, 100 mL, 200 mmol, 3.9 equiv) was added Boc anhydride (22 g, 101 mmol, 2.0 equiv) in DCM (30 mL) slowly at 0° C. After the addition, the mixture was stirred at rt for 8 h. The organic layer of the reaction mixture was then separated, and the aqueous fraction was extracted with DCM (2×100 mL). The combined organic fractions were then washed with brine (200 mL), dried over anhydrous sodium sulfate, filtered, and concentrated in vacuo. The residue was purified by silica gel column chromatography (5% DCM in MeOH) to afford tert-butyl 5-amino-4-methyl-3-(pyridin-4-yl)-1H-pyrazole-1-carboxylate (5.1 g, 18 mmol, 36% yield) as a light yellow solid. $^1$HNMR (400 MHz, DMSO-$d_6$): δ 8.64 (dd, J=4.5, 1.6 Hz, 2H), 7.61 (dd, J=4.5, 1.6 Hz, 2H), 6.21 (s, 2H), 1.99 (s, 3H), 1.59 (s, 9H). LCMS: ESI-MS m/z: 275.2 [M+H]$^+$.

Intermediate #29

N-(3-Bromo-1H-pyrazol-5-yl)-3-(4-chlorophenyl)propanamide

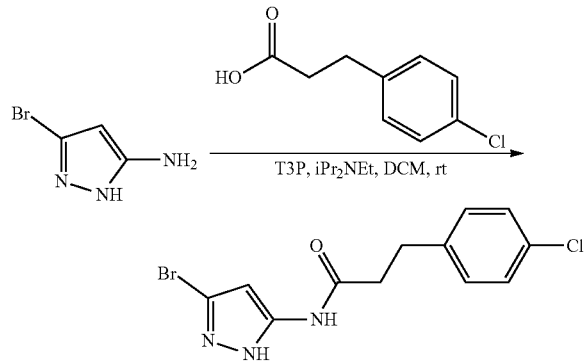

To a solution of 3-bromo-TH-pyrazol-5-amine (100 mg, 0.62 mmol, 1.0 equiv) in DCM (3.0 mL, 0.21 M) was added 3-(4-chlorophenyl)propanoic acid (150 mg, 0.81 mmol, 1.3 equiv), T3P (50% w/w in EtOAc, 300 mg, 0.81 mmol, 1.3 equiv), DIPEA (200 mL, 1.7 mmol, 2.7 equiv). After the addition, the mixture was stirred at rt for 2 h. The reaction mixture was concentrated in vacuo and purified by silica gel column chromatography (15-100% EtOAc in hexanes) to afford N-(3-bromo-1H-pyrazol-5-yl)-3-(4-chlorophenyl)propanamide (140 mg, 0.43 mmol, 69% yield) as a white solid. LCMS: ESI-MS m/z: 328.1 [M+H]$^+$.

General Procedures:

Below are general synthetic protocols that can be used, and where indicated, were used, to prepare the compounds of the invention.

General Procedure #1

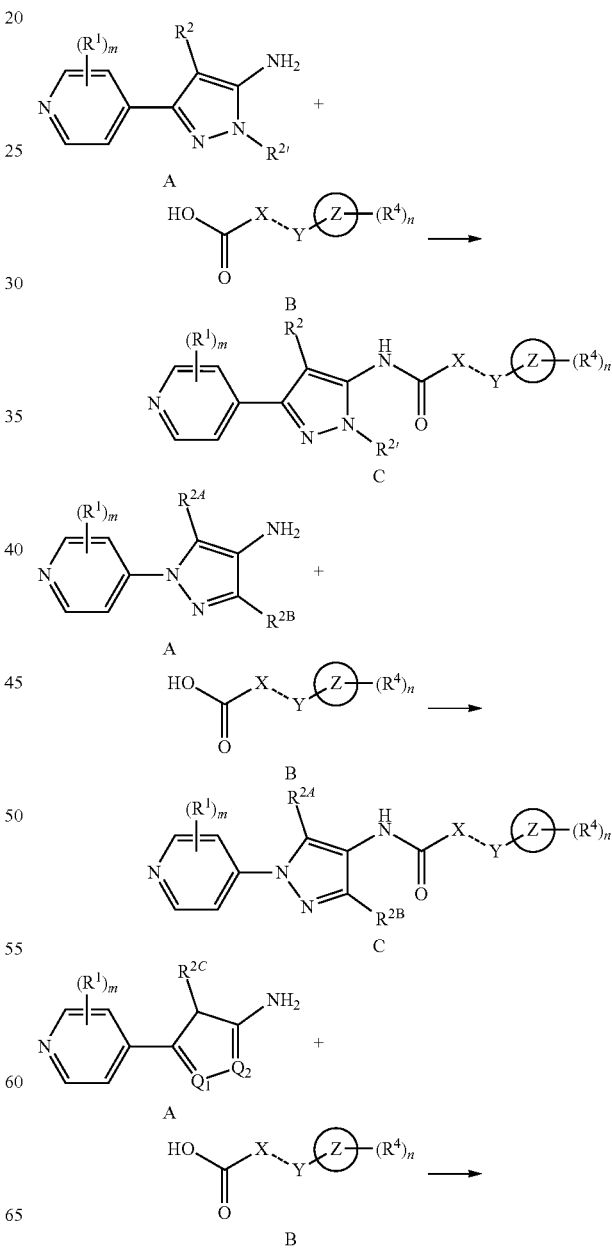

49

-continued

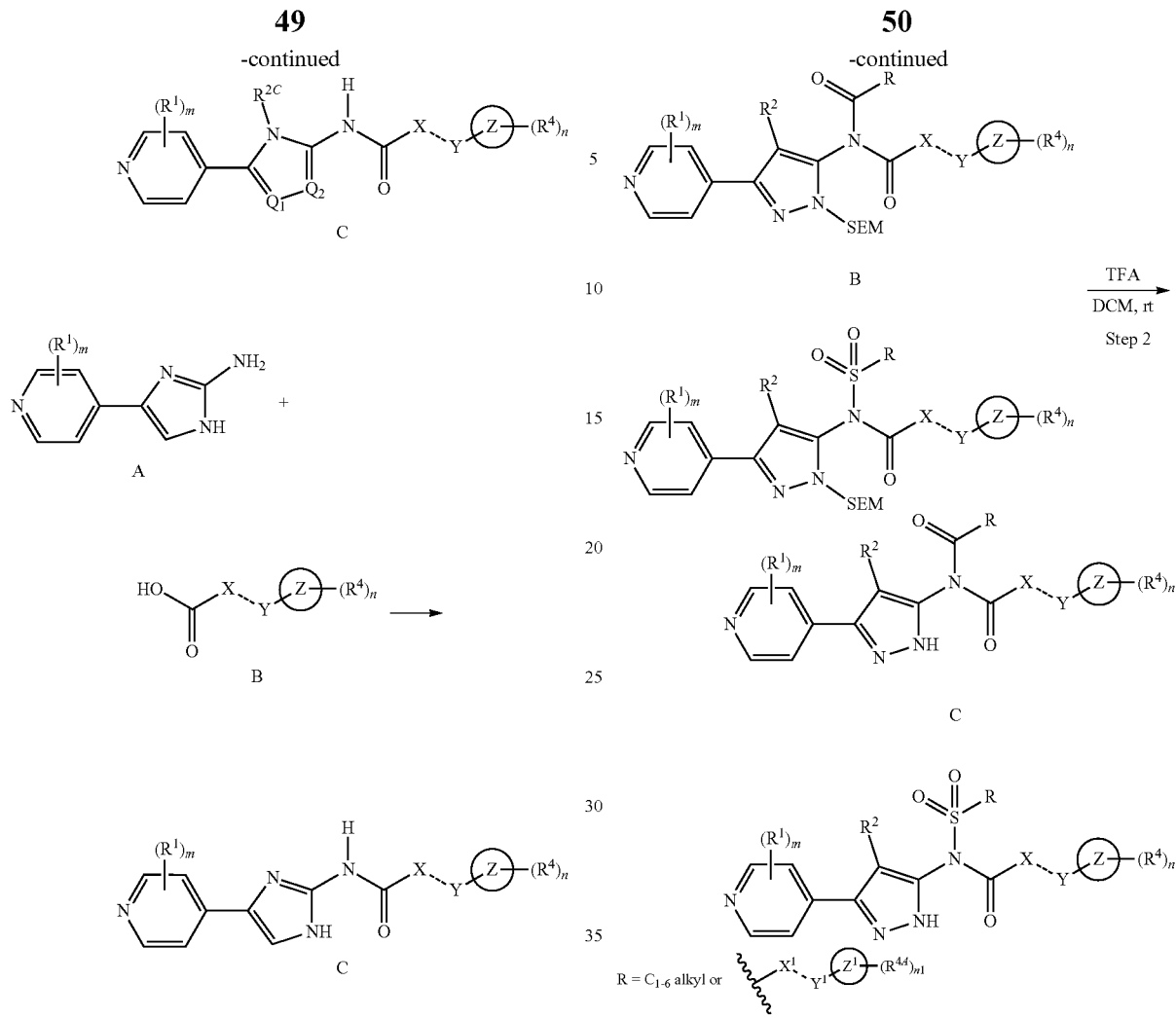

The appropriate acid (B) (1.0-1.5 equiv) is dissolved in either DCM, DMF, or DMA, (0.05-0.40 M) with either triethylamine or DIPEA (1.5-10 equiv) and stirred at 0° C. or rt for (5 min to 1 h). HATU (1.1-1.5 equiv) or T3P (50 w/v % in DMF or EtOAc, 1.5-2.0 equiv), is then added at 0° C. or rt and the reaction mixture is stirred for (5 min to 1 h). To the resulting reaction mixture, the appropriate amine (A, R2' is H or an amino protecting group like Boc) (1.0 equiv) (neat or in a DMF solution (1.0-1.8 M) is added and the reaction was warmed to rt (if at 0° C.) and was stirred for 5 min 16 h. Upon completion, the reaction mixture is concentrated and purified directly by silica gel column chromatography or RP-HPLC (either Method A: MeCN in H₂O+0.1% TFA, or Method C: MeCN in H₂O+10 mM NH₄HCO₃+0.025% NH₃·H₂O) to afford the desired amides (C) as either trifluoroacetic acid salts (Method A) or as the parent compound (silica gel column chromatography or Method C).

General Procedure #2

Step 1: A solution of amine (e.g., see Intermediate #3) (1.0 equiv) in anhydrous DMF (0.21 M) is treated with NaH (60 wt % dispersion in mineral oil, 1.2 equiv) for 0.5 h at 0° C. Subsequently, acid chloride (A) (1.2 equiv) is added to the mixture. After stirring for 1 h at rt, a saturated aqueous solution of NH₄Cl is added. The mixture is extracted with EtOAc (2×10 mL). The organic fractions are filtered over Na₂SO₄ and concentrated in vacuo to afford the desired compound (B) as a crude product. The material is carried forward to the next step without further purification.

Step 2: A mixture of N-SEM protected pyrazole (B) (1.0 equiv) and TFA (2.0 mL) in DCM (0.07 M) are stirred at rt for 5 min to 1 h. The reaction mixture is concentrated in vacuo. The crude material is purified by RP-HPLC (Method A or Method C). Fractions containing the desired mass are combined and concentrated by lyophilization to afford pyrazole (C) as the desired product.

General Procedure #3

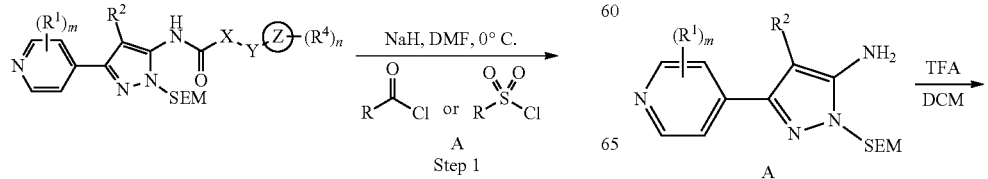

-continued

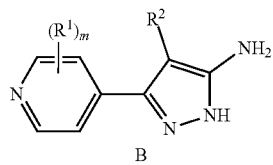

A mixture of N-SEM protected pyrazole (A) (1.0 equiv) and TFA (1-10 equiv) in DCM (0.05-0.60 M) is stirred at rt or 50° C. for 5 min to 1 h. The reaction mixture is concentrated in vacuo and the crude material is purified directly by RP-HPLC. Fractions containing the desired mass are combined and concentrated by lyophilization to afford pyrazole (B) as the desired product.

General Procedure #4

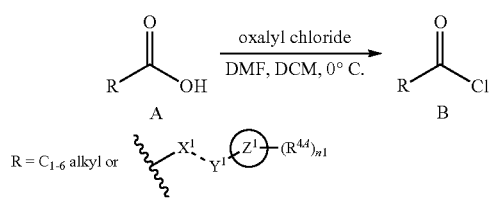

To a mixture of carboxylic acid A (1.0 equiv) in anhydrous DCM (x-x M) is added oxalyl chloride (1.5-3.0 equiv) and one drop of anhydrous DMF at 0° C. After the addition, the mixture is warmed to rt and stirred for 1 h. The solution is then concentrated in vacuo to afford crude product B. This material is used without further purification.

Example 1

N-Acetyl-3-(4-chlorophenyl)-N-(4-methyl-3-(pyridin-4-yl)-1H-pyrazol-5-yl)propenamide

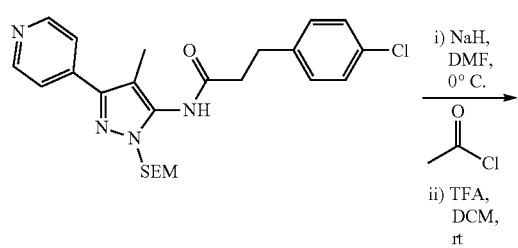

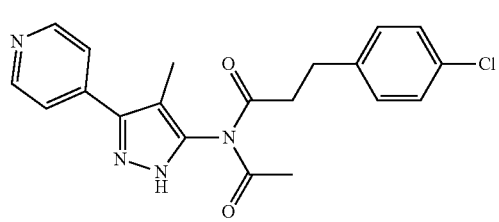

The product was prepared according to General Procedure #2 using Intermediate 3 and acetyl chloride to give N-acetyl-3-(4-chlorophenyl)-N-(4-methyl-3-(pyridin-4-yl)-1-((2-(trimethylsilyl)ethoxy)methyl)-1H-pyrazol-5-yl)propanamide (150 mg, 50% purity) as a crude intermediate. The crude material was then treated directly as outlined in Step 2 of the same general procedure to give N-acetyl-3-(4-chlorophenyl)-N-(4-methyl-3-(pyridin-4-yl)-1H-pyrazol-5-yl)propanamide (20 mg, 0.052 mmol, 13% yield over two steps) as a white solid. $^1$H NMR (400 MHz, DMSO-d$_6$) δ 13.7 (s, 1H), 8.73 (d, J=5.3 Hz, 2H), 7.72 (s, 2H), 7.37-7.29 (m, 2H), 7.27-7.20 (m, 2H), 2.84 (s, 4H), 2.23 (s, 3H), 1.99 (s, 3H). LCMS: ESI-MS m/z: 383.1 [M+H]$^+$.

Example 2

3-(4-Chlorophenyl)-N-(4-methyl-3-(pyridin-4-yl)-1H-pyrazol-5-yl)-N-propionylpropanamide

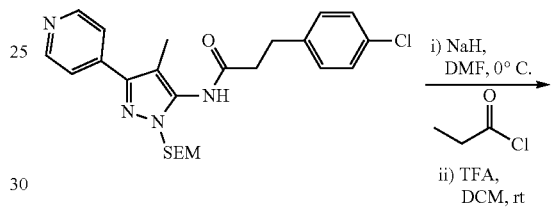

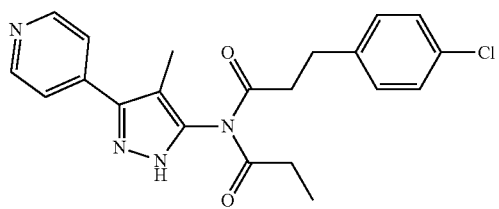

The product was prepared according to General Procedure #2 using Intermediate 3 and propionyl chloride. The resulting intermediate was then treated directly with TFA as described in Step 2 of General Procedure #2 to give 3-(4-chlorophenyl)-N-(4-methyl-3-(pyridin-4-yl)-1H-pyrazol-5-yl)-N-propionylpropanamide (28 mg, 0.072 mmol, 18% yield over two steps) as a white solid. $^1$H NMR (400 MHz, DMSO-d$_6$) δ 13.8 (s, 1H), 8.82 (s, 2H), 7.88 (s, 2H), 7.37-7.22 (m, 4H), 2.89 (dd, J=18.6, 6.4 Hz, 4H), 2.47 (s, 2H), 2.01 (s, 3H), 1.00 (t, J=7.3 Hz, 3H). LCMS: ESI-MS m/z: 397.1 [M+H]$^+$.

Example 3

3-(4-Chlorophenyl)-N-(3-(4-chlorophenyl)propanoyl)-N-(4-methyl-3-(pyridin-4-yl)-1H-pyrazol-5-yl)propanamide

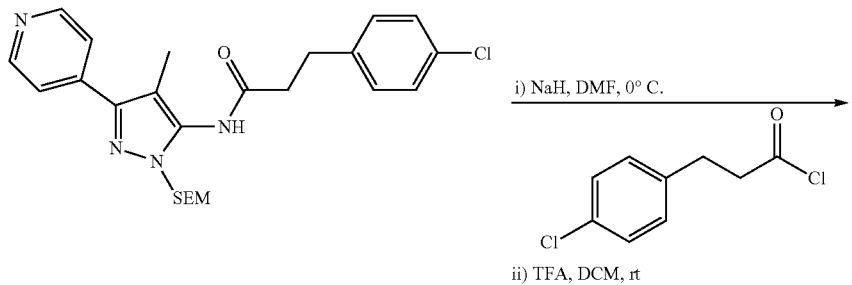

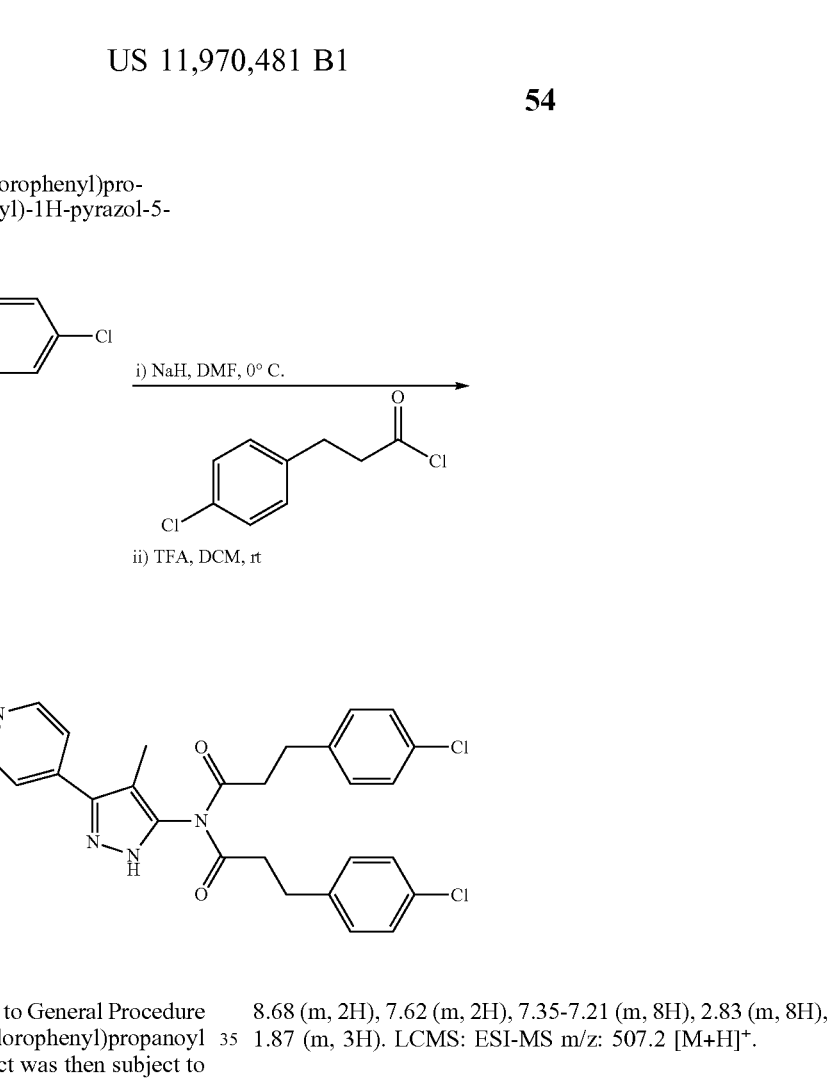

The product was prepared according to General Procedure #2 using Intermediate 3 and 3-(4-chlorophenyl)propanoyl chloride. The resulting acylated product was then subject to TFA according to Step 2 of the same general procedure to give 3-(4-chlorophenyl)-N-(3-(4-chlorophenyl)propanoyl)-N-(4-methyl-3-(pyridin-4-yl)-1H-pyrazol-5-yl)propanamide (38 mg, 0.10 mmol, 25% yield over two steps) as a white solid. $^1$H NMR (400 MHz, DMSO-$d_6$) δ 13.6 (s, 1H), 8.68 (m, 2H), 7.62 (m, 2H), 7.35-7.21 (m, 8H), 2.83 (m, 8H), 1.87 (m, 3H). LCMS: ESI-MS m/z: 507.2 [M+H]$^+$.

Example 4

3-(3-Chlorophenyl)-N-(3-(4-chlorophenyl)propanoyl)-N-(4-methyl-3-(pyridin-4-yl)-1H-pyrazol-5-yl)propanamide

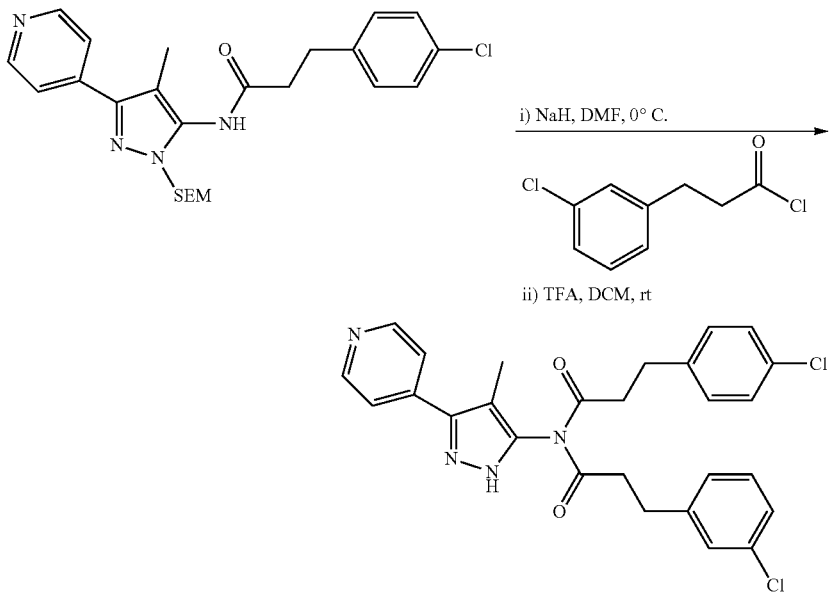

The product was prepared according to General Procedure #2 using Intermediate 3 and 3-(3-chlorophenyl)propanoyl chloride. The resulting intermediate was treated with TFA according to Step 2 of the same general procedure to give 3-(3-chlorophenyl)-N-(3-(4-chlorophenyl)propanoyl)-N-(4-methyl-3-(pyridin-4-yl)-1H-pyrazol-5-yl)propanamide (35 mg, 0.092 mmol, 23% yield over two steps) as a white solid. $^1$H NMR (400 MHz, DMSO-$d_6$) δ 13.6 (s, 1H), 8.68 (d, J=5.4 Hz, 2H), 7.62 (d, J=5.4 Hz, 2H), 7.32-7.26 (m, 4H), 7.25-7.20 (m, 3H), 7.16 (d, J=7.5 Hz, 1H), 2.84 (d, J=12.0 Hz, 8H), 1.88 (s, 3H). LCMS: ESI-MS m/z: 507.1 [M+H]$^+$.

Example 5

3-(2-Chlorophenyl)-N-(3-(4-chlorophenyl)propanoyl)-N-(4-methyl-3-(pyridin-4-yl)-1H-pyrazol-5-yl)propanamide

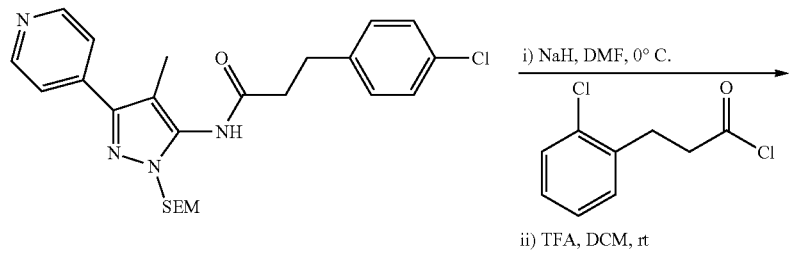

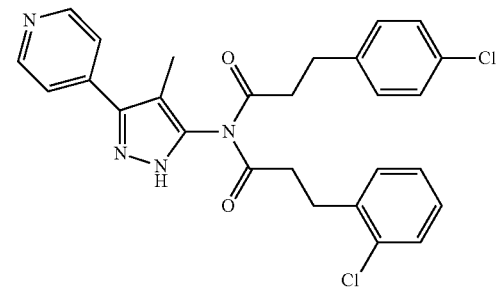

The product was prepared according to General Procedure #2 using Intermediate 3 and 3-(2-chlorophenyl)propanoyl chloride. The resulting acylated intermediate was then treated with TFA according to Step 2 of the same general procedure, to give 3-(2-chlorophenyl)-N-(3-(4-chlorophenyl)propanoyl)-N-(4-methyl-3-(pyridin-4-yl)-1H-pyrazol-5-yl)propanamide (35 mg, 0.092 mmol, 23% yield over two steps) as a white solid. $^1$H NMR (400 MHz, DMSO-$d_6$) δ 13.6 (s, 1H), 8.68 (d, J=5.8 Hz, 2H), 7.62 (d, J=6.0 Hz, 2H), 7.39 (dd, J=7.2, 1.9 Hz, 1H), 7.33-7.29 (m, 3H), 7.24 (ddd, J=8.4, 5.1, 2.8 Hz, 4H), 2.84 (m, 8H), 1.90 (s, 3H). LCMS: ESI-MS m/z: 507.1 [M+H]$^+$.

Example 6

3-(4-Chlorophenyl)-N-(4-methyl-3-(pyridin-4-yl)-1H-pyrazol-5-yl)-N-(3-phenylpropanoyl)propanamide

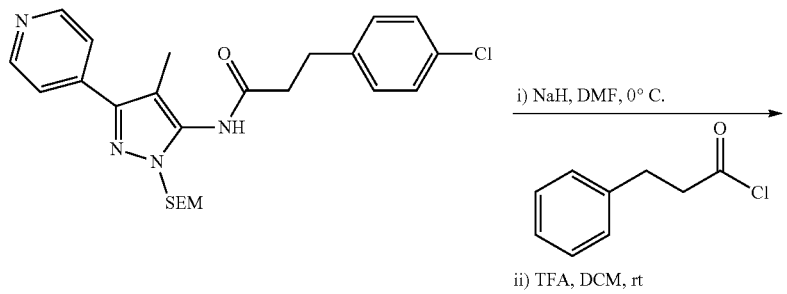

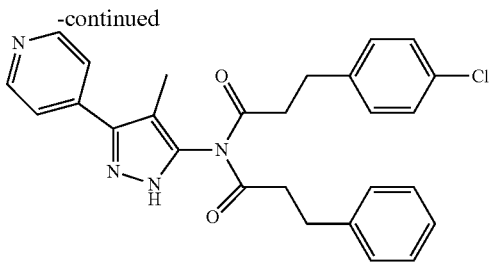

The product was prepared according to General Procedure #2 using Intermediate 3 and 3-phenylpropanoyl chloride. The resulting acylated intermediate was then treated with TFA according to Step 2 of the same general procedure to give 3-(4-chlorophenyl)-N-(4-methyl-3-(pyridin-4-yl)-1H-pyrazol-5-yl)-N-(3-phenylpropanoyl)propanamide (38 mg, 0.10 mmol, 25% yield over two steps) as a white solid. $^1$H NMR (400 MHz, DMSO-$d_6$) δ 13.6 (s, 1H), 8.68 (d, J=6.1 Hz, 2H), 7.62 (dd, J=4.6, 1.6 Hz, 2H), 7.31 (d, J=8.4 Hz, 2H), 7.27-7.21 (m, 4H), 7.19-7.15 (m, 3H), 2.84 (s, 8H), 1.87 (s, 3H). LCMS: ESI-MS m/z: 473.2 [M+H]$^+$.

Example 7

N-(3-(4-Chlorophenyl)propanoyl)-4-methyl-N-(4-methyl-3-(pyridin-4-yl)-1H-pyrazol-5-yl)pentanamide

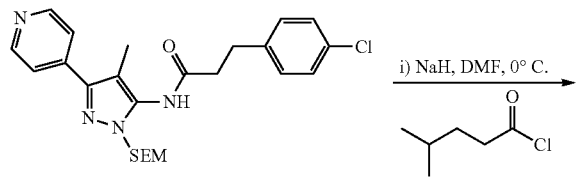

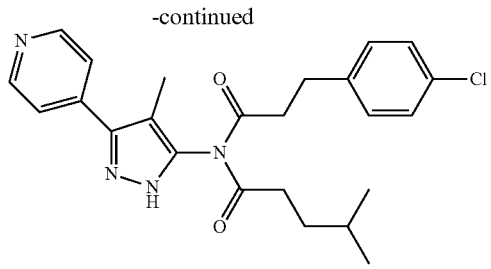

The product was prepared according to General Procedure #2 using Intermediate 3 and 4-methylpentanoyl chloride. The resulting acylated intermediate was then treated with TFA according to Step 2 of the same general procedure to give N-(3-(4-chlorophenyl)propanoyl)-4-methyl-N-(4-methyl-3-(pyridin-4-yl)-1H-pyrazol-5-yl)pentanamide (31 mg, 0.080 mmol, 20% yield over two steps) as a white solid. $^1$H NMR (400 MHz, DMSO-$d_6$) δ 13.6 (s, 1H), 8.69 (d, J=5.9 Hz, 2H), 7.63 (d, J=5.9 Hz, 2H), 7.32 (d, J=8.3 Hz, 2H), 7.24 (d, J=8.3 Hz, 2H), 2.86 (s, 4H), 2.47 (s, 2H), 1.95 (s, 3H), 1.53-1.45 (m, 1H), 1.40 (dd, J=14.5, 7.3 Hz, 2H), 0.80 (d, J=6.5 Hz, 6H). LCMS: ESI-MS m/z: 439.1 [M+H]$^+$.

Example 8

3-(4-Chlorophenyl)-N-(3-cyclopentylpropanoyl)-N-(4-methyl-3-(pyridin-4-yl)-1H-pyrazol-5-yl)propanamide

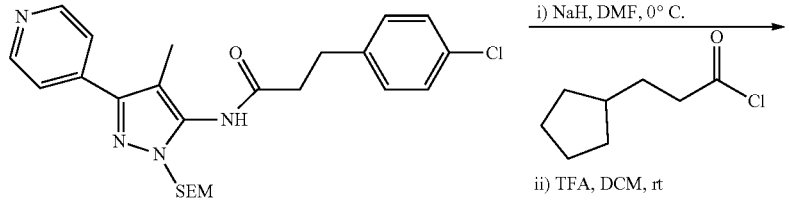

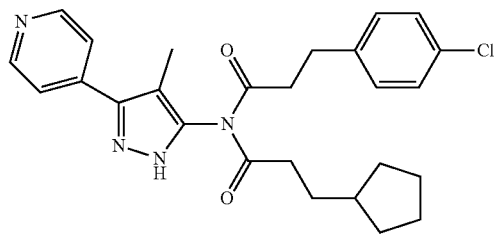

The product was prepared according to General Procedure #2 using Intermediate 3 and 3-cyclopentylpropanoyl chloride. The resulting acylated intermediate was treated with TFA according to Step 2 of the same general procedure to give 3-(4-chlorophenyl)-N-(3-cyclopentylpropanoyl)-N-(4-methyl-3-(pyridin-4-yl)-1H-pyrazol-5-yl)propanamide (46 mg, 0.12 mmol, 30% yield over two steps) as a white solid. $^1$H NMR (400 MHz, DMSO-$d_6$) δ 13.6 (s, 1H), 8.69 (d, J=5.3 Hz, 2H), 7.63 (d, J=5.7 Hz, 2H), 7.32 (d, J=8.4 Hz, 2H), 7.24 (d, J=8.4 Hz, 2H), 2.86 (s, 4H), 2.47 (s, 2H), 1.95 (s, 3H), 1.71-1.59 (m, 3H), 1.56-1.40 (m, 6H), 1.03-0.93 (m, 2H). LCMS: ESI-MS m/z: 465.1 [M+H]$^+$.

Example 9

3-(4-Chloro-3,5-difluorophenyl)-N-(3-(4-chloro-3,5-difluorophenyl)propanoyl)-N-(4-methyl-3-(pyridin-4-yl)-1H-pyrazol-5-yl)propanamide

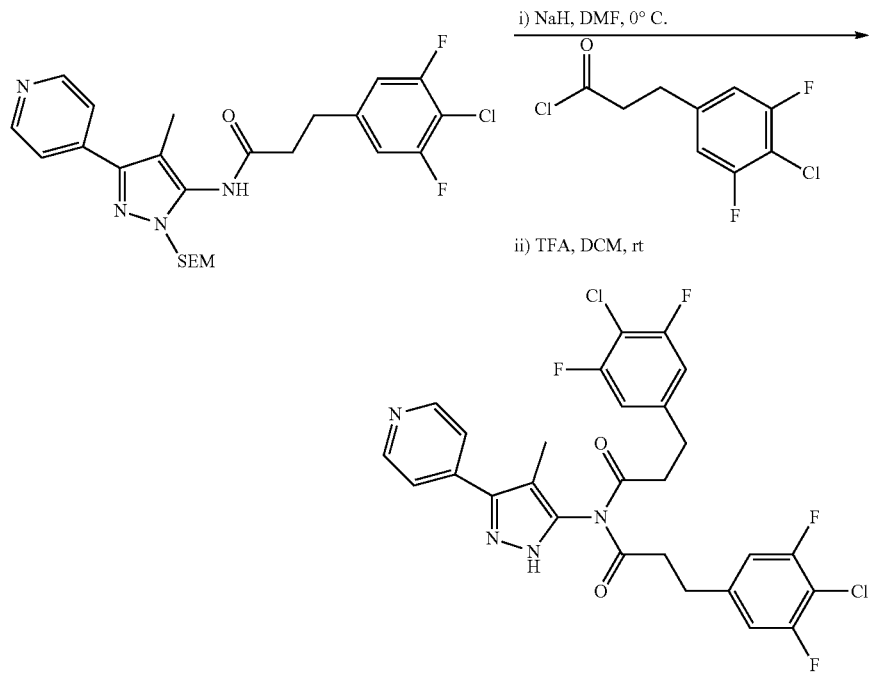

The product was prepared according to General Procedure #2 using Intermediate 24 and 3-(4-chloro-3,5-difluorophenyl)propanoyl chloride (prepared according to General Procedure #4 from carboxylic acid Intermediate 9) to afford 3-(4-chloro-3,5-difluorophenyl)-N-(3-(4-chloro-3,5-difluorophenyl)propanoyl)-N-(4-methyl-3-(pyridin-4-yl)-1H-pyrazol-5-yl)propanamide (16 mg, 0.028 mmol, 16% yield) as a white solid. $^1$H NMR (400 MHz, DMSO-$d_6$) δ 13.6 (s, 1H), 8.77 (s, 2H), 7.65 (d, J=4.3 Hz, 2H), 7.20 (d, J=8.4 Hz, 4H), 2.87 (s, 8H), 1.93 (s, 3H). LCMS: ESI-MS m/z: 579.2 [M+H]$^+$.

Example 10

N-(4-Methyl-3-(pyridin-4-yl)-1H-pyrazol-5-yl)-3-(3,4,5-trifluorophenyl)-N-(3-(3,4,5-trifluorophenyl)propanoyl)propanamide

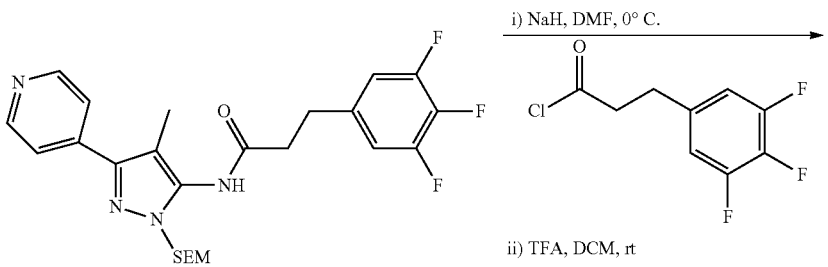

-continued

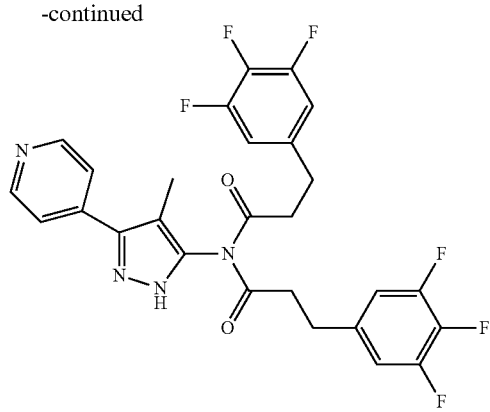

The product was prepared according to General Procedure #2 using Intermediate 25 and 3-(3,4,5-trifluorophenyl)propanoyl chloride (prepared according to General Procedure #4 from carboxylic acid 3-(3,4,5-trifluorophenyl)propanoic acid) to afford N-(4-methyl-3-(pyridin-4-yl)-1H-pyrazol-5-yl)-3-(3,4,5-trifluorophenyl)-N-(3-(3,4,5-trifluorophenyl)propanoyl)propanamide in 20% yield. $^1$H NMR (400 MHz, DMSO-d$_6$) δ 13.6 (s, 1H), 8.71 (d, J=5.9 Hz, 2H), 7.67 (s, 2H), 7.19 (dd, J=9.1, 6.9 Hz, 4H), 2.85 (s, 8H), 1.93 (s, 3H). LCMS: ESI-MS m/z: 547.2 [M+H]$^+$.

Example 11

3-(4-Chlorophenyl)-N-(4-methyl-3-(pyridin-4-yl)-1H-pyrazol-5-yl)-N-(methylsulfonyl)propanamide

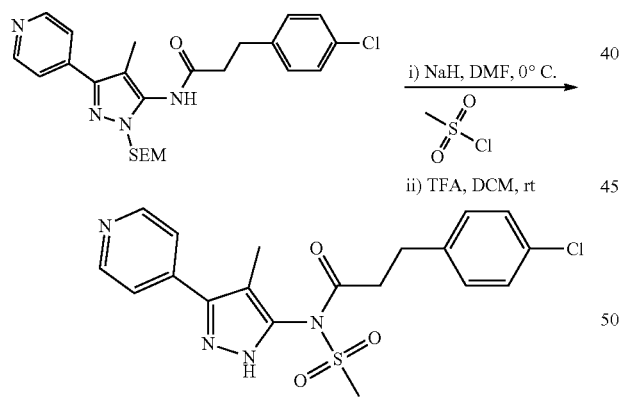

The product was prepared according to General Procedure #2 using Intermediate 3 and methanesulfonyl chloride. The resulting intermediate was then treated directly with TFA according to Step 2 of the same general procedure to give 3-(4-chlorophenyl)-N-(4-methyl-3-(pyridin-4-yl)-1H-pyrazol-5-yl)-N-(methylsulfonyl)propanamide (46 mg, 0.12 mmol, 30% yield over two steps) as a white solid. $^1$H NMR (400 MHz, DMSO-d$_6$) δ 13.8 (s, 1H), 8.69 (d, J=6.1 Hz, 2H), 7.64 (dd, J=4.6, 1.6 Hz, 2H), 7.31-7.28 (m, 2H), 7.19 (d, J=8.4 Hz, 2H), 3.51 (s, 3H), 2.81 (t, J=7.5 Hz, 2H), 2.47 (d, J=8.8 Hz, 2H), 2.12 (s, 3H). LCMS: ESI-MS m/z: 419.1 [M+H]$^+$.

Example 12

3-(4-Chlorophenyl)-N-isobutyryl-N-(4-methyl-3-(pyridin-4-yl)-1H-pyrazol-5-yl)propanamide

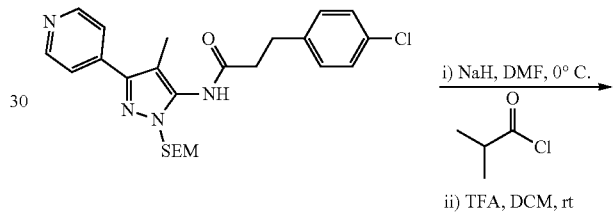

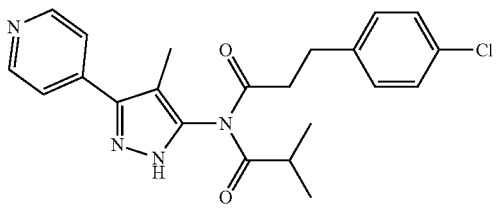

The product was prepared according to General Procedure #2 using Intermediate 3 and isobutyryl chloride. The resulting acylated intermediate was then treated directly with TFA according to Step 2 of the same general procedure to give 3-(4-chlorophenyl)-N-isobutyryl-N-(4-methyl-3-(pyridin-4-yl)-1H-pyrazol-5-yl)propanamide (38 mg, 0.10 mmol, 25% yield over two steps) as a white solid. $^1$H NMR (400 MHz, DMSO-d$_6$) δ 13.6 (s, 1H), 8.69 (d, J=5.8 Hz, 2H), 7.63 (d, J=6.1 Hz, 2H), 7.35-7.30 (m, 2H), 7.28-7.22 (m, 2H), 2.94-2.89 (m, 1H), 2.88 (d, J=3.7 Hz, 4H), 1.94 (s, 3H), 1.05 (d, J=6.8 Hz, 6H). LCMS: ESI-MS m/z: 411.2 [M+H]$^+$.

Example 13

3-(4-Chloro-3,5-difluorophenyl)-N-(4-ethyl-3-(pyridin-4-yl)-1H-pyrazol-5-yl)propanamide

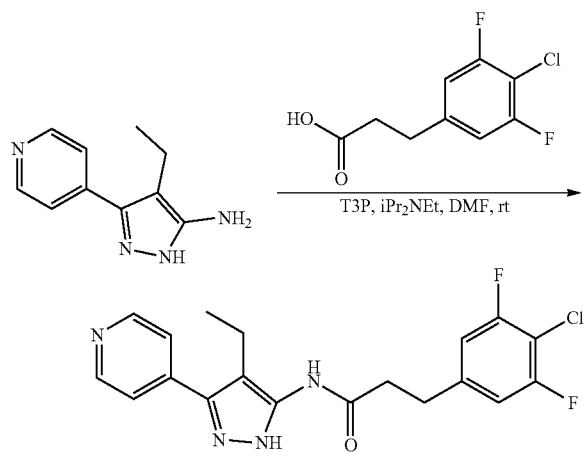

The product was prepared according to General Procedure #1 using Intermediate 4 and Intermediate 9 to yield the desired product 3-(4-chloro-3,5-difluorophenyl)-N-(4-ethyl-3-(pyridin-4-yl)-1H-pyrazol-5-yl)propenamide (31 mg, 0.079 mmol, 30% yield) as a white solid. $^1$H NMR (400 MHz, DMSO-$d_6$) δ 13.0 (s, 1H), 9.74 (d, J=113.7 Hz, 1H), 8.76-8.50 (m, 2H), 7.70-7.45 (m, 2H), 7.27 (d, J=8.6 Hz, 2H), 2.96 (t, J=7.2 Hz, 2H), 2.69 (s, 2H), 2.47-2.31 (m, 2H), 0.92 (s, 3H). LCMS: ESI-MS m/z: 391.0 [M+H]$^+$.

Example 14

3-(4-Chlorophenyl)-N-(4-ethyl-3-(pyridin-4-yl)-1H-pyrazol-5-yl)propanamide

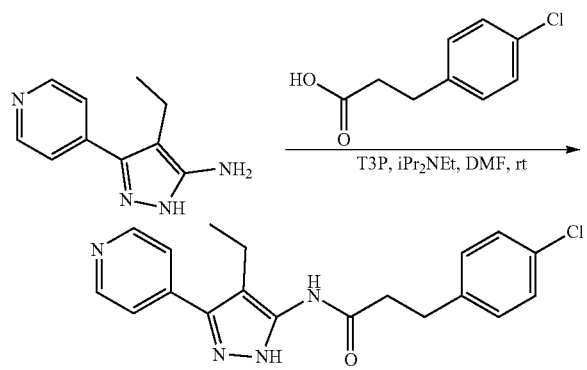

The product was prepared according to General Procedure #1 using Intermediate 4 and 3-(4-chlorophenyl)propanoic acid to give the desired product, 3-(4-chlorophenyl)-N-(4-ethyl-3-(pyridin-4-yl)-1H-pyrazol-5-yl)propanamide (31 mg, 0.079 mmol, 30% yield) as a white solid. $^1$H NMR (400 MHz, DMSO-$d_6$) δ 8.66 (m, 2H), 7.53 (m, 2H), 7.38-7.28 (m, 3H), 7.26-7.17 (m, 2H), 3.05 (m, 2H), 2.76 (m, 2H), 2.49 (m, 2H), 1.06 (t, J=7.2 Hz, 3H). LCMS: ESI-MS m/z: 355.1 [M+H]$^+$.

Example 15

3-(4-Cyano-3,5-difluorophenyl)-N-(4-ethyl-3-(pyridin-4-yl)-1H-pyrazol-5-yl)propanamide

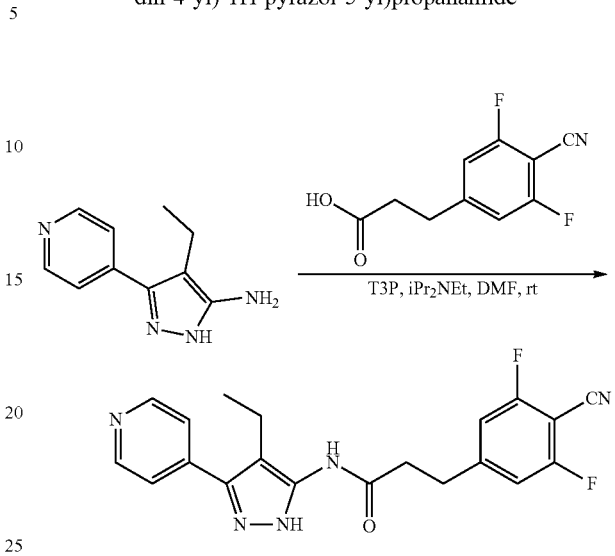

The product was prepared according to General Procedure #1 using Intermediate 4 and Intermediate 8 to give the desired product 3-(4-cyano-3,5-difluorophenyl)-N-(4-ethyl-3-(pyridin-4-yl)-1H-pyrazol-5-yl)propanamide (29 mg, 0.074 mmol, 28% yield) as a white solid. $^1$H NMR (400 MHz, DMSO-$d_6$) δ 13.1-12.9 (m, 1H), 9.92-9.63 (m, 1H), 8.65 (s, 2H), 7.55 (s, 2H), 7.41 (d, J=9.5 Hz, 2H), 3.04 (t, J=7.2 Hz, 2H), 2.68 (dd, J=14.1, 12.3 Hz, 2H), 2.35 (dd, J=20.4, 19.4 Hz, 2H), 0.93 (s, 3H). LCMS: ESI-MS m/z: 382.1 [M+H]$^+$.

Example 16

3-(4-Cyano-3-fluorophenyl)-N-(4-ethyl-3-(pyridin-4-yl)-1H-pyrazol-5-yl)propanamide

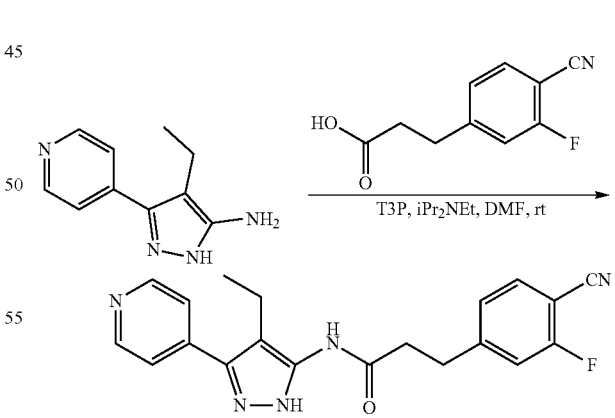

The product was prepared according to General Procedure #1 using Intermediate 4 and Intermediate 10 to afford the desire product, 3-(4-cyano-3-fluorophenyl)-N-(4-ethyl-3-(pyridin-4-yl)-1H-pyrazol-5-yl)propanamide (33 mg, 0.084 mmol, 32% yield) as a white solid. $^1$H NMR (400 MHz, DMSO-$d_6$) δ 13.0-12.9 (m, 1H), 9.92-9.63 (m, 1H), 8.65 (s, 2H), 7.87 (t, J=7.5 Hz, 1H), 7.55 (d, J=1.2 Hz, 2H), 7.47 (d, J=10.8 Hz, 1H), 7.35 (d, J=7.5 Hz, 1H), 3.03 (t, J=7.2 Hz, 2H), 2.72 (s, 2H), 2.41 (s, 2H), 0.93 (s, 3H). LCMS: ESI-MS m/z: 364.1 [M+H]⁺.

Example 17

3-(5-Chlorothiophen-2-yl)-N-(4-ethyl-3-(pyridin-4-yl)-1H-pyrazol-5-yl)propenamide

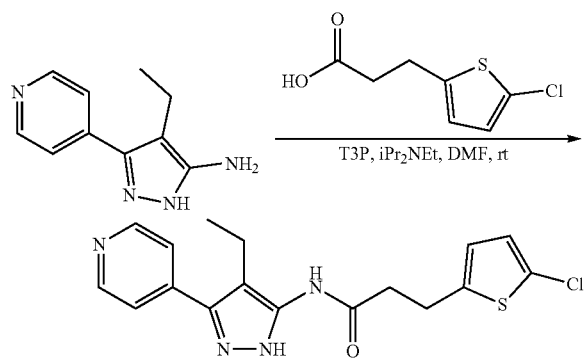

The product was prepared according to General Procedure 1 using Intermediate 4 and 3-(5-chlorothiophen-2-yl)propanoic acid to afford 3-(5-chlorothiophen-2-yl)-N-(4-ethyl-3-(pyridin-4-yl)-1H-pyrazol-5-yl)propenamide (23 mg, 58% yield) as a white solid, trifluoroacetic acid salt. ¹H NMR (400 MHz, DMSO-d₆) δ 9.92 (s, 1H), 8.81-8.74 (m, 2H), 7.94 (s, 1H), 6.94 (d, J=3.7 Hz, 1H), 6.79 (d, J=3.8 Hz, 1H), 3.07 (t, J=7.1 Hz, 2H), 2.70 (t, J=7.1 Hz, 2H), 2.56 (q, J=7.3 Hz, 2H), 1.00 (t, J=7.5 Hz, 3H). LCMS: ESI-MS m/z: 361.1 [M+H]⁺.

Example 18

(rac)-3-(4-chlorophenyl)-2-fluoro-N-(4-methyl-3-(pyridin-4-yl)-1H-pyrazol-5-yl)propanamide

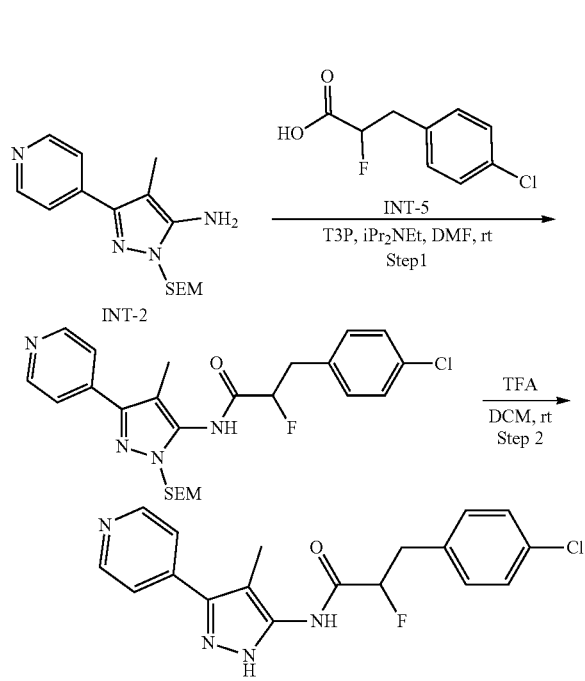

Step 1: (rac)-3-(4-Chlorophenyl)-2-fluoro-N-(4-methyl-3-(pyridin-4-yl)-1-((2-(trimethylsilyl)ethoxy)methyl)-1H-pyrazol-5-yl)propenamide. The product was prepared according to General Procedure #1 using Intermediate 2 and Intermediate 5 to give the desired product (rac)-3-(4-chlorophenyl)-2-fluoro-N-(4-methyl-3-(pyridin-4-yl)-1-((2-(trimethylsilyl)ethoxy)methyl)-1H-pyrazol-5-yl)propanamide (400 mg, 0.82 mmol, >95% crude yield, 65% purity) as an oil. The crude material was carried forward to the next step without further purification. LCMS: ESI-MS m/z: 489.2 [M+H]⁺.

Step 2: (rac)-3-(4-Chlorophenyl)-2-fluoro-N-(4-methyl-3-(pyridin-4-yl)-1H-pyrazol-5-yl)propanamide. A mixture of (rac)3-(4-chlorophenyl)-2-fluoro-N-(4-methyl-3-(pyridin-4-yl)-1-((2-(trimethylsilyl)ethoxy)methyl)-1H-pyrazol-5-yl)propanamide (400 mg, 0.82 mmol, 1.0 equiv) and TFA (3.0 mL) in DCM (6.0 mL, 0.14 M) was stirred at rt for 2 h. The reaction mixture was concentrated in vacuo and the crude material was purified directly by RP-HPLC (Method C, 15-40% MeCN in H₂O+10 mM NH₄HCO₃+0.025% NH₃·H₂O). Fractions containing the desired mass were combined and concentrated by lyophilization to afford (rac)-3-(4-chlorophenyl)-2-fluoro-N-(4-methyl-3-(pyridin-4-yl)-1H-pyrazol-5-yl)propanamide (110 mg, 0.32 mmol, 65% yield) as a white solid. ¹H NMR (400 MHz, DMSO-d₆) δ 13.2-13.1 (m, 1H), 10.2-10.0 (m, 1H), 8.67-8.62 (m, 2H), 7.65-7.59 (m, 2H), 7.42-7.34 (m, 4H), 5.43-5.29 (m, 1H), 3.31-3.12 (m, 2H), 1.94 (s, 3H). LCMS: ESI-MS m/z: 359.1 [M+H]⁺.

Example 19

3-(4-Chlorophenyl)-N-(4-methyl-3-(pyridin-4-yl)-1H-pyrazol-5-yl)propanamide

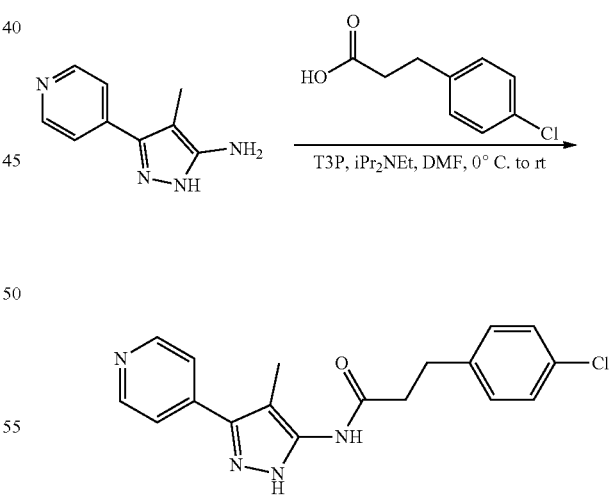

The product was prepared according to General Procedure #1 using Intermediate 1 and 3-(4-chlorophenyl)propanoic acid to afford 3-(4-chlorophenyl)-N-(4-methyl-3-(pyridin-4-yl)-1H-pyrazol-5-yl)propenamide (3.3 g, 48% yield) as an off-white solid. ¹H NMR (400 MHz, DMSO-d₆) δ 13.0 (s, 1H), 9.81 (s, 1H), 8.63 (d, J=5.6 Hz, 2H), 7.58 (d, J=5.6 Hz, 2H), 7.36-7.29 (m, 4H), 2.91 (t, J=7.6 Hz, 2H), 2.64 (t, J=7.6 Hz, 2H), 1.98 (s, 3H). LCMS: ESI-MS m/z: 341.1 [M+H]⁺.

Example 20

3-(Benzo[d][1,3]dioxol-5-yl)-N-(4-methyl-3-(pyridin-4-yl)-1H-pyrazol-5-yl)propanamide

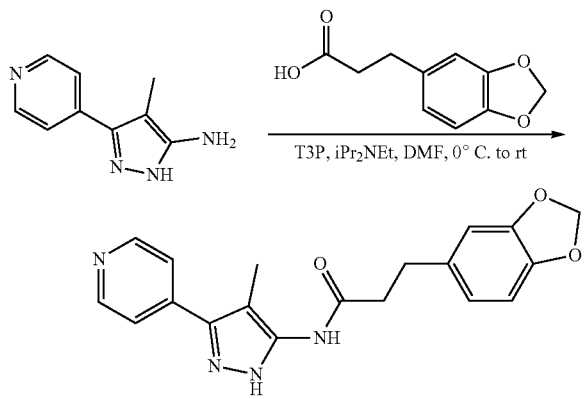

The product was prepared according to General Procedure #1 using Intermediate 1 and 3-(benzo[d][1,3]dioxol-5-yl)propanoic acid to afford 3-(benzo[d][1,3]dioxol-5-yl)-N-(4-methyl-3-(pyridin-4-yl)-1H-pyrazol-5-yl)propenamide (41% yield) as a white solid. $^1$H NMR (500 MHz, DMSO-d$_6$) δ 14.0 (s, 1H), 9.77 (s, 1H), 8.63 (d, J=5.5 Hz, 2H), 7.59 (d, J=6.0 Hz, 2H), 6.83-6.73 (m, 3H), 5.96 (s, 2H), 2.84 (t, J=7.0 Hz, 2H), 2.60 (t, J=7.5 Hz, 2H), 1.99 (s, 3H). LCMS: ESI-MS m/z: 351.1 [M+H]$^+$.

Example 21

3-(3,5-Dichlorophenyl)-N-(4-methyl-3-(pyridin-4-yl)-1H-pyrazol-5-yl)propanamide

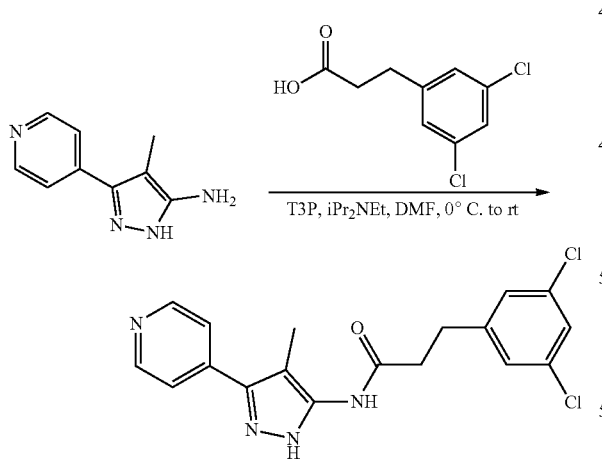

The product was prepared according to General Procedure #1 using Intermediate 1 and 3-(3,5-dichlorophenyl)propanoic acid to afford 3-(3,5-dichlorophenyl)-N-(4-methyl-3-(pyridin-4-yl)-1H-pyrazol-5-yl)propenamide (27% yield) as a white solid. $^1$H NMR (500 MHz, DMSO-d$_6$) δ 13.1-13.0 (m, 1H), 10.0-9.71 (m, 1H), 8.65-8.58 (m, 2H), 7.64-7.57 (m, 2H), 7.44-7.36 (m, 3H), 2.94 (t, J=7.2 Hz, 2H), 2.72-2.64 (m, 2H), 2.04-1.94 (m, 3H). LCMS: ESI-MS m/z: 375.0 [M+H]$^+$.

Example 22

N-(4-Methyl-3-(pyridin-4-yl)-1H-pyrazol-5-yl)-3-phenylpropanamide

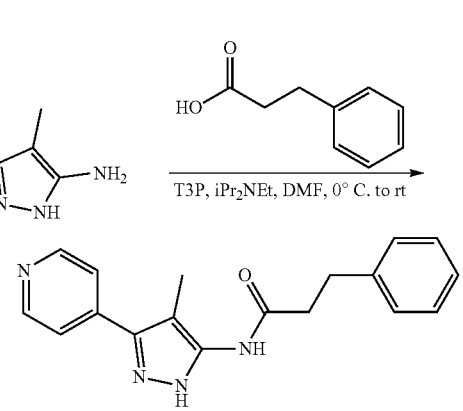

The product was prepared according to General Procedure #1 using Intermediate 1 and 3-phenylpropanoic acid to afford N-(4-methyl-3-(pyridin-4-yl)-1H-pyrazol-5-yl)-3-phenylpropanamide (42% yield). $^1$H NMR (500 MHz, DMSO-d$_6$) δ 13.1-13.0 (m, 1H), 9.97-9.70 (m, 1H), 8.65-8.59 (m, 2H), 7.64-7.57 (m, 2H), 7.31-7.18 (m, 5H), 2.91 (d, J=6.7 Hz, 2H), 2.74-2.57 (m, 2H), 2.05-1.95 (m, 3H). LCMS: ESI-MS m/z: 307.1 [M+H]$^+$.

Example 23

3-(2-Chlorophenyl)-N-(4-methyl-3-(pyridin-4-yl)-1H-pyrazol-5-yl)propanamide

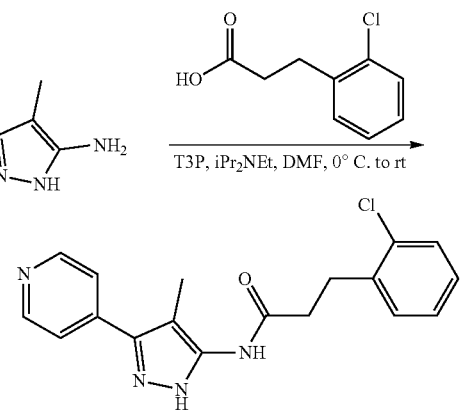

The product was prepared according to General Procedure #1 using Intermediate 1 and 3-(2-chlorophenyl)propanoic acid to afford 3-(2-chlorophenyl)-N-(4-methyl-3-(pyridin-4-yl)-1H-pyrazol-5-yl)propenamide (20% yield). $^1$H NMR (500 MHz, DMSO-d$_6$) δ 13.0 (s, 1H), 9.80 (s, 1H), 8.63 (d, J=5.2 Hz, 2H), 7.60 (d, J=5.5 Hz, 2H), 7.45-7.39 (m, 2H), 7.32-7.22 (m, 2H), 3.03 (t, J=7.7 Hz, 2H), 2.67 (t, J=7.6 Hz, 2H), 2.01 (s, 3H). LCMS: ESI-MS m/z: 341.0 [M+H]$^+$.

Example 24

N-(4-Methyl-3-(pyridin-4-yl)-1H-pyrazol-5-yl)-3-(p-tolyl)propanamide

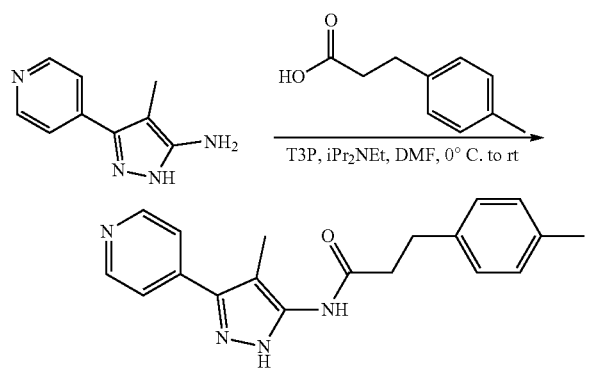

The product was prepared according to General Procedure #1 using Intermediate 1 and 3-(p-tolyl)propanoic acid to afford N-(4-methyl-3-(pyridin-4-yl)-1H-pyrazol-5-yl)-3-(p-tolyl)propenamide (37% yield). $^1$H NMR (500 MHz, DMSO-$d_6$) δ 13.1-12.9 (m, 1H), 9.96-9.68 (m, 1H), 8.66-8.58 (m, 2H), 7.64-7.56 (m, 2H), 7.16-7.09 (m, 4H), 2.88-2.85 (m, 2H), 2.67-2.57 (m, 2H), 2.26 (s, 3H), 2.05-1.95 (m, 3H). LCMS: ESI-MS m/z: 321.2 [M+H]$^+$.

Example 25

N-(4-Methyl-3-(pyridin-4-yl)-1H-pyrazol-5-yl)-3-(m-tolyl)propanamide

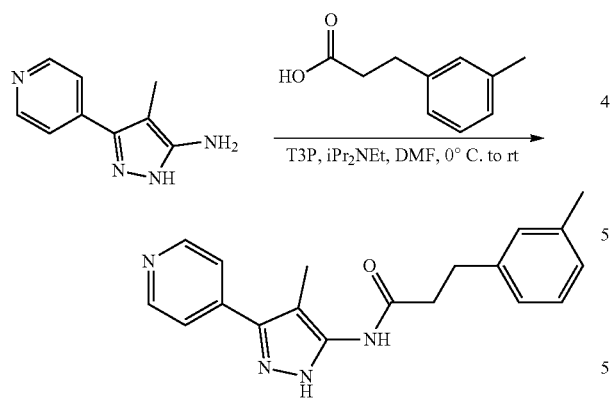

The product was prepared according to General Procedure #1 using Intermediate 1 and 3-(m-tolyl)propanoic acid to afford the desired compound, N-(4-methyl-3-(pyridin-4-yl)-1H-pyrazol-5-yl)-3-(m-tolyl)propenamide in 25% yield. $^1$H NMR (500 MHz, DMSO-$d_6$) δ 13.2-12.9 (m, 1H), 9.94-9.69 (m, 1H), 8.65 (s, 2H), 7.59 (s, 1H), 7.18 (t, J=7.5 Hz, 1H), 7.12-7.03 (m, 1H), 7.01 (d, J=7.4 Hz, 1H), 2.88 (t, J=7.6 Hz, 2H), 2.62 (s, 2H), 2.04-1.97 (m, 3H). LCMS: ESI-MS m/z: 321.1 [M+H]$^+$.

Example 26

N-(4-Methyl-3-(pyridin-4-yl)-1H-pyrazol-5-yl)-3-(o-tolyl)propanamide

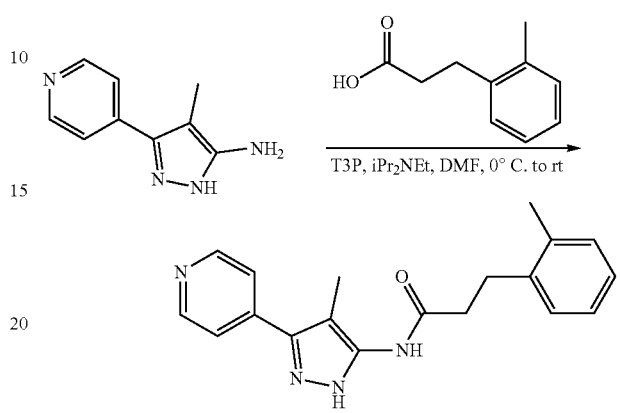

The product was prepared according to General Procedure #1 using Intermediate 1 and 3-(o-tolyl)propanoic acid to afford N-(4-methyl-3-(pyridin-4-yl)-1H-pyrazol-5-yl)-3-(o-tolyl)propenamide (40% yield). $^1$H NMR (500 MHz, DMSO-$d_6$) δ 13.1-13.0 (m, 1H), 10.0-9.63 (m, 1H), 8.66-8.59 (m, 2H), 7.65-7.57 (m, 2H), 7.20-7.09 (m, 4H), 2.90 (t, J=6.6 Hz, 2H), 2.64-2.57 (m, 2H), 2.32 (s, 3H), 2.07 (s, 3H). LCMS: ESI-MS m/z: 321.1 [M+H]$^+$.

Example 27

3-(4-Methoxyphenyl)-N-(4-methyl-3-(pyridin-4-yl)-1H-pyrazol-5-yl)propanamide

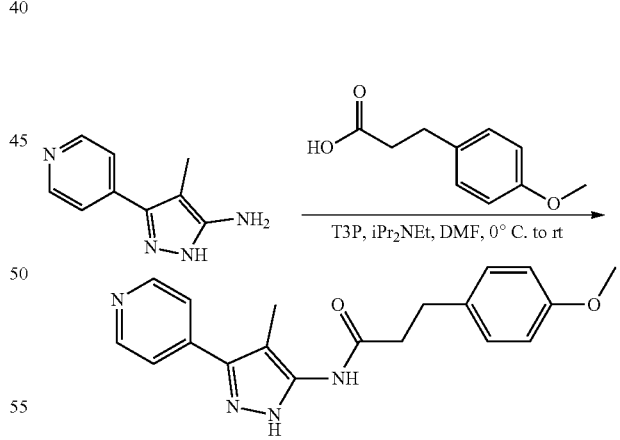

The product was prepared according to General Procedure #1 using Intermediate 1 and 3-(4-methoxyphenyl)propanoic acid to afford 3-(4-methoxyphenyl)-N-(4-methyl-3-(pyridin-4-yl)-1H-pyrazol-5-yl)propenamide (22% yield). $^1$H NMR (500 MHz, DMSO-$d_6$) δ 13.1-12.9 (m, 1H), 9.95-9.68 (m, 1H), 8.66-8.59 (m, 2H), 7.64-4.56 (m, 2H), 7.18 (d, J=8.4 Hz, 2H), 6.85 (d, J=8.4 Hz, 2H), 3.72 (s, 3H), 2.85-2.83 (m, 2H), 2.66-2.56 (m, 2H), 2.06-1.95 (m, 3H). LCMS: ESI-MS m/z: 337.1 [M+H]$^+$.

Example 28

N-(4-Methyl-3-(pyridin-4-yl)-1H-pyrazol-5-yl)-3-(naphthalen-2-yl)propanamide

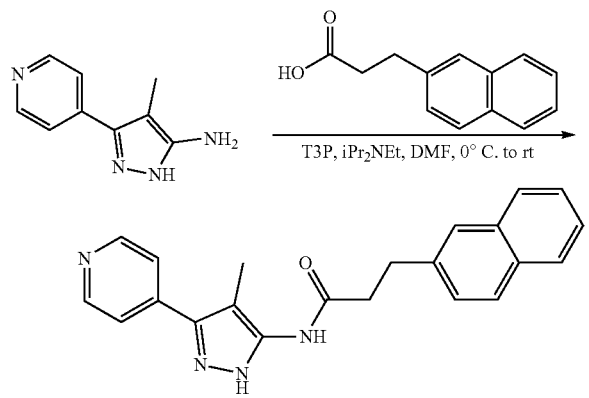

The product was prepared according to General Procedure #1 using Intermediate 1 and 3-(naphthalen-2-yl)propanoic acid to afford N-(4-methyl-3-(pyridin-4-yl)-1H-pyrazol-5-yl)-3-(naphthalen-2-yl)propenamide in 18% yield. $^1$H NMR (500 MHz, DMSO-$d_6$) δ 13.1-13.0 (m, 1H), 10.0-9.73 (m, 1H), 8.65-8.58 (m, 2H), 7.94-7.72 (m, 4H), 7.70-7.37 (m, 5H), 3.10 (s, 2H), 2.80-2.73 (m, 2H), 2.03-1.98 (m, 3H). LCMS: ESI-MS m/z: 357.1 [M+H]$^+$.

Example 29

N-(4-Methyl-3-(pyridin-4-yl)-1H-pyrazol-5-yl)-3-(naphthalen-1-yl)propanamide

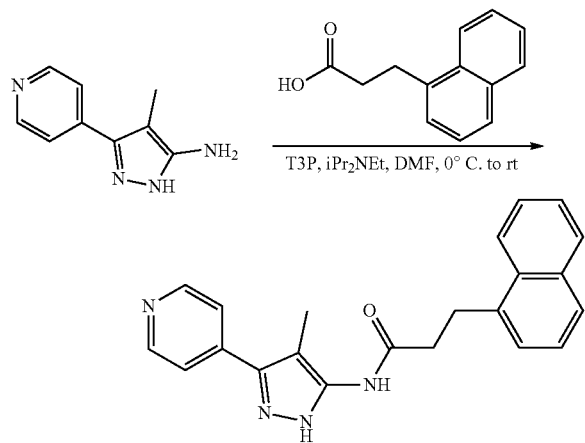

The product was prepared according to General Procedure #1 using Intermediate 1 and 3-(naphthalen-1-yl)propanoic acid to afford N-(4-methyl-3-(pyridin-4-yl)-1H-pyrazol-5-yl)-3-(naphthalen-1-yl)propenamide (29% yield). $^1$H NMR (500 MHz, DMSO-$d_6$) δ 13.1-13.0 (m, 1H), 10.0-9.75 (m, 1H), 8.67-8.58 (m, 2H), 8.21-8.06 (m, 1H), 7.94 (d, J=8.1 Hz, 1H), 7.84-7.74 (m, 1H), 7.67-7.50 (m, 4H), 7.44 (d, J=3.4 Hz, 2H), 3.41 (dd, J=14.9, 7.5 Hz, 2H), 2.83-2.73 (m, 2H), 2.06-1.98 (m, 3H). LCMS: ESI-MS m/z: 357.1 [M+H]$^+$.

Example 30

3-(3-Chlorophenyl)-N-(4-methyl-3-(pyridin-4-yl)-1H-pyrazol-5-yl)propanamide

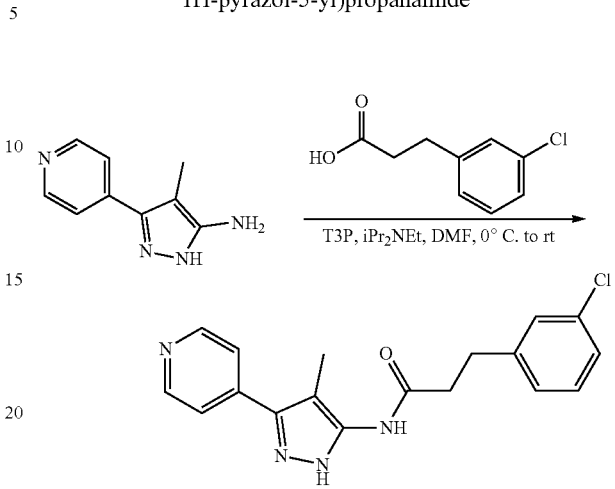

The product was prepared according to General Procedure #1 using Intermediate 1 and 3-(3-chlorophenyl)propanoic acid to afford 3-(3-chlorophenyl)-N-(4-methyl-3-(pyridin-4-yl)-1H-pyrazol-5-yl)propanamide (17% yield). $^1$H NMR (500 MHz, DMSO-$d_6$) δ 13.0 (s, 1H), 9.76 (s, 1H), 8.63 (s, 2H), 7.59 (s, 2H), 7.33 (dd, J=14.2, 6.3 Hz, 2H), 7.25 (t, J=8.7 Hz, 2H), 2.93 (t, J=7.5 Hz, 2H), 2.65 (dd, J=12.7, 5.0 Hz, 2H), 1.97 (s, 3H). LCMS: ESI-MS m/z: 341.1 [M+H]$^+$.

Example 31

3-(3,4-Dichlorophenyl)-N-(4-methyl-3-(pyridin-4-yl)-1H-pyrazol-5-yl)propanamide

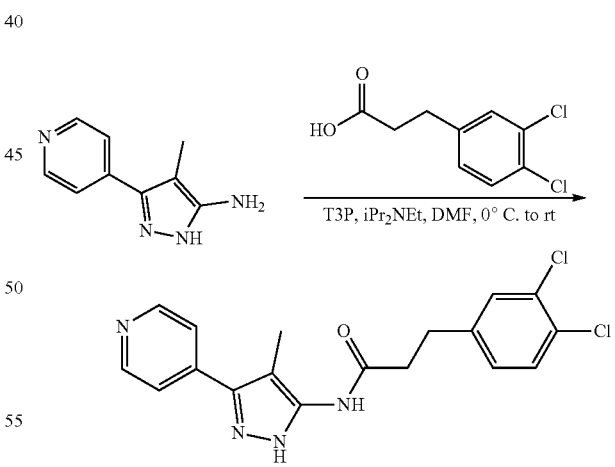

The product was prepared according to General Procedure #1 using Intermediate 1 and 3-(3,4-dichlorophenyl)propanoic acid to afford 3-(3,4-dichlorophenyl)-N-(4-methyl-3-(pyridin-4-yl)-1H-pyrazol-5-yl)propanamide in 23% yield. $^1$H NMR (400 MHz, DMSO-$d_6$) δ 13.1-13.0 (m, 1H), 9.97-9.71 (m, 1H), 8.65-8.59 (m, 2H), 7.64-7.55 (m, 4H), 7.28 (dd, J=8.3, 1.9 Hz, 2H), 2.93 (t, J=7.0 Hz, 2H), 2.66 (dd, J=18.5, 11.5 Hz, 2H), 2.04-1.94 (m, 3H). LCMS: ESI-MS m/z: 375.0 [M+H]$^+$.

Example 32

N-(4-Methyl-3-(pyridin-4-yl)-1H-pyrazol-5-yl)-3-(4-(trifluoromethyl)phenyl)propanamide

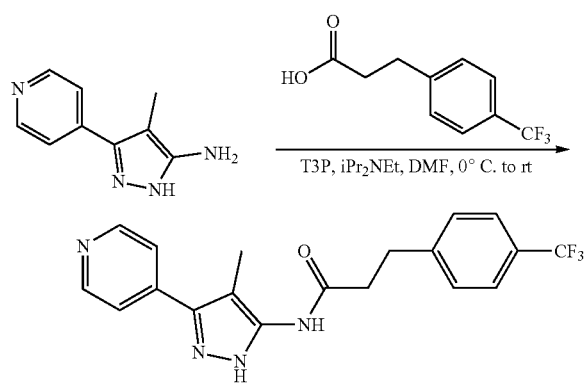

The product was prepared according to General Procedure #1 using Intermediate 1 and 3-(4-(trifluoromethyl)phenyl)propanoic acid to afford N-(4-methyl-3-(pyridin-4-yl)-1H-pyrazol-5-yl)-3-(4-(trifluoromethyl)phenyl)propenamide in 33% yield. $^1$H NMR (500 MHz, DMSO-$d_6$) δ 13.1-13.0 (m, 1H), 9.99-9.73 (m, 1H), 8.75-8.48 (m, 2H), 7.69-7.34 (m, 6H), 3.09-2.85 (m, 2H), 2.74-2.67 (m, 2H), 2.03-1.93 (m, 3H). LCMS: ESI-MS m/z: 375.1 [M+H]$^+$.

Example 33

3-(4-Fluorophenyl)-N-(4-methyl-3-(pyridin-4-yl)-1H-pyrazol-5-yl)propanamide

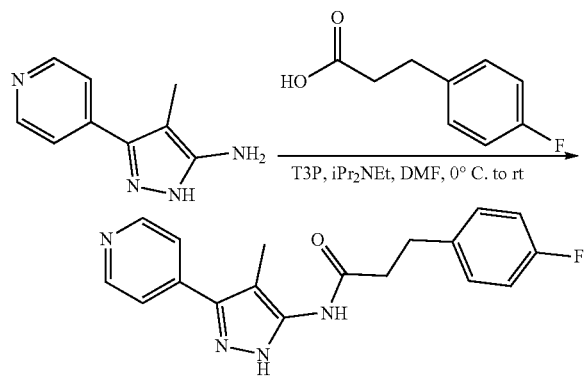

The product was prepared according to General Procedure #1 using Intermediate 1 and 3-(4-fluorophenyl)propanoic acid to afford 3-(4-fluorophenyl)-N-(4-methyl-3-(pyridin-4-yl)-1H-pyrazol-5-yl)propenamide in 26% yield. $^1$H NMR (500 MHz, DMSO-$d_6$) δ 13.1-12.9 (m, 1H), 9.96-9.69 (m, 1H), 8.66-8.58 (m, 2H), 7.65-7.56 (m, 2H), 7.30 (dd, J=8.1, 5.8 Hz, 2H), 7.11 (t, J=8.7 Hz, 2H), 2.94-2.89 (m, 2H), 2.69-2.60 (m, 2H), 2.05-1.94 (m, 3H). LCMS: ESI-MS m/z: 325.1 [M+H]$^+$.

Example 34

3-(4-Ethylphenyl)-N-(4-methyl-3-(pyridin-4-yl)-1H-pyrazol-5-yl)propanamide

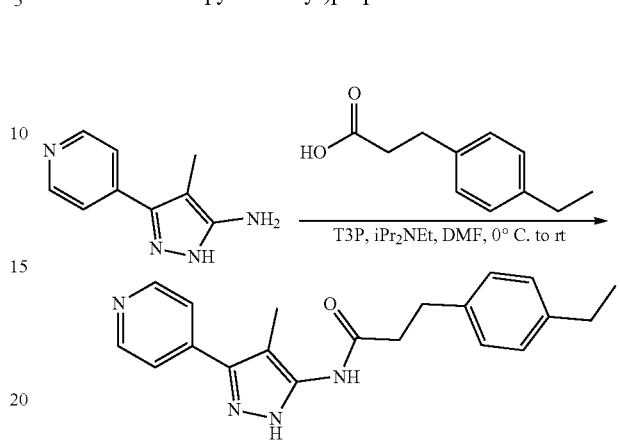

The product was prepared according to General Procedure #1 using Intermediate 1 and 3-(4-ethylphenyl)propanoic acid to afford 3-(4-ethylphenyl)-N-(4-methyl-3-(pyridin-4-yl)-1H-pyrazol-5-yl)propenamide (20% yield). $^1$H NMR (400 MHz, DMSO-$d_6$) δ 13.1-12.9 (m, 1H), 10.0-9.68 (m, 1H), 8.75-8.42 (m, 2H), 7.73-7.44 (m, 2H), 7.30-7.00 (m, 4H), 2.89 (dt, J=14.0, 4.0 Hz, 2H), 2.70-2.53 (m, 4H), 2.05-1.95 (m, 3H), 1.16 (t, J=7.6 Hz, 3H). LCMS: ESI-MS m/z: 335.1 [M+H]$^+$.

Example 35

3-(4-Bromophenyl)-N-(4-methyl-3-(pyridin-4-yl)-1H-pyrazol-5-yl)propanamide

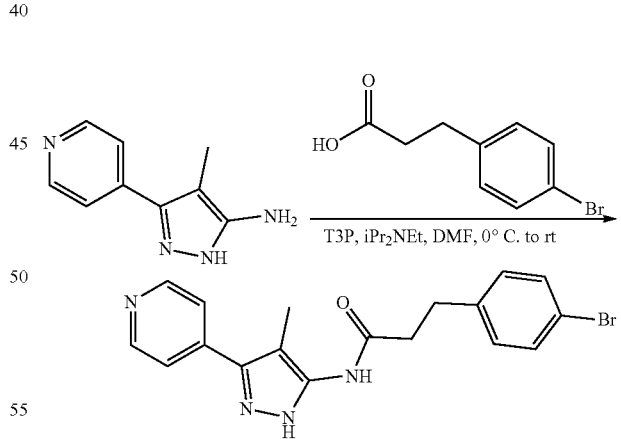

The product was prepared according to General Procedure #1 using Intermediate 1 and 3-(4-bromophenyl)propanoic acid to afford 3-(4-bromophenyl)-N-(4-methyl-3-(pyridin-4-yl)-1H-pyrazol-5-yl)propenamide in 34% yield. $^1$H NMR (500 MHz, DMSO-$d_6$) δ 13.1-12.9 (m, 1H), 9.97-9.70 (m, 1H), 8.66-8.58 (m, 2H), 7.65-7.56 (m, 2H), 7.48 (d, J=8.2 Hz, 2H), 7.24 (d, J=8.3 Hz, 2H), 2.90 (q, J=7.1 Hz, 2H), 2.70-2.60 (m, 2H), 2.05-1.94 (m, 3H). LCMS: ESI-MS m/z: 385.0 [M+H]$^+$.

Example 36

3-(4-Cyanophenyl)-N-(4-methyl-3-(pyridin-4-yl)-1H-pyrazol-5-yl)propanamide

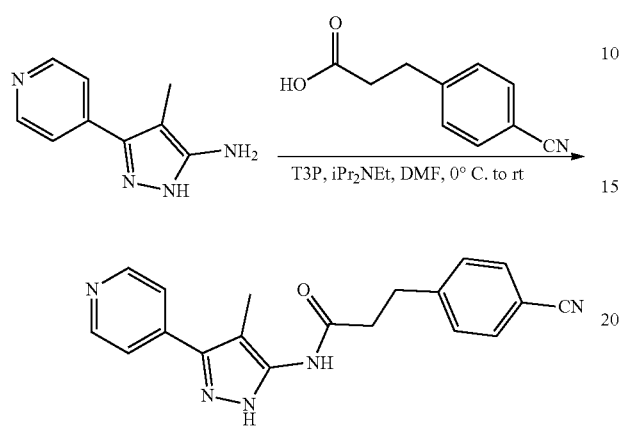

The product was prepared according to General Procedure #1 using Intermediate 1 and 3-(4-cyanophenyl)propanoic acid to afford 3-(4-cyanophenyl)-N-(4-methyl-3-(pyridin-4-yl)-1H-pyrazol-5-yl)propenamide in 14% yield. $^1$H NMR (500 MHz, DMSO-d$_6$) δ 13.1-12.9 (m, 1H), 10.0-9.73 (m, 1H), 8.66-8.59 (m, 2H), 7.77 (d, J=8.1 Hz, 2H), 7.64-7.48 (m, 4H), 3.01-2.99 (m, 2H), 2.75-2.64 (m, 2H), 2.05-1.93 (m, 3H). LCMS: ESI-MS m/z: 332.1 [M+H]$^+$.

Example 37

N-(4-Methyl-3-(pyridin-4-yl)-1H-pyrazol-5-yl)-3-(4-nitrophenyl)propanamide

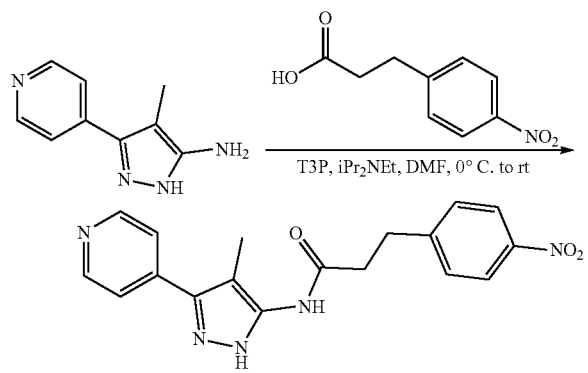

The product was prepared according to General Procedure #1 using Intermediate 1 and 3-(4-nitrophenyl)propanoic acid to afford N-(4-methyl-3-(pyridin-4-yl)-1H-pyrazol-5-yl)-3-(4-nitrophenyl)propenamide (13% yield). $^1$H NMR (500 MHz, DMSO-d$_6$) δ 13.0 (s, 1H), 9.84 (s, 1H), 8.63 (d, J=5.6 Hz, 2H), 7.58 (t, J=7.8 Hz, 4H), 8.18 (d, J=8.6 Hz, 2H), 3.10-2.92 (m, 2H), 2.72 (t, J=7.5 Hz, 2H), 1.97 (s, 3H). LCMS: ESI-MS m/z: 352.2 [M+H]$^+$.

Example 38

3-(6-Chloropyridin-3-yl)-N-(4-methyl-3-(pyridin-4-yl)-1H-pyrazol-5-yl)propanamide

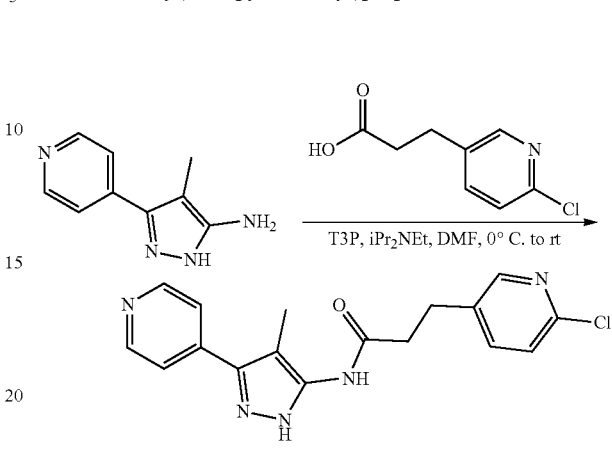

The product was prepared according to General Procedure #1 using Intermediate 1 and 3-(6-chloropyridin-3-yl)propanoic acid to afford 3-(6-chloropyridin-3-yl)-N-(4-methyl-3-(pyridin-4-yl)-1H-pyrazol-5-yl)propenamide in 26% yield. $^1$HNMR (400 MHz, DMSO-d$_6$) δ 13.1-12.9 (m, 1H), 10.0-9.73 (m, 1H), 8.67-8.58 (m, 2H), 8.33 (d, J=0.6 Hz, 1H), 7.78 (dd, J=8.2, 2.3 Hz, 1H), 7.65-7.55 (m, 2H), 7.45 (s, 1H), 2.94 (d, J=7.1 Hz, 2H), 2.74-2.63 (m, 2H), 2.04-1.92 (m, 3H). LCMS: ESI-MS m/z: 342.1 [M+H]$^+$.

Example 39

3-(5-Chloropyridin-2-yl)-N-(4-methyl-3-(pyridin-4-yl)-1H-pyrazol-5-yl)propanamide

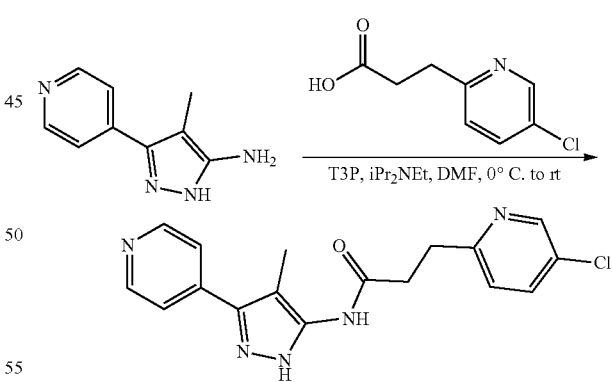

The product was prepared according to General Procedure #1 using Intermediate 1 and 3-(5-chloropyridin-2-yl)propanoic acid to afford 3-(5-chloropyridin-2-yl)-N-(4-methyl-3-(pyridin-4-yl)-1H-pyrazol-5-yl)propenamide in 24% yield. $^1$H NMR (400 MHz, DMSO-d$_6$) δ 13.0 (s, 1H), 9.83 (s, 1H), 8.63 (dd, J=3.7, 1.0 Hz, 2H), 8.54 (d, J=2.2 Hz, 1H), 7.84 (dd, J=8.4, 2.5 Hz, 1H), 7.70-7.54 (m, 2H), 7.37 (d, J=8.3 Hz, 1H), 3.07 (dd, J=9.6, 5.3 Hz, 2H), 2.78 (dd, J=9.0, 5.1 Hz, 2H), 2.00 (s, 3H). LCMS: ESI-MS m/z: 342.0 [M+H]$^+$.

Example 40

3-(4-Chloro-2,5-difluorophenyl)-N-(4-methyl-3-(pyridin-4-yl)-1H-pyrazol-5-yl)propanamide

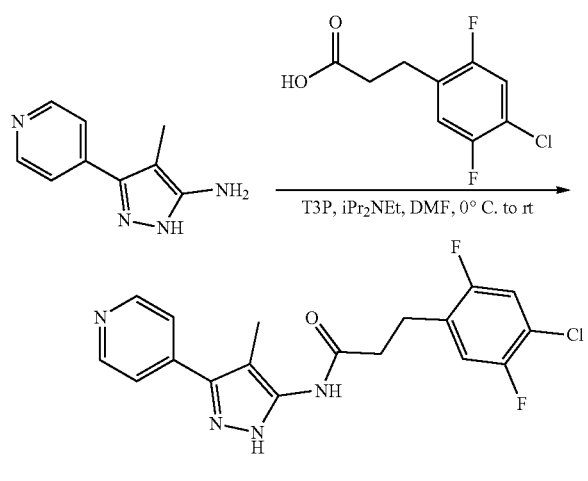

The product was prepared according to General Procedure #1 using Intermediate 1 and 3-(4-chloro-2,5-difluorophenyl) propanoic acid to afford 3-(4-chloro-2,5-difluorophenyl)-N-(4-methyl-3-(pyridin-4-yl)-1H-pyrazol-5-yl)propenamide in 38% yield. $^1$H NMR (400 MHz, DMSO-$d_6$) δ 13.1-12.9 (m, 1H), 10.0-9.75 (m, 1H), 8.67-8.58 (m, 2H), 7.60 (ddd, J=16.8, 9.3, 4.2 Hz, 3H), 7.51-7.36 (m, 1H), 2.93 (t, J=6.6 Hz, 2H), 2.68 (dt, J=14.5, 7.7 Hz, 2H), 2.05-1.94 (m, 3H). LCMS: ESI-MS m/z: 377.0 [M+H]$^+$.

Example 41

3-(4-Chloro-2-fluorophenyl)-N-(4-methyl-3-(pyridin-4-yl)-1H-pyrazol-5-yl)propanamide

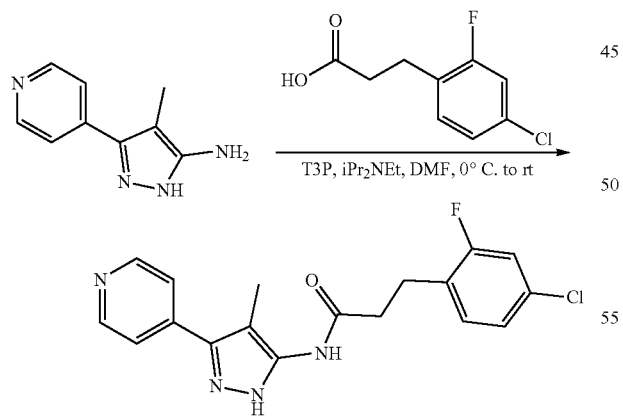

The product was prepared according to General Procedure #1 using Intermediate 1 and 3-(4-chloro-2-fluorophenyl) propanoic acid to afford 3-(4-chloro-2-fluorophenyl)-N-(4-methyl-3-(pyridin-4-yl)-1H-pyrazol-5-yl)propenamide in 45% yield. $^1$H NMR (400 MHz, DMSO-$d_6$) δ 13.1-12.9 (m, 1H), 10.0-9.74 (m, 1H), 8.66-8.60 (m, 2H), 7.64-7.58 (m, 2H), 7.38 (t, J=8.3 Hz, 2H), 7.24 (dd, J=8.2, 1.7 Hz, 1H), 2.93 (t, J=7.1 Hz, 2H), 2.64 (s, 2H), 2.04-1.95 (m, 3H). LCMS: ESI-MS m/z: 359.0 [M+H]$^+$.

Example 42

3-(4-Chloro-2-methylphenyl)-N-(4-methyl-3-(pyridin-4-yl)-1H-pyrazol-5-yl)propanamide

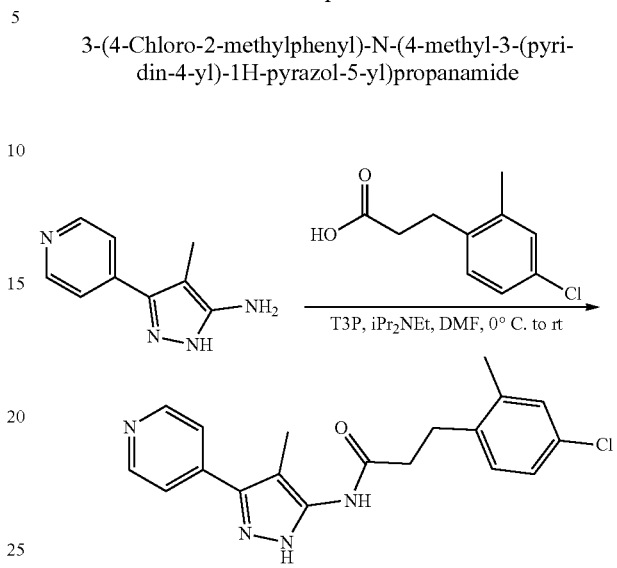

The product was prepared according to General Procedure #1 using Intermediate 1 and 3-(4-chloro-2-methylphenyl) propanoic acid to afford 3-(4-chloro-2-methylphenyl)-N-(4-methyl-3-(pyridin-4-yl)-1H-pyrazol-5-yl)propenamide in 26% yield. $^1$H NMR (400 MHz, DMSO-$d_6$) δ 13.1-12.9 (m, 1H), 10.0-9.73 (m, 1H), 8.66-8.59 (m, 2H), 7.64-7.58 (m, 2H), 7.44-6.96 (m, 3H), 2.89 (t, J=7.5 Hz, 2H), 2.58 (s, 2H), 2.32 (s, 3H), 2.17-1.90 (m, 3H). LCMS: ESI-MS m/z: 355.1 [M+H]$^+$.

Example 43

3-(4-Chloro-3-methylphenyl)-N-(4-methyl-3-(pyridin-4-yl)-1H-pyrazol-5-yl)propanamide

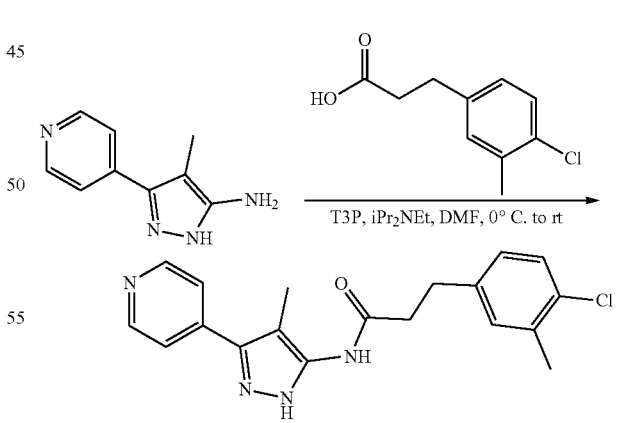

The product was prepared according to General Procedure #1 using Intermediate 1 and 3-(4-chloro-3-methylphenyl) propanoic acid to afford 3-(4-chloro-3-methylphenyl)-N-(4-methyl-3-(pyridin-4-yl)-1H-pyrazol-5-yl)propenamide in 35% yield. $^1$H NMR (400 MHz, DMSO-$d_6$) δ 13.1-12.9 (m, 1H), 9.96-9.69 (m, 1H), 8.73-8.52 (m, 2H), 7.64-7.57 (m, 2H), 7.32 (d, J=8.1 Hz, 1H), 7.26 (s, 1H), 7.12 (d, J=9.9 Hz, 1H), 2.88 (t, J=7.2 Hz, 2H), 2.75-2.57 (m, 2H), 2.30 (s, 3H), 2.05-1.95 (m, 3H). LCMS: ESI-MS m/z: 355.1 [M+H]⁺.

Example 44

3-(3,4-Difluorophenyl)-N-(4-methyl-3-(pyridin-4-yl)-1H-pyrazol-5-yl)propanamide

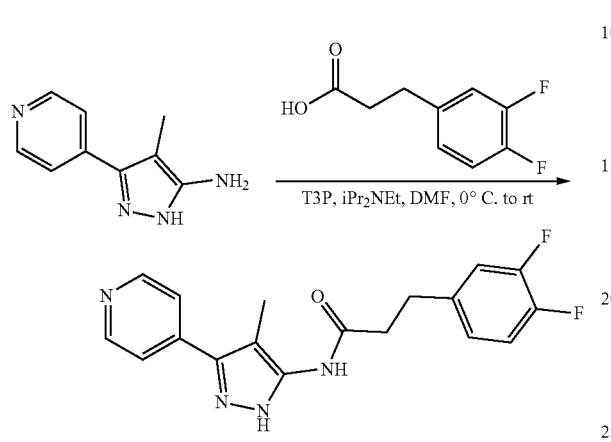

The product was prepared according to General Procedure #1 using Intermediate 1 and 3-(3,4-difluorophenyl)propanoic acid to afford 3-(3,4-difluorophenyl)-N-(4-methyl-3-(pyridin-4-yl)-1H-pyrazol-5-yl)propenamide in 29% yield. ¹H NMR (400 MHz, DMSO-d₆) δ 13.2-13.1 (m, 1H), 9.98-9.72 (m, 1H), 8.65 (s, 2H), 7.59 (s, 2H), 7.50-7.20 (m, 2H), 7.19-6.94 (m, 1H), 2.92 (t, J=7.4 Hz, 2H), 2.65 (s, 2H), 2.04-1.96 (m, 3H). LCMS: ESI-MS m/z: 343.0 [M+H]⁺.

Example 45

3-(2,4-Difluorophenyl)-N-(4-methyl-3-(pyridin-4-yl)-1H-pyrazol-5-yl)propanamide

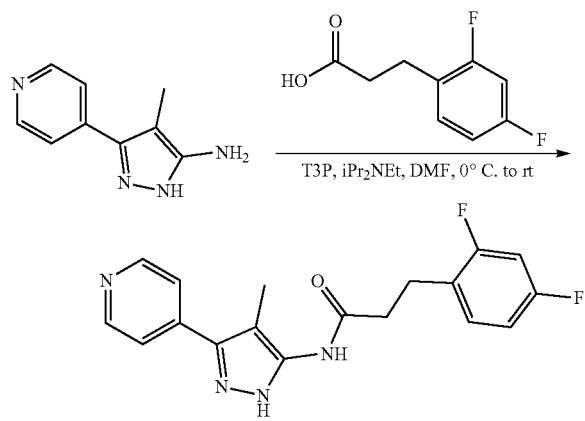

The product was prepared according to General Procedure #1 using Intermediate 1 and 3-(2,4-difluorophenyl)propanoic acid 3-(2,4-difluorophenyl)-N-(4-methyl-3-(pyridin-4-yl)-1H-pyrazol-5-yl)propenamide in 34% yield. ¹H NMR (400 MHz, DMSO-d₆) δ 13.1-12.9 (m, 1H), 10.0-9.73 (m, 1H), 8.66-8.59 (m, 2H), 7.63-7.57 (m, 2H), 7.47-6.90 (m, 3H), 2.92 (s, 2H), 2.74-2.56 (m, 2H), 2.05-1.94 (m, 3H). LCMS: ESI-MS m/z: 343.1 [M+H]⁺.

Example 46

3-(4-Iodophenyl)-N-(4-methyl-3-(pyridin-4-yl)-1H-pyrazol-5-yl)propanamide

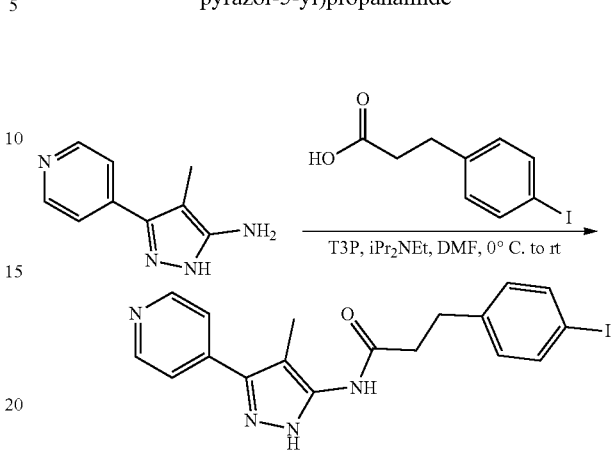

The product was prepared according to General Procedure #1 using Intermediate 1 and 3-(4-iodophenyl)propanoic acid to afford 3-(4-iodophenyl)-N-(4-methyl-3-(pyridin-4-yl)-1H-pyrazol-5-yl)propenamide in 72% yield. ¹H NMR (400 MHz, DMSO-d₆) δ 13.1-12.9 (m, 1H), 10.0-9.70 (m, 1H), 8.66-8.59 (m, 2H), 7.66-7.57 (m, 4H), 7.10 (d, J=8.2 Hz, 2H), 2.88 (t, J=7.2 Hz, 2H), 2.67-2.61 (m, 2H), 2.04-1.95 (m, 3H). LCMS: ESI-MS m/z: 433.0 [M+H]⁺.

Example 47

N-(4-Methyl-3-(pyridin-4-yl)-1H-pyrazol-5-yl)-3-(3,4,5-trichlorophenyl)propanamide

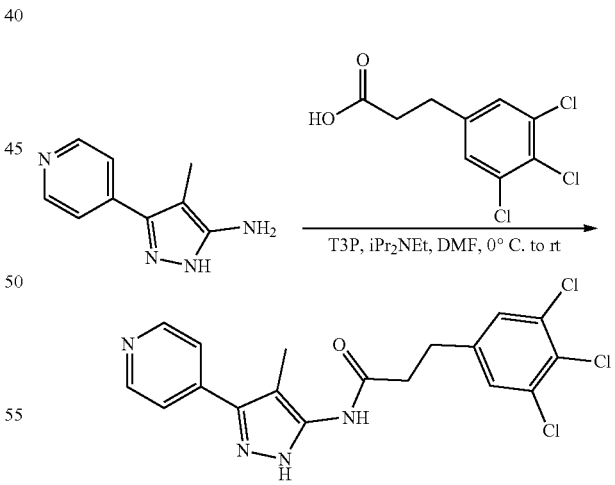

The product was prepared according to General Procedure #1 using Intermediate 1 and 3-(3,4,5-trichlorophenyl)propanoic acid to afford N-(4-methyl-3-(pyridin-4-yl)-1H-pyrazol-5-yl)-3-(3,4,5-trichlorophenyl)propenamide in 38% yield. ¹H NMR (400 MHz, DMSO-d₆) δ 13.1-12.9 (m, 1H), 9.92-9.72 (m, 1H), 8.65-8.59 (m, 2H), 7.76-7.44 (m, 4H), 2.95 (s, 2H), 2.68-2.66 (m, 2H), 2.04-1.94 (m, 3H). LCMS: ESI-MS m/z: 409.0 [M+H]⁺.

Example 48

3-(4-Chloro-3,5-difluorophenyl)-N-(4-methyl-3-(pyridin-4-yl)-1H-pyrazol-5-yl)propanamide

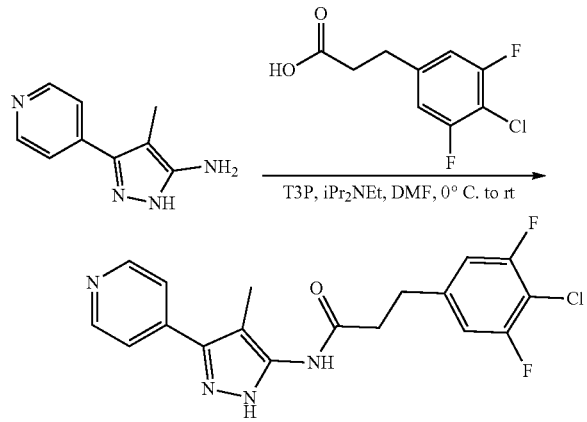

The product was prepared according to General Procedure #1 using Intermediate 1 and Intermediate 9 to afford 3-(4-chloro-3,5-difluorophenyl)-N-(4-methyl-3-(pyridin-4-yl)-1H-pyrazol-5-yl)propenamide in 45% yield. $^1$H NMR (400 MHz, DMSO-$d_6$) δ 13.1-13.0 (m, 1H), 9.99-9.72 (m, 1H), 8.65-8.57 (m, 2H), 7.63-7.57 (m, 2H), 7.27 (d, J=8.8 Hz, 2H), 2.96 (t, J=7.2 Hz, 2H), 2.73-2.61 (m, 2H), 2.04-1.94 (m, 3H). LCMS: ESI-MS m/z: 377.0 [M+H]$^+$.

Example 49

3-(4-Chloro-2,3-difluorophenyl)-N-(4-methyl-3-(pyridin-4-yl)-1H-pyrazol-5-yl)propanamide

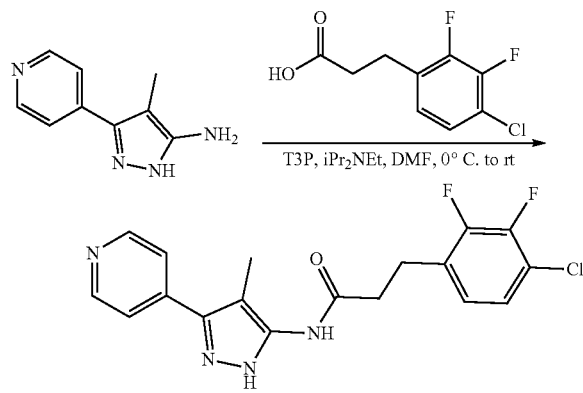

The product was prepared according to General Procedure #1 using Intermediate 1 and 3-(4-chloro-2,3-difluorophenyl) propanoic acid to afford 3-(4-chloro-2,3-difluorophenyl)-N-(4-methyl-3-(pyridin-4-yl)-1H-pyrazol-5-yl)propenamide in 25% yield. $^1$H NMR (400 MHz, DMSO-$d_6$) δ 13.1-13.0 (m, 1H), 10.0-9.74 (m, 1H), 8.66-8.59 (m, 2H), 7.64-7.57 (m, 2H), 7.39 (t, J=7.0 Hz, 1H), 7.22 (t, J=7.2 Hz, 1H), 2.98 (s, 2H), 2.67 (s, 2H), 2.04-1.94 (m, 3H). LCMS: ESI-MS m/z: 377.1 [M+H]$^+$.

Example 50

N-(4-Methyl-3-(pyridin-4-yl)-1H-pyrazol-5-yl)-3-(3,4,5-trifluorophenyl)propanamide

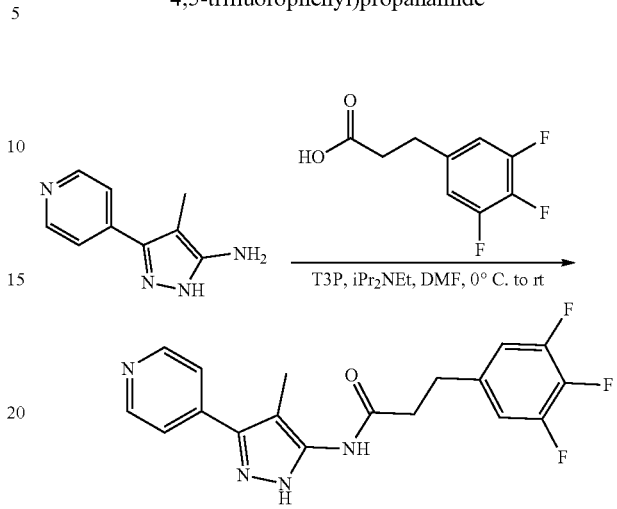

The product was prepared according to General Procedure #1 using Intermediate 1 and 3-(3,4,5-trifluorophenyl)propanoic acid to afford N-(4-methyl-3-(pyridin-4-yl)-1H-pyrazol-5-yl)-3-(3,4,5-trifluorophenyl)propenamide in 16% yield. $^1$H NMR (400 MHz, DMSO-$d_6$) δ 13.1 (s, 1H), 9.77 (s, 1H), 8.74-8.49 (m, 2H), 7.60 (d, J=1.6 Hz, 2H), 7.26 (dd, J=9.0, 6.9 Hz, 2H), 2.92 (t, J=7.4 Hz, 2H), 2.67 (dd, J=9.5, 4.3 Hz, 2H), 2.01 (d, J=28.1 Hz, 3H). LCMS: ESI-MS m/z: 361.1 [M+H]$^+$.

Example 51

N-(4-Methyl-3-(pyridin-4-yl)-1H-pyrazol-5-yl)-3-(2,3,4-trifluorophenyl)propanamide

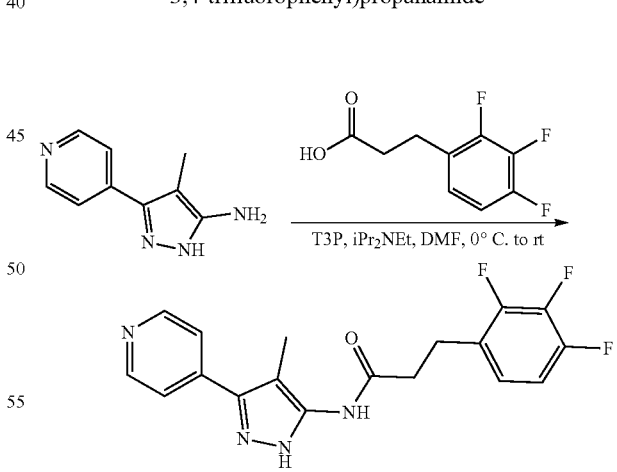

The product was prepared according to General Procedure #1 using Intermediate 1 and 3-(2,3,4-trifluorophenyl)propanoic acid to afford N-(4-methyl-3-(pyridin-4-yl)-1H-pyrazol-5-yl)-3-(2,3,4-trifluorophenyl)propenamide in 13% yield. $^1$H NMR (400 MHz, DMSO-$d_6$) δ 13.1-12.9 (m, 1H), 10.13-9.66 (m, 1H), 8.64 (s, 2H), 7.66-7.58 (m, 2H), 7.25 (dt, J=16.8, 8.7 Hz, 2H), 2.96 (t, J=7.3 Hz, 2H), 2.67 (s, 2H), 2.04-1.94 (m, 3H). LCMS: ESI-MS m/z: 361.1 [M+H]$^+$.

Example 52

N-(4-Methyl-3-(pyridin-4-yl)-1H-pyrazol-5-yl)-3-(2,4,5-trifluorophenyl)propanamide

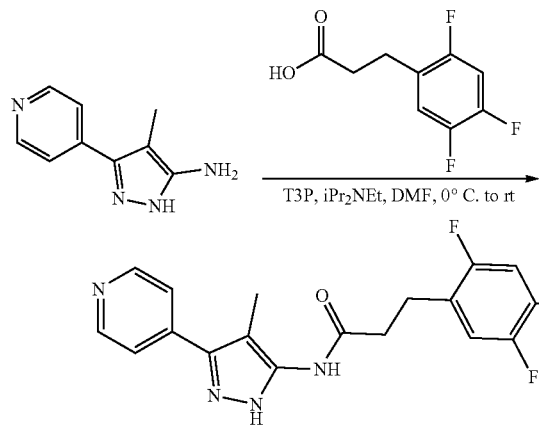

The product was prepared according to General Procedure #1 using Intermediate 1 and 3-(2,4,5-trifluorophenyl)propanoic acid to afford N-(4-methyl-3-(pyridin-4-yl)-1H-pyrazol-5-yl)-3-(2,4,5-trifluorophenyl)propanamide in 26% yield. $^1$H NMR (400 MHz, DMSO-$d_6$) δ 13.1-12.9 (m, 1H), 10.0-9.73 (m, 1H), 8.66-8.61 (m, 2H), 7.71-7.35 (m, 4H), 2.91 (t, J=7.2 Hz, 2H), 2.66 (s, 2H), 2.05-1.95 (m, 3H). LCMS: ESI-MS m/z: 361.1 [M+H]$^+$.

Example 53

3-(4-Cyano-3-fluorophenyl)-N-(4-methyl-3-(pyridin-4-yl)-1H-pyrazol-5-yl)propanamide

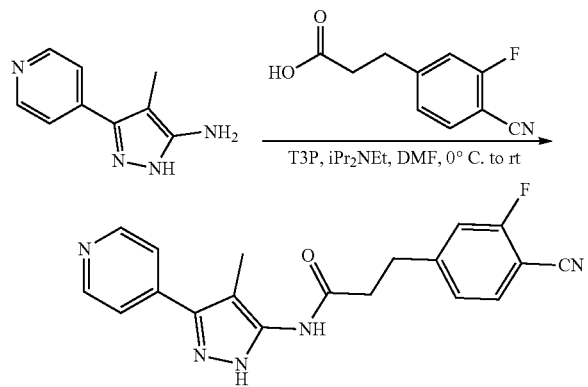

The product was prepared according to General Procedure #1 using Intermediate 1 and Intermediate 10 to afford 3-(4-cyano-3-fluorophenyl)-N-(4-methyl-3-(pyridin-4-yl)-1H-pyrazol-5-yl)propanamide (1.1 g, 3.1 mmol, 38% yield) as a white solid. $^1$H NMR (400 MHz, DMSO-$d_6$) δ 13.1 (s, 1H), 9.74 (s, 1H), 8.65 (s, 2H), 7.86 (t, J=7.5 Hz, 1H), 7.58 (s, 2H), 7.48 (d, J=10.6 Hz, 1H), 7.35 (d, J=8.0 Hz, 1H), 3.03 (t, J 7.4 Hz, 2H), 2.70 (s, 2H), 1.94 (s, 3H). LCMS: ESI-MS m/z: 350.2 [M+H]$^+$.

Example 54

N-(4-Methyl-3-(pyridin-4-yl)-1H-pyrazol-5-yl)-3-(4-(trifluoromethoxy)phenyl)propanamide

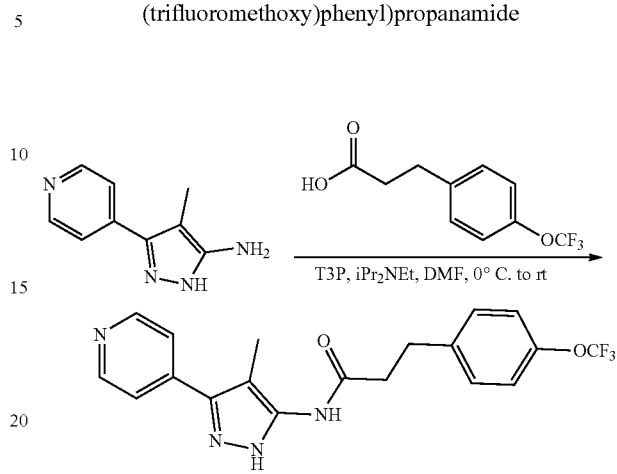

The product was prepared according to General Procedure #1 using Intermediate 1 and 3-(4-(trifluoromethoxy)phenyl)propanoic acid to afford N-(4-methyl-3-(pyridin-4-yl)-1H-pyrazol-5-yl)-3-(4-(trifluoromethoxy)phenyl)propenamide in 35% yield. $^1$H NMR (400 MHz, DMSO-$d_6$) δ 13.1-12.9 (m, 1H), 9.96-9.71 (m, 1H), 8.65 (s, 2H), 7.63-7.57 (m, 2H), 7.40 (d, J=8.6 Hz, 2H), 7.29 (d, J=8.2 Hz, 2H), 2.96 (t, J=7.3 Hz, 2H), 2.66 (s, 2H), 2.02-1.92 (s, 3H). LCMS: ESI-MS m/z: 391.1 [M+H]$^+$.

Example 55

3-(4-(Difluoromethoxy)phenyl)-N-(4-methyl-3-(pyridin-4-yl)-1H-pyrazol-5-yl)propanamide

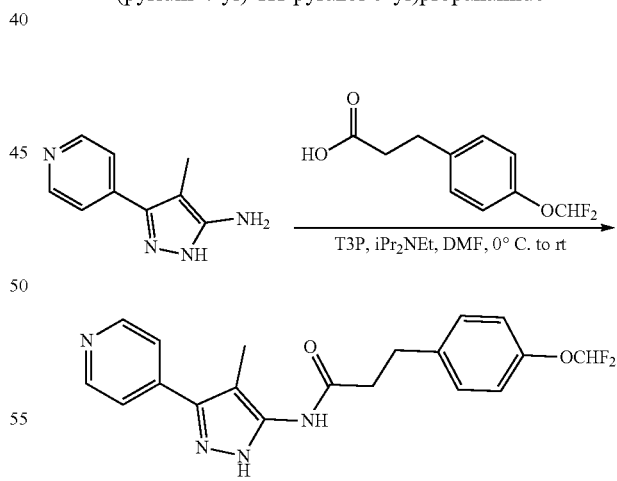

The product was prepared according to General Procedure #1 using Intermediate 1 and 3-(4-(difluoromethoxy)phenyl)propanoic acid to afford 3-(4-(difluoromethoxy)phenyl)-N-(4-methyl-3-(pyridin-4-yl)-1H-pyrazol-5-yl)propenamide in 25% yield. $^1$H NMR (400 MHz, DMSO-$d_6$) δ 13.1-12.9 (m, 1H), 10.0-9.71 (m, 1H), 8.65 (s, 2H), 7.58 (s, 2H), 7.42-6.96 (m, 5H), 2.92 (t, J=7.4 Hz, 2H), 2.64 (s, 2H), 2.04-1.95 (m, 3H). LCMS: ESI-MS m/z: 373.1 [M+H]$^+$.

Example 56

3-(4-(Fluoromethyl)phenyl)-N-(4-methyl-3-(pyridin-4-yl)-1H-pyrazol-5-yl)propanamide

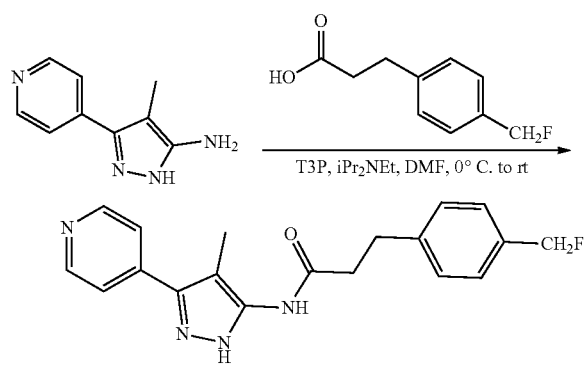

The product was prepared according to General Procedure #1 using Intermediate 1 and 3-(4-(fluoromethyl)phenyl)propanoic acid to afford 3-(4-(fluoromethyl)phenyl)-N-(4-methyl-3-(pyridin-4-yl)-1H-pyrazol-5-yl)propenamide in 26% yield. $^1$H NMR (400 MHz, DMSO-$d_6$) δ 13.1-12.9 (m, 1H), 9.96-9.70 (m, 1H), 8.64 (s, 2H), 7.58 (s, 2H), 7.34 (q, J=8.1 Hz, 4H), 5.37 (d, J=48.0 Hz, 2H), 2.95 (t, J=7.2 Hz, 2H), 2.66 (s, 2H), 2.04-1.96 (m, 3H). LCMS: ESI-MS m/z: 339.1 [M+H]$^+$.

Example 57

3-(4-(Difluoromethyl)phenyl)-N-(4-methyl-3-(pyridin-4-yl)-1H-pyrazol-5-yl)propanamide

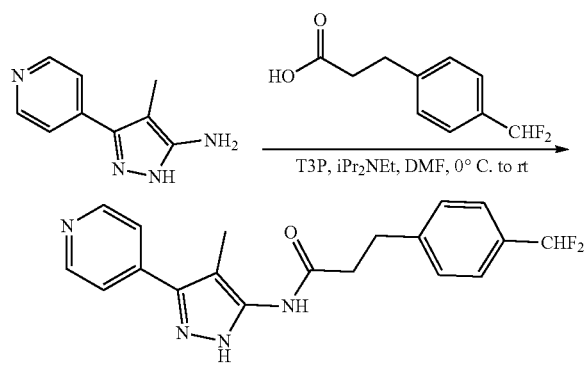

The product was prepared according to General Procedure #1 using Intermediate 1 and 3-(4-(difluoromethyl)phenyl)propanoic acid to afford 3-(4-(difluoromethyl)phenyl)-N-(4-methyl-3-(pyridin-4-yl)-1H-pyrazol-5-yl)propenamide in 30% yield. $^1$H NMR (400 MHz, DMSO-$d_6$) δ 13.1 (s, 1H), 9.71 (s, 1H), 8.65 (s, 2H), 7.58 (s, 2H), 7.50 (d, J=7.9 Hz, 2H), 7.42 (d, J=8.0 Hz, 2H), 6.99 (t, J=56.0 Hz, 1H), 2.98 (t, J=7.3 Hz, 2H), 2.67 (s, 2H), 2.03-1.94 (m, 3H). LCMS: ESI-MS m/z: 357.1 [M+H]$^+$.

Example 58

N-(4-Methyl-3-(pyridin-4-yl)-1H-pyrazol-5-yl)-3-(perfluorophenyl)propanamide

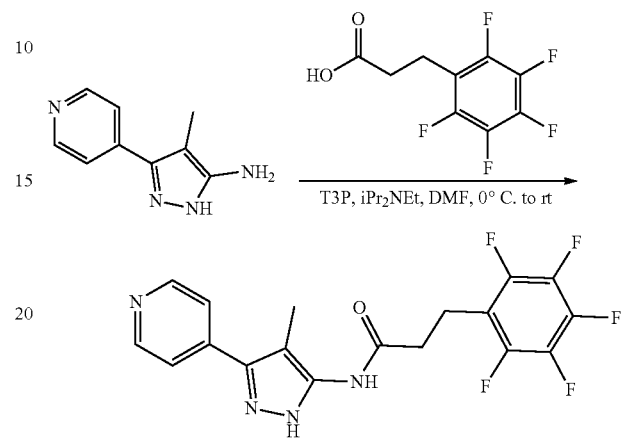

The product was prepared according to General Procedure #1 using Intermediate 1 and 3-(perfluorophenyl)propanoic acid to afford N-(4-methyl-3-(pyridin-4-yl)-1H-pyrazol-5-yl)-3-(perfluorophenyl)propenamide in 29% yield. $^1$H NMR (400 MHz, DMSO-$d_6$) δ 13.1 (s, 1H), 9.94 (d, J=80.2 Hz, 1H), 8.64 (s, 2H), 7.59 (s, 2H), 3.03 (t, J=7.2 Hz, 2H), 2.68 (s, 2H), 1.99 (s, 3H). LCMS: ESI-MS m/z: 397.0 [M+H]$^+$.

Example 59

3-(6-Fluoropyridin-3-yl)-N-(4-methyl-3-(pyridin-4-yl)-1H-pyrazol-5-yl)propanamide

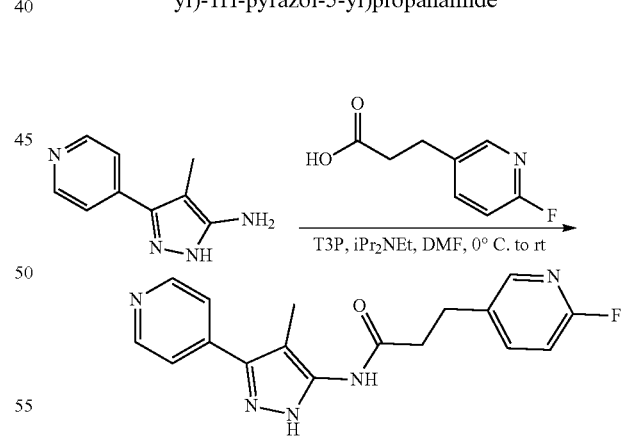

The product was prepared according to General Procedure #1 using Intermediate 1 and 3-(6-fluoropyridin-3-yl)propanoic acid to afford 3-(6-fluoropyridin-3-yl)-N-(4-methyl-3-(pyridin-4-yl)-1H-pyrazol-5-yl)propenamide in 31% yield. $^1$H NMR (400 MHz, DMSO-$d_6$) δ 13.0 (s, 1H), 9.94-9.73 (m, 1H), 8.63 (d, J=1.3 Hz, 2H), 8.14 (s, 1H), 7.90 (td, J=8.2, 2.3 Hz, 1H), 7.60 (t, J=8.1 Hz, 2H), 7.12 (dd, J=8.4, 2.7 Hz, 1H), 2.95 (t, J=7.3 Hz, 2H), 2.68 (s, 2H), 2.13-1.83 (m, 3H). LCMS: ESI-MS m/z: 326.1 [M+H]$^+$.

Example 60

3-(2-Fluoropyrimidin-5-yl)-N-(4-methyl-3-(pyridin-4-yl)-1H-pyrazol-5-yl)propanamide

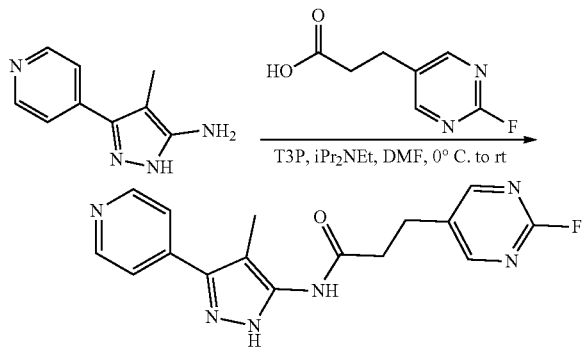

The product was prepared according to General Procedure #1 using Intermediate 1 and 3-(2-fluoropyrimidin-5-yl)propanoic acid to afford 3-(2-fluoropyrimidin-5-yl)-N-(4-methyl-3-(pyridin-4-yl)-1H-pyrazol-5-yl)propenamide in 10% yield. $^1$H NMR (500 MHz, DMSO-$d_6$) δ 13.1-12.9 (m, 1H), 10.0-9.74 (m, 1H), 8.73 (s, 2H), 8.65-8.59 (m, 2H), 7.63-7.57 (m, 2H), 2.97 (t, J=7.2 Hz, 2H), 2.72 (s, 2H), 2.10-1.84 (m, 3H). LCMS: ESI-MS m/z: 327.2 [M+H]$^+$.

Example 61

3-(2-Chloropyrimidin-5-yl)-N-(4-methyl-3-(pyridin-4-yl)-1H-pyrazol-5-yl)propanamide

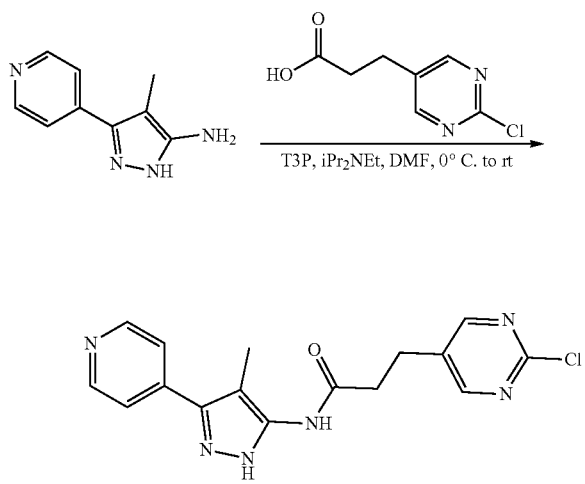 [SMILES: Cc1c(-c2ccncc2)n[nH]c1N ; O=C(O)CCc1ccc(Cl)c(F)c1F ; Cc1c(-c2ccncc2)n[nH]c1NC(=O)CCc1ccc(Cl)c(F)c1F]

The product was prepared according to General Procedure #1 using Intermediate 1 and 3-(2-chloropyrimidin-5-yl)propanoic acid to afford 3-(2-chloropyrimidin-5-yl)-N-(4-methyl-3-(pyridin-4-yl)-1H-pyrazol-5-yl)propenamide in 15% yield. $^1$H NMR (400 MHz, DMSO-$d_6$) δ 13.1 (s, 1H), 9.76 (s, 1H), 8.72 (s, 2H), 8.64 (s, 2H), 7.58 (s, 2H), 2.95 (t, J=7.2 Hz, 2H), 2.73 (s, 2H), 1.95 (s, 3H). LCMS: ESI-MS m/z: 343.0 [M+H]$^+$.

Example 62

2-(4-Chlorophenoxy)-N-(4-methyl-3-(pyridin-4-yl)-1H-pyrazol-5-yl)acetamide

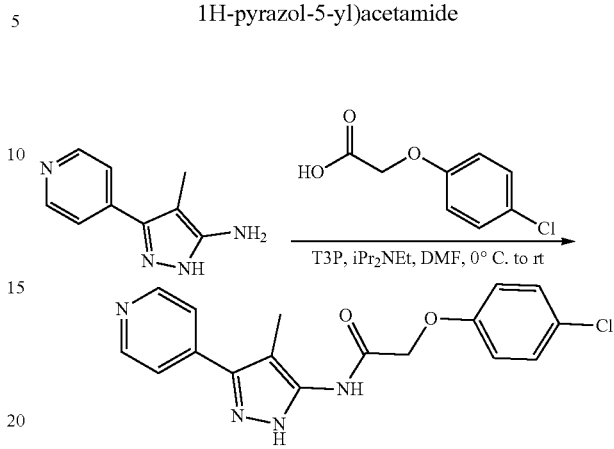

The product was prepared according to General Procedure #1 using Intermediate 1 and 2-(4-chlorophenoxy)acetic acid to afford 2-(4-chlorophenoxy)-N-(4-methyl-3-(pyridin-4-yl)-1H-pyrazol-5-yl)acetamide in 36% yield. $^1$H NMR (400 MHz, DMSO-$d_6$) δ 13.2 (s, 1H), 9.97 (s, 1H), 8.66 (s, 2H), 7.60 (s, 2H), 7.38 (d, J=8.9 Hz, 2H), 7.05 (d, J=8.9 Hz, 2H), 4.75 (s, 2H), 2.04 (s, 3H). LCMS: ESI-MS m/z: 343.0 [M+H]$^+$.

Example 63

2-((4-Chlorophenyl)thio)-N-(4-methyl-3-(pyridin-4-yl)-1H-pyrazol-5-yl)acetamide

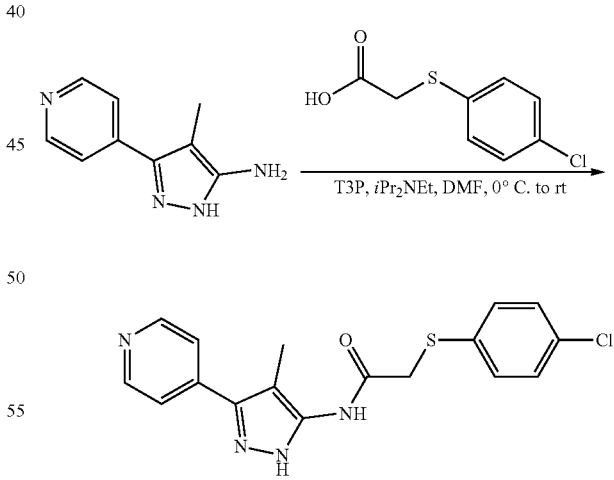

The product was prepared according to General Procedure #1 using Intermediate 1 and 2-((4-chlorophenyl)thio)acetic acid to afford 2-((4-chlorophenyl)thio)-N-(4-methyl-3-(pyridin-4-yl)-1H-pyrazol-5-yl)acetamide in 37% yield. $^1$H NMR (400 MHz, DMSO-$d_6$) δ 13.1-12.9 (m, 1H), 10.3-10.0 (m, 1H), 8.65-8.59 (m, 2H), 7.64-7.57 (m, 2H), 7.46 (d, J=8.7 Hz, 2H), 7.40 (d, J=8.6 Hz, 2H), 3.89 (s, 2H), 2.06-1.94 (m, 3H). LCMS: ESI-MS m/z: 359.0 [M+H]$^+$.

Example 64

3-(4-Chloro-3-fluorophenyl)-N-(4-methyl-3-(pyridin-4-yl)-1H-pyrazol-5-yl)propanamide

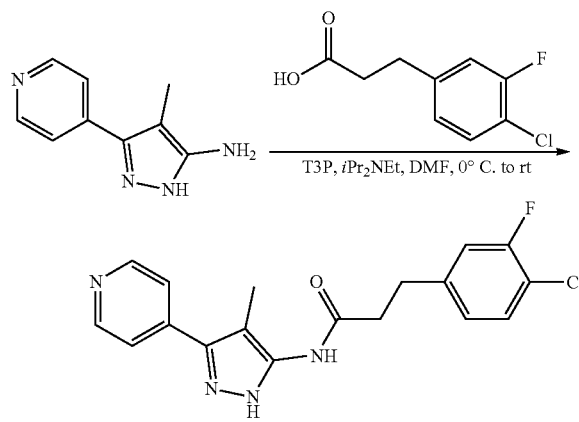

The product was prepared according to General Procedure #1 using Intermediate 1 and 3-(4-chloro-3-fluorophenyl)propanoic acid to afford 3-(4-chloro-3-fluorophenyl)-N-(4-methyl-3-(pyridin-4-yl)-1H-pyrazol-5-yl)propanamide in 42% yield. $^1$H NMR (400 MHz, DMSO-$d_6$) δ 13.1-12.9 (m, 1H), 9.96-9.72 (m, 1H), 8.64 (s, 2H), 7.58 (s, 2H), 7.50 (t, J=8.1 Hz, 1H), 7.34 (dd, J=10.7, 1.5 Hz, 1H), 7.15 (dd, J=8.2, 1.3 Hz, 1H), 2.94 (t, J=7.4 Hz, 2H), 2.67 (s, 2H), 2.04-1.95 (m, 3H). LCMS: ESI-MS m/z: 359.1 [M+H]$^+$.

Example 65

3-(4-Cyano-3,5-difluorophenyl)-N-(4-methyl-3-(pyridin-4-yl)-1H-pyrazol-5-yl)propanamide

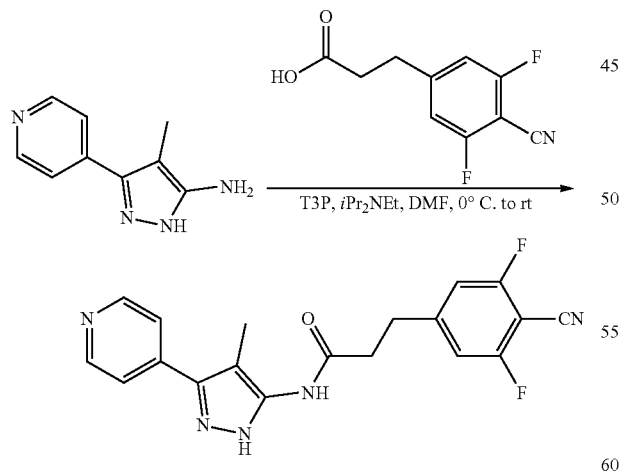

The product was prepared according to General Procedure #1 using Intermediate 1 and Intermediate 8 to afford 3-(4-cyano-3,5-difluorophenyl)-N-(4-methyl-3-(pyridin-4-yl)-1H-pyrazol-5-yl)propanamide in 25% yield. $^1$H NMR (400 MHz, DMSO-$d_6$) δ 13.1-12.9 (m, 1H), 10.0-9.75 (m, 1H), 8.65-8.59 (m, 2H), 7.64-7.57 (m, 2H), 7.41 (d, J=9.5 Hz, 2H), 3.04 (t, J=7.3 Hz, 2H), 2.71 (s, 2H), 2.11-1.88 (m, 3H). LCMS: ESI-MS m/z: 368.1 [M+H]$^+$.

Example 66

N-[4-Methyl-3-(pyridin-4-yl)-1H-pyrazol-5-yl]-2-(1,2,3,4-tetrahydronaphthalen-1-yl)acetamide

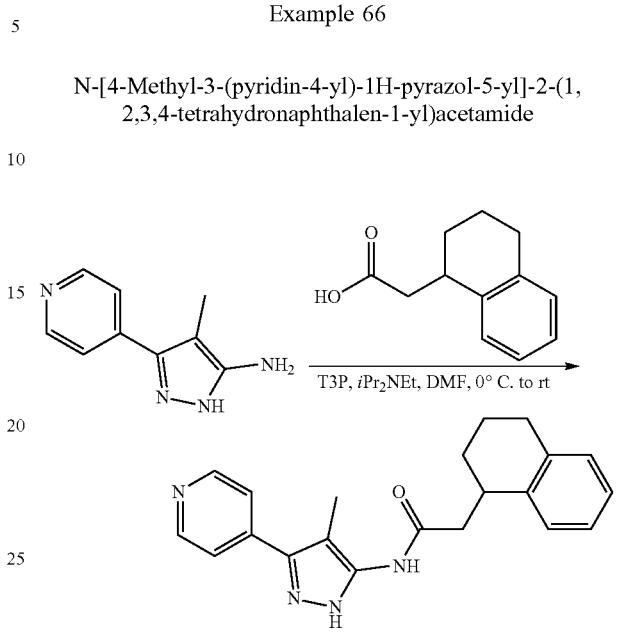

The product was prepared according to General Procedure #1 using Intermediate 1 and 2-(1,2,3,4-tetrahydronaphthalen-1-yl)acetic acid to afford N-[4-methyl-3-(pyridin-4-yl)-1H-pyrazol-5-yl]-2-(1,2,3,4-tetrahydronaphthalen-1-yl)acetamide (25 mg, 0.070 mmol, 50% yield) as colorless solid. LCMS: ESI-MS m/z: 347.1 [M+H]$^+$.

Example 67

2-(5-Chloro-2,3-dihydro-1H-inden-yl)-N-[4-methyl-3-(pyridin-4-yl)-1H-pyrazol-5-yl]acetamide

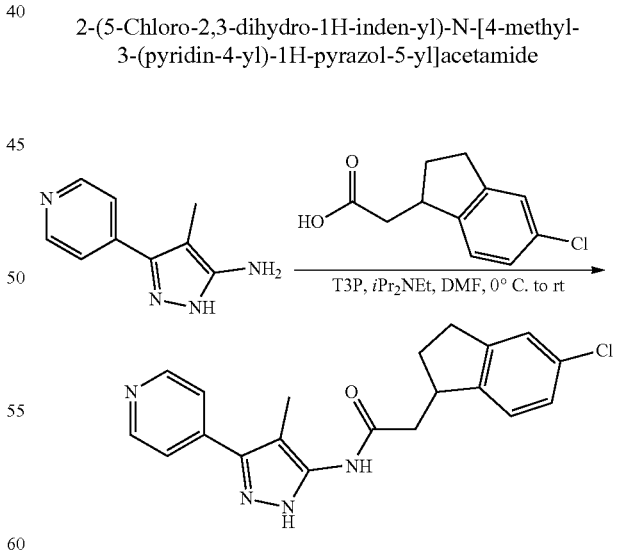

The product was prepared according to General Procedure #1 using Intermediate 1 and Intermediate 11 to afford 2-(5-chloro-2,3-dihydro-1H-inden-1-yl)-N-[4-methyl-3-(pyridin-4-yl)-1H-pyrazol-5-yl]acetamide (8.0 mg, 0.020 mmol, 64% yield) as white solid, trifluoroacetic acid salt. LCMS: ESI-MS m/z: 367.1 [M+H]$^+$.

Example 68

2-(6-Chloro-1,2,3,4-tetrahydronaphthalen-1-yl)-N-[4-methyl-3-(pyridin-4-yl)-1H-pyrazol-5-yl]acetamide

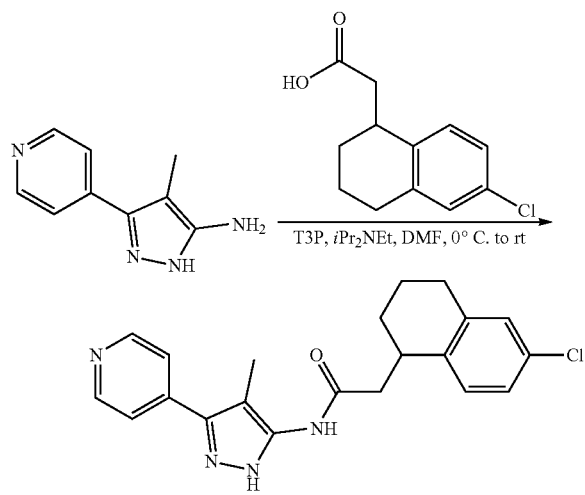

The product was prepared according to General Procedure #1 using Intermediate 1 and Intermediate 12 to afford 2-(6-chloro-1,2,3,4-tetrahydronaphthalen-1-yl)-N-[4-methyl-3-(pyridin-4-yl)-1H-pyrazol-5-yl]acetamide (54 mg, 0.11 mmol, 50% yield) as white solid, trifluoroacetic acid salt. LCMS: ESI-MS m/z: 381.1 [M+H]$^+$.

Example 69

(E)-3-(4-chlorophenyl)-2,3-difluoro-N-(4-methyl-3-(pyridin-4-yl)-1H-pyrazol-5-yl)acrylamide

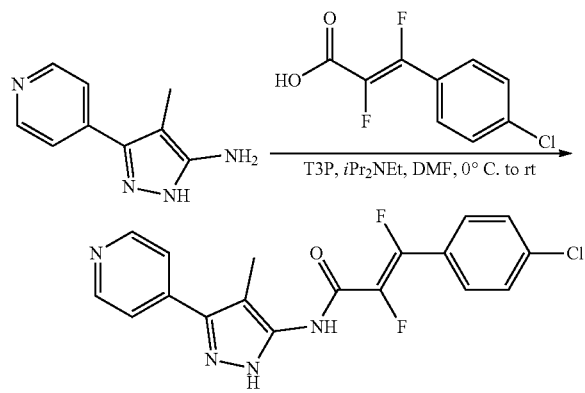

The product was prepared according to General Procedure #1 using Intermediate 1 and (2F)-3-(4-chlorophenyl)-2,3-difluoroprop-2-enoic acid to afford (E)-3-(4-chlorophenyl)-2,3-difluoro-N-(4-methyl-3-(pyridin-4-yl)-1H-pyrazol-5-yl)acrylamide (1.7 mg, 0.0040 mmol, 8.0% yield) as a white solid, trifluoroacetic acid salt. LCMS: ESI-MS m/z: 375.1 [M+H]$^+$.

Example 70

(rac)-3-(4-Cyano-3-fluorophenyl)-2-fluoro-N-(4-methyl-3-(pyridin-4-yl)-1H-pyrazol-5-yl)propanamide

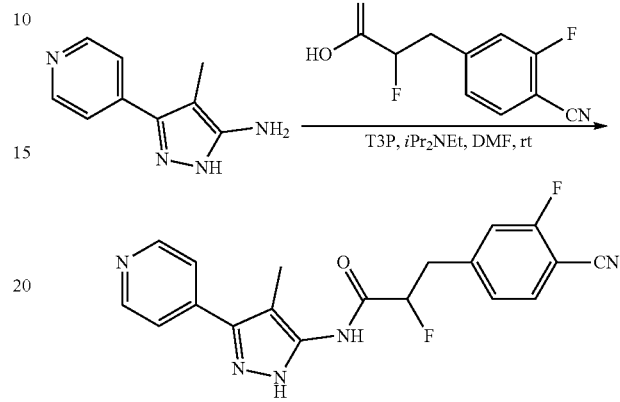

The product was prepared according to General Procedure #1 using Intermediate 1 and Intermediate 14 to afford (rac)-3-(4-cyano-3-fluorophenyl)-2-fluoro-N-(4-methyl-3-(pyridin-4-yl)-1H-pyrazol-5-yl)propenamide as a white solid in 17% yield. $^1$H NMR (400 MHz, DMSO-d$_6$) δ 13.2 (s, 1H), 10.1 (s, 1H), 8.66 (s, 2H), 7.93 (t, J=7.5 Hz, 1H), 7.60 (s, 2H), 7.53 (d, J=10.5 Hz, 1H), 7.40 (d, J=8.2 Hz, 1H), 5.49 (d, J=45.8 Hz, 1H), 3.47-3.38 (m, 2H), 1.95 (s, 3H). LCMS: ESI-MS m/z: 368.2 [M+H]$^+$.

Example 71

(rac)-3-(4-Chloro-3,5-difluorophenyl)-2-fluoro-N-(4-methyl-3-(pyridin-4-yl)-1H-pyrazol-5-yl)propanamide

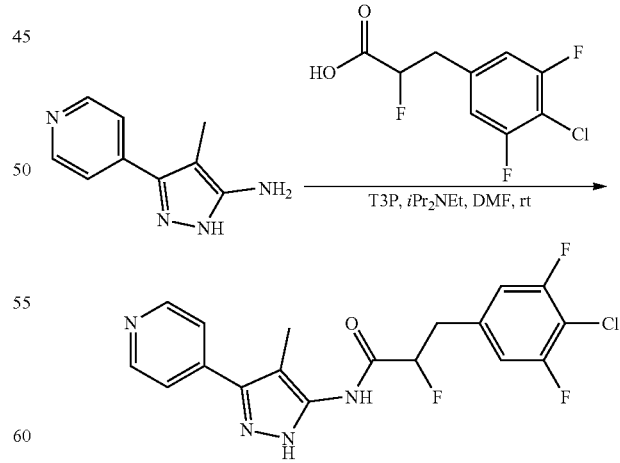

The product was prepared according to General Procedure #1 using Intermediate 1 and Intermediate 27 to afford (rac)-3-(4-chloro-3,5-difluorophenyl)-2-fluoro-N-(4-methyl-3-(pyridin-4-yl)-1H-pyrazol-5-yl)propanamide in 21% yield as a white solid. $^1$H NMR (400 MHz, DMSO-d$_6$)

δ 13.2-13.1 (m, 1H), 10.2-10.0 (m, 1H), 8.66 (s, 2H), 7.59 (s, 2H), 7.32 (d, J=8.0 Hz, 2H), 5.45 (d, J=48.0 Hz, 1H), 3.41-3.23 (m, 2H), 1.95 (s, 3H). LCMS: ESI-MS m/z: 395.0 [M+H]⁺.

Example 72

3-(4-Chlorophenyl)-N-(4-methyl-3-(pyridin-4-yl)-1H-pyrazol-5-yl)propiolamide

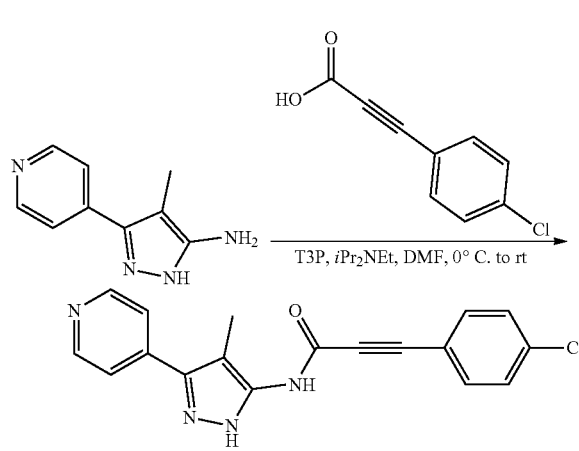

The product was prepared according to General Procedure #1 using Intermediate 1 and 3-(4-chlorophenyl)propiolic acid to afford 3-(4-chlorophenyl)-N-(4-methyl-3-(pyridin-4-yl)-1H-pyrazol-5-yl)propiolamide, trifluoroacetic acid salt (53 mg, >95% yield) as a white solid. LCMS: ESI-MS m/z: 337.1 [M+H]⁺.

Example 73

3-(4-Chlorothiophen-2-yl)-N-(4-methyl-3-(pyridin-4-yl)-1H-pyrazol-5-yl)propenamide

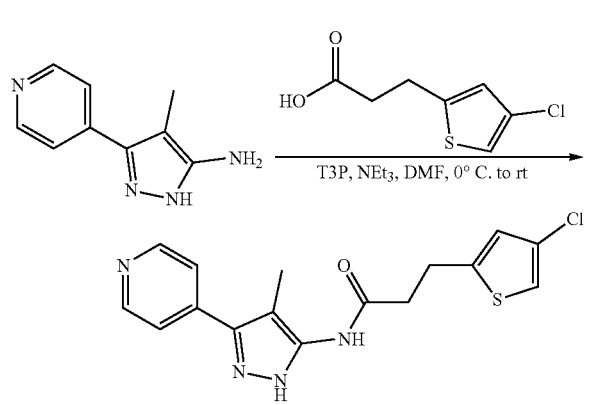

The product was prepared according to General Procedure #1 using Intermediate 1 and 3-(4-chlorothiophen-2-yl)propanoic acid to afford 3-(4-chlorothiophen-2-yl)-N-(4-methyl-3-(pyridin-4-yl)-1H-pyrazol-5-yl)propenamide (32 mg, 40% yield) as a white solid, trifluoroacetic acid salt. ¹H NMR (400 MHz, DMSO-d₆) δ 10.0 (s, 1H), 8.82-8.75 (m, 2H), 7.97 (s, 1H), 7.38 (d, J=1.6 Hz, 1H), 6.92 (d, J=1.5 Hz, 1H), 3.10 (d, J=14.3 Hz, 2H), 2.73 (t, J=7.2 Hz, 2H), 2.09 (s, 3H). LCMS: ESI-MS m/z: 347.1 [M+H]⁺.

Example 74

3-(5-Chlorothiophen-2-yl)-N-(4-methyl-3-(pyridin-4-yl)-1H-pyrazol-5-yl)propenamide

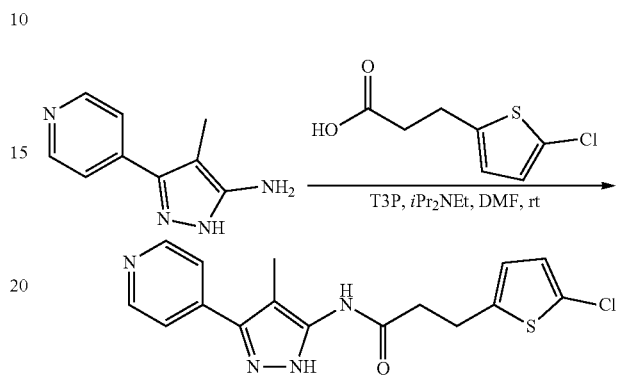

The product was prepared according to General Procedure #1 using Intermediate 1 and 3-(5-chlorothiophen-2-yl)propanoic acid to afford 3-(5-chlorothiophen-2-yl)-N-(4-methyl-3-(pyridin-4-yl)-1H-pyrazol-5-yl)propenamide (31 mg, 39% yield) as a white solid, trifluoroacetic acid salt. ¹H NMR (400 MHz, DMSO-d₆) δ 10.0 (s, 1H), 8.81-8.75 (m, 2H), 7.97 (s, 2H), 6.94 (d, J=3.7 Hz, 1H), 6.79 (d, J=3.7 Hz, 1H), 3.07 (t, J=7.1 Hz, 2H), 2.70 (t, J=7.2 Hz, 2H), 2.09 (s, 3H). LCMS: ESI-MS m/z: 347.1 [M+H]⁺.

Example 75

3-(2-Chlorothiazol-5-yl)-N-(4-methyl-3-(pyridin-4-yl)-1H-pyrazol-5-yl)propanamide

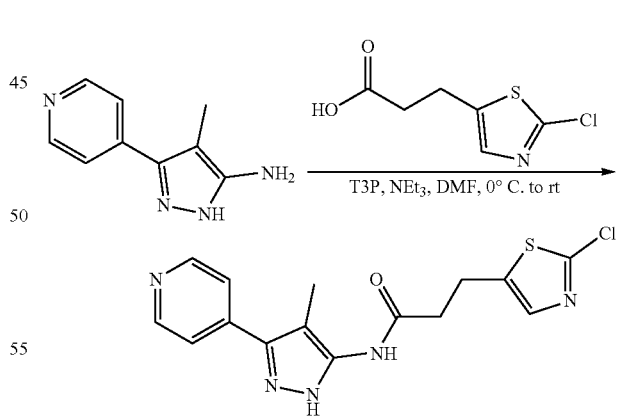

The product was prepared according to General Procedure #1 using Intermediate 1 and Intermediate 17 to afford 3-(2-chlorothiazol-5-yl)-N-(4-methyl-3-(pyridin-4-yl)-1H-pyrazol-5-yl)propenamide (62 mg, >95% yield), as a white solid, trifluoroacetic acid salt. ¹H NMR (400 MHz, DMSO-d₆) δ 10.0 (s, 1H), 8.83-8.71 (m, 2H), 7.96 (s, 2H), 7.50 (d, J=1.1 Hz, 1H), 3.13 (t, J=6.9 Hz, 2H), 2.74 (t, J=6.9 Hz, 2H), 2.09 (s, 3H). LCMS: ESI-MS m/z: 348.1 [M+H]⁺.

Example 76

3-(5-Chlorothiazol-2-yl)-N-(4-methyl-3-(pyridin-4-yl)-1H-pyrazol-5-yl)propenamide

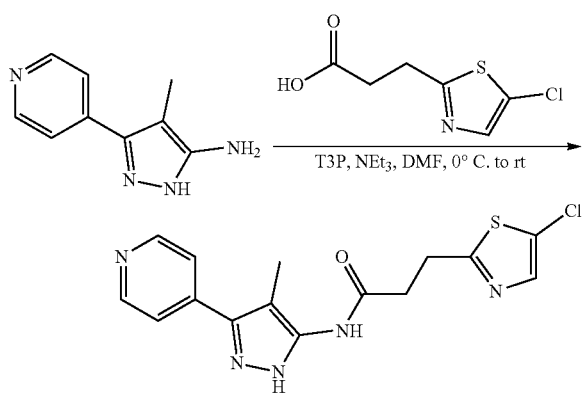

The product was prepared according to General Procedure #1 using Intermediate 1 and Intermediate 18 to afford 3-(4-chlorothiophen-2-yl)-N-(4-methyl-3-(pyridin-4-yl)-1H-pyrazol-5-yl)propenamide (29 mg, 36% yield) as a white solid, trifluoroacetic acid salt. $^1$H NMR (400 MHz, DMSO-$d_6$) δ 10.1 (s, 1H), 8.85-8.75 (m, 2H), 7.96 (s, 2H), 7.72 (s, 1H), 3.27 (d, J=14.1 Hz, 2H), 2.86 (t, J=7.0 Hz, H), 2.10 (s, 3H). LCMS: ESI-MS m/z: 348.1 [M+H]$^+$.

Example 77

3-(4-Chloro-1H-pyrazol-1-yl)-N-(4-methyl-3-(pyridin-4-yl)-1H-pyrazol-5-yl)propenamide

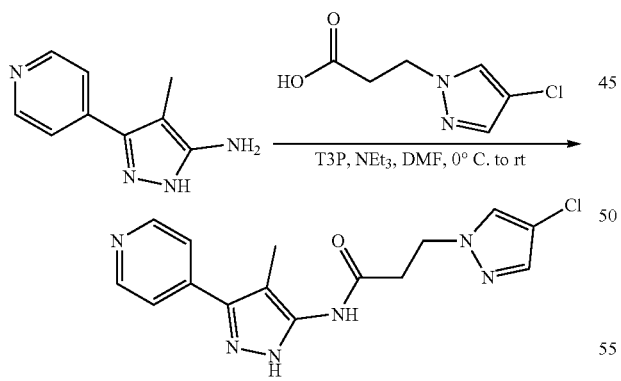

The product was prepared according to General Procedure #1 using Intermediate 1 and 3-(4-chloro-1H-pyrazol-1-yl)propanoic acid to afford 3-(4-chloro-1H-pyrazol-1-yl)-N-(4-methyl-3-(pyridin-4-yl)-1H-pyrazol-5-yl)propenamide (11 mg, 14% yield) as a white solid, trifluoroacetic acid salt. $^1$H NMR (400 MHz, DMSO-$d_6$) δ 10.1 (s, 1H), 8.80 (d, J=5.8 Hz, 2H), 8.01 (s, 2H), 7.95 (s, 1H), 7.56 (s, 1H), 4.39 (t, J=6.7 Hz, 2H), 2.93 (d, J=13.2 Hz, 2H), 2.07 (s, 3H). LCMS: ESI-MS m/z: 331.1 [M+H]$^+$.

Example 78

3-(3-Chloroisoxazol-5-yl)-N-(4-methyl-3-(pyridin-4-yl)-1H-pyrazol-5-yl)propanamide

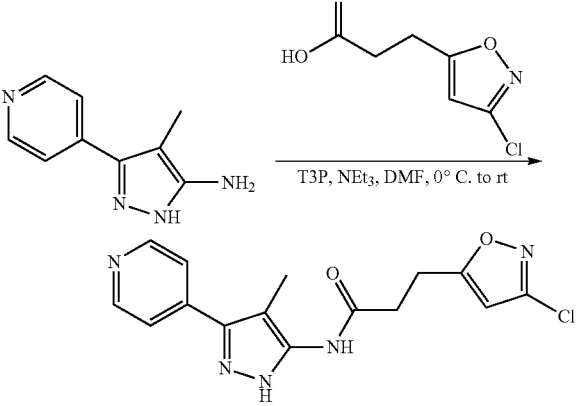

The product was prepared according to General Procedure #1 using Intermediate 1 and 3-(3-chloroisoxazol-5-yl)propanoic acid to afford 3-(3-chloroisoxazol-5-yl)-N-(4-methyl-3-(pyridin-4-yl)-1H-pyrazol-5-yl)propanamide (6.5 mg, 8.0% yield) as a white solid, trifluoroacetic acid salt. $^1$H NMR (400 MHz, DMSO-$d_6$) δ 10.1 (s, 1H), 8.78 (d, J=6.0 Hz, 2H), 7.97 (s, 2H), 6.64 (s, 1H), 3.11 (t, J=7.2 Hz, 2H), 2.81 (t, J=7.2 Hz, 2H), 2.10 (s, 3H). LCMS: ESI-MS m/z: 332.1 [M+H]$^+$.

Example 79

2-((4-Chlorophenyl)amino)-N-(4-methyl-3-(pyridin-4-yl)-1H-pyrazol-5-yl)acetamide

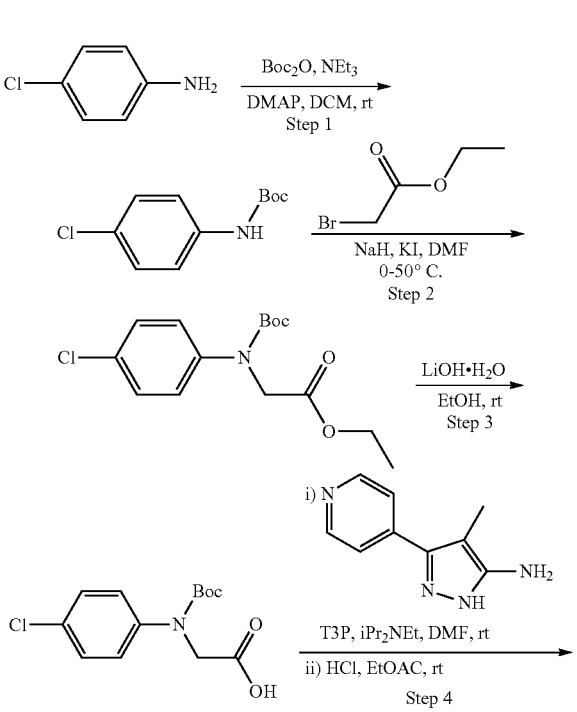

-continued

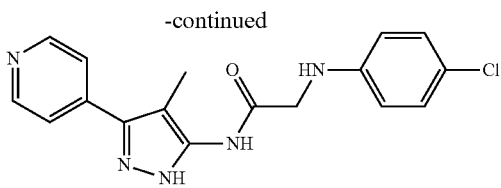

Step 1: tert-Butyl (4-chlorophenyl)carbamate: To a solution of 4-chloroaniline (3.0 g, 24 mmol, 1.0 equiv) in DCM (30 mL, 0.80 M) was added triethylamine (6.0 g, 59 mmol, 2.5 equiv), DMAP (290 mg, 2.4 mmol, 0.10 equiv) and Boc anhydride (5.7 g, 26 mmol, 1.1 equiv). After the addition, the mixture was stirred at rt for 8 h. The mixture was washed with water (15 mL), brine (15 mL), dried over anhydrous sodium sulfate, filtered, and concentrated in vacuo. The crude residue was purified by silica gel column chromatography (20-90% EtOAc in hexanes) to afford tert-butyl (4-chlorophenyl)carbamate (4.3 g, 19 mmol, 810% yield) as a light yellow liquid. LCMS: ESI-MS m/z: 172.1 [M−55]$^+$.

Step 2: Ethyl N-(tert-butoxycarbonyl)-N-(4-chlorophenyl)glycinate: To a solution of tert-butyl (4-chlorophenyl) carbamate (500 mg, 2.2 mmol, 1.0 equiv) in DMF (5.0 mL, 0.44 M) was added sodium hydride (60 wt % dispersion in mineral oil, 100 mg, 2.6 mmol, 60% in mineral oil, 1.2 equiv) at 0° C. After stirring for 5 min at 0° C., potassium iodide (360 mg, 2.2 mmol, 1.0 equiv) and ethyl 2-bromoacetate (470 mg, 2.4 mmol, 1.1 equiv) were added to the suspension. After the addition, the reaction mixture heated to 50° C. for 1 h. Then the mixture was cooled to rt, treated with water (20 mL) and extracted with ethyl acetate (3×20 mL). The combined organic fractions were washed with brine, dried over anhydrous sodium sulfate, filtered, and concentrated in vacuo. The crude material was purified directly by silica gel column chromatography (10-50% EtOAc in hexanes) to afford ethyl N-(tert-butoxycarbonyl)-N-(4-chlorophenyl)glycinate (400 mg, 1.3 mmol, 58% yield) as a light yellow liquid. LCMS: ESI-MS m/z: 214.1 [M−99]$^+$.

Step 3: N-(tert-Butoxycarbonyl)-N-(4-chlorophenyl)glycine: A mixture of N-(tert-butoxycarbonyl)-N-(4-chlorophenyl)glycinate (400 mg, 1.3 mmol, 1.0 equiv), lithium hydroxide monohydrate (270 mg, 6.4 mmol, 4.9 equiv) in a solution of ethanol (10 mL, 0.13 M) and water (5.0 mL, 0.26 M) was stirred at rt for 6 h. The reaction was concentrated in vacuo to remove ethanol, then the residual aqueous phase was diluted with water (10 mL) and washed with ethyl acetate (2×10 mL). The aqueous fraction was separated, and treated with a 1.0 M aqueous solution of HCl to adjust to pH 5~6. This solution was then extracted with ethyl acetate (3×20 mL). All combined organic fractions were then washed with brine (20 mL), dried over anhydrous sodium sulfate, filtered, and concentrated in vacuo to afford N-(tert-butoxycarbonyl)-N-(4-chlorophenyl)glycine (310 mg, 1.1 mmol, 85% yield) as a light yellow solid. This material was moved onto subsequent reactions with no further purification. LCMS: ESI-MS m/z: 186.1 [M−99]$^+$.

Step 4: 2-((4-Chlorophenyl)amino)-N-(4-methyl-3-(pyridin-4-yl)-1H-pyrazol-5-yl)acetamide. To a mixture of N-(tert-butoxycarbonyl)-N-(4-chlorophenyl)glycine (310 mg, 1.1 mmol, 1.0 equiv), 4-methyl-3-(pyridin-4-yl)-1H-pyrazol-5-amine (Intermediate 1, 210 mg, 1.2 mmol, 1.1 equiv) in anhydrous DMF (5.0 mL, 0.22 M) was added T3P (50% w/w in EtOAc, 890 mg, 1.4 mmol, 1.3 equiv) and DIPEA (280 mg, 2.2 mmol, 2.0 equiv). After the addition, the mixture was stirred at rt for 16 h. The mixture was then diluted with ethyl acetate (20 mL), washed with water (10 mL), and brine (10 mL). The organic fraction was separated and treated with a 4.0 M solution of HCl in 1,4-dioxane (10 mL). The mixture was stirred at rt for 2 h, and then concentrated in vacuo. The residue was dissolved in water (20 mL) and washed with ethyl acetate (10 mL). The aqueous fraction was separated, treated with a saturated solution of aqueous NH$_4$HCO$_3$ to adjust to pH 8, then extracted with a 10:1 solution of DCM:MeOH (3×15 mL). All organic fractions were combined and concentrated in vacuo, and the crude residue was purified by RP-HPLC (Method C, 5-25% MeCN in H$_2$O+10 mM NH$_4$HCO$_3$+ 0.025% NH$_3$·H$_2$O) to afford 2-((4-chlorophenyl)amino)-N-(4-methyl-3-(pyridin-4-yl)-1H-pyrazol-5-yl)acetamide (66 mg, 0.19 mmol, 18% yield) as a white solid. $^1$H NMR (400 MHz, DMSO-d$_6$) δ 13.1-13.0 (m, 1H), 10.0-9.79 (m, 1H), 8.65 (s, 2H), 7.59 (s, 2H), 7.13 (d, J=8.7 Hz, 2H), 6.63 (d, J=8.7 Hz, 2H), 6.24 (s, 1H), 3.89 (s, 2H), 2.02 (s, 3H). LCMS: ESI-MS m/z: 342.0 [M+H]$^+$.

Example 80

3-(4-Chlorophenyl)-2,2-difluoro-N-(4-methyl-3-(pyridin-4-yl)-1H-pyrazol-5-yl)propanamide

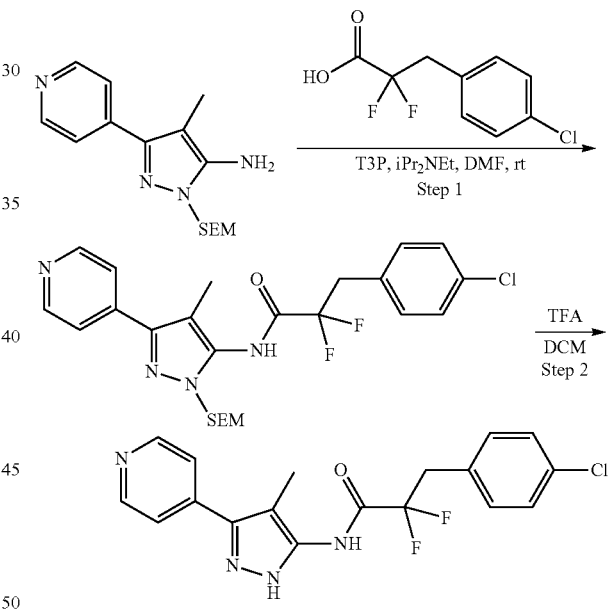

Step 1: 3-(4-Chlorophenyl)-2,2-difluoro-N-(4-methyl-3-(pyridin-4-yl)-1-((2-(trimethylsilyl)ethoxy)methyl)-1H-pyrazol-5-yl)propanamide. The product was prepared according to General Procedure #1 using Intermediate 2 and Intermediate 26 to afford 3-(4-chlorophenyl)-2,2-difluoro-N-(4-methyl-3-(pyridin-4-yl)-1-((2-(trimethylsilyl)ethoxy) methyl)-1H-pyrazol-5-yl)propanamide (30 mg, 0.059 mmol, 59%) as a light yellow oil which was carried forward without further purification. LCMS: ESI-MS m/z: 507.1 [M+H]$^+$.

Step 2: 3-(4-Chlorophenyl)-2,2-difluoro-N-(4-methyl-3-(pyridin-4-yl)-1H-pyrazol-5-yl)propenamide. The product was prepared according to General Procedure #3 using 3-(4-chlorophenyl)-2,2-difluoro-N-(4-methyl-3-(pyridin-4-yl)-1-((2-(trimethylsilyl)ethoxy)methyl)-1H-pyrazol-5-yl) propanamide to afford 3-(4-chlorophenyl)-2,2-difluoro-N-

(4-methyl-3-(pyridin-4-yl)-1H-pyrazol-5-yl)propenamide (12 mg, 0.032 mmol, 54%) as a white solid. $^1$H NMR (400 MHz, DMSO-$d_6$) δ 13.3 (s, 1H), 10.5 (s, 1H), 8.67 (s, 2H), 7.59-7.35 (m, 6H), 3.56 (t, J=17.6 Hz, 2H), 1.90 (s, 3H). LCMS: ESI-MS m/z: 377.0 [M+H]$^+$.

Example 81

2-((4-Chlorophenyl)thio)-N-(5-methyl-1-(pyridin-4-yl)-1H-pyrazol-4-yl)acetamide

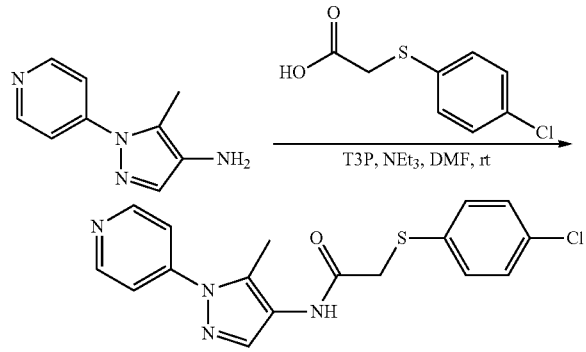

The product was prepared according to General Procedure #1 using Intermediate 6 and 2-((4-chlorophenyl)thio)acetic acid to afford 2-((4-chlorophenyl)thio)-N-(5-methyl-1-(pyridin-4-yl)-1H-pyrazol-4-yl)acetamide in 19% yield. $^1$H NMR (400 MHz, DMSO-$d_6$) δ 9.81 (s, 1H), 8.68 (d, J=5.6 Hz, 2H), 7.91 (s, 1H), 7.64 (dd, J=4.8, 1.6 Hz, 2H), 7.46-7.39 (m, 4H), 3.89 (s, 2H), 2.35 (s, 3H). LCMS: ESI-MS m/z: 359.0 [M+H]$^+$.

Example 82

3-(6-Chloropyridin-3-yl)-N-(5-methyl-1-(pyridin-4-yl)-1H-pyrazol-4-yl)propenamide

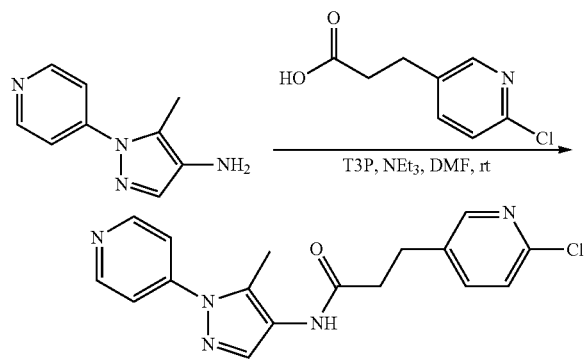

The product was prepared according to General Procedure #1 using Intermediate 6 and 3-(6-chloropyridin-3-yl)propanoic acid to afford 3-(6-chloropyridin-3-yl)-N-(5-methyl-1-(pyridin-4-yl)-1H-pyrazol-4-yl)propanamide in 20% yield. $^1$H NMR (400 MHz, DMSO-$d_6$) δ 9.51 (s, 1H), 8.67 (d, J=6.0 Hz, 2H), 8.31 (d, J=2.4 Hz, 1H), 7.91 (s, 1H), 7.76 (dd, J=2.4 Hz, 2.4 Hz, 1H), 7.63 (d, J=8.4 Hz, 2H), 7.45 (d, J=8.4 Hz, 1H), 2.93 (t, J=6.8 Hz, 2H), 2.67 (t, J=7.2 Hz, 2H), 2.32 (s, 3H). LCMS: ESI-MS m/z: 342.0 [M+H]$^+$.

Example 83

3-(4-Chloro-3,5-difluorophenyl)-N-(5-methyl-1-(pyridin-4-yl)-1H-pyrazol-4-yl)propanamide

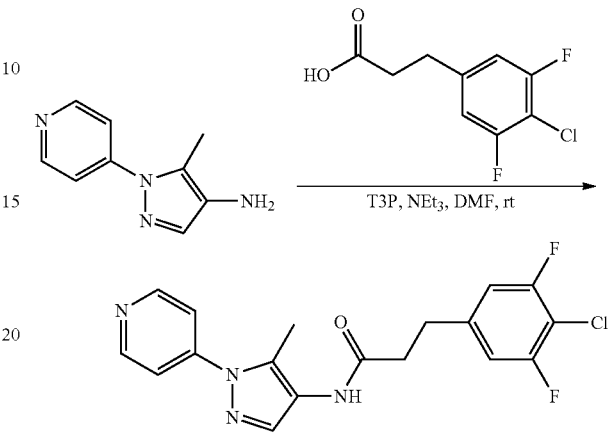

The product was prepared according to General Procedure #1 using Intermediate 6 and Intermediate 9 to afford 3-(4-chloro-3,5-difluorophenyl)-N-(5-methyl-1-(pyridin-4-yl)-1H-pyrazol-4-yl)propanamide in 25% yield. $^1$H NMR (400 MHz, DMSO-$d_6$) δ 9.51 (s, 1H), 8.67 (dd, J=1.6 Hz, 2H), 7.90 (s, 1H), 7.64 (dd, J=1.6 Hz, 2H), 7.26 (d, J=8.4 Hz, 2H), 2.95 (t, J=7.6 Hz, 2H), 2.68 (t, J=7.6 Hz, 2H), 2.32 (s, 3H). LCMS: ESI-MS m/z: 377.0 [M+H]$^+$.

Example 84

N-(5-Methyl-1-(pyridin-4-yl)-1H-pyrazol-4-yl)-3-(3,4,5-trifluorophenyl)propanamide

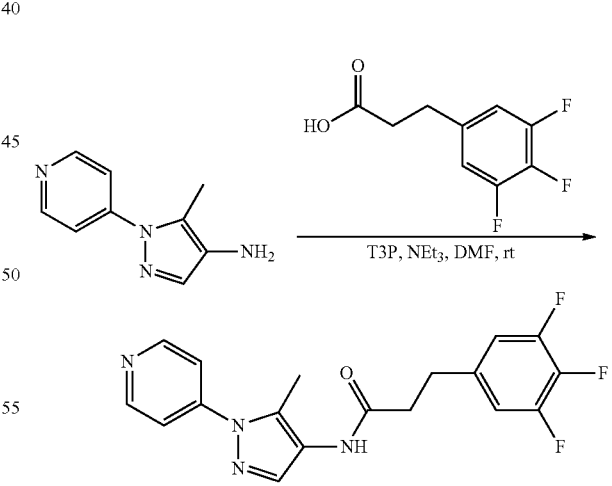

The product was prepared according to General Procedure #1 using Intermediate 6 and 3-(3,4,5-trifluorophenyl)propanoic acid to afford N-(5-methyl-1-(pyridin-4-yl)-1H-pyrazol-4-yl)-3-(3,4,5-trifluorophenyl)propanamide in 25% yield. $^1$H NMR (400 MHz, DMSO-$d_6$) δ 9.50 (s, 1H), 8.72 (d, J=6.0 Hz, 2H), 7.90 (s, 1H), 7.64 (dd, J=4.4, 1.6 Hz, 2H), 7.27-7.23 (m, 2H), 2.91 (t, J=7.6 Hz, 2H), 2.66 (t, J=7.6 Hz, 2H), 2.34 (s, 3H). LCMS: ESI-MS m/z: 361.0 [M+H]$^+$.

Example 85

2-(4-Chlorophenoxy)-N-(5-methyl-1-(pyridin-4-yl)-1H-pyrazol-4-yl)acetamide

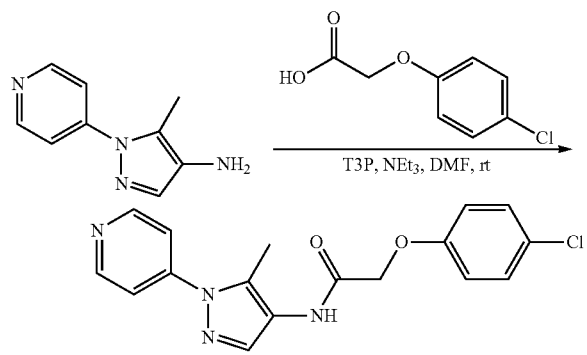

The product was prepared according to General Procedure #1 using Intermediate 6 and 2-(4-chlorophenoxy)acetic acid to afford 2-(4-chlorophenoxy)-N-(5-methyl-1-(pyridin-4-yl)-1H-pyrazol-4-yl)acetamide in 82% yield. $^1$H NMR (400 MHz, DMSO-$d_6$) δ 9.76 (s, 1H), 8.69 (d, J=1.6 Hz, 2H), 7.89 (s, 1H), 7.66 (d, J=1.6 Hz, 2H), 7.37 (d, J=9.2 Hz, 2H), 7.04 (d, J=8.8 Hz, 2H), 4.74 (s, 2H), 2.37 (s, 3H). LCMS: ESI-MS m/z: 343.0 [M+H]$^+$.

Example 86

3-(4-Chlorophenyl)-N-(5-methyl-1-(pyridin-4-yl)-1H-pyrazol-4-yl)propenamide

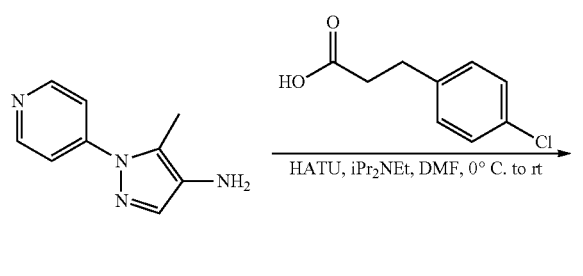

The product was prepared according to General Procedure #1 using intermediate 6 and 3-(4-chlorophenyl)propanoic acid to afford 3-(4-chlorophenyl)-N-(5-methyl-1-(pyridin-4-yl)-1H-pyrazol-4-yl)propenamide, trifluoroacetic acid salt (6.0 mg, 26% yield) as a beige solid. LCMS: ESI-MS m/z: 341.1 [M+H]$^+$.

Example 88

3-(4-Chloro-3,5-difluorophenyl)-N-[1-(pyridin-4-yl)-1H-pyrazol-4-yl]propanamide

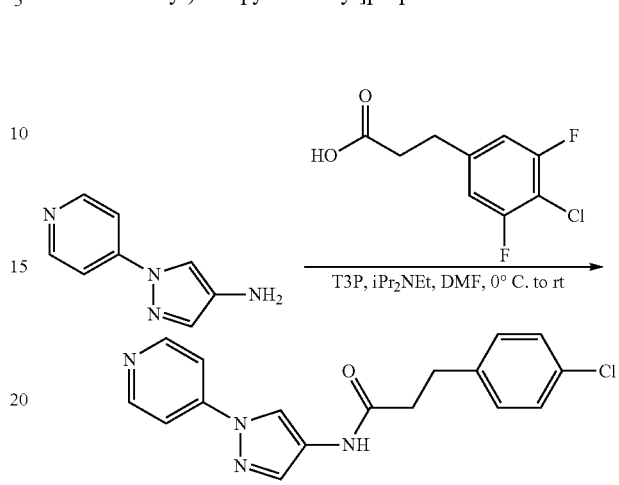

The product was prepared according to General Procedure #1 using Intermediate 21 and Intermediate 9 to afford 3-(4-chloro-3,5-difluorophenyl)-N-[1-(pyridin-4-yl)-1H-pyrazol-4-yl]propanamide (150 mg, 0.41 mmol, 88% yield) as a white solid. $^1$H NMR: (400 MHz, DMSO-$d_6$) δ 10.2 (s, 1H), 8.70 (s, 1H), 8.64-8.53 (m, 2H), 7.87-7.75 (m, 3H), 7.31-7.19 (m, 2H), 2.95 (t, J=7.5 Hz, 2H), 2.68 (t, J=7.5 Hz, 2H). LCMS: ESI-MS m/z: 363.1 [M+H]$^+$.

Example 89

3-(4-Chlorophenyl)-N-(1-(pyridin-4-yl)-1H-pyrazol-4-yl)propanamide

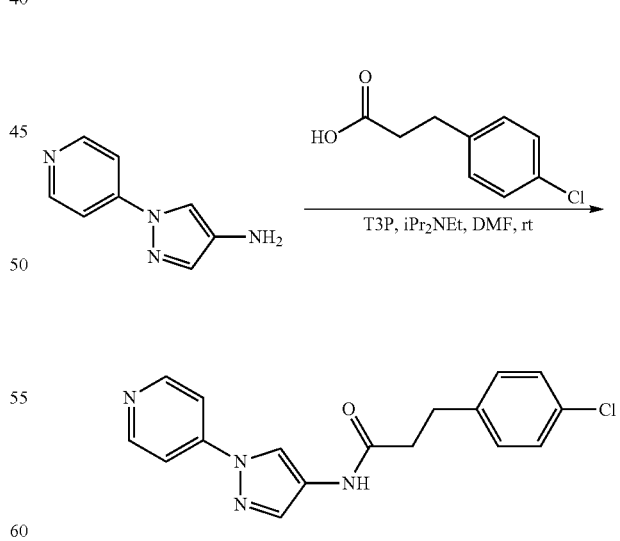

The product was prepared according to General Procedure #1 using Intermediate 21 and 3-(4-chlorophenyl)propanoic acid to afford 3-(4-chlorophenyl)-N-(1-(pyridin-4-yl)-1H-pyrazol-4-yl)propanamide (130 mg, 85% yield) as a white solid, trifluoroacetic acid salt. LCMS: ESI-MS m/z: 327.7 [M+H]$^+$.

Example 90

N-(5-Chloro-1-(pyridin-4-yl)-1H-pyrazol-4-yl)-3-(4-chlorophenyl)propenamide

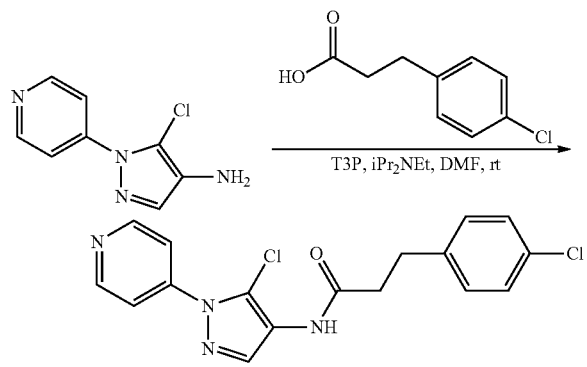

The product was prepared according to General Procedure #1 using Intermediate 7 and 3-(4-chlorophenyl)propanoic acid to afford N-(5-chloro-1-(pyridin-4-yl)-1H-pyrazol-4-yl)-3-(4-chlorophenyl)propenamide in 21% yield. $^1$H NMR (400 MHz, DMSO-d$_6$) δ 9.80 (s, 1H), 8.74 (dd, J=4.7, 1.6 Hz, 2H), 8.17 (s, 1H), 7.73 (dd, J=4.6, 1.6 Hz, 2H), 7.35 (d, J=8.5 Hz, 2H), 7.29 (d, J=8.5 Hz, 2H), 2.90 (t, J=7.5 Hz, 2H), 2.68 (t, J=7.6 Hz, 2H). LCMS: ESI-MS m/z: 361.0 [M+H]$^+$.

Example 91

N-(5-Chloro-1-(pyridin-4-yl)-1H-pyrazol-4-yl)-3-(4-chloro-3,5-difluorophenyl)propanamide

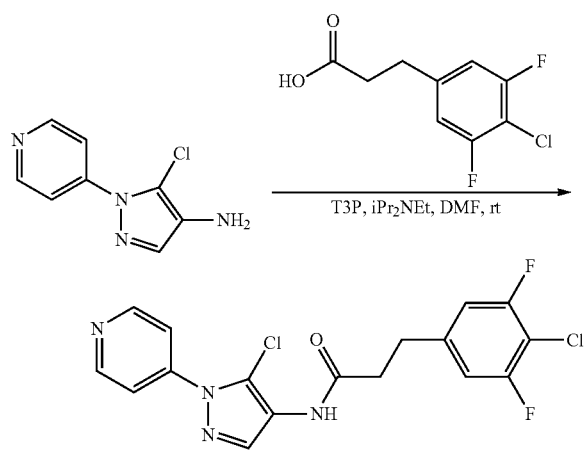

The product was prepared according to General Procedure #1 using Intermediate 7 and Intermediate 9 to afford N-(5-chloro-1-(pyridin-4-yl)-1H-pyrazol-4-yl)-3-(4-chloro-3,5-difluorophenyl)propanamide in 22% yield. $^1$H NMR (400 MHz, DMSO-d$_6$) δ 9.82 (s, 1H), 8.74 (dd, J=4.6, 1.6 Hz, 2H), 8.16 (s, 1H), 7.73 (dd, J=4.6, 1.6 Hz, 2H), 7.26 (d, J=8.4 Hz, 2H), 2.95 (t, J=7.5 Hz, 2H), 2.72 (t, J=7.5 Hz, 2H). LCMS: ESI-MS m/z: 397.0 [M+H]$^+$.

Example 92

N-(5-Chloro-1-(pyridin-4-yl)-1H-pyrazol-4-yl)-3-(3,4,5-trifluorophenyl)propanamide

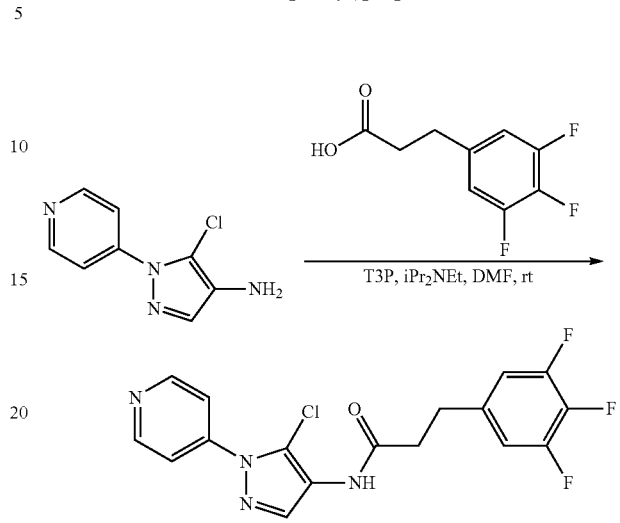

The product was prepared according to General Procedure #1 using Intermediate 7 and 3-(3,4,5-trifluorophenyl)propanoic acid to afford N-(5-chloro-1-(pyridin-4-yl)-1H-pyrazol-4-yl)-3-(3,4,5-trifluorophenyl)propanamide in 25% yield. $^1$H NMR (400 MHz, DMSO-d$_6$) δ 9.81 (s, 1H), 8.74 (dd, J=4.7, 1.6 Hz, 2H), 8.16 (s, 1H), 7.74 (dd, J=4.7, 1.6 Hz, 2H), 7.25 (dd, J=9.1, 6.9 Hz, 2H), 2.91 (t, J=7.6 Hz, 2H), 2.70 (t, J=7.5 Hz, 2H). LCMS: ESI-MS m/z: 381.0 [M+H]$^+$.

Example 93

N-(5-Chloro-1-(pyridin-4-yl)-1H-pyrazol-4-yl)-3-(4-cyano-3,5-difluorophenyl)propanamide

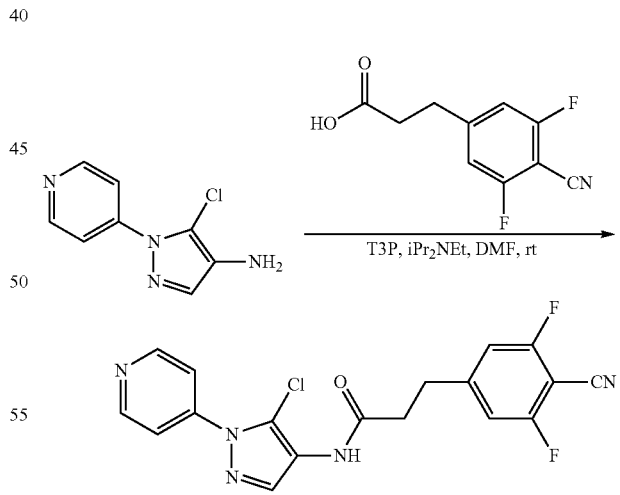

The product was prepared according to General Procedure #1 using Intermediate 7 and Intermediate 8 to afford N-(5-chloro-1-(pyridin-4-yl)-1H-pyrazol-4-yl)-3-(4-cyano-3,5-difluorophenyl)propanamide in 25% yield. $^1$H NMR (400 MHz, DMSO-d$_6$) δ 9.85 (s, 1H), 8.74 (dd, J=4.6, 1.6 Hz, 2H), 8.16 (s, 1H), 7.73 (dd, J=4.6, 1.6 Hz, 2H), 7.40 (d, J=9.4 Hz, 2H), 3.03 (t, J=7.5 Hz, 2H), 2.76 (t, J=7.5 Hz, 2H). LCMS: ESI-MS m/z: 388.0 [M+H]$^+$.

Example 94

N-(5-Chloro-1-(pyridin-4-yl)-1H-pyrazol-4-yl)-3-(4-cyano-3-fluorphenyl)propanamide

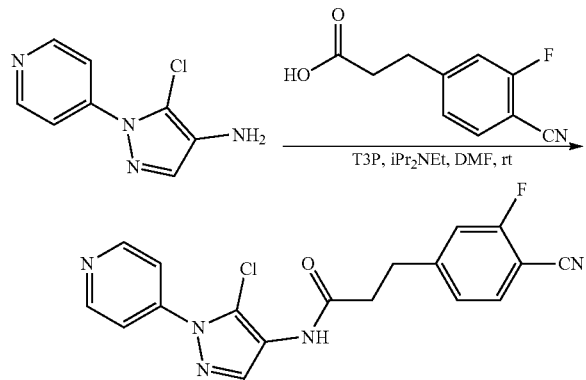

The product was prepared according to General Procedure #1 using Intermediate 7 and Intermediate 10 to afford N-(5-chloro-1-(pyridin-4-yl)-1H-pyrazol-4-yl)-3-(4-cyano-3-fluorophenyl)propanamide as a white solid in 22% yield. $^1$H NMR (400 MHz, DMSO-$d_6$) δ 9.83 (s, 1H), 8.74 (dd, J=4.7, 1.6 Hz, 2H), 8.16 (s, 1H), 7.88-7.83 (m, 1H), 7.73 (dd, J=4.6, 1.6 Hz, 2H), 7.47 (d, J=10.7 Hz, 1H), 7.33 (dd, J=8.0, 1.3 Hz, 1H), 3.02 (t, J=7.5 Hz, 2H), 2.75 (t, J=7.5 Hz, 2H). LCMS: ESI-MS m/z: 370.1 [M+H]$^+$.

Example 95

3-(4-Chlorophenyl)-N-(1-(pyridin-4-yl)-5-(trifluoromethyl)-1H-pyrazol-4-yl)propanamide

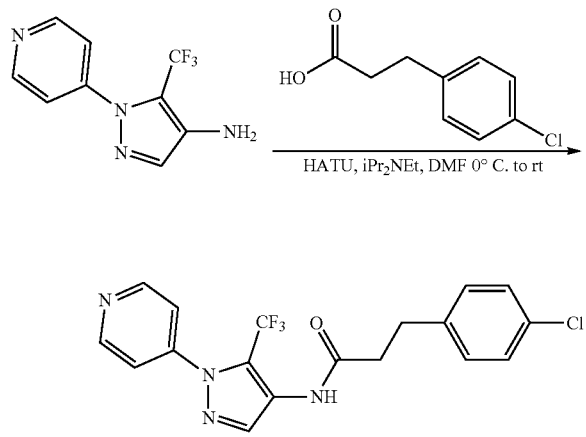

The product was prepared according to General Procedure #1 using 1-(pyridin-4-yl)-5-(trifluoromethyl)-1H-pyrazol-4-amine and 3-(4-chlorophenyl)propanoic acid to afford 3-(4-chlorophenyl)-N-(1-(pyridin-4-yl)-5-(trifluoromethyl)-1H-pyrazol-4-yl)propanamide (7.0 mg, 11% yield) as a pale yellow solid, trifluoroacetic acid salt. LCMS: ESI-MS m/z: 395.1 [M+H]$^+$.

Example 96

N-(4-Chloro-3-(pyridin-4-yl)-1H-pyrazol-5-yl)-3-(4-chlorophenyl)propanamide

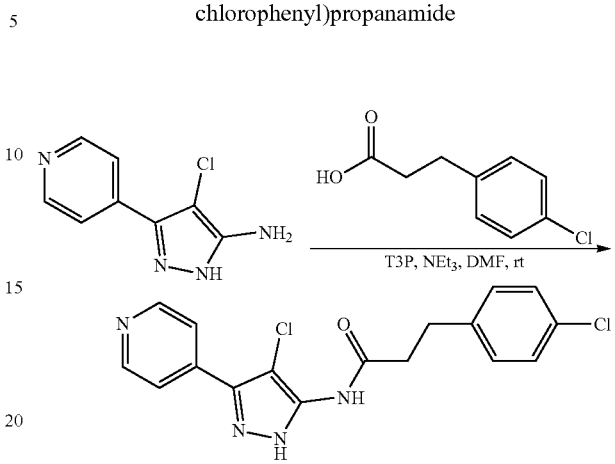

The product was prepared according to General Procedure #1 using Intermediate 23 and 3-(4-chlorophenyl)propanoic acid to afford N-(4-chloro-3-(pyridin-4-yl)-1H-pyrazol-5-yl)-3-(4-chlorophenyl)propanamide (10 mg, 0.028 mmol, 11%) as a white solid. $^1$H NMR (400 MHz, DMSO-$d_6$) δ 13.7 (br s, 1H), 10.1 (br s, 1H), 8.69 (s, 2H), 7.80 (s, 2H), 7.36-7.29 (m, 4H), 2.92 (t, J=7.4 Hz, 2H), 2.71-2.63 (m 2H). LCMS: ESI-MS m/z: 361.1 [M+H]$^+$.

Example 97

3-(4-Chloro-3,5-difluorophenyl)-N-(4-chloro-3-(pyridin-4-yl)-1H-pyrazol-5-yl)propanamide

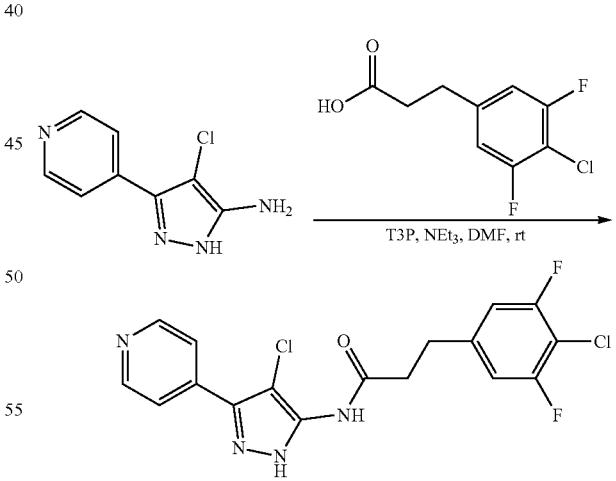

The product was prepared according to General Procedure #1 using Intermediate 23 and Intermediate 9 to afford 3-(4-chloro-3,5-difluorophenyl)-N-(4-chloro-3-(pyridin-4-yl)-1H-pyrazol-5-yl)propanamide in 12% yield. $^1$H NMR (400 MHz, DMSO-$d_6$) δ 13.6 (br s, 1H), 10.05 (br s, 1H), 8.69 (d, J=5.6 Hz, 2H), 7.80 (dd, J=1.6 Hz, J=4.8 Hz, 2H), 7.27 (d, J=8.8 Hz, 2H), 2.96 (t, J=7.4 Hz, 2H), 2.72 (t, J=7.0 Hz, 2H). LCMS: ESI-MS m/z: 397.1 [M+H]$^+$.

Example 98

3-(4-Chlorophenyl)-N-(3-(pyridin-4-yl)-1H-pyrazol-5-yl)propanamide

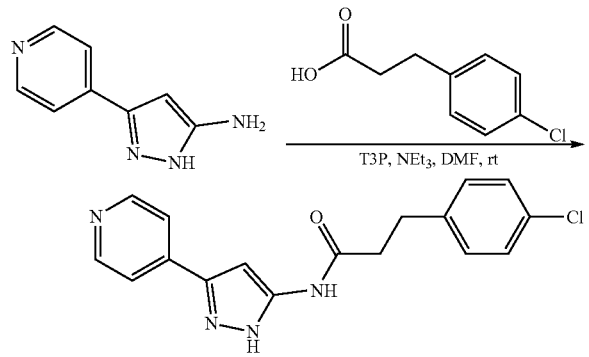

The product was prepared according to General Procedure #1 using Intermediate 13 and 3-(4-chlorophenyl)propanoic acid to afford 3-(4-chlorophenyl)-N-(3-(pyridin-4-yl)-1H-pyrazol-5-yl)propenamide (6.0 mg, 12% yield) as a white solid. $^1$H NMR (400 MHz, DMSO-d$_6$) δ 13.2 (s, 1H), 10.6 (s, 1H), 8.65-8.57 (m, 1H), 8.22-8.17 (m, 1H), 7.71 (s, 2H), 7.34 (d, J=8.0 Hz, 2H), 7.28 (d, J=8.4 Hz, 2H), 7.11-7.07 (m, 1H), 2.90 (t, J=11.8 Hz, 2H), 2.63 (t, J=11.6 Hz, 2H). LCMS: ESI-MS m/z: 327.1 [M+H]$^+$.

Example 99

3-(Benzo[d][1,3]dioxol-5-yl)-N-(3-(pyridin-4-yl)-1H-pyrazol-5-yl)propanamide

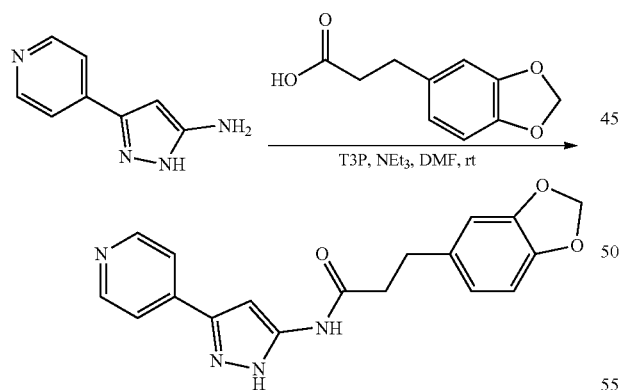

The product was prepared according to General Procedure #1 using Intermediate 13 and 3-(benzo[d][1,3]dioxol-5-yl)propanoic acid to afford 3-(benzo[d][1,3]dioxol-5-yl)-N-(3-(pyridin-4-yl)-1H-pyrazol-5-yl)propenamide as a white solid in 24% yield. $^1$H NMR (400 MHz, DMSO-d$_6$) δ 13.2 (s, 1H), 10.5 (s, 1H), 8.60 (s, 2H), 7.70 (d, J=6.4 Hz, 2H), 7.11 (s, 1H), 6.80-6.83 (m, 2H), 6.70 (dd, J=1.6 Hz, 1.6 Hz, 1H), 5.95 (s, 2H), 2.82 (t, 0.1=7.2 Hz, 2H), 2.59 (t, J=7.6 Hz, 2H). LCMS: ESI-MS m/z: 337.0 [M+H]$^+$.

Example 100

3-(3-Chlorophenyl)-N-(3-(pyridin-4-yl)-1H-pyrazol-5-yl)propanamide

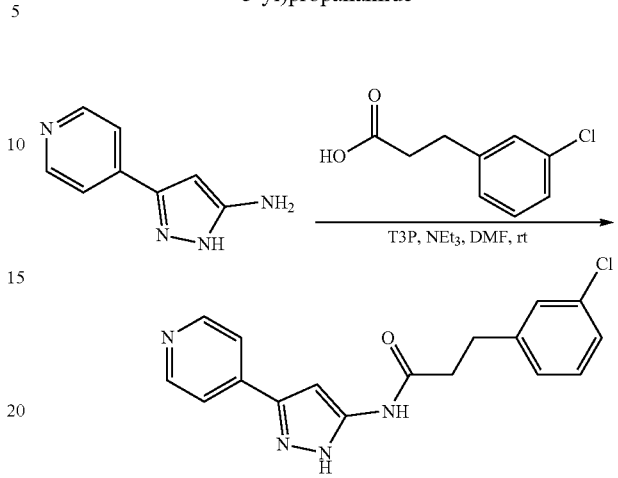

The product was prepared according to General Procedure #1 using Intermediate 13 and 3-(3-chlorophenyl)propanoic acid to afford 3-(3-chlorophenyl)-N-(3-(pyridin-4-yl)-1H-pyrazol-5-yl)propenamide as a white solid in 26% yield. $^1$H NMR (400 MHz, DMSO-d$_6$) δ 13.2 (s, 1H), 10.5 (s, 1H), 8.61-8.60 (m, 2H), 7.70 (d, J=5.6 Hz, 2H), 7.40-7.21 (m, 4H), 7.10 (s, 1H), 2.93-2.89 (m, 2H), 2.67-2.63 (m, 2H). LCMS: ESI-MS m/z: 327.0 [M+H]$^+$.

Example 101

3-(4-Chloro-3,5-difluorophenyl)-N-(3-(pyridin-4-yl)-1H-pyrazol-5-yl)propanamide

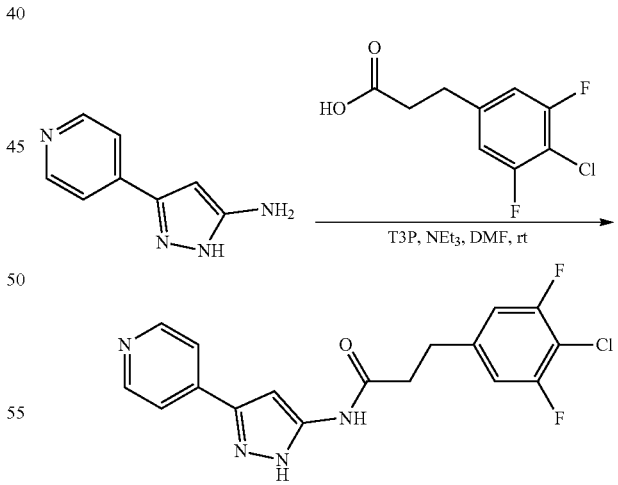

The product was prepared according to General Procedure #1 using Intermediate 13 and Intermediate 9 to afford 3-(4-chloro-3,5-difluorophenyl)-N-(3-(pyridin-4-yl)-1H-pyrazol-5-yl)propanamide as a white solid in 23% yield. $^1$H NMR (400 MHz, DMSO-d$_6$) δ 13.2 (s, 1H), 10.6 (s, 1H), 8.61 (d, J=4 Hz, 2H), 7.69 (d, J=5.2 Hz, 2H), 7.25 (d, J=8.8 Hz, 2H), 7.10 (s, 1H), 2.94 (t, J=7.2 Hz, 2H), 2.67 (t, J=7.2 Hz, 2H). LCMS: ESI-MS m/z: 363.0 [M+H]$^+$.

Example 102

N-(3-(Pyridin-4-yl)-1H-pyrazol-5-yl)-3-(3,4,5-trifluorophenyl)propanamide

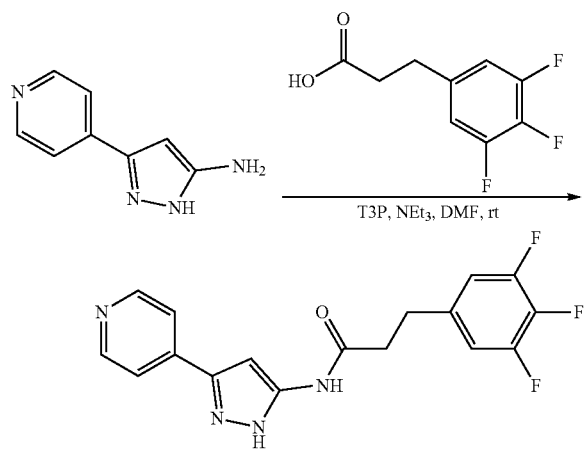

The product was prepared according to General Procedure #1 using Intermediate 13 and 3-(3,4,5-trifluorophenyl)propanoic acid to afford N-(3-(pyridin-4-yl)-1H-pyrazol-5-yl)-3-(3,4,5-trifluorophenyl)propenamide as a white solid in 23% yield. $^1$H NMR (400 MHz, DMSO-$d_6$) δ 13.2 (s, 1H), 10.6 (s, 1H), 8.61 (s, 2H), 7.70 (d, J=4.4 Hz, 2H), 7.25 (t, J=4.4 Hz, 2H), 7.11 (s, 1H), 2.90 (t, J=7.4 Hz, 2H), 2.67 (t, J=4.2 Hz, 2H). LCMS: ESI-MS m/z: 347.1 [M+H]$^+$.

Example 103

3-(4-Cyano-3-fluorophenyl)-N-(3-(pyridin-4-yl)-1H-pyrazol-5-yl)propanamide

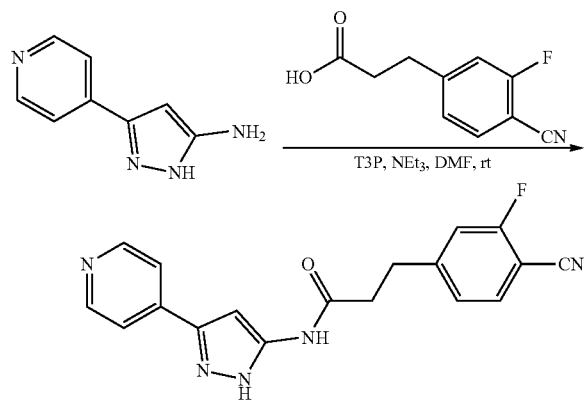

The product was prepared according to General Procedure #1 using Intermediate 13 and Intermediate 10 to afford 3-(4-cyano-3-fluorophenyl)-N-(3-(pyridin-4-yl)-1H-pyrazol-5-yl)propenamide as a white solid in 25% yield. $^1$H NMR (400 MHz, DMSO-$d_6$) δ 10.6 (s, 1H), 8.61 (dd, J=6.4 Hz, 2H), 7.86 (t, J=14.8 Hz, 1H), 7.70 (dd, J=6.4 Hz, 2H), 7.47 (d, J=10.0 Hz, 1H), 7.33 (dd, J=8.4 Hz, 1H), 7.00 (s, 1H), 3.02 (t, J=15.2 Hz, 2H), 2.70 (t, J=15.2 Hz, 2H). LCMS: ESI-MS m/z: 336.0 [M+H]$^+$.

Example 104

3-(4-Cyano-3,5-difluorophenyl)-N-(3-(pyridin-4-yl)-1H-pyrazol-5-yl)propanamide

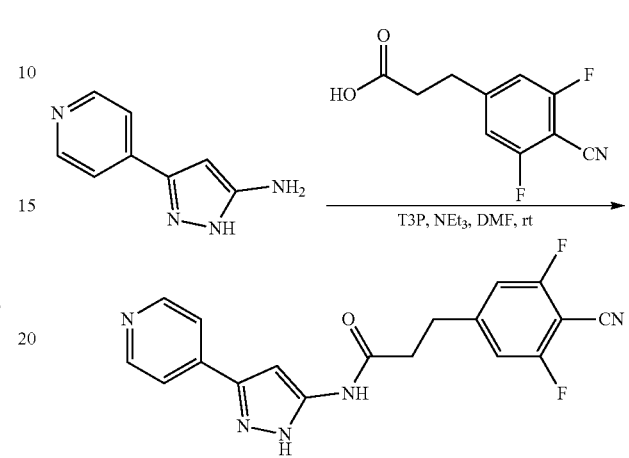

The product was prepared according to General Procedure #1 using Intermediate 13 and Intermediate 8 to afford 3-(4-cyano-3,5-difluorophenyl)-N-(3-(pyridin-4-yl)-1H-pyrazol-5-yl)propanamide as a white solid in 20% yield. $^1$H NMR (400 MHz, DMSO-$d_6$) δ 13.2 (s, 1H), 10.6 (s, 1H), 8.62 (d, J=5.2 Hz, 2H), 7.73 (s, 2H), 7.40 (d, J=9.2 Hz, 2H), 7.10 (s, 1H), 3.03 (t, J=14.8 Hz, 2H), 2.72 (t, J=14.8 Hz, 2H). LCMS: ESI-MS m/z: 354.1 [M+H]$^+$.

Example 105

3-(4-Chlorophenyl)-N-(1-methyl-2-(pyridin-4-yl)-1H-imidazol-5-yl)propanamide

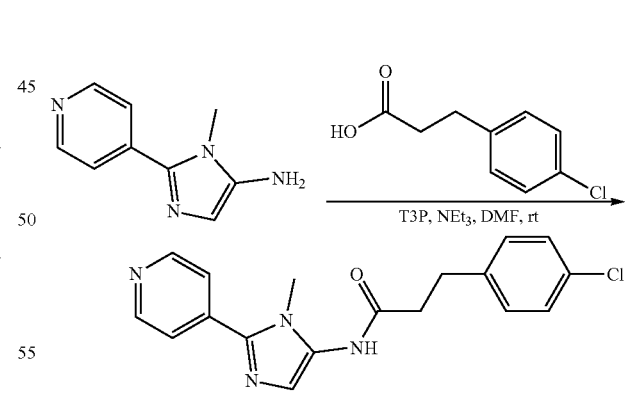

The product was prepared according to General Procedure #1 using Intermediate 15 and 3-(4-chlorophenyl)propanoic acid to afford 3-(4-chlorophenyl)-N-(1-methyl-2-(pyridin-4-yl)-1H-imidazol-5-yl)propanamide (3.0 mg, 7.0% yield) as a white solid. $^1$H NMR (400 MHz, CDCl$_3$) δ 8.70 (d, J=4.8 Hz, 2H), 7.56 (d, J=5.2 Hz, 2H), 7.29 (d, J=8.4 Hz, 2H), 7.20 (d, J=8.4 Hz, 2H), 7.09-7.08 (m, 1H), 6.99 (s, 1H), 3.44 (s, 3H), 3.06 (t, J=7.0 Hz, 2H), 2.74 (t, J=7.0 Hz, 2H). LCMS: ESI-MS m/z: 341.1 [M+H]$^+$.

Example 106

3-(4-Chlorophenyl)-N-(3-(3-methylpyridin-4-yl)-1H-pyrazol-5-yl)propanamide

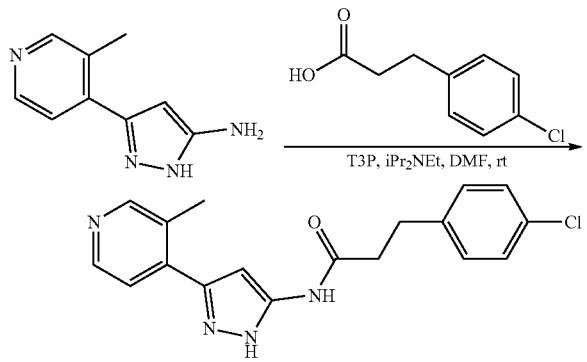

The product was prepared according to General Procedure #1 using Intermediate 16 and 3-(4-chlorophenyl)propanoic acid to afford 3-(4-chlorophenyl)-N-(3-(3-methylpyridin-4-yl)-1H-pyrazol-5-yl)propanamide (30 mg, 15% yield) as a white solid. $^1$H NMR (400 MHz, DMSO-$d_6$) δ 10.6 (s, 1H), 8.52 (s, 1H), 8.46 (d, J=5.2 Hz, 1H), 7.50 (d, J=4.8 Hz, 1H), 7.34 (d, J=8.4 Hz, 2H), 7.28 (d, J=8.4 Hz, 2H), 6.80 (s, 1H), 2.89 (t, J=8 Hz, 2H), 2.63 (t, J=7.6 Hz, 2H), 2.42 (s, 3H). LCMS: ESI-MS m/z: 341.0 [M+H]$^+$.

Example 107

3-(4-Chlorophenyl)-N-(3-methyl-1-(pyridin-4-yl)-1H-pyrazol-4-yl)propenamide

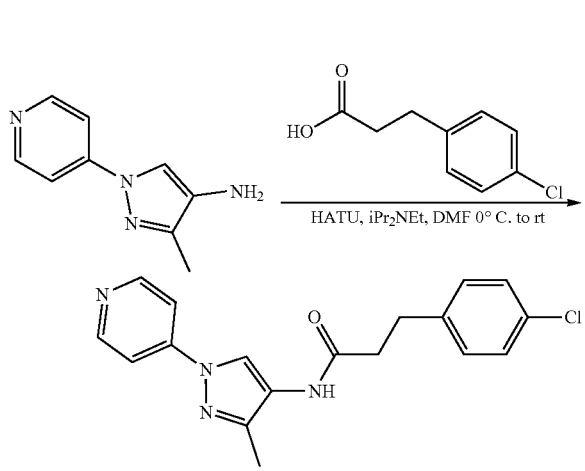

The product was prepared according to General Procedure #1 using 3-methyl-1-(pyridin-4-yl)-1H-pyrazol-4-amine and 3-(4-chlorophenyl)propanoic acid to afford 3-(4-chlorophenyl)-N-(3-methyl-1-(pyridin-4-yl)-1H-pyrazol-4-yl)propenamide, trifluoroacetic acid salt (77 mg, 74% yield) as a white solid. $^1$H NMR (400 MHz, MeOD) δ 8.85 (s, 1H), 8.72-8.67 (m, 2H), 8.23-8.17 (m, 2H), 7.31-7.21 (m, 4H), 3.01 (t, J=7.5 Hz, 2H), 2.77 (t, J=7.5 Hz, 2H), 2.32 (s, 3H). LCMS: ESI-MS m/z: 341.1 [M+H]$^+$.

Example 108

3-(4-Chlorophenyl)-N-(4-(pyridin-4-yl)-1H-imidazol-2-yl)propenamide

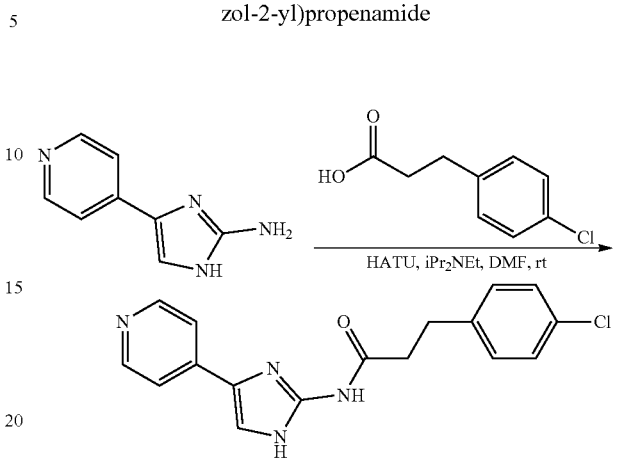

The product was prepared according to General Procedure #1 using 4-(pyridin-4-yl)-1H-imidazol-2-amine and 3-(4-chlorophenyl)propanoic acid to afford 3-(4-chlorophenyl)-N-(4-(pyridin-4-yl)-1H-imidazol-2-yl)propenamide, trifluoroacetic acid salt (20 mg, 36% yield) as a white solid. LCMS: ESI-MS m/z: 327.1 [M+H]$^+$.

Example 109

3-(4-Chlorophenyl)-N-(1-(3-methylpyridin-4-yl)-1H-pyrazol-4-yl)propanamide

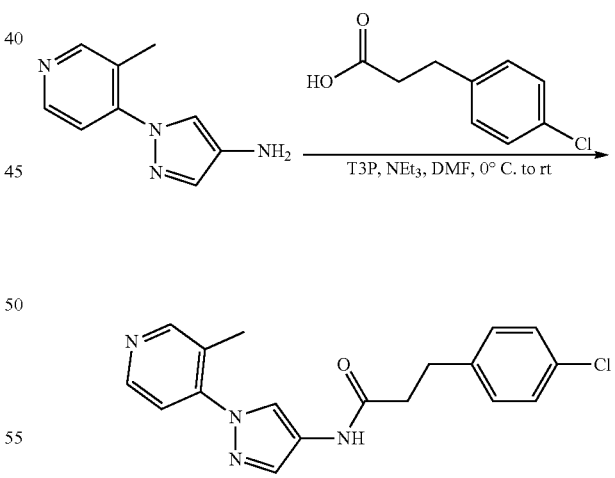

The product was prepared according to General Procedure #1 using Intermediate 19 and 3-(4-chlorophenyl)propanoic acid to afford 3-(4-chlorophenyl)-N-(1-(3-methylpyridin-4-yl)-1H-pyrazol-4-yl)propanamide (1.9 mg, 15% yield) as a white solid, trifluoroacetic acid salt. $^1$H NMR (400 MHz, CD$_3$OD) δ 8.73 (s, 1H), 8.62 (s, 1H), 8.01 (d, J=5.6 Hz, 1H), 1.88 (s, 1H), 7.33-7.11 (m, 6H), 3.00 (t, J=7.5 Hz, 2H), 2.78-2.70 (m, 2H), 2.69 (s, 3H). LCMS: ESI-MS m/z: 341.1 [M+H]$^+$.

Example 110

3-(4-Chlorophenyl)-N-(4-methyl-3-(3-methylpyridin-4-yl)-1H-pyrazol-5-yl)propenamide

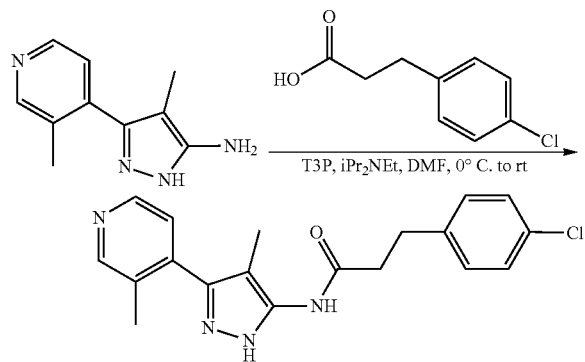

The product was prepared according to General Procedure #1 using Intermediate 20 and 3-(4-chlorophenyl)propanoic acid to afford 3-(4-chlorophenyl)-N-(4-methyl-3-(3-methylpyridin-4-yl)-1H-pyrazol-5-yl)propenamide in 33% yield. $^1$HNMR (500 MHz, DMSO-$d_6$) δ 12.8-12.6 (m, 1H), 9.95-9.71 (m, 1H), 8.54-8.46 (m, 2H), 7.35 (d, J=8.4 Hz, 2H), 7.30 (d, J=8.4 Hz, 2H), 7.24 (d, J=5.0 Hz, 1H), 2.91 (t, J=7.3 Hz, 2H), 2.64 (s, 2H), 2.24 (s, 3H), 1.71 (s, 3H). LCMS: ESI-MS m/z: 355.2 [M+H]$^+$.

Example 111

3-(4-Chloro-3,5-difluorophenyl)-N-(4-methyl-3-(3-methylpyridin-4-yl)-1H-pyrazol-5-yl)propanamide

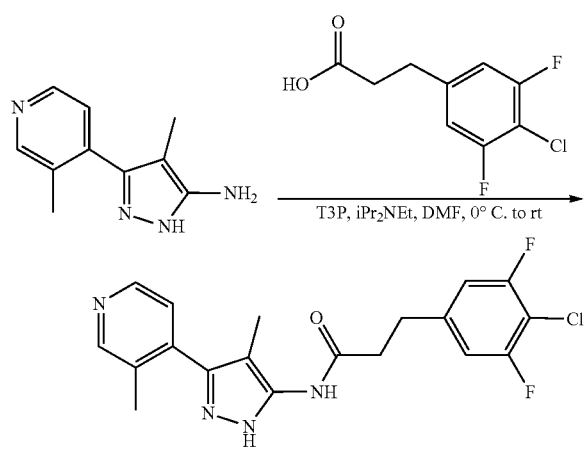

The product was prepared according to General Procedure #1 using Intermediate 20 and Intermediate 9 to afford 3-(4-chloro-3,5-difluorophenyl)-N-(4-methyl-3-(3-methylpyridin-4-yl)-1H-pyrazol-5-yl)propanamide in 34% yield. $^1$H NMR (500 MHz, DMSO-$d_6$) δ 12.8-12.6 (s, 1H), 9.72 (s, 1H), 8.51 (d, J=39.3 Hz, 2H), 7.26 (dd, J=14.2, 6.8 Hz, 3H), 2.95 (t, J=7.3 Hz, 2H), 2.66 (d, J=13.6 Hz, 2H), 2.23 (s, 3H), 1.70 (s, 3H). LCMS: ESI-MS m/z: 391.1 [M+H]$^+$.

Example 112

3-(4-Cyano-3-fluorophenyl)-N-(4-methyl-3-(3-methylpyridin-4-yl)-1H-pyrazol-5-yl)propanamide

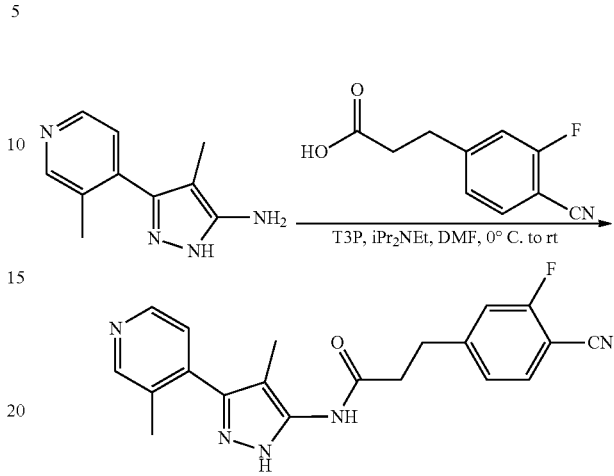

The product was prepared according to General Procedure #1 using Intermediate 20 and Intermediate 10 to afford 3-(4-cyano-3-fluorophenyl)-N-(4-methyl-3-(3-methylpyridin-4-yl)-1H-pyrazol-5-yl)propanamide in 36% yield. $^1$H NMR (500 MHz, DMSO-$d_6$) δ 12.8-12.6 (m, 1H), 9.76 (s, 1H), 8.65-8.36 (m, 2H), 7.86 (t, J=7.5 Hz, 1H), 7.48 (d, J=10.7 Hz, 1H), 7.35 (d, J=7.8 Hz, 1H), 7.25 (d, J=4.9 Hz, 1H), 3.03 (t, J=7.3 Hz, 2H), 2.70 (s, 2H), 2.24 (s, 3H), 1.76-1.70 (m, 3H). LCMS: ESI-MS m/z: 364.3 [M+H]+

Example 113

3-(4-Cyano-3,5-difluorophenyl)-N-(4-methyl-3-(3-methylpyridin-4-yl)-1H-pyrazol-5-yl)propenamide

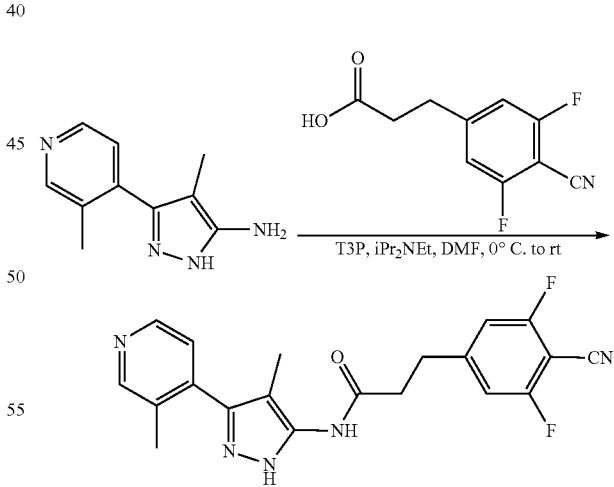

The product was prepared according to General Procedure #1 using Intermediate 20 and Intermediate 8 to afford 3-(4-cyano-3,5-difluorophenyl)-N-(4-methyl-3-(3-methylpyridin-4-yl)-1H-pyrazol-5-yl)propenamide in 36% yield. $^1$H NMR (500 MHz, DMSO-$d_6$) δ 12.6 (s, 1H), 9.77 (s, 1H), 8.51 (d, J=40.8 Hz, 2H), 7.41 (d, J=9.5 Hz, 2H), 7.25 (d, J=4.9 Hz, 1H), 3.04 (t, J=7.3 Hz, 2H), 2.71 (s, 2H), 2.23 (s, 3H), 1.71 (s, 3H). LCMS: ESI-MS m/z: 382.2 [M+H]$^+$.

Example 114

3-(4-Bromophenyl)-N-(1-(pyridin-4-yl)-1H-pyrazol-4-yl)propanamide

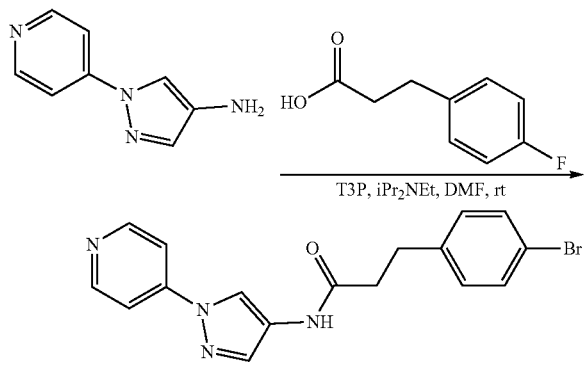

The product was prepared according to General Procedure #1 using Intermediate 21 and 3-(4-bromophenyl)propanoic acid to afford 3-(4-bromophenyl)-N-(1-(pyridin-4-yl)-1H-pyrazol-4-yl)propanamide in 20% yield. $^1$H NMR (400 MHz, DMSO-$d_6$) δ 10.3 (s, 1H), 8.69 (s, 1H), 8.60 (d, J=6.0 Hz, 2H), 7.83-7.82 (m, 3H), 7.47 (d, J=8.4 Hz, 2H), 7.22 (d, J=8.4 Hz, 2H), 2.90 (t, J=7.6 Hz, 2H), 2.62 (t, J=7.4 Hz, 2H). LCMS: ESI-MS m/z: 327.0 [M+H]$^+$.

Example 115

3-(4-Fluorophenyl)-N-(1-(pyridin-4-yl)-1H-pyrazol-4-yl)propenamide

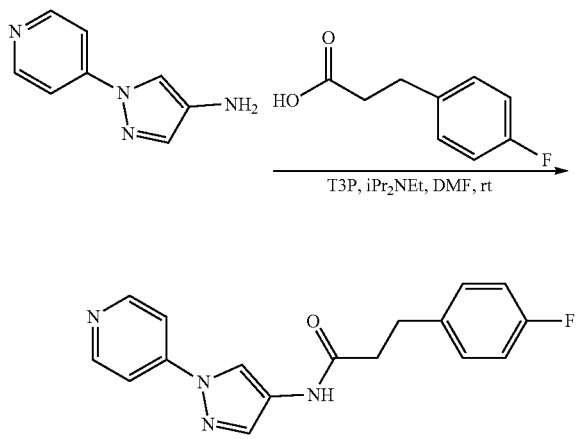 [SMILES: Nc1cnn(-c2ccncc2)c1 ; O=C(O)CCc1ccc(F)cc1 ; O=C(CCc1ccc(F)cc1)Nc1cnn(-c2ccncc2)c1]

The product was prepared according to General Procedure #1 using Intermediate 21 and 3-(4-fluorophenyl)propanoic acid to afford 3-(4-fluorophenyl)-N-(1-(pyridin-4-yl)-1H-pyrazol-4-yl)propenamide in 50% yield. $^1$H NMR (400 MHz, DMSO-$d_6$) δ 10.3 (s, 1H), 8.70 (s, 1H), 8.60 (dd, J=6.4 Hz, 2H), 7.83-7.81 (m, 3H), 7.30-7.26 (m, 2H), 7.13-7.07 (m, 2H), 2.91 (t, J=16.0 Hz, 2H), 2.62 (t, J=15.2 Hz, 2H). LCMS: ESI-MS m/z: 311.0 [M+H]$^+$.

Example 116

3-(4-Chlorophenyl)-N-(4-(hydroxymethyl)-3-(pyridin-4-yl)-1H-pyrazol-5-yl)propanamide

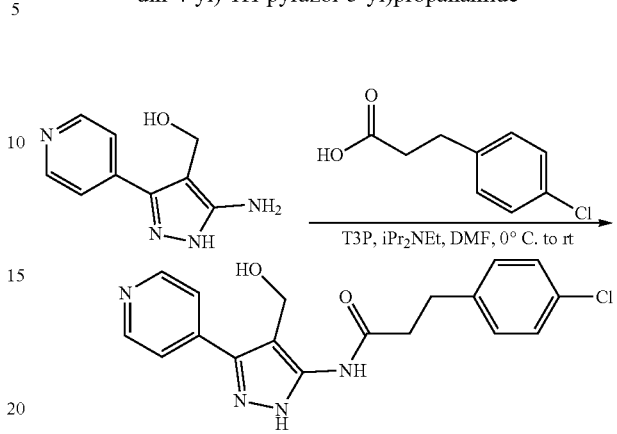

The product was prepared according to General Procedure #1 using Intermediate 22 and 3-(4-chlorophenyl)propanoic acid to afford 3-(4-chlorophenyl)-N-(4-(hydroxymethyl)-3-(pyridin-4-yl)-1H-pyrazol-5-yl)propanamide in 31% yield. $^1$H NMR (400 MHz, CD$_3$OD) δ 8.63 (d, J=22.0 Hz, 2H), 7.88-7.78 (m, 2H), 7.32-7.21 (m, 4H), 4.45-4.38 (m, 2H), 3.04 (t, J=15.2 Hz, 2H), 2.78 (t, J=14.4 Hz, 2H). LCMS: ESI-MS m/z: 357.1 [M+H]$^+$.

Example 117

3-(4-Chloro-3,5-difluorophenyl)-N-(4-(hydroxymethyl)-3-(pyridin-4-yl)-1H-pyrazol-5-yl)propanamide

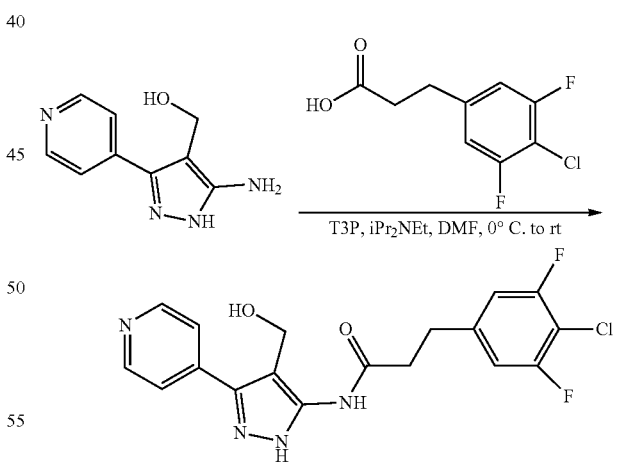

The product was prepared according to General Procedure #1 using Intermediate 22 and Intermediate 9 to afford 3-(4-chloro-3,5-difluorophenyl)-N-(4-(hydroxymethyl)-3-(pyridin-4-yl)-1H-pyrazol-5-yl)propenamide in 33% yield. $^1$H NMR (400 MHz, DMSO-$d_6$) δ 13.3-13.0 (br s, 1H), 10.2-10.0 (br s, 1H), 8.67 (s, 2H), 7.80-7.72 (m, 2H), 7.28 (d, J=8.4 Hz, 2H), 4.90-4.69 (m, 1H), 4.42-3.65 (m, 2H), 2.96 (t, J=7.4 Hz, 2H), 2.78-2.67 (m, 2H). LCMS: ESI-MS m/z: 393.0 [M+H]$^+$.

Example 118

3-(4-Chloro-3-fluorophenyl)-N-(4-(hydroxymethyl)-3-(pyridin-4-yl)-1H-pyrazol-5-yl)propenamide

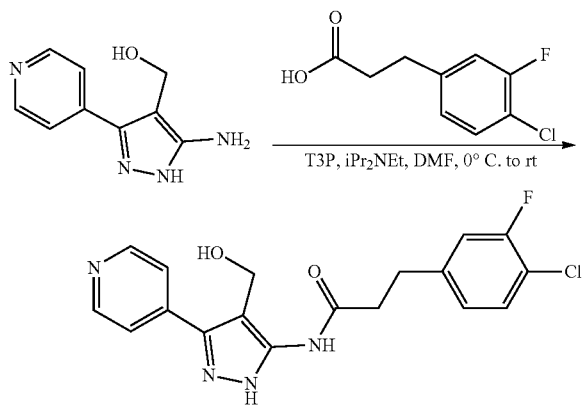

The product was prepared according to General Procedure #1 using Intermediate 22 and 3-(4-chloro-3-fluorophenyl) propanoic acid to afford 3-(4-chloro-3-fluorophenyl)-N-(4-(hydroxymethyl)-3-(pyridin-4-yl)-1H-pyrazol-5-yl)propenamide in 32% yield. $^1$H NMR (400 MHz, DMSO-$d_6$) δ 13.3 (s, 1H), 10.1 (s, 1H), 8.65 (s, 2H), 7.75 (s, 2H), 7.51 (t, J=16.0 Hz, 1H), 7.36 (d, J=10.4 Hz, 1H), 7.16 (d, J=8.4 Hz, 1H), 4.30 (s, 2H), 2.95 (t, J=14.8 Hz, 2H), 2.71 (t, J=14.8 Hz, 2H). LCMS: ESI-MS m/z: 375.0 [M+H]$^+$.

Example 119

N-(4-(Hydroxymethyl)-3-(pyridin-4-yl)-1H-pyrazol-5-yl)-3-(3,4,5-trifluorophenyl)propenamide

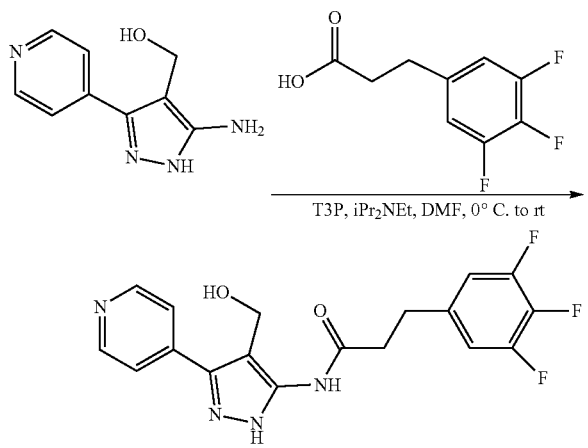

The product was prepared according to General Procedure #1 using Intermediate 22 and 3-(3,4,5-trifluorophenyl)propanoic acid to afford N-(4-(hydroxymethyl)-3-(pyridin-4-yl)-1H-pyrazol-5-yl)-3-(3,4,5-trifluorophenyl)propenamide in 32% yield. $^1$H NMR (400 MHz, DMSO-$d_6$) δ 13.3-13.0 (br s, 1H), 10.2-10.0 (br s, 1H), 8.67 (s, 2H), 7.83-7.72 (m, 2H), 7.28 (dd, J=8.8 Hz, 6.8 Hz, 2H), 4.88-4.71 (m, 1H), 4.38-4.24 (m, 2H), 2.93 (t, J=7.4 Hz, 2H), 2.71-2.67 (m, 2H). LCMS: ESI-MS m/z: 377.0 [M+H]$^+$.

Examples 120 and 121

2-((4-chlorophenyl)sulfinyl)-N-(4-methyl-3-(pyridin-4-yl)-1H-pyrazol-5-yl)acetamide (Ex. 120) and 2-((4-chlorophenyl)sulfonyl)-N-(4-methyl-3-(pyridin-4-yl)-1H-pyrazol-5-yl)acetamide (Ex. 121)

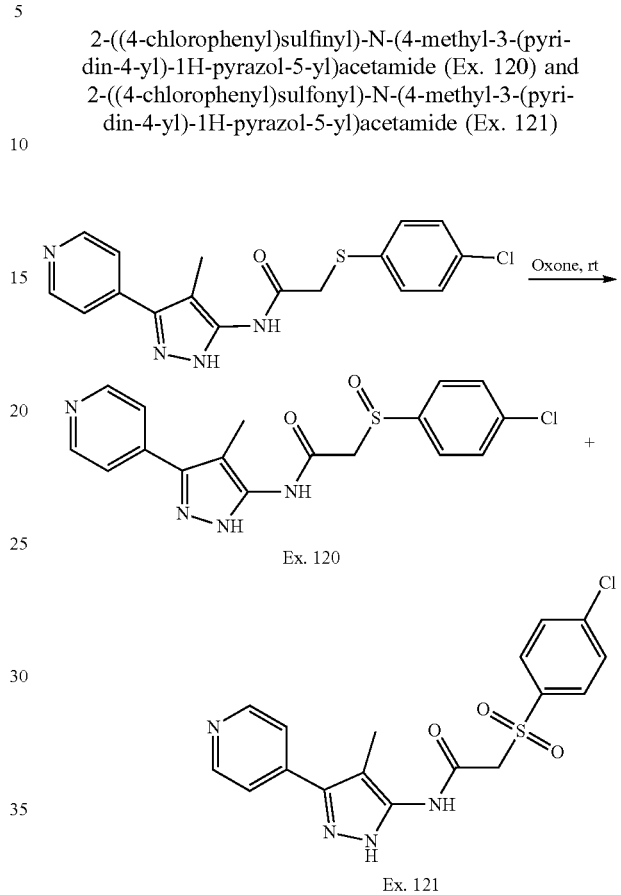

To a solution of 2-((4-chlorophenyl)thio)-N-(4-methyl-3-(pyridin-4-yl)-1H-pyrazol-5-yl)acetamide (Example 63, 65 mg, 0.18 mmol, 1.0 equiv) in DMF (3.0 mL, 0.060 M) was added Oxone® (110 mg, 0.18 mmol, 1.0 equiv) in water (1 mL). The mixture was stirred at rt for 2 h. The mixture was then treated with a saturated aqueous solution of $Na_2SO_3$ (5 mL) and extracted with EtOAc (3×5.0 mL). The combined organic extracts were washed with brine, dried over anhydrous sodium sulfate, filtered, and concentrated in vacuo. The resulting residue was purified by RP-HPLC (Method C, 5-25% MeCN in $H_2O$+10 mM $NH_4HCO_3$+0.025% $NH_3·H_2O$) to afford 2-((4-chlorophenyl)sulfinyl)-N-(4-methyl-3-(pyridin-4-yl)-1H-pyrazol-5-yl)acetamide (Ex. 120) (18 mg, 0.048 mmol, 26% yield) and 2-((4-chlorophenyl)sulfonyl)-N-(4-methyl-3-(pyridin-4-yl)-1H-pyrazol-5-yl)acetamide (Ex. 121) (41 mg, 0.11 mmol 58% yield) as white solids.

Ex. 120: $^1$H NMR (400 MHz, DMSO-$d_6$) δ 13.2 (s, 1H), 10.1 (s, 1H), 8.66 (s, 2H), 7.78 (d, J=8.6 Hz, 2H), 7.70 (d, J=8.6 Hz, 2H), 7.59 (s, 2H), 4.05 (dd, J=61.3, 13.3 Hz, 2H), 2.01 (s, 3H). LCMS: ESI-MS m/z: 375.0 [M+H]$^+$; first eluting peak (retention time=1.64 min).

Ex. 121: $^1$H NMR (400 MHz, DMSO-$d_6$) δ 13.2 (s, 1H), 10.2 (s, 1H), 8.65 (s, 2H), 7.93 (d, J=8.6 Hz, 2H), 7.80-7.71 (m, 2H), 7.58 (s, 2H), 4.66 (d, J=66.9 Hz, 2H), 1.98 (s, 3H). LCMS: ESI-MS m/z: 391.0 [M+H]$^+$; second eluting peak (retention time=1.71 min).

Example 122

3-(4-Chlorophenyl)-N-(4-methoxy-3-(pyridin-4-yl)-1H-pyrazol-5-yl)propanamide

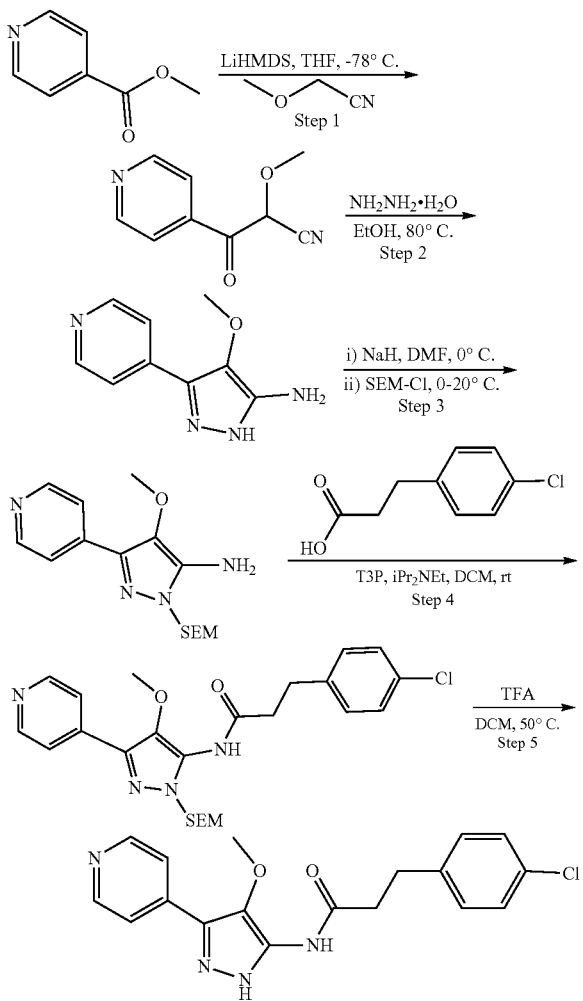

Step 1: 2-Methoxy-3-oxo-3-(pyridin-4-yl)propanenitrile. To a solution of 2-methoxyacetonitrile (210 mg, 3.7 mmol, 2.5 equiv) in anhydrous THF (10 mL, 0.14 M) was added LiHMDS (1.0 M in THF, 3.7 mL, 3.7 mmol, 2.5 equiv) dropwise at −78° C. under a $N_2$ atmosphere. The mixture was then warmed to rt and stirred for 30 min. Subsequently, methyl isonicotinate (200 mg, 1.5 mmol, 1.0 equiv) was added. After 1 h at rt, saturated aqueous solution of $NH_4Cl$ (20 mL) was added. The mixture was extracted with EtOAc (3×20 mL). The organic material was filtered over anhydrous sodium sulfate and concentrated in vacuo to afford 2-methoxy-3-oxo-3-(pyridin-4-yl)propanenitrile (130 mg, 0.73 mmol, 50% yield) as a light yellow liquid. The material was carried forward to the next step without further purification. LCMS: ESI-MS m/z: 177.1 [M+H]$^+$.

Step 2: 4-Methoxy-3-(pyridin-4-yl)-1H-pyrazol-5-amine. A mixture of crude 2-methoxy-3-oxo-3-(pyridin-4-yl)propanenitrile (200 mg, 1.1 mmol, 1.0 equiv) and hydrazine hydrate (210 mg, 3.7 mmol, 3.2 equiv) in EtOH (10 mL, 0.11 M) was stirred at 80° C. for 3 h. The mixture was concentrated in vacuo. The crude product was purified directly by RP-HPLC (Method C, 10-90% MeCN in $H_2O$+10 mM $NH_4HCO_3$+0.025% $NH_3 \cdot H_2O$) Fractions containing the desired mass were combined and concentrated by lyophilization to afford 4-methoxy-3-(pyridin-4-yl)-1H-pyrazol-5-amine (140 mg, 0.73 mmol, 65% yield) as a white solid. LCMS: ESI-MS m/z: 191.1 [M+H]$^+$.

Step 3: 4-Methoxy-3-(pyridin-4-yl)-1-((2-(trimethylsilyl)ethoxy)methyl)-1H-pyrazol-5-amine. A solution of 4-methoxy-3-(pyridin-4-yl)-1H-pyrazol-5-amine (90 mg, 0.47 mmol, 1.0 equiv) in anhydrous DMF (2.0 mL, 0.24 M) under an $N_2$ atmosphere was cooled 0° C. and treated with sodium hydride (60 wt % dispersion in mineral oil, 29 mg, 0.71 mmol, 1.5 equiv). The resulting suspension was stirred for 30 min at 0° C. Subsequently, (2-chloromethoxyethyl)trimethylsilane (117 mg, 0.71 mmol, 1.5 equiv) was added to the mixture, and the reaction was warmed to rt. After 1 h at rt, the mixture was diluted with EtOAc (20 mL) and washed with a saturated aqueous solution of $NH_4Cl$ (2×10 mL). The organic material was filtered over anhydrous sodium sulfate and concentrated in vacuo. The crude product was purified by silica gel column chromatography (0-25% MeOH in DCM) to afford 4-methoxy-3-(pyridin-4-yl)-1-((2-(trimethylsilyl)ethoxy)methyl)-1H-pyrazol-5-amine (100 mg, 0.31 mmol, 66% yield) as a light yellow oil. LCMS: ESI-MS m/z: 321.2 [M+H]$^+$.

Step 4: 3-(4-Chlorophenyl)-N-(4-methoxy-3-(pyridin-4-yl)-1-((2-(trimethylsilyl)ethoxy)methyl)-1H-pyrazol-5-yl)propenamide. The product was prepared according to General Procedure #1 using 4-methoxy-3-(pyridin-4-yl)-1-((2-(trimethylsilyl)ethoxy)methyl)-1H-pyrazol-5-amine and 3-(4-chlorophenyl)propanoic acid to afford 3-(4-chlorophenyl)-N-(4-methoxy-3-(pyridin-4-yl)-1-((2-(trimethylsilyl)ethoxy)methyl)-1H-pyrazol-5-yl)propanamide (70 mg, 0.14 mmol, 46% yield) as a light yellow solid. LCMS: ESI-MS m/z: 487.2 [M+H]$^+$.

Step 5: 3-(4-chlorophenyl)-N-(4-methoxy-3-(pyridin-4-yl)-1H-pyrazol-5-yl)propenamide. The product was prepared according to General Procedure #3 to afford 3-(4-chlorophenyl)-N-(4-methoxy-3-(pyridin-4-yl)-1H-pyrazol-5-yl)propenamide (12 mg, 0.034 mmol, 23% yield) as a white solid. $^1$H NMR (400 MHz, DMSO-$d_6$) δ 13.1 (s, 1H), 10.2 (s, 1H), 8.63-8.52 (m, 2H), 7.79-7.66 (m, 2H), 7.35 (d, J=8.4 Hz, 2H), 7.30 (d, J=8.4 Hz, 2H), 3.63 (s, 3H), 2.91 (t, J=7.6 Hz, 2H), 2.73-2.58 (m, 2H). LCMS: ESI-MS m/z: 357.0 [M+H]$^+$.

Example 123

3-(4-Chlorophenyl)-N-(4-cyclopropyl-3-(pyridin-4-yl)-1H-pyrazol-5-yl)propanamide

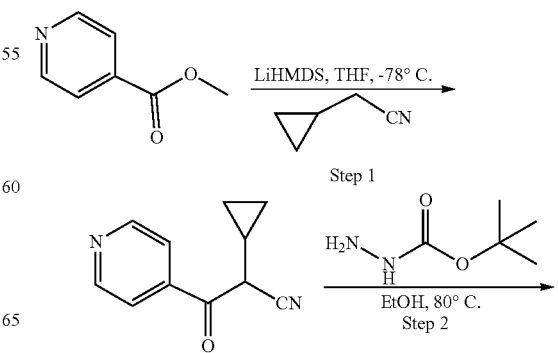

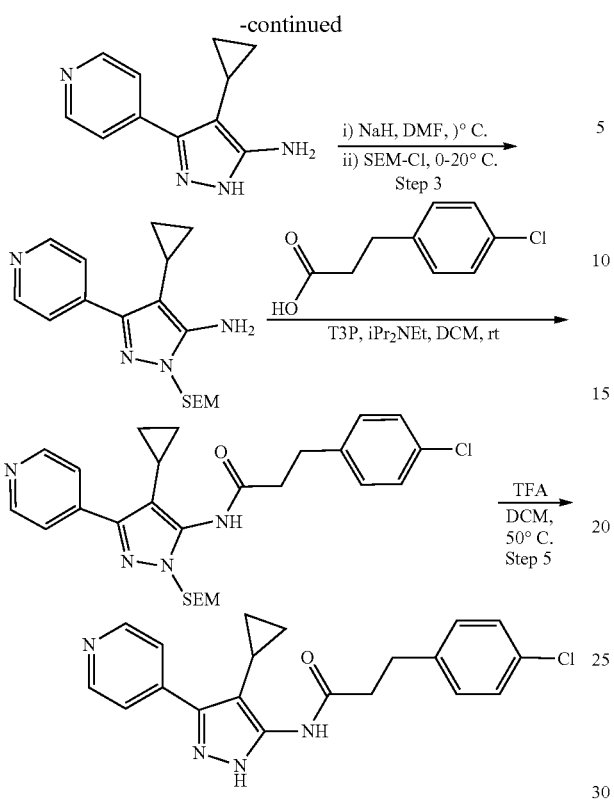

Step 1: 2-Cyclopropyl-3-oxo-3-(pyridin-4-yl)propanenitrile. To a solution of 2-cyclopropylacetonitrile (240 mg, 2.9 mmol, 1.9 equiv) in anhydrous THF (10 mL, 0.15 M) was added LiHMDS (1.0 M solution in THF, 3.7 mL, 3.7 mmol, 2.5 equiv) dropwise at −78° C. under an atmosphere of nitrogen gas. After the addition, the mixture was stirred at that temperature for 30 min. Then, methyl isonicotinate (200 mg, 1.5 mmol, 1.0 equiv) was added, and the mixture was stirred at rt for 1 h. The mixture was then treated with a saturated solution of NH$_4$Cl (30 mL) and extracted with ethyl acetate (3×20 mL). The combined organic fractions were dried over anhydrous sodium sulfate, filtered, and concentrated in vacuo to get afford crude 2-cyclopropyl-3-oxo-3-(pyridin-4-yl)propanenitrile (230 mg, 0.62 mmol, 42% yield, 50% purity) as a light yellow liquid. LCMS: ESI-MS m/z: 187.0 [M+H]$^+$.

Step 2: 4-Cyclopropyl-3-(pyridin-4-yl)-1H-pyrazol-5-amine. A mixture of crude 2-cyclopropyl-3-oxo-3-(pyridin-4-yl)propanenitrile (230 mg, 0.62 mmol, 50% purity, 1.0 equiv) and tert-butyl carbazate (120 mg, 0.92 mmol, 1.5 equiv) in ethanol (10 mL, 0.062 M) was stirred at reflux for 3 h. LCMS indicated product formation though the Boc group had cleaved during the reaction. The mixture was concentrated in vacuo, and the residue was purified directly by RP-HPLC (Method C, 10-90% MeCN in H$_2$O+10 mM NH$_4$HCO$_3$+0.025% NH$_3$·H$_2$O) to afford 4-cyclopropyl-3-(pyridin-4-yl)-1H-pyrazol-5-amine (100 mg, 0.50 mmol, 81% yield) as a white solid. LCMS: ESI-MS m/z: 201.1 [M+H]$^+$.

Step 3: 3-(4-chlorophenyl)-N-(4-cyclopropyl-3-(pyridin-4-yl)-1H-pyrazol-5-yl)propanamide. The product was prepared according to General Procedure #1 using 4-cyclopropyl-3-(pyridin-4-yl)-1H-pyrazol-5-amine and 3-(4-chlorophenyl)propanoic acid to afford 3-(4-chlorophenyl)-N-(4-cyclopropyl-3-(pyridin-4-yl)-1H-pyrazol-5-yl)propanamide (20 mg, 0.054 mmol, 22% yield) as a white solid. $^1$H NMR (400 MHz, DMSO-d$_6$) δ 13.1 (s, 1H), 9.66 (s, 1H), 8.67 (d, J=5.2 Hz, 2H), 7.73 (d, J=5.2 Hz, 2H), 7.33 (dd, J=8.4 Hz, 19.2 Hz, 4H), 2.95-2.90 (m, 2H), 2.72-2.61 (m, 2H), 1.66-1.64 (m, 1H), 0.79-0.66 (m, 2H), 0.23-0.14 (m, 2H). LCMS: ESI-MS m/z: 367.0 [M+H]$^+$.

Example 124

3-(4-Chlorophenyl)-N-[4-methyl-3-(pyridin-4-yl)-1H-pyrazol-5-yl]propanethioamide

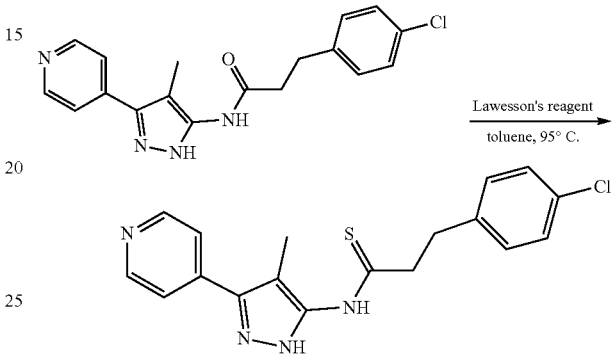

A suspension of 3-(4-chlorophenyl)-N-[4-methyl-3-(pyridin-4-yl)-1H-pyrazol-5-yl]propanamide (Example 19, 10 mg, 0.020 mmol, 1.0 equiv) in toluene (300 μL, 0.067 M) was treated with Lawesson's reagent (78 μL, 0.060 mmol, 3.0 equiv) and the reaction mixture was heated to 95° C. for 14 h. The reaction mixture was then cooled to rt and concentrated in vacuo. The residue was diluted with water (1.0 mL) and purified directly by RP-HPLC (Method A, 10-100% MeCN in H$_2$O+0.1% TFA). Fractions containing the desired product were combined and concentrated by lyophilization to afford 3-(4-chlorophenyl)-N-[4-methyl-3-(pyridin-4-yl)-1H-pyrazol-5-yl]propanethioamide (4.4 mg, 0.010 mmol, 44% yield) as a white solid, trifluoroacetic acid salt. LCMS: ESI-MS m/z: 357.1 [M+H]$^+$.

Example 125

3-(4-Chlorophenyl)-N-[3-(pyridin-4-yl)-4-(trifluoromethyl)-1H-pyrazol-5-yl]propanamide

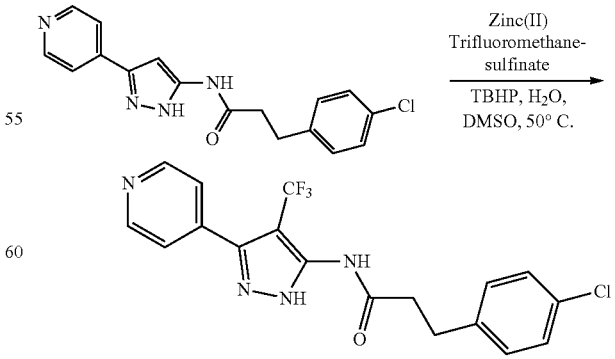

To a solution of 3-(4-chlorophenyl)-N-[3-(pyridin-4-yl)-1H-pyrazol-5-yl]propanamide (Example 98, 16 mg, 0.040 mmol, 1.0 equiv) in DMSO (300 μL, 0.13 M) was added zinc(II) bis(trifluoromethyl)-λ⁶-sulfanoylolate (48 mg, 0.18 mmol, 5.0 equiv), followed by TBHP (70 wt. % in water, 32 μL, 0.36, 10 equiv). The reaction mixture was heated to 50° C. and stirred for 2 h, after which it was cooled to rt and diluted with MeCN:water (1:1, 1 mL). The material was directly purified by RP-HPLC (Method A, 10-100% MeCN in H₂O+0.1% TFA). Fractions containing the desired product were combined and concentrated by lyophilization to afford 3-(4-chlorophenyl)-N-[3-(pyridin-4-yl)-4-(trifluoromethyl)-1H-pyrazol-5-yl]propanamide (2.0 mg, 0.030 mmol, 11% yield) as white solid, trifluoroacetic acid salt. LCMS: ESI-MS m/z: 463.1 [M+H]⁺.

Example 126

N-[5-Chloro-1-(pyridin-4-yl)-1H-pyrazol-4-yl]-3-(3-chlorophenyl)propanamide

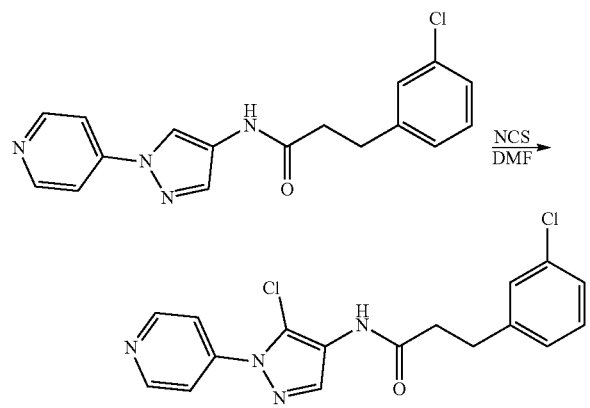

A solution of 3-(3-chlorophenyl)-N-[1-(pyridin-4-yl)-1H-pyrazol-4-yl]propanamide (9.7 mg, 0.030 mmol, 1.0 equiv) in DMF (300 μL) was treated with N-chlorosuccinimide (5.1 mg, 0.040 mmol, 1.3 equiv) and the reaction mixture was heated to 40° C. and stirred for 24 h. The reaction mixture was then cooled to rt and purified directly by silica gel column chromatography (100% EtOAc) to afford N-[5-chloro-1-(pyridin-4-yl)-1H-pyrazol-4-yl]-3-(3-chlorophenyl)propanamide (4.8 mg, 0.010 mmol, 45% yield) as a white solid. ¹H NMR (400 MHz, CDCl₃) δ 8.74 (d, J=5.5 Hz, 2H), 8.37 (s, 1H), 7.79 (d, J=5.3 Hz, 2H), 7.28-7.14 (m, 4H), 6.89 (s, 1H), 3.08 (t, J=7.5 Hz, 2H), 2.76 (t, J=7.5 Hz, 2H). LCMS: ESI-MS m/z: 361.1 [M+H]⁺.

Example 127

N-[5-Bromo-1-(pyridin-4-yl)-1H-pyrazol-4-yl]-3-(4-chloro-3,5-difluorophenyl)propanamide

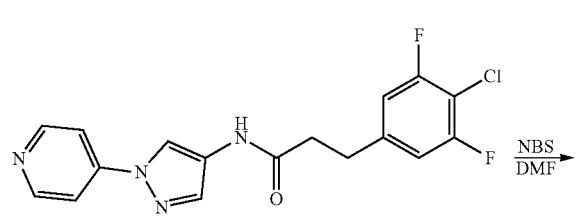

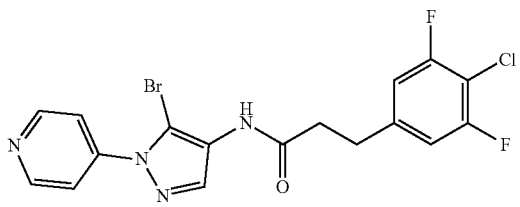

A solution of 3-(4-chloro-3,5-difluorophenyl)-N-[1-(pyridin-4-yl)-1H-pyrazol-4-yl]propanamide (Example 88, 23 mg, 0.060 mmol, 1.0 equiv) in DMF (630 μL, 0.10 M) was treated with N-bromosuccinimide (18 mg, 0.10 mmol, 1.6 equiv). After stirring at rt for 48 h, the reaction mixture was diluted with EtOAc (20 mL) and a saturated aqueous solution of NH₄Cl (20 mL). The layers were separated and the aqueous layer was extracted with ethyl acetate (3×10 mL). The combined organic fractions were washed with brine (30 mL), dried over anhydrous sodium sulfate, filtered, and concentrated in vacuo. The crude material was purified by silica gel column chromatography (100% EtOAc) to afford N-[5-bromo-1-(pyridin-4-yl)-1H-pyrazol-4-yl]-3-(4-chloro-3,5-difluorophenyl)propanamide (13 mg, 0.030 mmol, 47% yield) as a white solid. ¹H NMR (400 MHz, CDCl₃) δ 8.76 (d, J=5.5 Hz, 2H), 8.40 (d, J=1.8 Hz, 1H), 7.81 (s, 2H), 6.96-6.89 (m, 2H), 3.08 (t, J=7.3 Hz, 2H), 2.76 (t, J=7.3 Hz, 2H). LCMS: ESI-MS m/z: 443.0 [M+H]⁺.

Example 128

N-(4-Chloro-3-(pyridin-4-yl)-1H-pyrazol-5-yl)-3-(4-cyano-3,5-difluorophenyl) propenamide

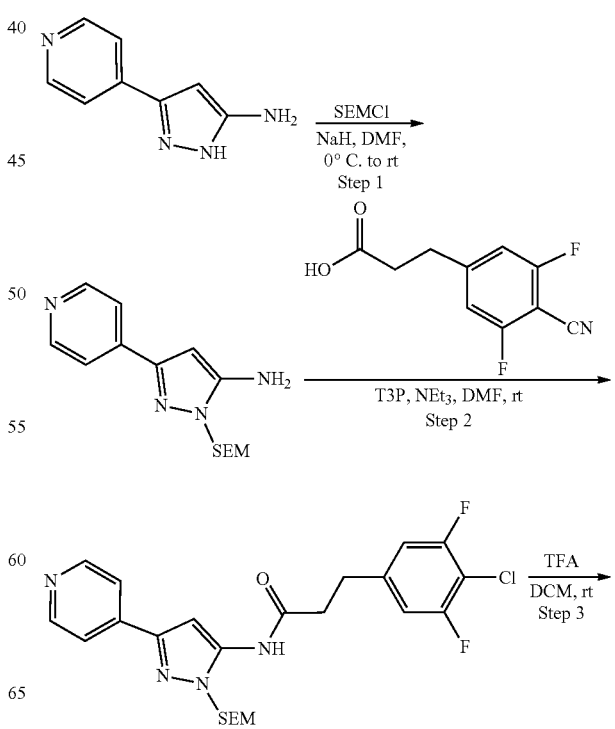

-continued

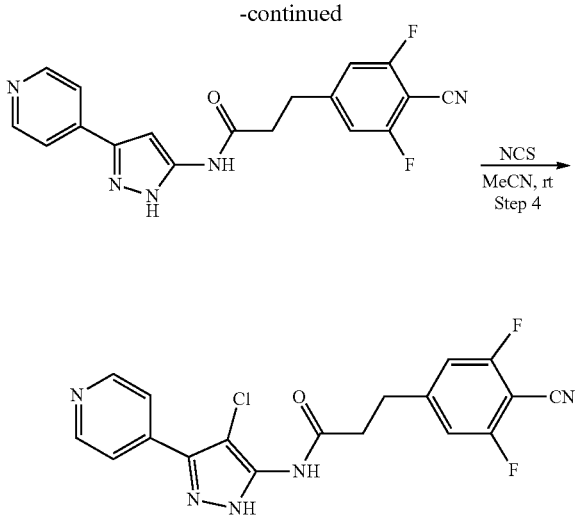

Step 1: 3-(Pyridin-4-yl)-1-((2-(trimethylsilyl)ethoxy)methyl)-1H-pyrazol-5-amine. To a solution of 3-(pyridin-4-yl)-1H-pyrazol-5-amine (Intermediate 13, 500 mg, 3.1 mmol, 1.0 equiv) in anhydrous DMF (10 mL, 0.31 M) was added sodium hydride (60 wt % dispersion in mineral oil, 190 mg, 4.7 mmol, 1.5 equiv) at 0° C. under an atmosphere of nitrogen gas. After the addition, the mixture was stirred at 0° C. for 40 min. Then SEM-Cl (780 mg, 4.7 mmol, 1.4 equiv) was added dropwise at 0° C. After the addition, the mixture was stirred at 0° C. for 2 h. The mixture was then treated with EtOAc (50 mL), washed with a saturated solution of NH$_4$Cl (2×30 mL).

The organic fraction was separated and concentrated in vacuo, and the resulting residue was purified by silica gel column chromatography (5% DCM in MeOH) to afford 3-(pyridin-4-yl)-1-((2-(trimethylsilyl)ethoxy)methyl)-1H-pyrazol-5-amine (500 mg, 1.7 mmol, 55% yield) as a light yellow solid. LCMS: ESI-MS m/z: 291.0 [M+H]$^+$.

Step 2: 3-(4-Cyano-3,5-difluorophenyl)-N-(3-(pyridin-4-yl)-1-((2-(trimethylsilyl)ethoxy) methyl)-1H-pyrazol-5-yl)propenamide. To a stirred solution of 3-(pyridin-4-yl)-1-((2-(trimethylsilyl)ethoxy)methyl)-1H-pyrazol-5-amine (22 mg, 0.080 mmol, 1.0 equiv) in DCM (5 mL, 0.016 M) was added Intermediate 8 (21 mg, 0.10 mmol, 1.3 equiv), T3P (50 w/v % in EtOAc, 96 mg, 0.15 mmol, 1.9 equiv) at 0° C. The mixture was stirred at rt for 30 min, then DIPEA (20 mg, 0.15 mmol, 1.9 equiv) was added. The mixture was stirred at rt for 1.5 h. The mixture was diluted with ethyl acetate (30 mL) and then was washed with water (2×10 mL), followed by brine (10 mL). The organic fraction was dried over anhydrous sodium sulfate, filtered, and concentrated in vacuo to afford the crude product. The crude material was purified by silica gel column chromatography (50% EtOAc in petroleum ether) to afford 3-(4-cyano-3,5-difluorophenyl)-N-(3-(pyridin-4-yl)-1-((2-(trimethylsilyl)ethoxy)methyl)-1H-pyrazol-5-yl)propenamide (14 mg, 36% yield) as a white solid. LCMS: ESI-MS m/z: 484.0 [M+H]$^+$.

Step 3: 3-(4-Cyano-3,5-difluorophenyl)-N-(3-(pyridin-4-yl)-1H-pyrazol-5-yl)propenamide. To a stirred solution of 3-(4-cyano-3,5-difluorophenyl)-N-(3-(pyridin-4-yl)-1-((2-(trimethylsilyl)ethoxy) methyl)-1H-pyrazol-5-yl)propenamide (14 mg, 0.030 mmol, 1.0 equiv) in DCM (1 mL, 0.030 M) was added TFA (0.20 mL, 2.7 mmol, 90 equiv) at rt. The mixture was stirred at rt for 1 h, concentrated in vacuo, and then the resulting residue was treated with ammonia in methanol (7M) to adjust to pH 8, and concentrated again in vacuo to afford the crude product. The crude material was purified by silica gel column chromatography (5% MeOH in DCM) to afford 3-(4-cyano-3,5-difluorophenyl)-N-(3-(pyridin-4-yl)-1H-pyrazol-5-yl)propenamide (5.0 mg, 47% yield) as a white solid. LCMS: ESI-MS m/z: 354.0 [M+H]$^+$.

Step 4: N-(4-Chloro-3-(pyridin-4-yl)-1H-pyrazol-5-yl)-3-(4-cyano-3,5-difluorophenyl) propenamide. To a stirred solution of 3-(4-cyano-3,5-difluorophenyl)-N-(3-(pyridin-4-yl)-1H-pyrazol-5-yl)propenamide (18 mg, 0.050 mmol, 1.0 equiv) in acetonitrile (3 mL, 0.017 M) was added NCS (7.1 mg, 0.050 mmol, 1.0 equiv) at 0° C. The mixture was stirred at rt for 1 h, concentrated in vacuo, then purified directly by silica gel column chromatography (5% MeOH in DCM) to afford N-(4-chloro-3-(pyridin-4-yl)-1H-pyrazol-5-yl)-3-(4-cyano-3,5-difluorophenyl) propenamide (10 mg, 52% yield) as a white solid. $^1$H NMR (400 MHz, DMSO-d$_6$) δ 13.7 (s, 1H), 10.4 (s, 1H), 8.70 (s, 2H), 7.80 (s, 2H), 7.42 (d, J=9.6 Hz, 2H), 3.04 (t, J=14.4 Hz, 2H), 2.79 (t, J=19.6 Hz, 2H). LCMS: ESI-MS m/z: 388.0 [M+H]$^+$.

Example 129

N-(4-Chloro-3-(pyridin-4-yl)-1H-pyrazol-5-yl)-3-(4-cyano-3-fluorophenyl)propenamide

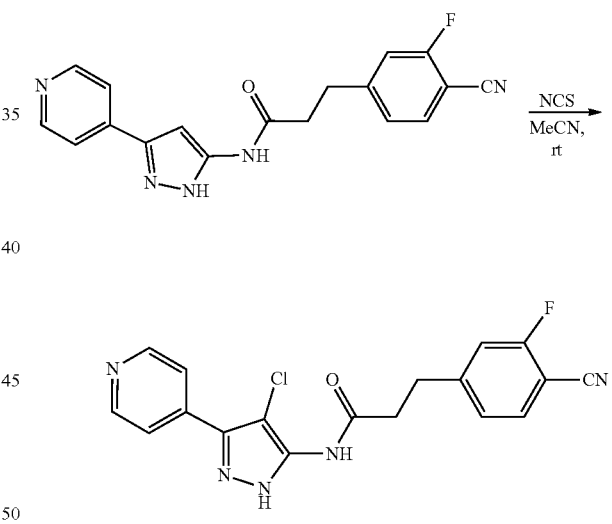

To a stirred solution of 3-(4-cyano-3-fluorophenyl)-N-(3-(pyridin-4-yl)-1H-pyrazol-5-yl)propanamide (12 mg, 0.036 mmol, 1.0 equiv) in anhydrous DMF (1 mL, 0.036 M) was added NCS (7.1 mg, 0.050 mmol, 1.4 equiv) at 0° C. After the addition, the mixture was stirred at rt for 1 h, concentrated in vacuo, and purified directly by RP-HPLC (Method C, 10-90% MeCN in H$_2$O+10 mM NH$_4$HCO$_3$+0.025% NH$_3$·H$_2$O) to afford N-(4-chloro-3-(pyridin-4-yl)-1H-pyrazol-5-yl)-3-(4-cyano-3-fluorophenyl)propenamide (5.0 mg, 0.014 mmol, 38% yield) as a white solid. $^1$H NMR (400 MHz, DMSO-d$_6$) δ 13.7 (s, 1H), 9.97 (s, 1H), 8.69 (s, 2H), 7.87 (t, J=15.2 Hz, 1H), 7.80 (d, J=4.8 Hz, 2H), 7.49 (d, J=10.4 Hz, 1H), 7.35 (d, J=8.0 Hz, 1H), 3.03 (t, J=14.8 Hz, 2H), 2.73 (t, J=15.2 Hz, 2H). LCMS: ESI-MS m/z: 370.2 [M+H]$^+$.

Example 130

4-Chlorobenzyl (4-methyl-3-(pyridin-4-yl)-1H-pyrazol-5-yl)carbamate

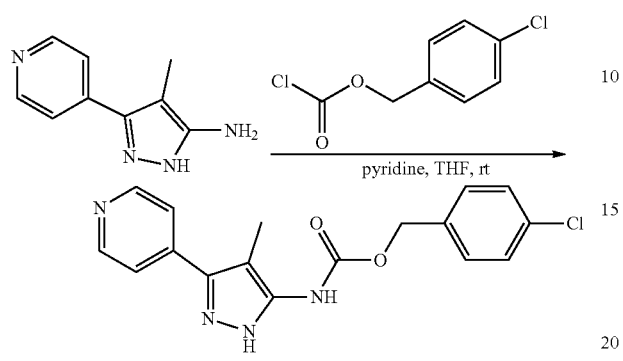

Pyridine (13 mg, 0.16 mmol, 1.5 equiv) was added to a solution of Intermediate 1 (22 mg, 0.12 mmol, 1.1 equiv) and 4-chlorobenzyl carbonochloridate (22 mg, 0.11 mmol, 1.0 equiv) in anhydrous THF (5 ml, 0.022 M) and was stirred for 2 h at rt. The mixture was then concentrated in vacuo and directly purified by RP-HPLC (Method A, 10-90% MeCN in $H_2O$+0.1% TFA) to afford 4-chlorobenzyl (4-methyl-3-(pyridin-4-yl)-1H-pyrazol-5-yl)carbamate (5.0 mg, 10% yield) as a white solid, trifluoroacetic acid salt. $^1$H NMR (400 MHz, DMSO-$d_6$) δ 9.58 (s, 1H), 8.86-8.65 (m, 2H), 7.92 (s, 2H), 7.46 (d, J=5.9 Hz, 4H), 5.14 (s, 2H), 2.11 (s, 3H). LCMS: ESI-MS m/z: 343.1 [M+H]$^+$.

Example 131

1-(4-Chlorobenzyl)-1-methyl-3-(4-methyl-3-(pyridin-4-yl)-1H-pyrazol-5-yl)urea

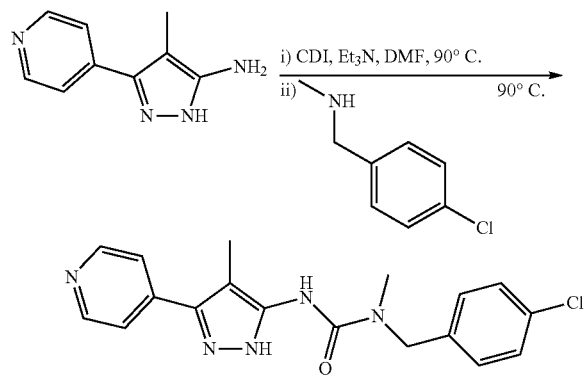

A solution of 4-methyl-3-(pyridin-4-yl)-1H-pyrazol-5-amine (50 mg, 0.29 mmol, 1.0 equiv) and CDI (70 mg, 0.43 mmol, 1.5 equiv) in DMF (1.5 mL, 0.19 M) was treated with triethylamine (0.16 mL, 1.2 mmol, 4 equiv), and the resulting solution was heated to 90° C. and stirred for 2 h. The reaction mixture was then cooled to rt and treated with 1-(4-chlorophenyl)-N-methylmethanamine (45 mg, 0.29 mmol, 1.0 equiv). Heating was then resumed at 90° C. and the reaction was stirred for a subsequent 6 h. The reaction mixture was cooled to rt and purified directly by RP-HPLC (Method A, 5-100% MeCN in $H_2O$+0.1% TFA) to give 1-(4-Chlorobenzyl)-1-methyl-3-(4-methyl-3-(pyridin-4-yl)-1H-pyrazol-5-yl)urea (34 mg, 25% yield) as an off-white solid, trifluoroacetic acid salt. $^1$H NMR (400 MHz, DMSO-$d_6$) δ 8.80-8.82 (m, 2H), 8.55 (s, 1H), 8.09 (br s, 2H), 7.42-7.46 (m, 2H), 7.29-7.32 (m, 2H), 4.54 (s, 2H), 2.93 (s, 3H), 2.14 (s, 3H). LCMS: ESI-MS m/z: 356.2 [M+H]$^+$.

Examples 132 and 133

3-(4-Chlorophenyl)-N-(1-methyl-5-(pyridin-4-yl)-1H-imidazol-2-yl)propenamide and 3-(4-chlorophenyl)-N-methyl-N-(1-methyl-5-(pyridin-4-yl)-1H-imidazol-2-yl)propanamide

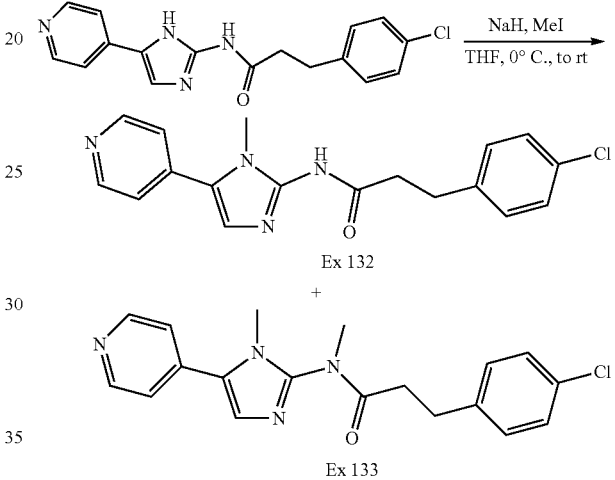

A solution of 3-(4-chlorophenyl)-N-(5-(pyridin-4-yl)-1H-imidazol-2-yl)propenamide (Example 108, 40 mg, 0.091 mmol, 1 equiv) in anhydrous THF (1.0 mL, 0.091 M) was cooled to 0° C. and treated with NaH (60 wt % dispersion in mineral oil, 7.3 mg, 0.18 mmol, 2.0 equiv). The resulting suspension was stirred at 0° C. for 15 min, then treated with methyl iodide (0.0073 mL, 0.12 mmol, 1.2 equiv).

The reaction mixture was then warmed to rt and stirred for 0.5 h until the starting material was consumed (as monitored by LCSM). The mixture was the purified directly by RP-HPLC (Method A, 5-100% MeCN in $H_2O$+0.1% TFA) to give (Ex. 132) 3-(4-chlorophenyl)-N-(1-methyl-5-(pyridin-4-yl)-1H-imidazol-2-yl)propenamide (3.5 mg, 0.0077 mmol, 8.5% yield) and (Ex. 133) 3-(4-chlorophenyl)-N-methyl-N-(1-methyl-5-(pyridin-4-yl)-1H-imidazol-2-yl)propenamide (7.0 mg, 0.015 mmol, 16% yield), both as white solid, trifluoroacetic acid salts.

Ex. 132: 3-(4-Chlorophenyl)-N-(1-methyl-5-(pyridin-4-yl)-1H-imidazol-2-yl)propenamide: $^1$H NMR (400 MHz, CD$_3$OD) δ 8.63 (dd, J=7.1, 2.1 Hz, 2H), 8.33-8.18 (m, 2H), 8.00 (d, J=2.0 Hz, 1H), 7.35-7.19 (m, 4H), 4.27 (s, 3H), 3.03 (t, J=7.5 Hz, 2H), 2.77 (t, J=7.6, 2H). LCMS: ESI-MS m/z: 341.1 [M+H]$^+$; second eluting peak (retention time=0.82 min).

Ex. 133: 3-(4-Chlorophenyl)-N-methyl-N-(1-methyl-5-(pyridin-4-yl)-1H-imidazol-2-yl)propenamide: $^1$H NMR (400 MHz, CD$_3$OD) δ 8.71-8.63 (m, 2H), 8.30-8.18 (m, 2H), 8.16 (s, 1H), 7.41-7.24 (m, 4H), 4.29 (s, 3H), 3.51 (s, 3H), 3.04 (t, J=7.4 Hz, 2H), 2.82 (t, 0.1=7.4 Hz, 2H). LCMS: ESI-MS m/z: 355.2 [M+H]⁺; first eluting peak (retention time=0.80 min).

Example 134

3-(4-Chlorophenyl)-N-methyl-N-(1-(pyridin-4-yl)-1H-pyrazol-4-yl)propanamide

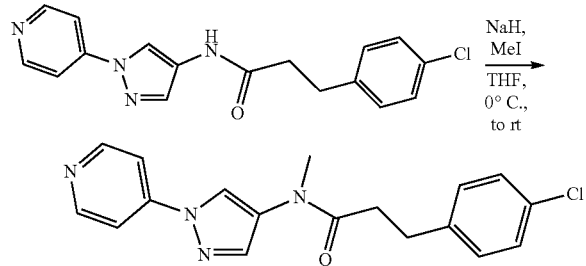

A solution of 3-(4-chlorophenyl)-N-(1-(pyridin-4-yl)-1H-pyrazol-4-yl)propanamide (Example 89, 40 mg, 0.12 mmol, 1 equiv) in anhydrous THF (1.0 mL, 0.12 M) was cooled to 0° C. and treated with NaH (60 wt % dispersion in mineral oil, 11 mg, 0.27 mmol, 2.2 equiv). The resulting suspension was stirred at 0° C. for 15 min, then treated with methyl iodide (0.011 mL, 0.18 mmol, 1.5 equiv). The reaction mixture was then warmed to rt and stirred for 3 h until the starting material was consumed (as monitored by LCSM). The mixture was the purified directly by RP-HPLC (Method A, 10-100% MeCN in H₂O+0.1% TFA) to give 3-(4-chlorophenyl)-N-methyl-N-(1-(pyridin-4-yl)-1H-pyrazol-4-yl)propenamide (30 mg, 0.066 mmol, 54% yield) as a white solid, trifluoroacetic acid salt. LCMS: ESI-MS m/z: 341.1 [M+H]⁺.

Example 135

2-(4-Chlorophenyl)-N-(4-methyl-3-(pyridin-4-yl)-1H-pyrazol-5-yl)cyclopropane-1-carboxamide

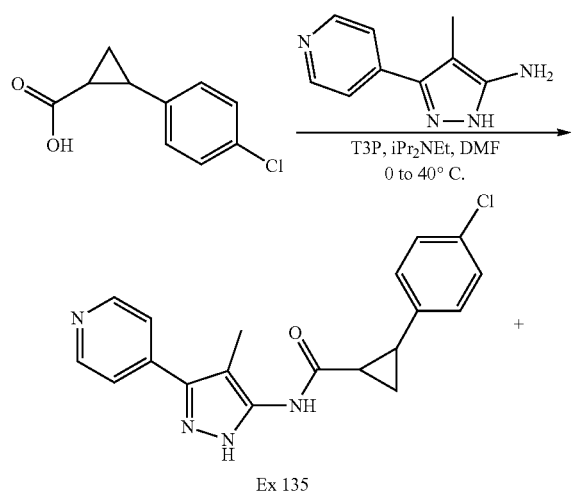

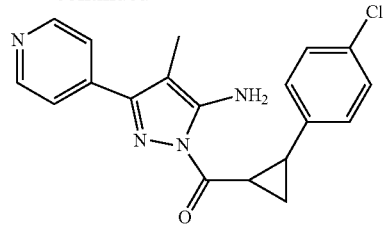

A vial was charged with 2-(4-chlorophenyl)cyclopropane-1-carboxylic acid (95 mg, 0.48 mmol, 1.2 equiv). After dissolving in DMF (1.0 mL, 0.40 M), the solution was cooled to 0° C. and DIPEA (100 mg, 0.80 mmol, 2.0 equiv) and T3P (50% w/v % solution in DMF, 380 mg, 0.60 mmol, 1.5 equiv) were added. After 5 min at rt, 4-methyl-3-(pyridin-4-yl)-1H-pyrazol-5-amine (70 mg, 0.40 mmol, 1.0 equiv) was subsequently added. The solution was stirred at 40° C. for 4 h. The crude material was purified directly by RP-HPLC (Method A, 10-35% MeCN in H₂O+0.1% TFA). Fractions containing the desired mass were combined and concentrated by lyophilization to afford 2-(4-chlorophenyl)-N-(4-methyl-3-(pyridin-4-yl)-1H-pyrazol-5-yl)cyclopropane-1-carboxamide (P1, Ex. 135), 100 mg, 0.21 mmol, 53% yield) and the regioisomer (5-amino-4-methyl-3-(pyridin-4-yl)-1H-pyrazol-1-yl)(2-(4-chlorophenyl)cyclopropyl)methanone (P2), 83 mg, 0.18 mmol, 44% yield) as a white and pale yellow solid respectively, trifluoroacetic acid salts.

P1 (Ex. 135): LCSM: ESI-MS m/z: 353.1 [M+H]⁺; first eluting peak (retention time=1.09 min).

P2: LCMS: ESI-MS m/z: 353.1 [M+H]⁺; second eluting peak (retention time=1.32 min).

Example 136

4-Chlorobenzyl (5-methyl-1-(pyridin-4-yl)-1H-pyrazol-4-yl)carbamate

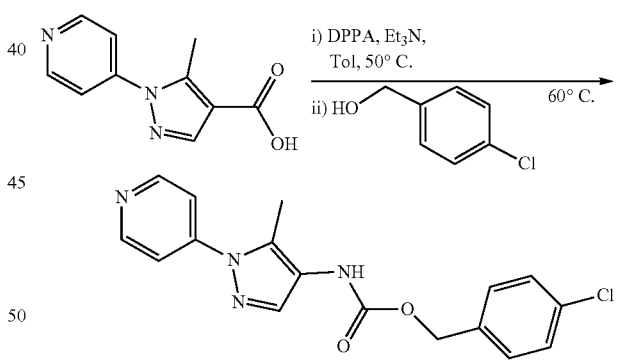

A vial was charged with 5-methyl-1-(pyridin-4-yl)-1H-pyrazole-4-carboxylic acid (100 mg, 0.49 mmol, 1.0 equiv). After dissolving in anhydrous toluene (3.0 mL, 0.16 M), triethylamine (120 mg, 1.2 mmol, 2.5 equiv) and DPPA (270 mg, 0.98 mmol, 2.0 equiv) were subsequently added and the mixture was heated to 50° C. After 17 h, (4-chlorophenyl)methanol (84 mg, 0.59 mmol, 1.2 equiv) was added. The solution was heated to 60° C. and stirred for 4 h. The crude material was purified directly by RP-HPLC (Method A, 10-90 MeCN in H₂O+0.1% TFA). Fractions containing the desired mass were combined and concentrated by lyophilization. The material was subsequently recrystallized in hexanes to afford 4-chlorobenzyl (5-methyl-1-(pyridin-4-yl)-1H-pyrazol-4-yl)carbamate (2.0 mg, 0.0044 mmol, 0.90% yield) as a white solid, trifluoroacetic acid salt. LCMS: ESI-MS m/z: 343.1 [M+H]⁺.

Example 137

3-(4-Chlorophenyl)-N-(5-methyl-1-(pyridin-4-yl)-1H-pyrazol-4-yl)propanethioamide

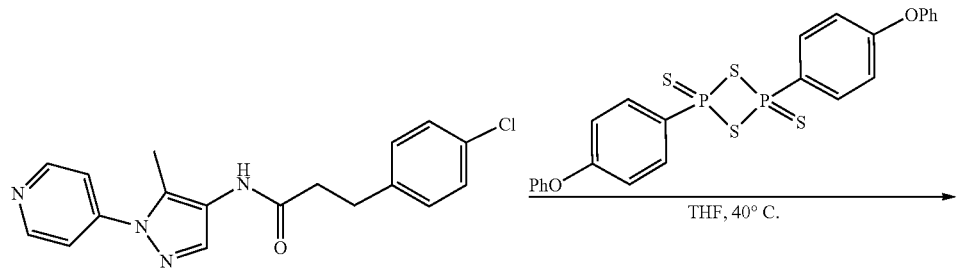

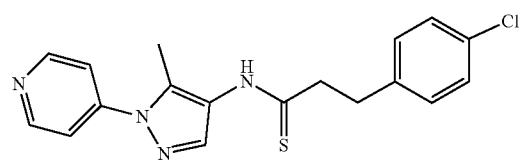

A vial was charged with 3-(4-chlorophenyl)-N-(5-methyl-1-(pyridin-4-yl)-1H-pyrazol-4-yl)propanamide (Example 86, 20 mg, 0.044 mmol, 1.0 equiv). After dissolving in THF (0.60 mL, 0.073 M), 2,4-bis(4-phenoxyphenyl)-1,3-dithia-2,4-diphosphetane 2,4-disulfide (67 mg, 0.13 mmol, 2.9 equiv) was subsequently added. The solution was heated to 40° C. and stirred for 2 h. The reaction mixture was quenched with water, filtered, and purified directly by RP-HPLC (Method A, 10-50% MeCN in $H_2O$+0.10% TFA). Fractions containing the desired mass were combined and concentrated by lyophilization to afford 3-(4-chlorophenyl)-N-(5-methyl-1-(pyridin-4-yl)-1H-pyrazol-4-yl)propanethioamide (1.4 mg, 0.0030 mmol, 6.7% yield) as a solid, trifluoroacetic acid salt. LCMS: ESI-MS m/z: 357.1 [M+H]$^+$.

Example 138

4-(4-Chlorophenyl)-1-(4-methyl-3-(pyridin-4-yl)-1H-pyrazol-5-yl)piperidin-2-one

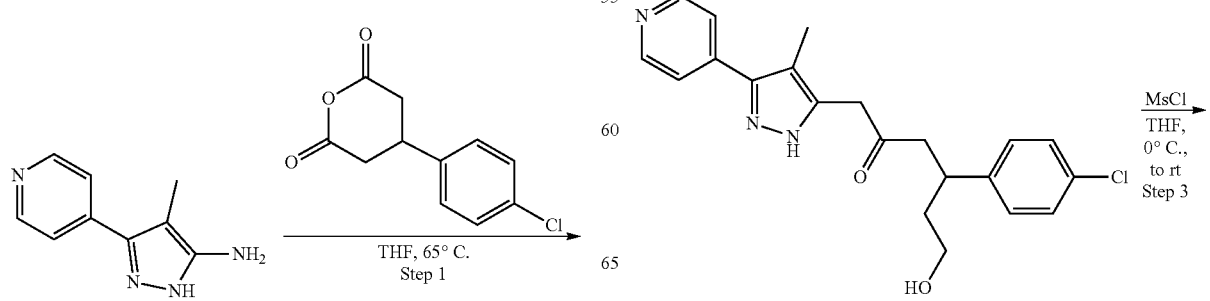

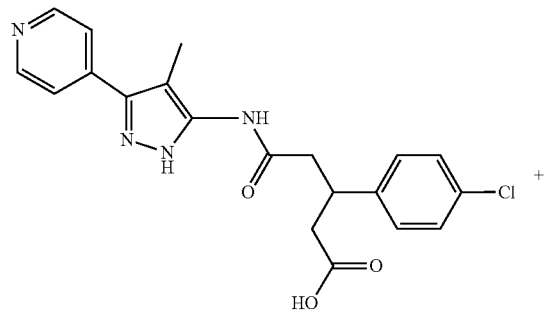

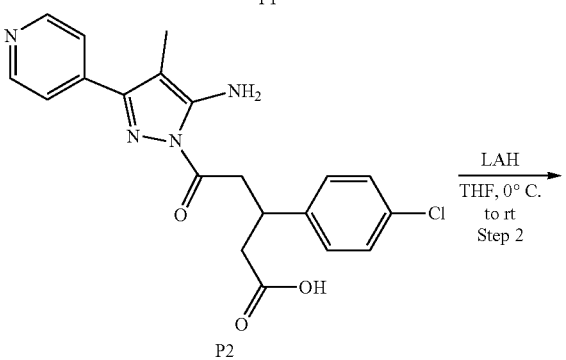

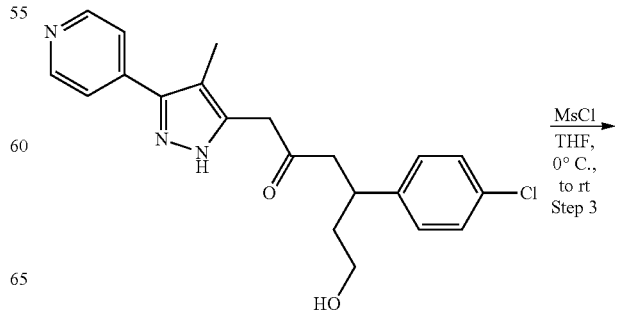

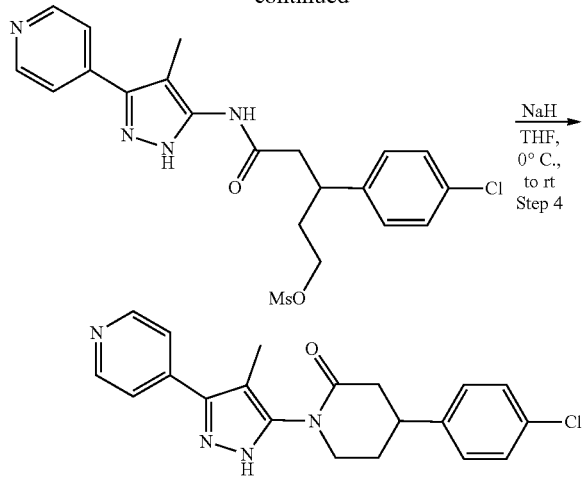

Step 1: 3-(4-Chlorophenyl)-5-((4-methyl-3-(pyridin-4-yl)-1H-pyrazol-5-yl)amino)-5-oxopentanoic acid. A vial was charged with 4-methyl-3-(pyridin-4-yl)-1H-pyrazol-5-amine (160 mg, 0.94 mmol, 1.0 equiv) and 4-(4-chlorophenyl)dihydro-2H-pyran-2,6(3H)-dione (210 mg, 0.94 mmol, 1.0 equiv). After dissolving in anhydrous THF (5.0 mL, 0.19 M), the mixture was heated to 65° C. After 17 h, the reaction mixture was then concentrated in vacuo, re-dissolved in a minimal amount of DMSO and directly purified by RP-HPLC (Method A, 10-30% MeCN in H$_2$O+0.1% TFA). Fractions containing the desired mass were combined and concentrated by lyophilization to afford 3-(4-chlorophenyl)-5-((4-methyl-3-(pyridin-4-yl)-1H-pyrazol-5-yl)amino)-5-oxopentanoic acid (P1, 180 mg, 0.35 mmol, 38% yield) and undesired regioisomer 5-(5-amino-4-methyl-3-(pyridin-4-yl)-1H-pyrazol-1-yl)-3-(4-chlorophenyl)-5-oxopentanoic acid (P2, 10 mg, 0.016 mmol, 1.7% yield) as white solids, trifluoroacetic acid salts.

P1: $^1$H NMR (400 MHz, DMSO-d$_6$) δ 12.1 (s, 1H), 9.89 (s, 1H), 8.76 (d, J=5.8 Hz, 2H), 7.94 (s, 2H), 7.35 (d, J=8.7 Hz, 2H), 7.32 (d, J=8.7 Hz, 2H), 3.55 (quint, J=7.2, 6.7 Hz, 1H), 2.79-2.54 (m, 4H), 1.91 (s, 3H). LCMS: ESI-MS m/z: 399.1 [M+H]$^+$; first eluting peak (retention time=0.77 min).

P2: $^1$H NMR (400 MHz, DMSO-d$_6$) δ 8.76 (d, J=5.5 Hz, 2H), 7.89 (s, 2H), 7.36 (d, J=8.7 Hz, 2H), 7.33 (d, J=8.2 Hz, 2H), 6.45 (s, 1H), 3.72-3.50 (m, 2H), 3.41 (dd, J=16.9, 5.8 Hz, 1H), 2.77 (dd, J=16.0, 6.1 Hz, 1H), 2.63 (dt, J=16.1, 8.2 Hz, 1H), 2.01 (s, 3H). LCMS: ESI-MS m/z: 399.1 [M+H]$^+$; second eluting peak (retention time=0.89 min).

Step 2: 3-(4-Chlorophenyl)-5-hydroxy-N-(4-methyl-3-(pyridin-4-yl)-1H-pyrazol-5-yl)pentanamide. A vial was charged with 3-(4-chlorophenyl)-5-((4-methyl-3-(pyridin-4-yl)-1H-pyrazol-5-yl)amino)-5-oxopentanoic acid (45 mg, 0.11 mmol, 1.0 equiv). After dissolving in anhydrous THF (3.0 mL, 0.038 M), the solution was cooled to 0° C. and LAH (1.0 M solution in THF, 42 mg, 1.1 mmol, 10 equiv) was added dropwise and the mixture was slowly warmed to rt and stirred for 2 h. The crude material was purified directly by RP-HPLC (Method A, 10-90% MeCN in H$_2$O+0.1% TFA). Fractions containing the desired mass were combined and concentrated by lyophilization to afford 3-(4-chlorophenyl)-5-hydroxy-N-(4-methyl-3-(pyridin-4-yl)-1H-pyrazol-5-yl)pentanamide (10 mg, 0.026 mmol, 23% yield) as a white solid, trifluoroacetic acid salt. LCMS: ESI-MS m/z: 385.2 [M+H]$^+$.

Step 3: 3-(4-Chlorophenyl)-5-((4-methyl-3-(pyridin-4-yl)-1H-pyrazol-5-yl)amino)-5-oxopentyl methanesulfonate. A vial was charged with 3-(4-chlorophenyl)-5-hydroxy-N-(4-methyl-3-(pyridin-4-yl)-1H-pyrazol-5-yl)pentanamide (9.0 mg, 0.023 mmol, 1.0 equiv). After dissolving in anhydrous THF (1.0 mL, 0.023 M), the solution was cooled to 0° C. and triethylamine (7.1 mg, 0.070 mmol, 3.0 equiv) was added. After 10 min, methanesulfonyl chloride (4.0 mg, 0.035 mmol, 1.5 equiv) was slowly added. The mixture was warmed to rt and stirred for 3 h. The reaction mixture was concentrated in vacuo to afford crude 3-(4-chlorophenyl)-5-((4-methyl-3-(pyridin-4-yl)-1H-pyrazol-5-yl)amino)-5-oxopentyl methanesulfonate (10 mg, 0.022 mmol, >95% crude yield), which was used in the next step directly without purification. LCMS: ESI-MS m/z: 463.2 [M+H]$^+$.

Step 4: 4-(4-Chlorophenyl)-1-(4-methyl-3-(pyridin-4-yl)-1H-pyrazol-5-yl)piperidin-2-one. A vial was charged with 3-(4-chlorophenyl)-5-((4-methyl-3-(pyridin-4-yl)-1H-pyrazol-5-yl)amino)-5-oxopentyl methanesulfonate (10 mg, 0.022 mmol, 1.0 equiv). After dissolving in anhydrous THF (1.0 mL, 0.022 M), the solution was cooled to 0° C. and NaH (60% w/w dispersion in mineral oil, 8.7 mg, 0.22 mmol, equiv) was added. The suspension was warmed to rt and stirred for 3 h. The reaction mixture was quenched with water, filtered and purified directly by RP-HPLC (Method B, 10-90% MeCN in H$_2$O+0.1% FA). Fractions containing the desired mass were combined and concentrated by lyophilization to afford 4-(4-chlorophenyl)-1-(4-methyl-3-(pyridin-4-yl)-1H-pyrazol-5-yl)piperidin-2-one (1.6 mg, 0.0040 mmol, 18% yield) as a solid, formic acid salt. $^1$H NMR (400 MHz, CD$_3$OD) δ 8.65 (d, J=5.2 Hz, 2H), 8.52 (s, 1H), 7.66 (s, 2H), 7.37 (s, 4H), 3.91-3.79 (m, 1H), 3.71 (d, J=12.2 Hz, 1H), 3.41-3.34 (m, 1H), 2.84 (dd, J=17.7, 5.3 Hz, 1H), 2.72 (dd, J=17.6, 10.9 Hz, 1H), 2.24 (td, J=9.1, 8.4, 4.6 Hz, 2H), 2.14 (s, 3H). LCMS: ESI-MS m/z: 367.2 [M+H]$^+$.

Example 139

3-(4-Chlorophenyl)-N-methyl-N-(4-methyl-3-(pyridin-4-yl)-1H-pyrazol-5-yl)propenamide

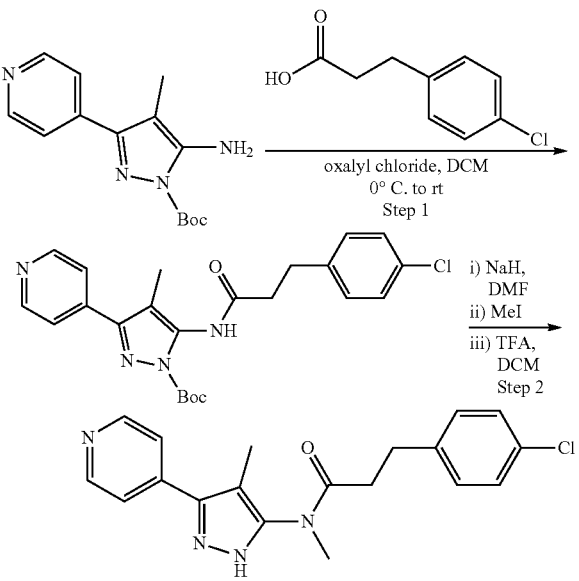

Step 1: tert-Butyl 5-(3-(4-chlorophenyl)propanamido)-4-methyl-3-(pyridin-4-yl)-1H-pyrazole-1-carboxylate. To a solution of 3-(4-chlorophenyl)propanoic acid (340 mg, 1.8 mmol, 2.5 equiv) was added DCM (3 mL, 0.6 M) was added oxalyl chloride (2.0 M in DCM, 1.1 mL, 2.1 mmol, 3.0 equiv) and 1 drop of anhydrous DMF. The resulting mixture was stirred at rt for 4.5 h. The mixture was concentrated in vacuo to afford a crude residue. In a separate flask, a solution of tert-butyl 5-amino-4-methyl-3-(pyridin-4-yl)-1H-pyrazole-1-carboxylate (Intermediate 28, 190 mg, 0.70 mmol, 1.0 equiv) in DCM (5.0 mL, 0.14 M) at 0° C. was treated with triethylamine (280 mg, 2.8 mmol, 4.0 equiv). The acid chloride was then dissolved in DCM (1.0 mL) and added to the cold solution. The mixture was warmed to rt and stirred for 16 h. It was then diluted with DCM (100 ml), washed with a saturated solution of NaHCO$_3$, water, and brine. The organic fractions were dried over anhydrous sodium sulfate, filtered, and concentrated in vacuo. The resulting crude product was purified by silica gel column chromatography (5-55% EtOAc in DCM) to afford tert-butyl 5-(3-(4-chlorophenyl)propanamido)-4-methyl-3-(pyridin-4-yl)-1H-pyrazole-1-carboxylate (54 mg, 17% yield) as a white solid. LCMS: ESI-MS m/z: 441.2 [M+H]$^+$.

Step 2: 3-(4-Chlorophenyl)-N-methyl-N-(4-methyl-3-(pyridin-4-yl)-1H-pyrazol-5-yl)propenamide. To a solution of tert-butyl 5-(3-(4-chlorophenyl)propanamido)-4-methyl-3-(pyridin-4-yl)-1H-pyrazole-1-carboxylate (26 mg, 0.059 mmol, 1.0 equiv) in anhydrous DMF (2 mL, 0.030 M) at 0° C. was added NaH (60% w/w dispersion in mineral oil, 4.7 mg, 0.12 mmol, 2.0 equiv). The resulting suspension was stirred at 0° C. for 15 min. Then, methyl iodide (10 mg, 0.071 mmol, 1.2 equiv) was added and stirring was continued at 0° C. for a subsequent 40 min. After 40 min, the reaction was carefully quenched with water (0.20 mL) and the reaction was concentrated in vacuo. The resulting residue was then treated with a 1:6 solution of TFA:DCM (2.0 mL) and stirred at rt for 15 h. The mixture was again concentrated in vacuo and purified directly by RP-HPLC (Method A, 10-90% MeCN in H$_2$O+0.1% TFA) to afford 3-(4-chlorophenyl)-N-methyl-N-(4-methyl-3-(pyridin-4-yl)-1H-pyrazol-5-yl)propenamide (3.7 mg, 13% yield) as a white solid, trifluoroacetic acid salt. LCMS: ESI-MS m/z: 355.2 [M+H]$^+$.

Example 140

3-(4-Ethynylphenyl)-N-(4-methyl-3-(pyridin-4-yl)-1H-pyrazol-5-yl)propenamide

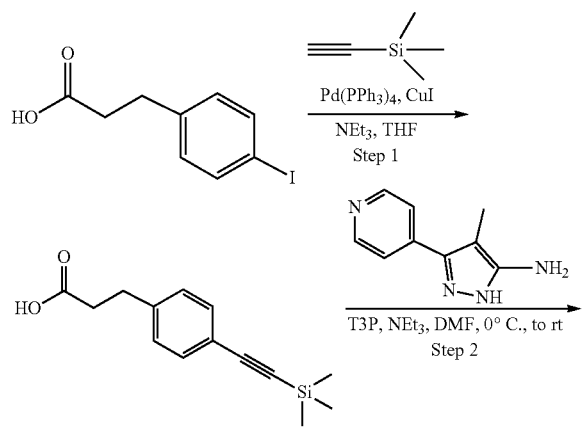

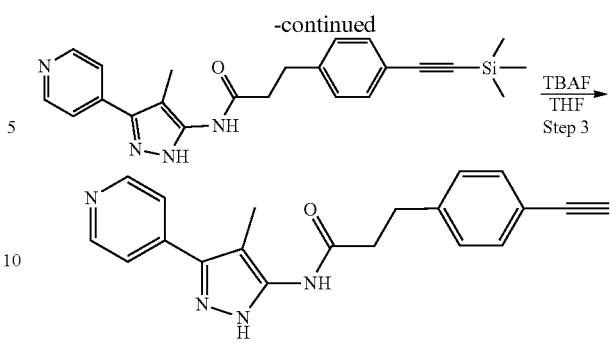

Step 1: 3-(4-((Trimethylsilyl)ethynyl)phenyl)propanoic acid. A flask was charged with 3-(4-iodophenyl)propanoic acid (400 mg, 1.5 mmol, 1.0 equiv), which was azeotroped with toluene. Then CuI (28 mg, 0.15 mmol, 0.10 equiv), tetrakis(triphenylphosphine) palladium(0) (34 mg, 0.029 mmol, 0.020 equiv) and anhydrous THF (6.0 mL, 0.25 M) were added. The resulting mixture was degassed with nitrogen gas for 30 min, then triethylamine (6.1 mL, 4.4 g, 44 mmol, 30 equiv) and ethynyltrimethylsilane (0.24 mL, 170 mg, 1.7 mmol, 1.2 equiv) were added. The resulting mixture was stirred at rt for 17 h. Subsequently, the solution was diluted with EtOAc (140 ml) and washed with an aqueous solution of 1 N HCl (20 mL), and brine (20 mL). The organic layer was separated and dried over anhydrous sodium sulfate, filtered, and concentrated in vacuo to afford a crude residue. The crude product was purified by silica gel column chromatography (20-40% EtOAc in DCM) to afford 3-(4-((trimethylsilyl)ethynyl)phenyl)propanoic acid (210 mg, 58% yield) as a white solid. $^1$H NMR (400 MHz, DMSO-d$_6$) δ 12.2 (s, 1H), 7.40-7.32 (m, 2H), 7.28-7.17 (m, 2H), 2.82 (d, J=7.6 Hz, 2H), 2.54 (d, J=7.6 Hz, 2H), 0.22 (s, 9H).

Step 2: N-(4-Methyl-3-(pyridin-4-yl)-1H-pyrazol-5-yl)-3-(4-((trimethylsilyl)ethynyl)phenyl) propenamide. To a solution of 3-(4-((trimethylsilyl)ethynyl)phenyl)propanoic acid (55 mg, 0.22 mmol, 1.0 equiv) in DMF (3 mL, 0.073 M) at 0° C. was added T3P (50 w/v % in DMF, 140 mg, 0.22 mmol, 1.0 equiv) and triethylamine (68 mg, 0.68 mmol, 3.0 equiv). The resulting solution was stirred at 0° C. for 10 min, followed then by the addition of 4-methyl-3-(pyridin-4-yl)-1H-pyrazol-5-amine (Intermediate 1, 43 mg, 0.25 mmol, 1.1 equiv). The resulting mixture was stirred at rt for 3 h, then concentrated in vacuo and purified directly by RP-HPLC (Method A, 10-90% MeCN in H$_2$O+0.1% TFA) to afford N-(4-methyl-3-(pyridin-4-yl)-1H-pyrazol-5-yl)-3-(4-((trimethylsilyl)ethynyl)phenyl) propenamide (41 mg, 46% yield) as a white solid, trifluoroacetic acid salt. LCMS: ESI-MS m/z: 403.2 [M+H]$^+$.

Step 3: 3-(4-Ethynylphenyl)-N-(4-methyl-3-(pyridin-4-yl)-1H-pyrazol-5-yl)propenamide. To a solution of N-(4-methyl-3-(pyridin-4-yl)-1H-pyrazol-5-yl)-3-(4-((trimethylsilyl)ethynyl)phenyl) propenamide (37 mg, 0.092 mmol, 1.0 equiv) in THF (2 mL, 0.046 M) was added TBAF (1 M solution in THF, 0.18 mL, 0.18 mmol, 2.0 equiv). The resulting solution was stirred at rt for 30 min, then the reaction mixture was concentrated in vacuo and purified directly by RP-HPLC (Method A, 10-90% MeCN in H$_2$O+ 0.1% TFA) to afford 3-(4-ethynylphenyl)-N-(4-methyl-3-(pyridin-4-yl)-1H-pyrazol-5-yl)propenamide (22 mg, 54% yield), a white solid, trifluoroacetic acid salt. $^1$H NMR (400 MHz, DMSO-d$_6$) δ 9.93 (s, 1H), 8.76 (d, J=5.7 Hz, 2H), 7.93 (s, 2H), 7.46-7.37 (m, 2H), 7.29 (d, J=8.1 Hz, 2H), 4.13 (s, 1H), 2.94 (t, J=7.6 Hz, 2H), 2.67 (t, J=7.5 Hz, 2H), 2.04 (s, 3H). LCMS: ESI-MS m/z: 331.1 [M+H]⁺.

Example 141

1-[(4-Cyanophenyl)methyl]-3-[4-methyl-3-(pyridin-4-yl)-1H-pyrazol-5-yl]urea

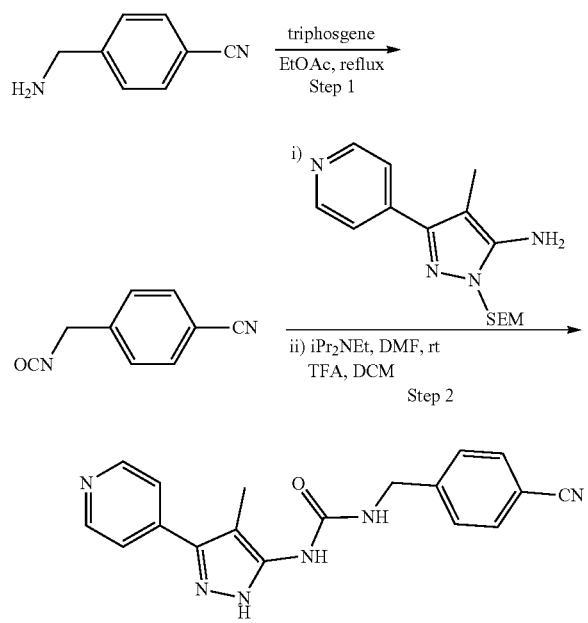

Step 1: 4-(Isocyanatomethyl)benzonitrile. To a stirred solution of 4-(aminomethyl)benzonitrile (150 mg, 1.2 mmol, 1.0 equiv) in EtOAc (10 mL, 0.12 M) at 0° C. was added triphosgene (400 mg, 1.3 mmol, 1.1 equiv). The reaction mixture was heated to reflux for 2 h. The reaction mixture was concentrated in vacuo and the residue was used in the next step without further purification.

Step 2: 1-[(4-Cyanophenyl)methyl]-3-[4-methyl-3-(pyridin-4-yl)-1H-pyrazol-5-yl]urea. To a stirred solution of crude 4-(isocyanatomethyl)benzonitrile (1.2 mmol, 1.0 equiv) in anhydrous DMF (2 mL, 0.60 M), was added DIPEA (390 mg, 3.1 mmol, 2.6 equiv) and 4-methyl-3-(pyridin-4-yl)-1-{[2-(trimethylsilyl)ethoxy]methyl}-1H-pyrazol-5-amine (Intermediate 2, 410 mg, 1.3 mmol, 1.1 equiv). The mixture was stirred for 16 h at rt. The mixture was diluted with water (10 mL) and extracted with EtOAc (10 mL). The organic layer was separated and washed with brine, dried over anhydrous sodium sulfate, filtered, and concentrated in vacuo. The crude residue was dissolved in DCM (6 mL) and to this mixture was added TFA (2 mL). The reaction mixture was stirred for 2 h at rt then concentrated in vacuo and purified by RP-HPLC (Method C, 5-95% MeCN in H₂O+10 mM NH₄HCO₃+0.025% NH₃·H₂O) to afford 1-[(4-cyanophenyl)methyl]-3-[4-methyl-3-(pyridin-4-yl)-1H-pyrazol-5-yl]urea (12 mg, 3.0% yield) as a white solid. ¹H NMR (400 MHz, DMSO-d₆) δ 12.8 (d, J=50.0 Hz, 1H), 8.65 (s, 4H), 7.81 (d, J=8.2 Hz, 2H), 7.74-7.53 (m, 3H), 7.49 (d, J=8.3 Hz, 2H), 4.42 (s, 2H), 2.10 (s, 3H). LCMS: ESI-MS: m/z: 333.1 [M+H]⁺.

Example 142

1-[(4-Fluorophenyl)methyl]-3-[4-methyl-3-(pyridin-4-yl)-1H-pyrazol-5-yl]urea

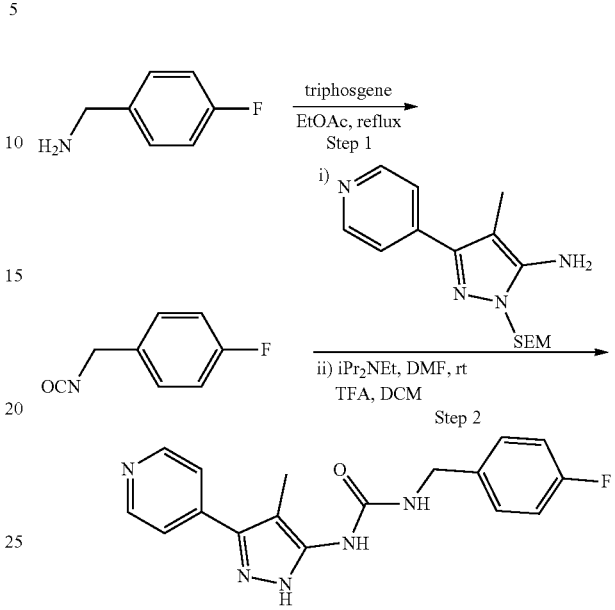

The product was prepared following the same procedure as Example #141 to afford 1-[(4-fluorophenyl)methyl]-3-[4-methyl-3-(pyridin-4-yl)-1H-pyrazol-5-yl]urea in 10% yield (over two steps) as a white solid. ¹H NMR (400 MHz, DMSO-d₆) δ 12.9 (s, 1H), 8.66-8.58 (m, 2H), 8.44 (s, 1H), 7.64-7.56 (m, 3H), 7.35 (dd, J=8.6, 5.7 Hz, 2H), 7.16 (t, J=8.9 Hz, 2H), 4.33 (s, 2H), 2.09 (s, 3H). LCMS: ESI-MS m/z: 326.1 [M+H]⁺.

Example 143

1-[(6-Chloropyridin-3-yl)methyl]-3-[4-methyl-3-(pyridin-4-yl)-1H-pyrazol-5-yl]urea

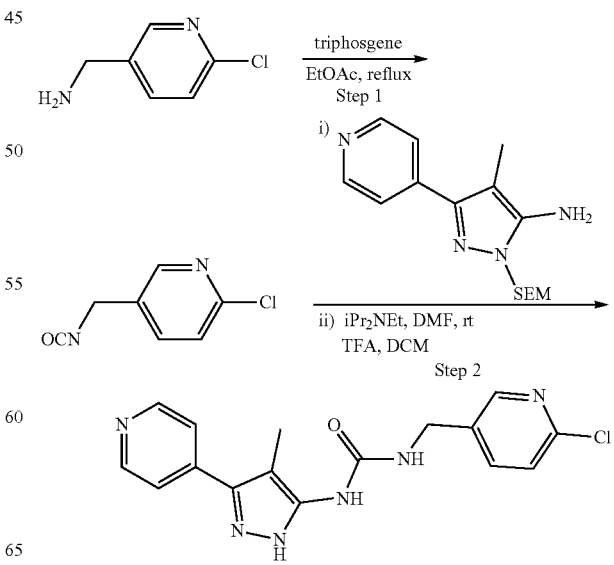

The product was prepared following the same procedure as Example #141 to afford 1-[(6-chloropyridin-3-yl)methyl]-3-[4-methyl-3-(pyridin-4-yl)-1H-pyrazol-5-yl]urea in 8.0% yield (over two steps) as a white solid. ¹H NMR (400 MHz, DMSO-d₆) δ 12.9 (s, 1H), 8.64 (s, 2H), 8.49 (s, 1H), 8.35 (d, J=2.2 Hz, 1H), 7.79 (dd, J=8.2, 2.4 Hz, 1H), 7.58 (s, 2H), 7.50 (d, J=8.2 Hz, 1H), 4.35 (d, J=5.0 Hz, 2H), 2.08 (s, 3H). LCMS: ESI-MS m/z: 343.1 [M+H]⁺.

Example 144

1-(4-Chlorobenzyl)-3-(5-methyl-1-(pyridin-4-yl)-1H-pyrazol-4-yl)urea

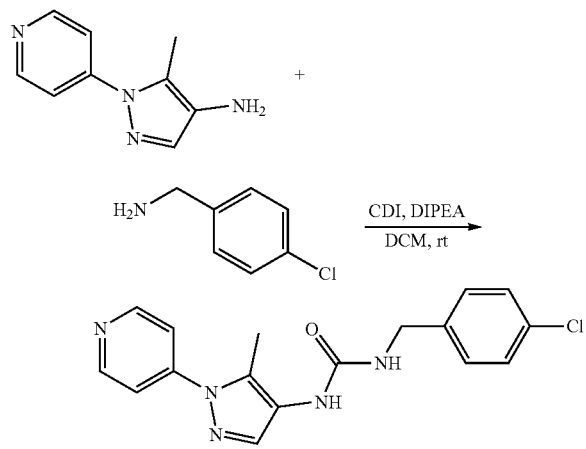

A solution of 5-methyl-1-(pyridin-4-yl)-1H-pyrazol-4-amine (Intermediate 6, 50 mg, 0.29 mmol, 1.0 equiv), (4-chlorophenyl)methanamine (41 mg, 0.29 mmol, 1.0 equiv) CDI (50 mg, 0.31 mmol, 1.1 equiv), and DIPEA (75 mg, 0.57 mmol, 2.0 equiv) in DCM (3.0 mL, 0.10 M) was stirred at rt for 16 h. The mixture was then washed with water and the organic fraction was separated and concentrated in vacuo. The crude material was purified directly by RP-HPLC (Method C, 15-40% MeCN in H₂O+10 mM NH₄HCO₃+0.025% NH₃·H₂O) to afford 1-(4-chlorobenzyl)-3-(5-methyl-1-(pyridin-4-yl)-1H-pyrazol-4-yl)urea (10 mg, 0.029 mmol, 10% yield) as a white solid. ¹H NMR (400 MHz, DMSO-d₆) δ 8.66 (dd, J=6.0 Hz, 2H), 7.98 (s, 1H), 7.85 (s, 1H), 7.63 (dd, J=6.4 Hz, 2H), 7.41-7.38 (m, 2H), 7.32 (d, J=8.4 Hz, 2H), 6.66 (t, J=12.0 Hz, 1H), 4.28 (d, J=6.0 Hz, 2H), 2.36 (s, 3H). LCMS: ESI-MS m/z: 342.0 [M+H]⁺.

Example 145

1-(4-Chloro-3-(pyridin-4-yl)-1H-pyrazol-5-yl)-3-(3,4,5-trifluorobenzyl)urea

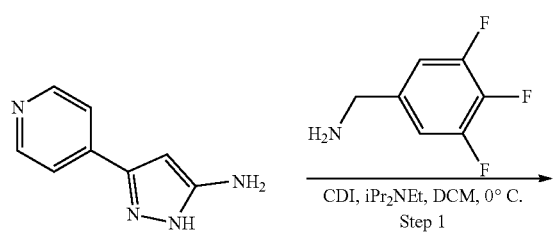

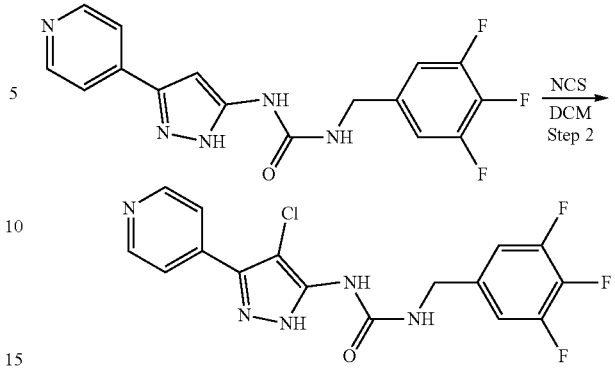

Step 1. 1-(3-(Pyridin-4-yl)-1H-pyrazol-5-yl)-3-(3,4,5-trifluorobenzyl)urea. To a solution of (3,4,5-trifluorophenyl)methanamine (100 mg, 0.63 mmol, 1.0 equiv) and CDI (110 mg, 0.70 mmol, 1.2 equiv) in DCM (10 mL, 0.063 M) was added ethylbis(propan-2-yl)amine (120 mg, 0.94 mmol, 1.5 equiv), and the reaction mixture was stirred for 1 h at rt. 3-(Pyridin-4-yl)-1H-pyrazol-5-amine (100 mg, 0.63 mmol, 1.0 equiv) was then added and the reaction mixture was stirred for 8 h at rt. The reaction mixture was washed with water (20 mL), the layers were separated, and the organic layer was concentrated in vacuo. The resulting crude residue was then purified RP-HPLC (Method C, 5-25% MeCN in H₂O+10 mM NH₄HCO₃+0.025% NH₃·H₂O). Fractions containing the desired product were combined and concentrated by lyophilization to afford 1-(3-(pyridin-4-yl)-1H-pyrazol-5-yl)-3-(3,4,5-trifluorobenzyl)urea (20 mg, 0.31 mmol, 50% yield) as a colorless solid. ¹H NMR (DMSO-d₆, 400 MHz) δ 13.01 (s, 1H), 9.12 (s, 1H), 8.61 (s, 2H), 7.68 (d, J=5.8 Hz, 2H), 7.33-7.20 (m, 2H), 7.14 (s, 1H), 6.79 (s, 1H), 4.32 (d, J=5.6 Hz, 2H). LCMS: ESI-MS m/z: 348 [M+H]⁺.

Step 2. 1-(4-Chloro-3-(pyridin-4-yl)-1H-pyrazol-5-yl)-3-(3,4,5-trifluorobenzyl)urea. A mixture of 1-(3-(pyridin-4-yl)-1H-pyrazol-5-yl)-3-(3,4,5-trifluorobenzyl)urea (20 mg, 0.057 mmol, 1.0 equiv) and N-chlorosuccinimide (8.0 mg, 0.060 mmol, 1.1 equiv) in DCM (1 mL, 0.057 M) was stirred for 1 h at rt, and then concentrated in vacuo. The resulting residue was then purified RP-HPLC (Method C, 5-50% MeCN in H₂O+10 mM NH₄HCO₃+0.025% NH₃·H₂O).

Fractions containing the desired product were combined and concentrated by lyophilization to afford 1-(4-chloro-3-(pyridin-4-yl)-1H-pyrazol-5-yl)-3-(3,4,5-trifluorobenzyl)urea (5.0 mg, 0.013 mmol, 23% yield) as a colorless solid. ¹H NMR (DMSO-d₆, 400 MHz) δ 13.4 (s, 1H), 8.98 (s, 1H), 8.67 (s, 2H), 7.81 (d, J=4.4 Hz, 2H), 7.27-7.20 (m, 3H), 4.31 (d, J=6.0 Hz, 2H). LCMS: ESI-MS m/z: 348 [M+H]⁺.

Example 146

2,6-Difluoro-4-((2-oxo-1-(3-(pyridin-4-yl)-1H-pyrazol-5-yl)pyrrolidin-3-yl)methyl)benzonitrile

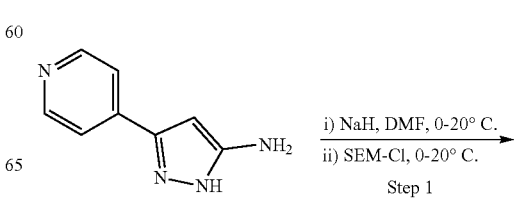

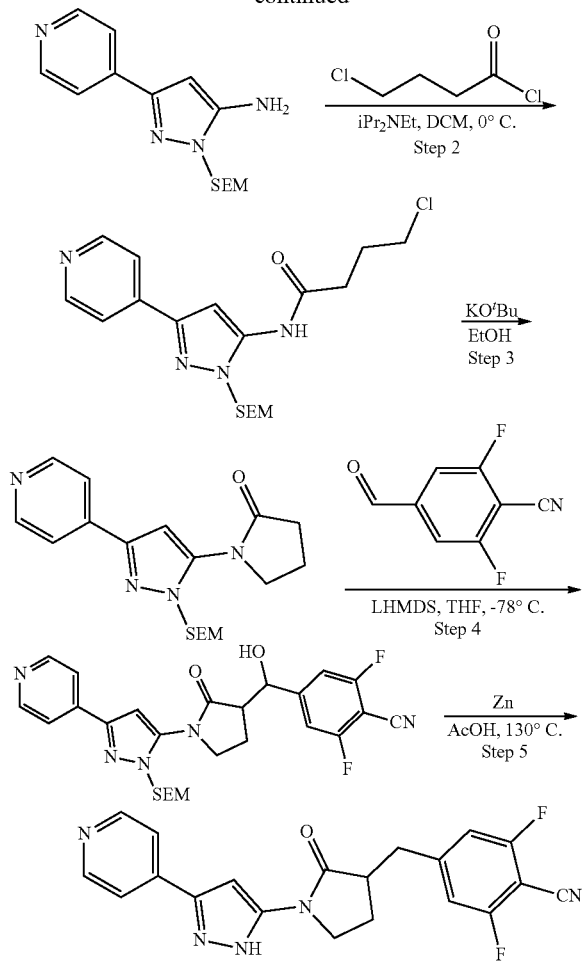

Step 1: 3-(Pyridin-4-yl)-1-((2-(trimethylsilyl)ethoxy)methyl)-1H-pyrazol-5-amine. To a solution of 3-(pyridin-4-yl)-1H-pyrazol-5-amine (Intermediate 13, 500 mg, 3.1 mmol, 1.0 equiv) in anhydrous DMF (10 mL, 0.31 M) was added sodium hydride (60 wt % dispersion in mineral oil, 190 mg, 4.7 mmol, 1.5 equiv) at 0° C. under an atmosphere of nitrogen gas. After the addition, the mixture was stirred at 0° C. for 40 min. Next, SEM-Cl (780 mg, 4.7 mmol, 1.5 equiv) was added dropwise at 0° C. After the addition, the mixture was stirred at 0° C. for 2 h. The mixture was then diluted with ethyl acetate (50 mL) and washed with a saturated solution of aqueous NH$_4$Cl (2×30 mL). The organic layer was separated, dried over anhydrous sodium sulfate, filtered, and concentrated in vacuo. The crude residue was purified by silica gel column chromatography (5% DCM in MeOH) to afford 3-(pyridin-4-yl)-1-((2-(trimethylsilyl)ethoxy)methyl)-1H-pyrazol-5-amine (500 mg, 1.7 mmol, 55% yield) as a light yellow solid. LCMS: ESI-MS m/z: 291.1 [M+H]$^+$.

Step 2: 4-Chloro-N-(3-(pyridin-4-yl)-1-((2-(trimethylsilyl)ethoxy)methyl)-1H-pyrazol-5-yl)butanamide. To a solution of 3-(pyridin-4-yl)-1-((2-(trimethylsilyl)ethoxy)methyl)-1H-pyrazol-5-amine (200 mg, 0.69 mmol, 1.0 equiv) in DCM (4 mL, 0.17 M) was added 4-chlorobutanoyl chloride (120 mg, 0.83 mmol, 1.2 equiv) at 0° C. DIPEA (110 mg, 0.83 mmol, 1.2 equiv) was then added dropwise and the reaction mixture was stirred at rt for 2 h. The reaction mixture was then concentrated in vacuo, and the resulting residue purified directly by RP-HPLC (Method C, 5-95% MeCN in H$_2$O+10 mM NH$_4$HCO$_3$+0.025% NH$_3$·H$_2$O). The fractions containing the desired compound were concentrated by lyophilization to afford 4-chloro-N-(3-(pyridin-4-yl)-1-((2-(trimethylsilyl)ethoxy)methyl)-1H-pyrazol-5-yl)butanamide (120 mg, 0.30 mmol, 36% yield) as a yellow oil. LCMS: ESI-MS m/z: 395.0 [M+H]$^+$.

Step 3: 1-(3-(Pyridin-4-yl)-1-((2-(trimethylsilyl)ethoxy)methyl)-1H-pyrazol-5-yl)pyrrolidin-2-one. To a solution of 4-chloro-N-(3-(pyridin-4-yl)-1-((2-(trimethylsilyl)ethoxy)methyl)-1H-pyrazol-5-yl)butanamide (100 mg, 0.25 mmol, 1.0 equiv) in EtOH (4 mL, 0.063 M) was added potassium tert-butoxide (85 mg, 0.76 mmol, 3.0 equiv) at rt and the reaction was stirred for 2 h. The reaction mixture was then concentrated in vacuo, and the resulting residue was purified by RP-HPLC (Method C, 5-95% MeCN in H$_2$O+10 mM NH$_4$HCO$_3$+0.025% NH$_3$·H$_2$O). Fractions containing the desired product were concentrated by lyophilization to afford 1-(3-(pyridin-4-yl)-1-((2-(trimethylsilyl)ethoxy)methyl)-1H-pyrazol-5-yl)pyrrolidin-2-one (50 mg, 0.14 mmol, 41% yield) as a yellow oil. LCMS: ESI-MS m/z: 359.0 [M+H]$^+$.

Step 4: 2,6-Difluoro-4-(hydroxy(2-oxo-1-(3-(pyridin-4-yl)-1-((2-(trimethylsilyl)ethoxy)methyl)-1H-pyrazol-5-yl)pyrrolidin-3-yl)methyl)benzonitrile. To a solution of 1-(3-(pyridin-4-yl)-1-((2-(trimethylsilyl)ethoxy)methyl)-1H-pyrazol-5-yl)pyrrolidin-2-one (170 mg, 0.47 mmol, 1.0 equiv) in THF (3 mL, 0.16 M), was added LiHMDS (1.0 M in THF, 0.95 mL, 0.95 mmol, 2.0 equiv) dropwise at −78° C. A solution of 2,6-difluoro-4-formylbenzonitrile (120 mg, 0.71 mmol, 1.5 equiv) in THF (2 ml) was then added at to the cold solution, and the resulting mixture was stirred at −78° C. for 1 h. Water (20 mL) was then added, and the mixture was extracted with DCM (3×30 mL). The combined organic fractions were washed with brine (2×20 mL), dried over anhydrous sodium sulfate, filtered and concentrated in vacuo. The residue was purified by RP-HPLC (Method C, 5-95% MeCN in H$_2$O+10 mM NH$_4$HCO$_3$+0.025% NH$_3$·H$_2$O) and fractions containing the desired product were concentrated by lyophilization to afford 2,6-difluoro-4-(hydroxy(2-oxo-1-(3-(pyridin-4-yl)-1-((2-(trimethylsilyl)ethoxy)methyl)-1H-pyrazol-5-yl)pyrrolidin-3-yl)methyl)benzonitrile (40 mg, 0.076 mmol, 16%) as a white solid. LCMS: ESI-MS m/z: 526.2 [M+H]$^+$.

Step 5: 2,6-Difluoro-4-((2-oxo-1-(3-(pyridin-4-yl)-1H-pyrazol-5-yl)pyrrolidin-3-yl)methyl)benzonitrile. A mixture of 2,6-difluoro-4-(hydroxy(2-oxo-1-(3-(pyridin-4-yl)-1-((2-(trimethylsilyl)ethoxy)methyl)-1H-pyrazol-5-yl)pyrrolidin-3-yl)methyl)benzonitrile (40 mg, 0.070 mmol, 1.0 equiv) and Zn dust (27 mg, 0.42 mmol, 6.0 equiv) in acetic acid (2 mL, 0.035 M) was stirred at 130° C. for 18 h. The mixture was filtered, and the filtrate was concentrated in vacuo. The residue was treated with NH$_3$/MeOH (7 M) to adjust to pH 8-9 and further purified by RP-HPLC (Method C, 5-95% MeCN in H$_2$O+10 mM NH$_4$HCO$_3$+0.025% NH$_3$·H$_2$O). The desired fractions were concentrated to afford 2,6-difluoro-4-((2-oxo-1-(3-(pyridin-4-yl)-1H-pyrazol-5-yl)pyrrolidin-3-yl)methyl)benzonitrile (2.0 mg, 0.0050 mmol, 7.5% yield) as a white solid. $^1$H NMR (400 MHz, DMSO-d$_6$) δ 13.3 (s, 1H), 8.64 (d, J=5.5 Hz, 2H), 7.81-7.71 (m, 2H), 7.46 (d, J=9.4 Hz, 2H), 7.28 (s, 1H), 3.86 (d, J=9.1 Hz, 1H), 3.71 (dd, J=17.1, 9.3 Hz, 1H), 3.24 (dd, J=13.7, 5.2 Hz, 1H), 3.14-3.04 (m, 1H), 2.85 (dd, J=13.7, 9.5 Hz, 1H), 2.13 (d, J=4.5 Hz, 1H), 1.89-1.73 (m, 1H). LCMS: ESI-MS m/z: 380.0 [M+H]$^+$.

Example 147

N-(4-Bromo-3-(pyridin-4-yl)-1H-pyrazol-5-yl)-3-(4-chlorophenyl)propanamide

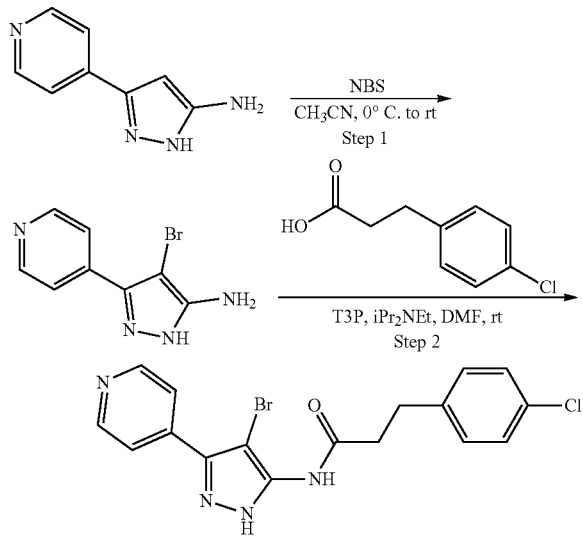

Step 1: 4-Bromo-3-(pyridin-4-yl)-1H-pyrazol-5-amine. To a stirred solution of 3-(pyridin-4-yl)-1H-pyrazol-5-amine (200 mg, 1.3 mmol, 1.0 equiv) in acetonitrile (3 mL, 0.43 M) was added NBS (250 mg, 1.4 mmol, 1.1 equiv) portionwise at 0° C. under an atmosphere of nitrogen gas. After the addition, the reaction was stirred at rt for 3 h. The reaction mixture was then concentrated in vacuo and the residue was purified by silica gel column chromatography (10% MeOH in DCM) to afford 4-bromo-3-(pyridin-4-yl)-1H-pyrazol-5-amine (160 mg, 0.66 mmol, 53% yield) as a light yellow solid. LCMS: ESI-MS m/z: 240.0 [M+H]$^+$.

Step 2. N-(4-Bromo-3-(pyridin-4-yl)-1H-pyrazol-5-yl)-3-(4-chlorophenyl)propanamide. The product was prepared according to General Procedure #1 using 4-bromo-3-(pyridin-4-yl)-1H-pyrazol-5-amine and 3-(4-chlorophenyl)propanoic acid to afford N-(4-bromo-3-(pyridin-4-yl)-1H-pyrazol-5-yl)-3-(4-chlorophenyl)propanamide (78 mg, 0.19 mmol, 46%) as a light yellow solid. $^1$H NMR (400 MHz, CDCl$_3$) δ 8.71 (d, J=4.4 Hz, 2H), 7.89 (d, J=4.8 Hz, 2H), 7.56 (s, 1H), 7.32 (d, J=8.0 Hz, 2H), 7.21 (d, J=8.0 Hz, 2H), 3.09 (t, J=6.8 Hz, 2H), 2.84 (t, J=7.2 Hz, 2H). LCMS: ESI-MS m/z: 405.0 [M+H]$^+$.

Example 148

(R)-1-(1-(4-Chlorophenyl)ethyl)-3-(4-methyl-3-(pyridin-4-yl)-1H-pyrazol-5-yl)urea

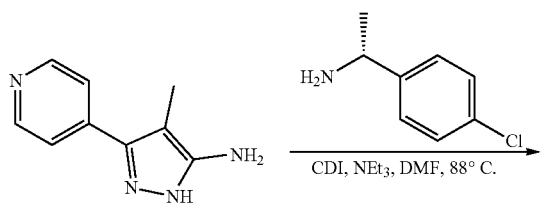

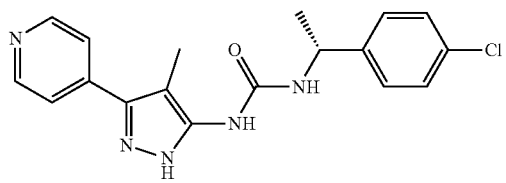

A mixture of Intermediate 1 (50 mg, 0.28 mmol, 1.0 equiv), CDI (70 mg, 0.43 mmol, 1.5 equiv), triethylamine (0.16 mL, 1.2 mmol, 4.0 equiv), and DMF (1.5 mL, 0.19 M) was heated to 88° C. for 2 h. (R)-1-(4-Chlorophenyl)ethan-1-amine (45 mg, 0.29 mmol, 1.0 equiv) was then added and the reaction mixture was heated to 88° C. for 6 h. The crude material was purified by RP-HPLC (Method A, 40-45% MeCN in H$_2$O+0.1% TFA) to give (R)-1-(1-(4-chlorophenyl)ethyl)-3-(4-methyl-3-(pyridin-4-yl)-1H-pyrazol-5-yl)urea (26 mg, 19% yield) as a pale white solid. $^1$H NMR (400 MHz, DMSO-d$_6$) δ 8.77 (d, J=6.2 Hz, 2H), 8.47 (s, 1H), 7.96 (s, 2H), 7.60-7.12 (m, 4H), 4.84 (q, J=7.0 Hz, 1H), 2.13 (s, 3H), 1.36 (dd, J=24.9, 7.0 Hz, 3H). LCMS: ESI-MS m/z: 356.1 [M+H]$^+$.

Example 149

(5-Chlorothiophen-2-yl)methyl (5-methyl-1-(pyridin-4-yl)-1H-pyrazol-4-yl)carbamate

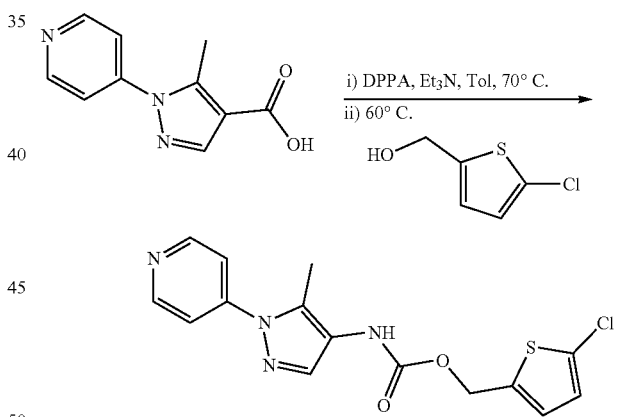

To a suspension of 5-methyl-1-(pyridin-4-yl)-1H-pyrazole-4-carboxylic acid (100 mg, 0.49 mmol, 1.0 equiv) in toluene (3.0 mL, 0.16 M) was added triethylamine (0.17 mL, 1.2 mmol, 2.5 equiv), and DPPA (0.21 mL. 0.98 mmol, 2.0 equiv). The reaction was heated to 70° C. After 17 h, (5-chlorothiophen-2-yl)methanol (88 mg, 0.59 mmol, 1.2 equiv) was added. The solution was heated to 60° C. and stirred for 4 h. After cooling to rt, the crude material was purified directly by RP-HPLC (Method A, 10-90 MeCN in H$_2$O+0.1% TFA). Fractions containing the desired mass were combined and concentrated by lyophilization. The material was subsequently recrystallized in hexanes to afford (5-chlorothiophen-2-yl)methyl (5-methyl-1-(pyridin-4-yl)-1H-pyrazol-4-yl)carbamate (10 mg, 4.0% yield). LCMS: ESI-MS m/z: 349.1 [M+H]$^+$.

Example 150

(rac)-3-(4-Chlorophenyl)-2-hydroxy-N-(5-methyl-1-(pyridin-4-yl)-1H-pyrazol-4-yl)propanamide

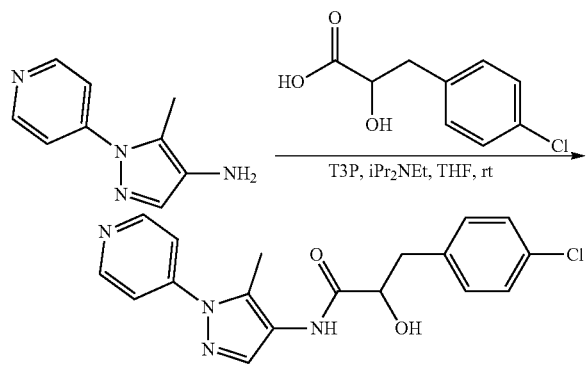

The product was prepared according to General Procedure #1 using Intermediate 6 and (rac)-3-(4-chlorophenyl)-2-hydroxypropanoic acid to afford (rac)-3-(4-chlorophenyl)-2-hydroxy-N-(5-methyl-1-(pyridin-4-yl)-1H-pyrazol-4-yl)propanamide in 16% yield as a white solid. $^1$H NMR (400 MHz, CDCl$_3$) δ 8.96 (s, 0.34H), 8.69 (d, J=4 Hz, 1.34H), 8.57 (d, J=4 Hz, 0.54H), 8.17-8.10 (m, 2H), 8.05 (s, 0.31H), 7.93 (s, 0.62H), 7.65-7.61 (m, 2H), 7.34-7.21 (m, 4H), 5.00-4.95 (m, 0.3H), 4.56-4.53 (m, 0.62H), 3.28-3.22 (m, 1H), 3.11-2.98 (m, 1H), 2.33 (s, 1.90H), 2.22 (s, 1.1H). LCMS: ESI-MS m/z: 357.1 [M+H]$^+$.

Example 151

(R)-2-Amino-3-(4-chlorophenyl)-N-(3-(pyridin-4-yl)-1H-pyrazol-5-yl)propanamide

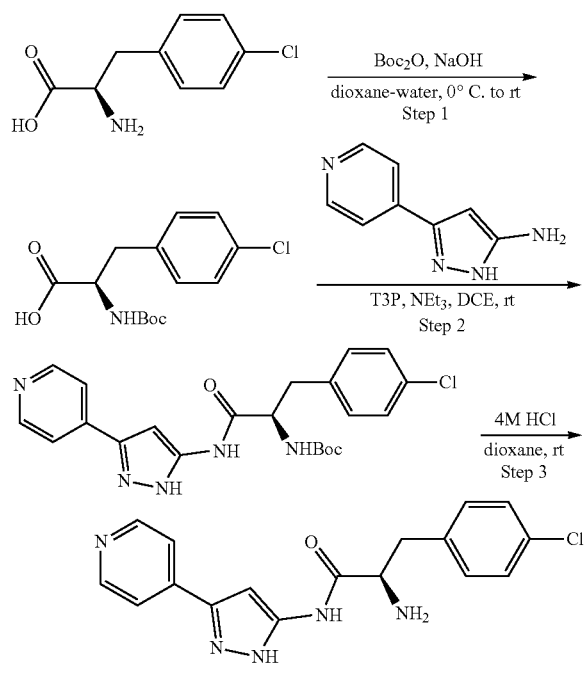

Step 1: (R)-2-((tert-Butoxycarbonyl)amino)-3-(4-chlorophenyl)propanoic acid. To a solution of (R)-2-amino-3-(4-chlorophenyl)propanoic acid (500 mg, 2.5 mmol, 1.0 equiv) dissolved in a 1:1 mixture of dioxane:water (5.0 mL, 0.50 M) was added solid sodium hydroxide (200 mg, 5.0 mmol, 5.0 equiv). The resulting solution was cooled to 5° C. and Boc anhydride (160 mg, 3.8 mmol, 1.5 equiv) was slowly added as a solution in dioxane (2.0 mL). The resulting mixture was stirred at 0° C. for 1 h and then to rt and stirred for 15 h. Water was added and the aqueous layer was extracted with EtOAc (2×20 mL). The combined organic fractions were washed with a saturated solution of sodium bicarbonate (2×20 mL). The combined aqueous fractions were acidified with an aqueous solution of 10% HCl until pH~ 1, then extracted with EtOAc (3×10 mL). The combined organic fractions were dried over anhydrous sodium sulfate and concentrated in vacuo to give (R)-2-((tert-butoxycarbonyl)amino)-3-(4-chlorophenyl)propanoic acid (750 mg, >95% yield) as a clear viscous oil. LCMS: ESI-MS m/z: 322.1 [M+Na]$^+$.

Step 2: tert-Butyl (R)-(3-(4-chlorophenyl)-1-oxo-1-((3-(pyridin-4-yl)-1H-pyrazol-5-yl)amino)propan-2-yl)carbamate. To a solution (R)-2-((tert-butoxycarbonyl)amino)-3-(4-chlorophenyl)propanoic acid (94 mg, 0.31 mmol, 1.0 equiv) in DCE (2.0 mL, 0.16 M) was added triethylamine (0.13 mL, 0.94 mmol, 3.0 equiv), then a solution of T3P (50% w/w in EtOAc, 0.11 mL, 0.38 mmol, 1.2 equiv). The reaction mixture was stirred at rt for 30 min then 3-(pyridin-4-yl)-1H-pyrazol-5-amine (50 mg, 0.31 mmol, 1.0 equiv) was added. The reaction mixture was stirred at rt for 15 h. The mixture was purified directly by RP-HPLC (Method A, 10-90% MeCN in H$_2$O+0.1% FA) to afford tert-butyl (R)-(3-(4-chlorophenyl)-1-oxo-1-((3-(pyridin-4-yl)-1H-pyrazol-5-yl)amino)propan-2-yl)carbamate (25 mg, 18% yield) as a white solid. LCMS: ESI-MS m/z: 442.2 [M+H]$^+$.

Step 3: (R)-2-Amino-3-(4-chlorophenyl)-N-(3-(pyridin-4-yl)-1H-pyrazol-5-yl)propanamide. To a solution of tert-butyl (R)-(3-(4-chlorophenyl)-1-oxo-1-((3-(pyridin-4-yl)-1H-pyrazol-5-yl)amino)propan-2-yl)carbamate (100 mg, 0.23 mmol, 1.0 equiv) and anhydrous 1,4-dioxane (1.0 mL, 0.23 M) was added 4 M HCl in dioxane (0.57 mL, 2.3 mmol, 10 equiv). The reaction mixture was stirred at rt for 2 h. The reaction mixture was concentrated in vacuo to give (R)-2-amino-3-(4-chlorophenyl)-N-(3-(pyridin-4-yl)-1H-pyrazol-5-yl)propanamide (77 mg, >95% yield) as a light-yellow solid, hydrochloric acid salt. $^1$H NMR (400 MHz, DMSO-d$_6$) δ 13.3 (br s, 1H), 8.61 (d, J=4 Hz, 2H), 7.71 (d, J=4 Hz, 2H), 7.34 (d, J=8 Hz, 2H), 7.28 (d, J=8 Hz, 2H), 7.11 (br s, 1H), 3.65-3.60 (m, 1H), 3.04-2.97 (m, 1H), 2.76-2.65 (m, 1H). LCMS: ESI-MS m/z: 342.1 [M+H]$^+$.

Example 152

(S)-5-(4-Chlorobenzyl)-2,2-dimethyl-3-(5-methyl-1-(pyridin-4-yl)-1H-pyrazol-4-yl)imidazolidin-4-one

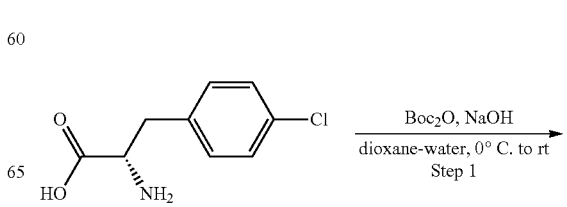

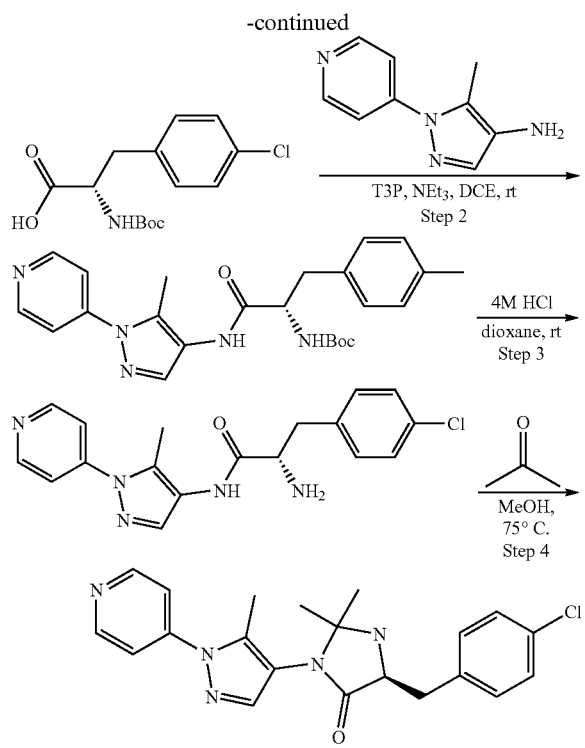

Step 1: (S)-2-((tert-Butoxycarbonyl)amino)-3-(4-chlorophenyl)propanoic acid. To a solution of (S)-2-amino-3-(4-chlorophenyl)propanoic acid (500 mg, 2.5 mmol, 1.0 equiv) and a 1:1 mixture of 1,4-dioxane:water (10 mL, 0.25 M) was added solid sodium hydroxide (210 mg, 5.0 mmol, 2.0 equiv). The resulting solution was cooled to 5° C. and Boc anhydride (820 mg, 3.8 mmol, 1.5 equiv) in 1,4-dioxane (2.0 mL) was slowly added. The reaction mixture was stirred at 0° C. for 1 h, then warmed to rt and stirred for 15 h. Water was added and the aqueous layer was extracted with EtOAc (2×20 mL). The combined organic fractions were washed twice with a saturated solution of sodium bicarbonate. The combined aqueous fractions were acidified with an aqueous solution of 10% HCl until pH~ 1, then extracted with EtOAc (3×10 mL). The combined organic fractions were dried over anhydrous sodium sulfate and concentrated in vacuo to afford (S)-2-((tert-butoxycarbonyl)amino)-3-(4-chlorophenyl)propanoic acid (810 mg, >95% yield) as a white solid. LCMS: ESI-MS m/z: 322.1 [M+Na]+.

Step 2: tert-Butyl (S)-(3-(4-chlorophenyl)-1-((5-methyl-1-(pyridin-4-yl)-1H-pyrazol-4-yl)amino)-1-oxopropan-2-yl)carbamate. To a solution of (S)-2-((tert-butoxycarbonyl)amino)-3-(4-chlorophenyl)propanoic acid (270 mg, 0.90 mmol, 1.0 equiv) in DCM (3.0 mL, 0.30 M) at 0° C. was added DIPEA (0.47 mL, 2.7 mmol, 3.0 equiv) followed by dropwise addition of T3P (50% w/w in EtOAc, 0.69 mL, 1.2 mmol, 1.3 equiv). After 10 min, 5-methyl-1-(pyridin-4-yl)-1H-pyrazol-4-amine (Intermediate 6, 160 mg, 0.90 mmol, 1.0 equiv) in DCM (6.0 mL) was added and the reaction mixture was stirred at rt for 4 h. The reaction mixture was then concentrated in vacuo to afford a light orange residue. The crude product was purified by silica gel column chromatography (0-10% MeOH in DCM) to afford tert-butyl (S)-(3-(4-chlorophenyl)-1-((5-methyl-1-(pyridin-4-yl)-1H-pyrazol-4-yl)amino)-1-oxopropan-2-yl)carbamate (160 mg, 39% yield) as a white solid. LCMS: ESI-MS m/z: 456.2 [M+H]+.

Step 3: (S)-2-Amino-3-(4-chlorophenyl)-N-(5-methyl-1-(pyridin-4-yl)-1H-pyrazol-4-yl)propanamide. To a solution of tert-butyl (S)-(3-(4-chlorophenyl)-1-((5-methyl-1-(pyridin-4-yl)-1H-pyrazol-4-yl)amino)-1-oxopropan-2-yl)carbamate (150 mg, 0.33 mmol, 1.0 equiv) and anhydrous 1,4-dioxane (3.0 mL, 0.11 M) was added 4 M HCl in dioxane (0.51 mL, 1.0 mmol, 3.0 equiv). After stirring for 30 min at rt, the reaction mixture was concentrated in vacuo to afford (S)-2-amino-3-(4-chlorophenyl)-N-(5-methyl-1-(pyridin-4-yl)-1H-pyrazol-4-yl)propanamide as a white solid. This material was moved forward with no further purification. LCMS: ESI-MS m/z: 356.2 [M+H]+.

Step 4: (S)-5-(4-Chlorobenzyl)-2,2-dimethyl-3-(5-methyl-1-(pyridin-4-yl)-1H-pyrazol-4-yl)imidazolidin-4-one. A solution of (S)-2-amino-3-(4-chlorophenyl)-N-(5-methyl-1-(pyridin-4-yl)-1H-pyrazol-4-yl)propanamide (30 mg, 0.084 mmol, 1.0 equiv) in acetone (0.025 mL) and methanol (1.0 mL) was heated to 75° C. for 15 h. The crude product was purified directly by RP-HPLC (Method A, 10-90% MeCN in H2O+0.1% FA) to afford (S)-5-(4-chlorobenzyl)-2,2-dimethyl-3-(5-methyl-1-(pyridin-4-yl)-1H-pyrazol-4-yl)imidazolidin-4-one (2.0 mg, 6.0% yield) as a light yellow solid. 1H NMR (400 MHz, CD3OD) 8.70-8.64 (m, 2H), 7.82 (s, 1H), 7.70-7.62 (m, 2H), 7.34-7.24 (m, 4H), 4.09-4.03 (m, 1H), 3.23-3.15 (m, 1H), 3.06-2.95 (m, 1H), 2.26 (s, 3H), 1.40 (s, 3H), 1.28 (s, 3H). LCMS: ESI-MS m/z: 396.2 [M+H]+.

Example 153

(S)-2-Amino-3-(4-chlorophenyl)-N-(3-(pyridin-4-yl)-1H-pyrazol-5-yl)propanamide

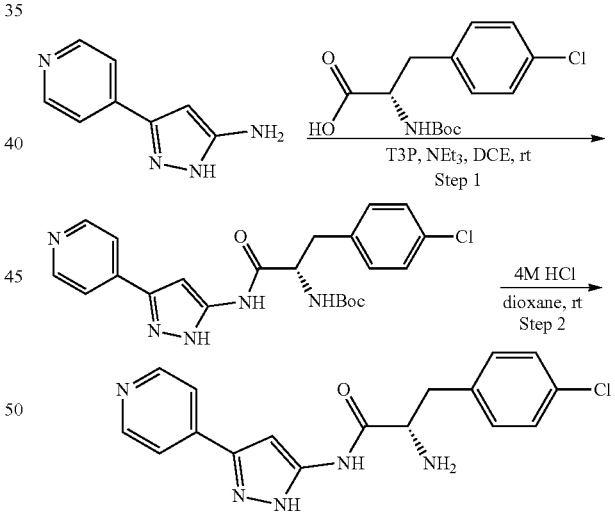

Step 1: tert-Butyl (S)-(3-(4-chlorophenyl)-1-oxo-1-((3-(pyridin-4-yl)-1H-pyrazol-5-yl)amino)propan-2-yl)carbamate. To a solution (S)-2-((tert-butoxycarbonyl)amino)-3-(4-chlorophenyl)propanoic acid (94 mg, 0.31 mmol, 1.0 equiv) in DCE (2.0 mL, 0.16 M) was added triethylamine (0.13 mL, 0.94 mmol, 3.0 equiv) then a solution of T3P (50% w/w in EtOAc, 0.11 mL, 0.38 mmol, 1.3 equiv). The reaction mixture was stirred at rt for 30 min then 3-(pyridin-4-yl)-1H-pyrazol-5-amine (50 mg, 0.31 mmol, 1.0 equiv) was added. The reaction mixture was stirred at rt for 15 h. The crude reaction mixture was directly purified by RP-HPLC (Method A, 10-90% MeCN in H2O+0.1% FA) to afford tert-butyl (S)-(3-(4-chlorophenyl)-1-oxo-1-((3-(pyridin-4-yl)-1H-pyrazol-5-yl)amino)propan-2-yl)carbamate (25 mg, 18% yield) as a white solid. LCMS: ESI-MS m/z: 442.2 [M+H]⁺.

Step 3: (S)-2-Amino-3-(4-chlorophenyl)-N-(3-(pyridin-4-yl)-1H-pyrazol-5-yl)propanamide. To tert-butyl (S)-(3-(4-chlorophenyl)-1-oxo-1-((3-(pyridin-4-yl)-1H-pyrazol-5-yl)amino)propan-2-yl)carbamate (25 mg, 0.057 mmol, 1.0 equiv) was added 4 M HCl in dioxane (1.0 mL, 4.0 mmol, 70 equiv). The reaction mixture was stirred at rt for 1 h. The reaction mixture was concentrated in vacuo to give (S)-2-amino-3-(4-chlorophenyl)-N-(3-(pyridin-4-yl)-1H-pyrazol-5-yl)propanamide (20 mg, >95% yield) as a light-yellow solid, hydrochloric acid salt. ¹H NMR (400 MHz, DMSO-d₆) δ 13.3 (br s, 1H), 8.66-8.59 (m, 2H), 8.23 (s, 1H), 7.72 (d, J=4 Hz, 2H), 7.35 (d, J=8 Hz, 2H), 7.29 (d, J=8 Hz, 2H), 7.14 (br s, 2H), 3.63-3.59 (m, 1H), 3.05-2.96 (m, 1H), 2.76-2.66 (m, 1H). LCMS: ESI-MS m/z: 342.2 [M+H]⁺.

Example 154

(rac)-3-(4-Chlorobenzyl)-1-(4-methyl-3-(pyridin-4-yl)-1H-pyrazol-5-yl)pyrrolidine-2,5-dione

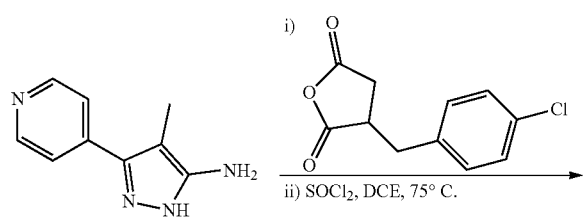

A mixture of 4-methyl-3-(pyridin-4-yl)-1H-pyrazol-5-amine (Intermediate 1, 100 mg, 0.57 mmol, 1.0 equiv), 3-(4-chlorobenzyl)dihydrofuran-2,5-dione (130 mg, 0.57 mmol, 1.0 equiv) and THF (4.0 mL, 0.14 M) was heated to 75° C. and stirred for 1 h. After 1 h, the reaction mixture was cooled to rt and concentrated in vacuo. The resulting yellow solid was diluted with 2 mL of DCE then treated with thionyl chloride (68 mg, 0.57 mmol, 1.0 equiv). The reaction mixture was heated to 75° C. for 1 h. The reaction mixture was cooled to rt and filtered to afford (rac)-3-(4-chlorobenzyl)-1-(4-methyl-3-(pyridin-4-yl)-1H-pyrazol-5-yl)pyrrolidine-2,5-dione (150 mg, 67% yield) as a tan colored solid. ¹H NMR (400 MHz, DMSO-d₆) δ 8.91 (d, J=4 Hz, 2H), 8.16-8.04 (br m, 2H), 7.44-7.31 (m, 4H), 3.21-3.12 (m, 2H), 3.05-2.99 (m, 2H), 2.74-2.65 (m, 1H), 2.03 (s, 3H). LCMS: ESI-MS m/z: 381.1 [M+H]⁺.

Example 155

(rac)-4-(4-Chlorophenyl)-1-(3-(pyridin-4-yl)-1H-pyrazol-5-yl)piperidine-2,6-dione

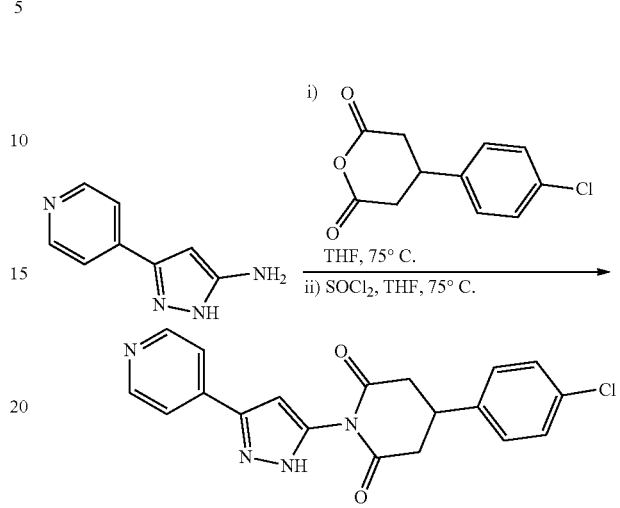

A mixture of 3-(pyridin-4-yl)-1H-pyrazol-5-amine (Intermediate 13, 100 mg, 0.62 mmol, 1.0 equiv), 4-(4-chlorophenyl)dihydro-2H-pyran-2,6(3H)-dione (140 mg, 0.62 mmol, 1.0 equiv) and THF (4.0 mL, 0.16 M) was heated to 75° C. for 1 h. The reaction mixture was cooled to rt and thionyl chloride (74 mg, 0.62 mmol) was added. The reaction mixture was heated to 75° C. for 1 h. The reaction mixture was cooled to r then concentrated in vacuo. The resulting crude product was purified by RP-HPLC (Method A, 10-90% MeCN in H₂O+0.1% FA) to afford (rac)-4-(4-chlorophenyl)-1-(3-(pyridin-4-yl)-1H-pyrazol-5-yl)piperidine-2,6-dione (69 mg, 23% yield) as a tan colored solid. ¹H NMR (400 MHz, DMSO-d₆) δ 13.9 (br s, 1H), 8.84-8.74 (m, 2H), 8.17-7.97 (m, 2H), 7.50-7.28 (m, 4H), 7.00 (br s, 1H), 3.22-3.10 (m, 2H), 3.04-2.94 (m, 2H). LCMS: ESI-MS m/z: 367.1 [M+H]⁺.

Example 156

(rac)-3-(4-Chlorobenzyl)-1-(3-(pyridin-4-yl)-1H-pyrazol-5-yl)pyrrolidine-2,5-dione

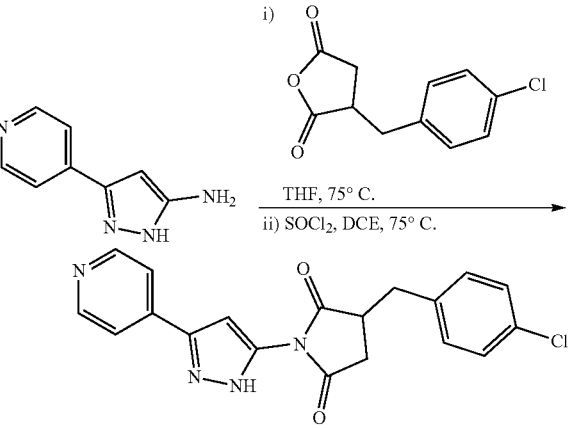

A mixture of 3-(pyridin-4-yl)-1H-pyrazol-5-amine (Intermediate 13, 50 mg, 0.31 mmol, 1.0 equiv), 3-(4-chlorobenzyl)dihydrofuran-2,5-dione (70 mg, 0.31 mmol, 1.0 equiv) and THF (4.0 mL, 0.078 M) was heated to 75° C. for 1 hr. The reaction mixture was cooled to rt and a light-colored solid was filtered. The crude solid was taken up in DCE (4.0 mL) and treated with thionyl chloride (37 mg, 0.31 mmol, 1.0 equiv). The reaction mixture was heated to 75° C. with stirring for 1 hr. The reaction mixture was cooled to rt and filtered to afford (rac)-3-(4-chlorobenzyl)-1-(3-(pyridin-4-yl)-1H-pyrazol-5-yl)pyrrolidine-2,5-dione (55 mg, 48% yield) as a tan colored solid. $^1$H NMR (400 MHz, DMSO-$d_6$) δ 8.92-8.90 (m, 2H), 8.38-8.27 (m, 2H), 7.46-7.32 (m, 4H), 7.23 (s, 1H), 3.24-3.13 (m, 2H), 3.03-2.84 (m, 2H), 2.69-2.59 (m, 1H). LCMS: ESI-MS m/z: 367.1 [M+H]$^+$.

Example 157

(rac)-4-(4-Chlorophenyl)-1-(4-methyl-3-(pyridin-4-yl)-1H-pyrazol-5-yl)piperidine-2,6-dione

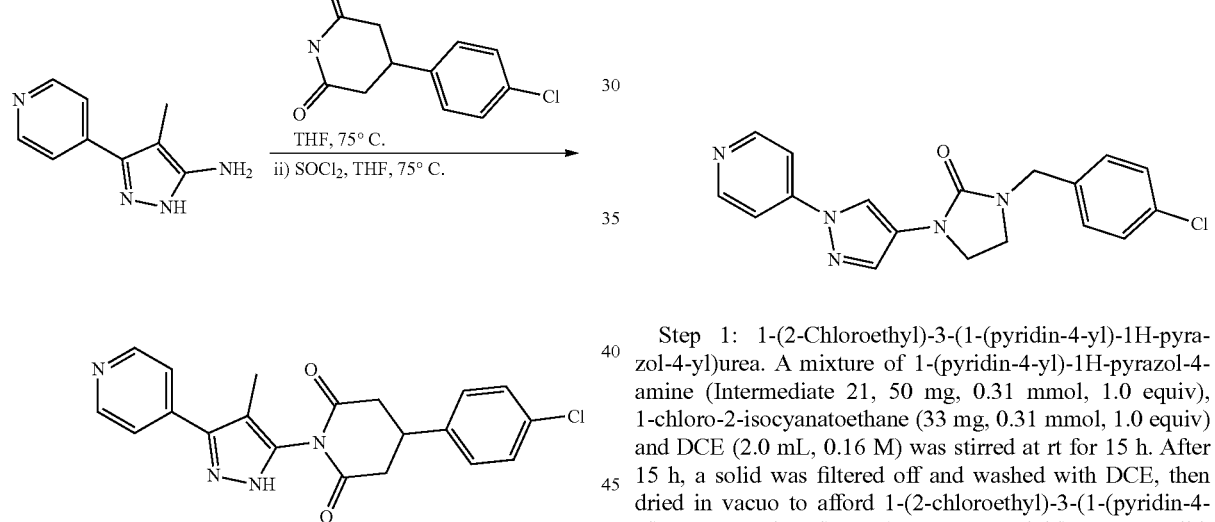

A solution of 4-methyl-3-(pyridin-4-yl)-1H-pyrazol-5-amine (Intermediate 1, 100 mg, 0.57 mmol, 1.0 equiv) and 4-(4-chlorophenyl)dihydro-2H-pyran-2,6(3H)-dione (130 mg, 0.57 mmol, 1.0 equiv) in anhydrous THF (2.0 mL, 0.29 M) was heated to 95° C. for 2 h. The mixture was cooled to rt and was directly purified by RP-HPLC (Method A, 10-90% MeCN in H$_2$O+0.1% TFA) to afford a viscous, light yellow oil. The purified intermediate (assume 0.57 mmol) was dissolved in DCE (4.0 mL, 0.14 M), treated with thionyl chloride (0.42 mL, 5.7 mmol, 1.0 equiv) and heated to 75° C. for 1 h. The mixture was again cooled to rt and purified directly by RP-HPLC (Method A, 10-90% MeCN in H$_2$O+0.1% TFA) to afford (rac)-4-(4-chlorophenyl)-1-(4-methyl-3-(pyridin-4-yl)-1H-pyrazol-5-yl)piperidine-2,6-dione (56 mg, 20% yield) as a yellow solid, trifluoroacetic acid salt. $^1$H NMR (400 MHz, DMSO-$d_6$) δ 13.7 (br s, 1H), 8.85-8.77 (m, 2H), 8.00-7.84 (m, 2H), 7.51-7.43 (m, 4H), 3.83-3.59 (m, 1H), 3.31-3.14 (m, 2H), 3.08-2.93 (m, 2H), 2.09 (s, 1.5H), 1.96 (s, 1.5H). LCMS: ESI-MS m/z: 381.1[M+H]$^+$.

Example 158

1-(4-Chlorobenzyl)-3-(1-(pyridin-4-yl)-1H-pyrazol-4-yl)imidazolidin-2-one

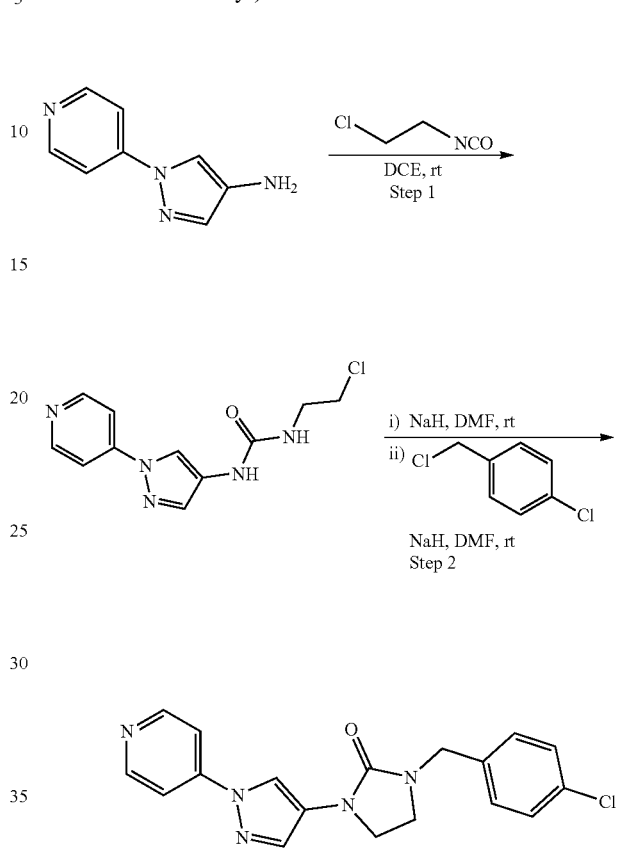

Step 1: 1-(2-Chloroethyl)-3-(1-(pyridin-4-yl)-1H-pyrazol-4-yl)urea. A mixture of 1-(pyridin-4-yl)-1H-pyrazol-4-amine (Intermediate 21, 50 mg, 0.31 mmol, 1.0 equiv), 1-chloro-2-isocyanatoethane (33 mg, 0.31 mmol, 1.0 equiv) and DCE (2.0 mL, 0.16 M) was stirred at rt for 15 h. After 15 h, a solid was filtered off and washed with DCE, then dried in vacuo to afford 1-(2-chloroethyl)-3-(1-(pyridin-4-yl)-1H-pyrazol-4-yl)urea (60 mg, 73% yield) as a tan solid. LCMS: ESI-MS m/z: 266.1 [M+H]$^+$.

Step 2: 1-(4-Chlorobenzyl)-3-(1-(pyridin-4-yl)-1H-pyrazol-4-yl)imidazolidin-2-one. To a solution of 1-(2-chloroethyl)-3-(1-(pyridin-4-yl)-1H-pyrazol-4-yl)urea (83 mg, 0.31 mmol, 1.0 equiv) and DMF (2.0 mL, 0.16 M) was added sodium hydride (60 wt % dispersion in mineral oil, 31 mg, 0.78 mmol, 2.5 equiv). The reaction was stirred at rt for 15 min. Subsequently, 1-chloro-4-(chloromethyl)benzene (50 mg, 0.31 mmol, 1.0 equiv) was added in one portion. The reaction was stirred at rt for 1 h. The reaction mixture was quenched carefully with water and purified directly by RP-HPLC (Method A, 10-90% MeCN in H$_2$O+0.10% TFA) to afford 1-(4-chlorobenzyl)-3-(1-(pyridin-4-yl)-1H-pyrazol-4-yl)imidazolidin-2-one (98 mg, 67% yield) as a white solid, trifluoroacetic acid salt. $^1$H NMR (400 MHz, DMSO-$d_6$) δ 8.78 (d, J=4 Hz, 2H), 8.69 (s, 1H), 8.28 (s, 1H), 7.45 (d, J=8 Hz, 2H), 7.35 (d, J=8 Hz, 2H), 4.40 (s, 2H), 3.79-3.73 (m, 2H), 3.49-3.43 (m, 2H). LCMS: ESI-MS m/z: 354.2 [M+H]$^+$.

Example 159

1-(4-Chlorobenzyl)-3-(1-(pyridin-4-yl)-1H-pyrazol-4-yl)tetrahydropyrimidin-2(1H)-one

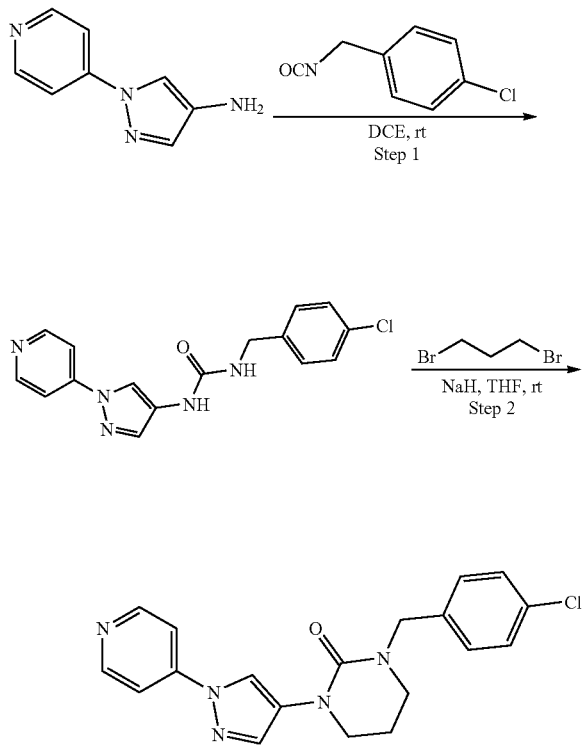

Step 1: 1-(4-Chlorobenzyl)-3-(1-(pyridin-4-yl)-1H-pyrazol-4-yl)urea. To a mixture of 1-(pyridin-4-yl)-1H-pyrazol-4-amine (Intermediate 21, 200 mg, 1.3 mmol, 1.0 equiv) and anhydrous DCE (4.0 mL, 0.33 M) was added 1-chloro-4-(isocyanatomethyl)benzene (410 mg, 2.5 mmol, 1.9 equiv) and the reaction mixture was stirred at rt for 15 h. After 15 h, the reaction mixture was concentrated in vacuo. The resulting solid was filtered and washed with hexanes to afford 1-(4-chlorobenzyl)-3-(1-(pyridin-4-yl)-1H-pyrazol-4-yl)urea (370 mg, 87% yield) as a light tan solid. LCMS: ESI-MS m/z: 328.1 [M+H]+.

Step 2: 1-(4-Chlorobenzyl)-3-(1-(pyridin-4-yl)-1H-pyrazol-4-yl)tetrahydropyrimidin-2(1H)-one. To a solution of 1-(4-chlorobenzyl)-3-(1-(pyridin-4-yl)-1H-pyrazol-4-yl)urea (35 mg, 0.079 mmol) in anhydrous THF (2.0 mL, 0.040 M) was added sodium hydride (60 wt % dispersion in mineral oil, 6.3 mg, 0.15 mmol). After stirring at rt for 5 min, 1,3-dibromopropane (8.0 uL, 0.079 mmol, 1.0 equiv) was added and the reaction mixture was stirred at rt for 1 h. After 1 h, the reaction mixture was carefully quenched with water and purified directly by RP-HPLC (Method A, 10-90% MeCN in H$_2$O+0.1% TFA) to afford 1-(4-chlorobenzyl)-3-(1-(pyridin-4-yl)-1H-pyrazol-4-yl)tetrahydropyrimidin-2(1H)-one (8.2 mg, 21% yield) as a tan solid, trifluoroacetic acid salt. $^1$H NMR (400 MHz, DMSO-d$_6$) δ 13.7 (br s, 1H), 8.85-8.77 (m, 2H), 8.00-7.84 (m, 2H), 7.51-7.43 (m, 4H), 3.83-3.59 (m, 1H), 3.31-3.14 (m, 2H), 3.08-2.93 (m, 2H), 2.09 (s, 1.5H), 1.96 (s, 1.5H). LCMS: ESI-MS m/z: 367.8 [M+H]+.

Example 160

1-(4-Chlorobenzyl)-3-(1-(pyridin-4-yl)-1H-pyrazol-4-yl)thiourea

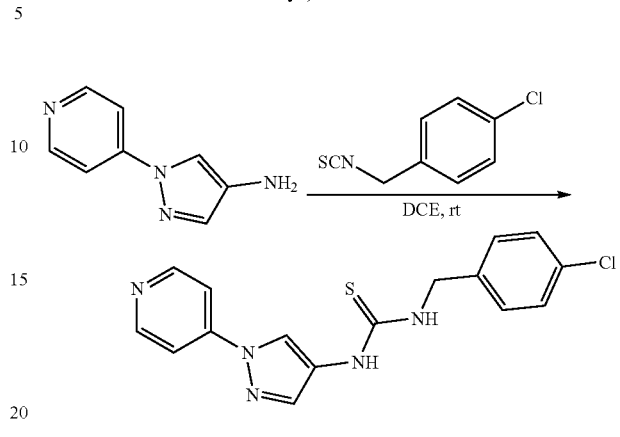

To a mixture of 1-(pyridin-4-yl)-1H-pyrazol-4-amine (Intermediate 21, 50 mg, 0.31 mmol, 1.0 equiv) and anhydrous DCE (4.0 mL, 0.078 M) was added 1-chloro-4-(isothiocyanatomethyl)benzene (57 mg, 0.31 mmol, 1.0 equiv). The heterogeneous reaction mixture was stirred at rt for 15 h. The reaction mixture was then concentrated in vacuo, and dissolved in 1.0 mL of DMSO. This solution was then purified by RP-HPLC (Method A, 10-90% MeCN in H$_2$O+0.1% TFA) to afford 1-(4-chlorobenzyl)-3-(1-(pyridin-4-yl)-1H-pyrazol-4-yl)thiourea (50 mg, 35% yield) as a white solid, trifluoroacetic acid salt. LCMS: ESI-MS m/z: 344.1 [M+H]+.

Example 161

1-(4-Chlorobenzyl)-3-(4-methyl-3-(pyridin-4-yl)-1H-pyrazol-5-yl)urea

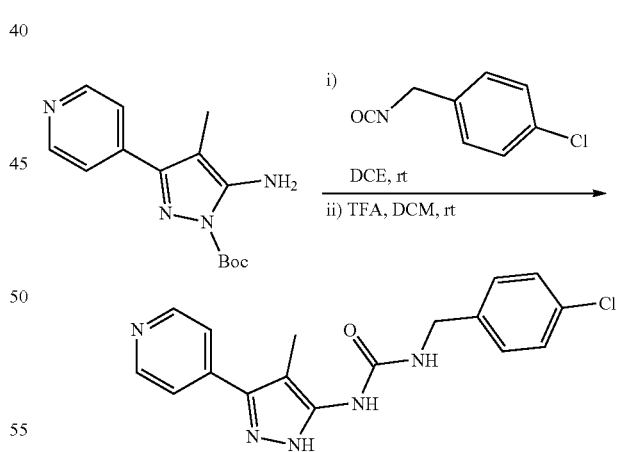

To a solution of tert-butyl 5-amino-4-methyl-3-(pyridin-4-yl)-1H-pyrazole-1-carboxylate (Intermediate 28, 100 mg, 0.37 mmol, 1.0 equiv) in anhydrous DCE (1.0 mL, 0.37 M) was added 1-chloro-4-(isocyanatomethyl)benzene (61 mg, 0.37 mmol, 1.0 equiv). The reaction mixture was stirred at rt for 15 h, then concentrated in vacuo. The resulting residue was diluted with DCM (0.5 mL) and TFA (0.1 mL) was added. After stirring at rt for 1 h, the reaction mixture was concentrated in vacuo and purified directly by RP-HPLC (Method A, 10-90% MeCN in H$_2$O+0.1% TFA) to afford 1-(4-chlorobenzyl)-3-(4-methyl-3-(pyridin-4-yl)-1H-pyrazol-5-yl)urea (15 mg, 9.3% yield) as a white solid, trifluoroacetic acid salt. LCMS: ESI-MS m/z: 342.1 [M+H]⁺.

Example 162

3-(4-Chlorophenyl)-N-(5-(pyridin-4-yl)-4H-1,2,4-triazol-3-yl)propanamide

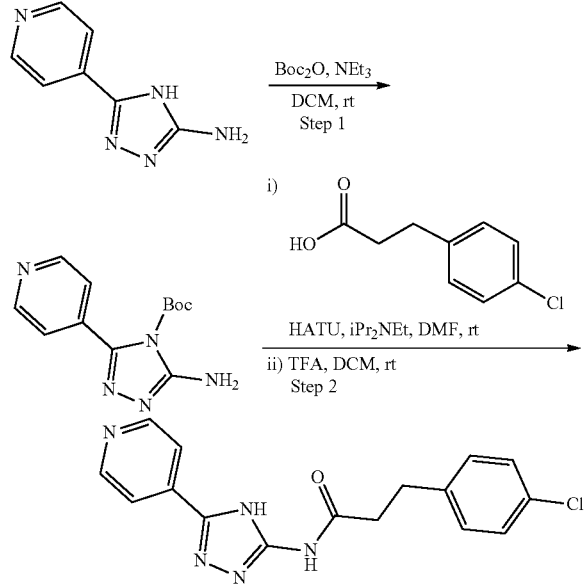

Step 1: tert-Butyl 3-amino-5-(pyridin-4-yl)-4H-1,2,4-triazole-4-carboxylate. To a solution of 5-(pyridin-4-yl)-4H-1,2,4-triazol-3-amine (200 mg, 1.2 mmol, 1.0 equiv) in DCM (3.0 mL, 0.40 M) was added triethylamine (250 mg, 2.5 mmol, 2.0 equiv), followed by Boc anhydride (270 mg, 1.2 mmol, 1.0 equiv). The resulting solution was stirred at rt for 3 h. The reaction mixture was then concentrated in vacuo and the crude residue was purified by silica gel column chromatography (50-100% EtOAc in hexanes) to afford tert-butyl 3-amino-5-(pyridin-4-yl)-4H-1,2,4-triazole-4-carboxylate (130 mg, 40% yield) as a white solid. ¹H NMR (400 MHz, DMSO-d₆) δ 8.69-8.68 (m, 2H), 7.84-7.82 (m, 2H), 7.49 (br s, 2H), 1.60 (s, 9H). LCMS: ESI-MS m/z: 262.1 [M+H]⁺.

Step 2: 3-(4-Chlorophenyl)-N-(5-(pyridin-4-yl)-4H-1,2,4-triazol-3-yl)propanamide. A solution of 3-(4-chlorophenyl)propanoic acid (110 mg, 0.59 mmol, 1.2 equiv) in DMF (2.5 mL, 0.20 M) was treated with DIPEA (0.17 mL, 0.98 mmol, 1.7 equiv) at rt for 5 min. The mixture was cooled to 0° C. and HATU (220 mg, 0.59 mmol, 2.0 equiv) was added and the mixture was stirred for 10 min at rt. Subsequently, tert-butyl 3-amino-5-(pyridin-4-yl)-4H-1,2,4-triazole-4-carboxylate (130 mg, 0.49 mmol, 1.0 equiv) was added at 0° C. and the mixture was slowly warmed to rt and stirred for 3 h. After 3 h, the reaction mixture was purified directly by RP-HPLC (Method A, 10-90% MeCN in H₂O+0.1% TFA) to afford 3-(4-chlorophenyl)-N-(5-(pyridin-4-yl)-4H-1,2,4-triazol-3-yl)propanamide (1.3 mg, 0.81% yield) as a white solid, trifluoroacetic acid salt. LCMS: ESI-MS m/z: 328.1 [M+H]⁺.

Example 163

1-(4-Chloro-3,5-difluorobenzyl)-3-(3-(pyridin-4-yl)-1H-pyrazol-5-yl)urea

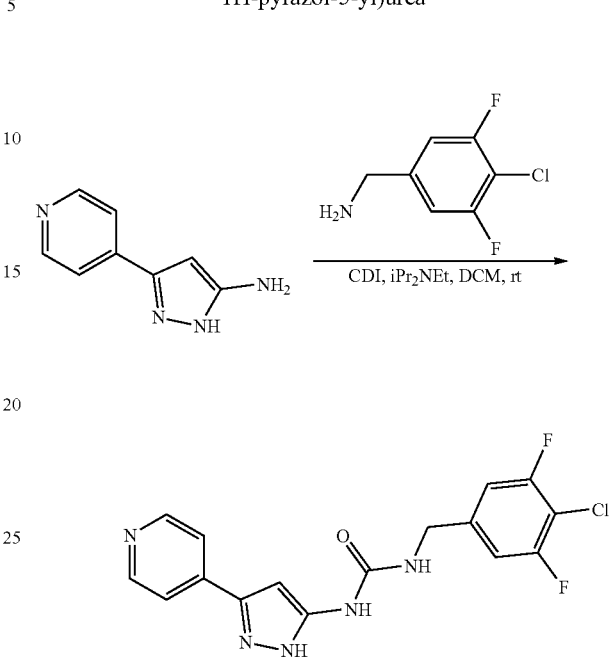

A solution of 3-(pyridin-4-yl)-1H-pyrazol-5-amine (Intermediate 13, 50 mg, 0.31 mmol, 1.0 equiv), DIPEA (81 mg, 0.63 mmol, 2.0 equiv) and CDI (100 mg, 0.63 mmol, 2.0 equiv) in DCM (3.0 mL, 0.10 M) was stirred at rt for 30 min. Subsequently (4-chloro-3,5-difluorophenyl)methanamine (55 mg, 0.31 mmol, 1.0 equiv) was added. The resulting mixture was stirred at rt for 1 h then heated to 50° C. for a subsequent 3 h. The reaction mixture was cooled to rt and concentrated in vacuo, then purified directly by RP-HPLC (Method C, 15-40% MeCN in H₂O+10 mM NH₄HCO₃+ 0.025% NH₃·H₂O) to afford 1-(4-chloro-3,5-difluorobenzyl)-3-(3-(pyridin-4-yl)-1H-pyrazol-5-yl)urea (20 mg, 0.055 mmol, 18% yield) as a white solid. ¹H NMR (400 MHz, CDCl₃) δ 8.71 (d, J=9.2 Hz, 2H), 7.52 (s, 1H), 7.42 (d, J=4.8 Hz, 2H), 7.01-6.99 (m, 3H), 6.79 (s, 1H), 6.22 (s, 1H), 4.52 (d, J=6.4 Hz, 2H). LCMS: ESI-MS m/z: 364.1 [M+H]⁺.

Example 164

1-(3-(Pyridin-4-yl)-1H-pyrazol-5-yl)-3-(3,4,5-trifluorobenzyl)urea

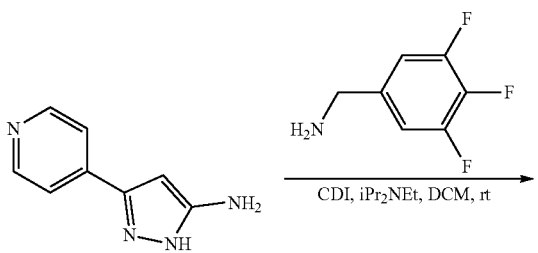

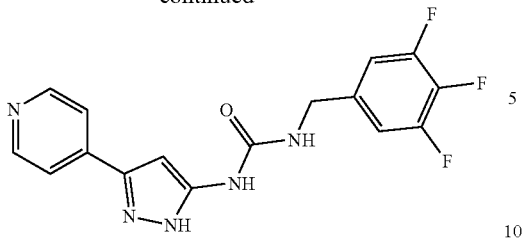

The product was prepared according to the same procedure as Example #163 to afford 1-(3-(pyridin-4-yl)-1H-pyrazol-5-yl)-3-(3,4,5-trifluorobenzyl)urea in 18% yield. $^1$H NMR (400 MHz, DMSO-$d_6$) δ 13.0 (s, 1H), 9.12 (s, 1H), 8.61 (s, 2H), 7.68 (d, J=5.8 Hz, 2H), 7.33-7.20 (m, 2H), 7.14 (s, 1H), 6.79 (s, 1H), 4.32 (d, J=5.6 Hz, 2H). LCMS: ESI-MS m/z: 348.1 [M+H]$^+$.

Example 165

1-(4-Chlorobenzyl)-3-(3-(pyridin-4-yl)-1H-pyrazol-5-yl)urea

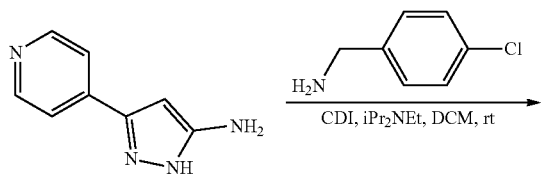

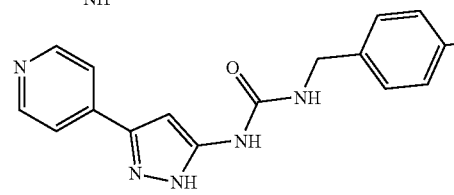

The product was prepared according to the same procedure as Example #163 to afford 1-(4-chlorobenzyl)-3-(3-(pyridin-4-yl)-1H-pyrazol-5-yl)urea in 20% yield. $^1$H NMR (400 MHz, DMSO-$d_6$) δ 13.0 (s, 1H), 9.04 (s, 1H), 8.61 (s, 2H), 7.68 (d, J=5.6 Hz, 2H), 7.47-7.29 (m, 4H), 7.09 (s, 1H), 6.77 (s, 1H), 4.33 (d, J=6.0 Hz, 2H). LCMS: ESI-MS m/z: 328.1 [M+H]$^+$.

Example 166

3-(4-Chloro-3,5-difluorophenyl)-N-(4-chloro-3-(pyridin-4-yl)-1H-pyrazol-5-yl)propanamide

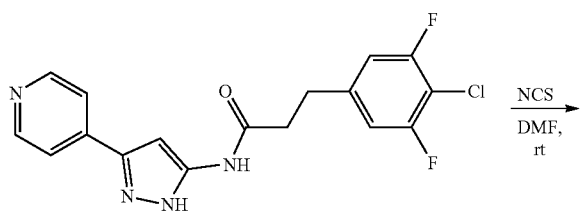

A solution of 3-(4-chloro-3,5-difluorophenyl)-N-(3-(pyridin-4-yl)-1H-pyrazol-5-yl)propanamide (Example 101, 30 mg, 0.082 mmol, 1.0 equiv) and N-chlorosuccinimide (22 mg, 0.17 mmol, 2.0 equiv) in DMF (1.5 mL, 0.055 M) was stirred at rt for 5 h. The reaction mixture was then concentrated in vacuo and purified directly by RP-HPLC (Method C, 15-40% MeCN in H$_2$O+10 mM NH$_4$HCO$_3$+0.025% NH$_3$·H$_2$O) to afford 3-(4-chloro-3,5-difluorophenyl)-N-(4-chloro-3-(pyridin-4-yl)-1H-pyrazol-5-yl)propanamide (13 mg, 0.034 mmol, 41% yield) as a white solid. $^1$H NMR (400 MHz, DMSO-$d_6$) δ 13.4 (br s, 1H), 9.08 (br s, 1H), 8.68 (s, 2H), 7.81 (d, J=4.8 Hz, 2H), 7.26-7.24 (m, 3H), 4.34 (d, J=6.0 Hz, 2H). LCMS: ESI-MS m/z: 398.1 [M+H]$^+$.

Example 167

N-(4-Chloro-3-(pyridin-4-yl)-1H-pyrazol-5-yl)-3-(3,4,5-trifluorophenyl)propanamide

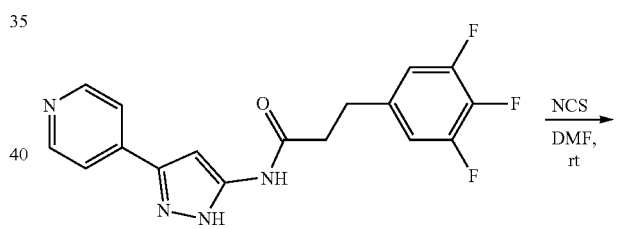

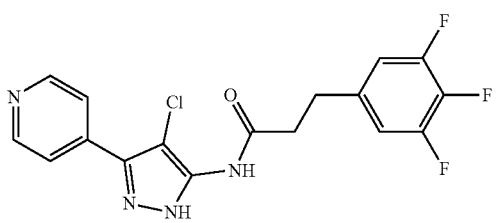

The product was prepared according to the same procedure as Example #166 to afford N-(4-chloro-3-(pyridin-4-yl)-1H-pyrazol-5-yl)-3-(3,4,5-trifluorophenyl)propanamide in 42% yield. $^1$H NMR (400 MHz, CD$_3$OD) δ 7.09 (d, J=4.7 Hz, 2H), 6.37 (s, 2H), 5.57-5.49 (m, 2H), 1.46 (dd, J=18.2, 11.0 Hz, 2H), 1.24 (t, J=7.4 Hz, 2H). LCMS: ESI-MS m/z: 381.1 [M+H]$^+$.

Example 168

1-(4-Chloro-3-(pyridin-4-yl)-1H-pyrazol-5-yl)-3-(4-chlorobenzyl)urea

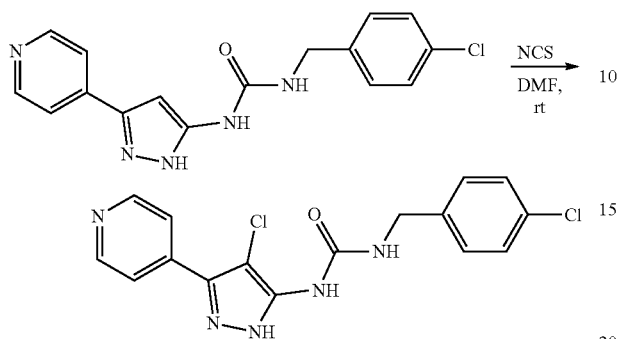

The product was prepared according to the same procedure as Example #166 to afford 1-(4-chloro-3-(pyridin-4-yl)-1H-pyrazol-5-yl)-3-(4-chlorobenzyl)urea in 45% yield. $^1$H NMR (400 MHz, DMSO-$d_6$) δ 13.4-13.2 (m, 1H), 8.95 (s, 1H), 8.67 (s, 2H), 7.82 (s, 2H), 7.38 (dd, J=29.7, 8.5 Hz, 4H), 7.17 (s, 1H), 4.33 (d, J=6.0 Hz, 2H). LCMS: ESI-MS m/z: 362.1 [M+H]$^+$.

Example 169

3-(4-Chlorophenyl)-N-(3-(3-methoxypyridin-4-yl)-1H-pyrazol-5-yl)propanamide

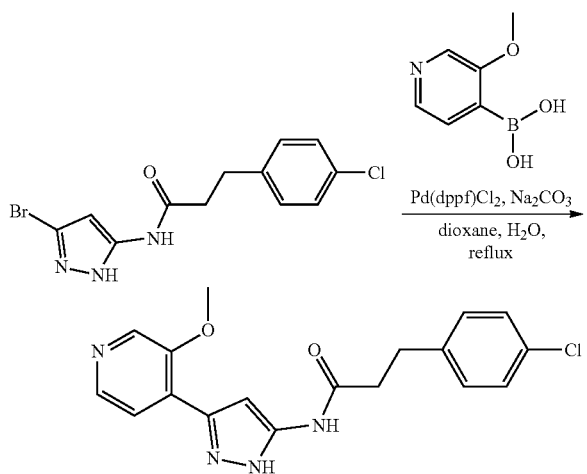

A mixture of N-(3-bromo-1H-pyrazol-5-yl)-3-(4-chlorophenyl)propanamide (Intermediate 29, 50 mg, 0.15 mmol, 1.0 equiv), (3-methoxypyridin-4-yl)boronic acid (25 mg, 0.16 mmol, 1.1 equiv), Pd(dppf)Cl$_2$ (11 mg, 0.015 mmol, 0.1 equiv), and sodium carbonate (32 mg, 0.30 mmol, 2.0 equiv) in a solution of 4.0 mL of 1,4-dioxane and 1.0 mL water (0.030 M) was stirred at reflux under an atmosphere of nitrogen gas for 3 h. The reaction mixture was then cooled to rt and diluted with EtOAc (10 mL), filtered, the filtrate was concentrated in vacuo and purified directly by RP-HPLC (Method C, 15-40% MeCN in H$_2$O+10 mM NH$_4$HCO$_3$+0.025% NH$_3$·H$_2$O) to afford 3-(4-chlorophenyl)-N-(3-(3-methoxypyridin-4-yl)-1H-pyrazol-5-yl)propanamide (15 mg, 0.042 mmol, 28% yield) as a white solid. $^1$H NMR (400 MHz, DMSO-$d_6$) δ 12.8 (s, 1H), 10.49 (s, 1H), 8.49 (s, 1H), 8.26 (d, J=4.8 Hz, 1H), 7.66 (d, J=5.2 Hz, 1H), 7.35 (d, J=8.4 Hz, 2H), 7.28 (d, J=8.4 Hz, 2H), 7.13 (s, 1H), 4.02 (s, 3H), 2.90 (t, J=7.6 Hz, 2H), 2.63 (t, J=7.6 Hz, 2H). LCMS: ESI-MS m/z: 357.1 [M+H]$^+$.

Example 170

3-(4-Chlorophenyl)-N-(3-(3-fluoropyridin-4-yl)-1H-pyrazol-5-yl)propanamide

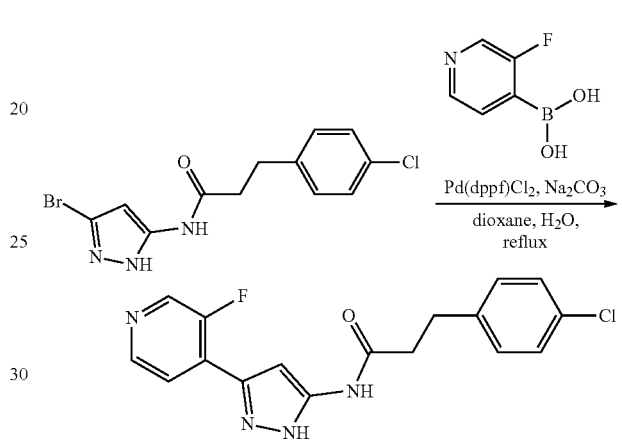

The product was prepared following the same procedure as Example #169 to afford 3-(4-chlorophenyl)-N-(3-(3-fluoropyridin-4-yl)-1H-pyrazol-5-yl)propanamide in 30% yield. $^1$H NMR (400 MHz, DMSO-$d_6$) δ 8.66 (s, 1H), 8.47 (s, 2H), 7.87 (t, J=12.0 Hz, 1H), 7.34 (d, J=8.8 Hz, 2H), 7.27 (d, J=8.4 Hz, 2H), 2.89 (t, J=15.2 Hz, 2H), 2.63 (t, J=15.2 Hz, 2H). LCMS: ESI-MS m/z: 345.1 [M+H]$^+$.

Example A

Biological Assay

Each reaction was run at a volume of 20 μL containing 50 μM compound (dissolved in DMSO; final concentration of DMSO is 1% v/v), 40 nM human SARM1$_{(50-724)}$, 0.3 mM NMN, 20 μM NAD, 1 mM TCEP, 25 mM HEPES pH 7.4, 10 mM KCl and 10 mM MgCl$_2$. The reaction was incubated at room temperature for 60 minutes and quenched with 20 μL of 0.4% formic acid. The samples were run on Agilent HPLC 1260 Infinity II with Synergi 2.5 μM Fusion-RP 100 Å (100×3.0 mm) LC column from Phenomenex. Total run time for each sample was 4 minutes. The run was isocratic with 1.5% methanol in 40 mM ammonium acetate pH 6.0. Samples were run at a flow rate of 0.8 m/min at 55° C. Peak areas of NAD and NAM were determined using OpenLAB CDS (Chem Station edition) software. For dose-response, the compound was diluted serially 1:3 in DMSO and added to the reaction starting at a final compound concentration of 100 μM in 1% DMSO.

IC$_{50}$ data according to the assay described above is provided in Table 1 below. IC$_{50}$<1 (+); 1≤IC$_{50}$<10 (++); and 10≤IC$_{50}$≤100 (+++) μM for the exemplified compounds.

TABLE 1

| Ex. No. | Average IC$_{50}$ (microM) |
|---|---|
| 1 | + |
| 2 | ++ |
| 3 | + |
| 4 | + |
| 5 | + |
| 6 | + |
| 7 | ++ |
| 8 | + |
| 9 | + |
| 10 | + |
| 11 | + |
| 12 | ++ |
| 13 | + |
| 14 | + |
| 15 | + |
| 16 | + |
| 17 | + |
| 18 | + |
| 19 | + |
| 20 | + |
| 21 | ++ |
| 22 | ++ |
| 23 | ++ |
| 24 | + |
| 25 | ++ |
| 26 | ++ |
| 27 | ++ |
| 28 | ++ |
| 29 | ++ |
| 30 | + |
| 31 | + |
| 32 | + |
| 33 | + |
| 34 | ++ |
| 35 | + |
| 36 | + |
| 37 | + |
| 38 | + |
| 39 | ++ |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | ++ |
| 67 | + |
| 68 | ++ |
| 69 | ++ |
| 70 | ++ |
| 71 | + |
| 72 | ++ |
| 73 | + |
| 74 | + |
| 75 | + |
| 76 | ++ |
| 77 | ++ |
| 78 | + |
| 79 | + |
| 80 | ++ |
| 81 | + |
| 82 | + |
| 83 | + |
| 84 | + |
| 85 | ++ |
| 86 | + |
| 88 | + |
| 89 | ++ |
| 90 | + |
| 91 | + |
| 92 | + |
| 93 | + |
| 94 | + |
| 95 | + |
| 96 | + |
| 97 | + |
| 98 | + |
| 99 | ++ |
| 100 | ++ |
| 101 | + |
| 102 | + |
| 103 | + |
| 104 | + |
| 105 | + |
| 106 | + |
| 107 | ++ |
| 108 | ++ |
| 109 | ++ |
| 110 | + |
| 111 | + |
| 112 | ++ |
| 113 | ++ |
| 114 | + |
| 115 | ++ |
| 116 | + |
| 117 | + |
| 118 | + |
| 119 | + |
| 120 | + |
| 121 | + |
| 122 | + |
| 123 | + |
| 124 | + |
| 125 | + |
| 126 | ++ |
| 127 | + |
| 128 | + |
| 129 | + |
| 130 | + |
| 131 | ++ |
| 132 | ++ |
| 133 | ND |
| 134 | ++ |
| 135 | ++ |
| 136 | + |
| 137 | ++ |
| 138 | + |
| 139 | + |
| 140 | + |
| 141 | + |
| 142 | + |
| 143 | + |
| 144 | + |
| 145 | + |
| 146 | + |
| 147 | + |
| 148 | ++ |
| 149 | ++ |
| 150 | ++ |
| 151 | + |
| 152 | ++ |
| 153 | + |

TABLE 1-continued

| Ex. No. | Average IC$_{50}$ (microM) |
|---|---|
| 154 | ++ |
| 155 | + |
| 156 | + |
| 157 | ++ |
| 158 | ++ |
| 159 | ++ |
| 160 | ++ |
| 161 | + |
| 162 | + |
| 163 | + |
| 164 | + |
| 165 | + |
| 166 | + |
| 167 | + |
| 168 | + |
| 169 | ++ |
| 170 | + |

Example B

Assessment of the Protective Effect of SARM1 Inhibitors in Multiple Sclerosis

To evaluate the ability of a SARM1 inhibitor to delay, prevent, or treat multiple sclerosis, a preclinical mouse model of experimental autoimmune encephalomyelitis (EAE) may be used (Lyons J A et al., Eur J of Immunology, 1999 29(11):3432-9). To induce EAE, female mice, 9-13 weeks old, may receive 0.1 ml subcutaneous injection (s.c.) of myelin oligo glycoprotein peptide (MOG35-55) suspension in complete Freund's adjuvant (CFA) in the upper and lower back, followed by intraperitoneal injection (i.p.) of pertussis toxin (100 ng) within 3 hours of MOG injection and again within 24 hours of MOG injection. Weight and clinical score of paralysis may be recorded daily starting at day 7 until day 28 post-MOG injection. A SARM1 inhibitor can be dosed orally (p.o.) daily or with the use of osmotic pumps implanted s.c. or i.p. as a stand-alone treatment, or in conjunction with current standard of care medication(s) either on the same day as MOG treatment or at the start of symptoms. Effective compounds will slow the development of disease and/or to decrease the severity of the symptoms.

Example C

Assessment of the Protective Effect of SARM1 Inhibitors in Chemotherapy-Induced Peripheral Neuropathy (CIPN)

To evaluate the ability of a SARM1 inhibitor to prevent CIPN, a mouse model of CIPN may be used. To induce peripheral neuropathy, mice may be treated with a specific chemotherapeutic known to cause peripheral neuropathy in humans (e.g., vincristine, paclitaxel, or oxaliplatin) (Geisler et al., *Brain* 2016, 139 (Pt 12):3092-3108; Wang M S et al., Ann. Neurol., 2002, 52(4)442-7; Sprowl et al., *Proc Natl Acad Sci* 2013, 110(27):11199). Peripheral neuropathy may be assessed with behavior tests of mechanical allodynia by measuring sensitivity in the footpad by increasing applied force of Von Frey filament, cold or heat sensitivity by measuring escape/pain behavior (e.g., jumping, paw licking or paw lifts) on a thermally controlled enclosed platform. Furthermore, behavior may be correlated with biomarkers of neuropathy (e.g., plasma neurofilament light) and by histologically examining intra-epidermal nerve fiber density in hind paw pad biopsies. SARM1 inhibitors may be dosed orally (p.o.) daily, or with the use of osmotic pumps implanted s.c. or i.p. at the start of the experiment. Effective compounds will prevent allodynia, prevent the increase of the neuropathy biomarker and/or prevent the decrease in IENF density relative to vehicle treated cohorts.

Example D

Assessment of the Protective Effect of SARM1 Inhibitors in Amyotrophic Lateral Sclerosis (ALS) To evaluate the ability of a SARM1 inhibitor to delay, prevent, or treat ALS, a genetic mouse model of the disease may be used. Transgenic mice with the mutation TDP43Q331K have been shown to develop progressive motor deficits as measured by performance on the accelerating rotarod and by progressive hind limb weakness as measured by hind paw grip strength. Furthermore, plasma NfL levels may appear to be increased in the mutants. SARM1 inhibitors may be dosed with the use of osmotic pumps implanted s.c. or i.p. Effective compounds will protect from the neurodegeneration and show a decrease in plasma NfL, as well as delay and/or prevent progression of the motor deficits and hind limb weakness.

Example E

Assessment of the Protective Effect of SARM1 Inhibitors in Glaucoma

To evaluate the ability of SARM1 inhibitor to prevent glaucoma, several mouse models of the disease are utilized. The optic nerve crush (ONC) model of glaucoma is generated by applying transient pressure to the optic nerve with forceps to induces retrograde retinal ganglion cell death and replicate many of the changes observed in glaucomatous retinas, excluding increased ocular pressure. Other models of glaucoma mimic increased intraocular pressure and are generated by blockade of the trabecular network by injection of exogenous oil/microbeads or by laser-induced coagulation. At select time points in all of the aforementioned glaucoma models, eyes and optic nerves are harvested for histology to evaluate ocular damage. Retinal cross sections or flatmounts stained with markers of retinal ganglion cells, such as RBPMS or BRN2A, are used to determine the number of surviving cells. Optic nerve sections stained with neuronal specific markers such as SMI32 are used to determine surviving axon number and morphology. In both histological sample types, markers of neuroinflammation, such as GFAP or IBA1, are used to assess injury extent. SARM1 inhibitors will be dosed orally (p.o.) everyday with the use of osmotic pumps implanted s.c. or i.p. at the start of the experiment. Additionally, SARM1 inhibitors may be dosed via topical eye drops or by intravitreal, subconjunctival, subtenon, or retrobulbar injection. We expect our compounds to prevent degeneration of retinal ganglion cells and their axons in the optic nerve, attenuate neuroinflammatory responses, and preserve visual function relative to vehicle treated cohorts.

Example F

Assessment of the Protective Effect of SARM1 Inhibitors in Traumatic Brain Injury (TBI)

To evaluate the ability of a SARM1 inhibitor to protect against TBI, a genetic mouse model of the disease may be used. Closed head TBI will be produced using a weight drop device as previously described in detail and as adapted for use in mice (Henninger et al., Brain 2016, 139 (Pt 4):1094). SARM1 inhibitors will be dosed orally (p.o.) everyday with the use of osmotic pumps implanted s.c. or i.p. at the start of the experiment. Effective compounds will be evaluated using multiple endpoints, primary endpoint being PAPP immunohistology after TBI. Secondary outcomes will include neurobehavioral deficits measured throughout the 4-week observation period using the NSS scale (Flierl et al., 2009, 4(9):1328), plasma phosphorylated neurofilament heavy chain (pNFH) and plasma neurofilament light chain (NfL) levels and cerebral neurochemical profiling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula Ic:

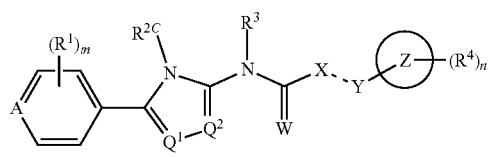

Ic or a pharmaceutically acceptable salt thereof, wherein:
A is N or $N^+$—O—;
$Q^1$ and $Q^2$ are each independently selected from CH and N;
W is O, S, or $NR^N$;
--- is a single bond;
X is $CR^5R^6$ and Y is $CR^8R^9$;
Ring Z is $C_{6-10}$ aryl, $C_{3-7}$ cycloalkyl, 5-10 membered heteroaryl, or 4-10 membered heterocycloalkyl;
$R^N$ is H, $C_{1-4}$ alkyl, or CN;
$R^1$ is halo, $C_{1-4}$ alkyl, $C_{1-4}$ haloalkyl, $C_{1-4}$ alkoxy, or $C_{1-4}$ haloalkoxy;
$R^{2C}$ is selected from H, $C_{1-4}$ alkyl, $C_{1-4}$ hydroxyalkyl, $C_{1-4}$cyanoalkyl, and $C_{3-7}$ cycloalkyl;
$R^3$ and $R^5$, together with the atoms to which they are attached and together with any intervening atoms, form a 5-7 membered heterocycloalkyl ring optionally substituted by 1, 2, or 3 substituents independently selected from oxo, halo, $C_{1-4}$ alkyl, $C_{1-4}$ haloalkyl, $C_{1-4}$ alkoxy, and $C_{1-4}$ haloalkoxy;
each $R^4$ is independently halo, nitro, cyano, $C_{1-4}$ alkyl, $C_{2-4}$ alkenyl, $C_{2-4}$ alkynyl, $C_{1-4}$ haloalkyl, $C_{1-4}$ alkoxy, or $C_{1-4}$ haloalkoxy;
$R^6$, $R^8$, and $R^9$ are each independently selected from H, halo, $NH_2$, OH, $C_{1-4}$ alkyl, $C_{1-4}$ haloalkyl, $C_{1-4}$ cyanoalkyl, $C_{1-4}$ alkoxy, and $C_{1-4}$ haloalkoxy;
m is 0, 1, or 2; and
n is 0, 1, 2, 3, 4, or 5.

2. The compound of claim 1, or a pharmaceutically acceptable salt thereof, wherein A is N.

3. The compound of claim 2, or a pharmaceutically acceptable salt thereof, wherein W is O or S.

4. The compound of claim 2, or a pharmaceutically acceptable salt thereof, wherein W is O.

5. The compound of claim 4, or a pharmaceutically acceptable salt thereof, wherein Ring Z is $C_{6-10}$ aryl or 5-10 membered heteroaryl.

6. The compound of claim 5, or a pharmaceutically acceptable salt thereof, wherein Ring Z is 5-6 membered heteroaryl.

7. The compound of claim 6, or a pharmaceutically acceptable salt thereof, wherein Ring Z is pyridyl, pyrimidinyl, thienyl, thiazolyl, isoxazolyl, or pyrazolyl.

8. The compound of claim 5, or a pharmaceutically acceptable salt thereof, wherein Ring Z is selected from the following (a)-(i).

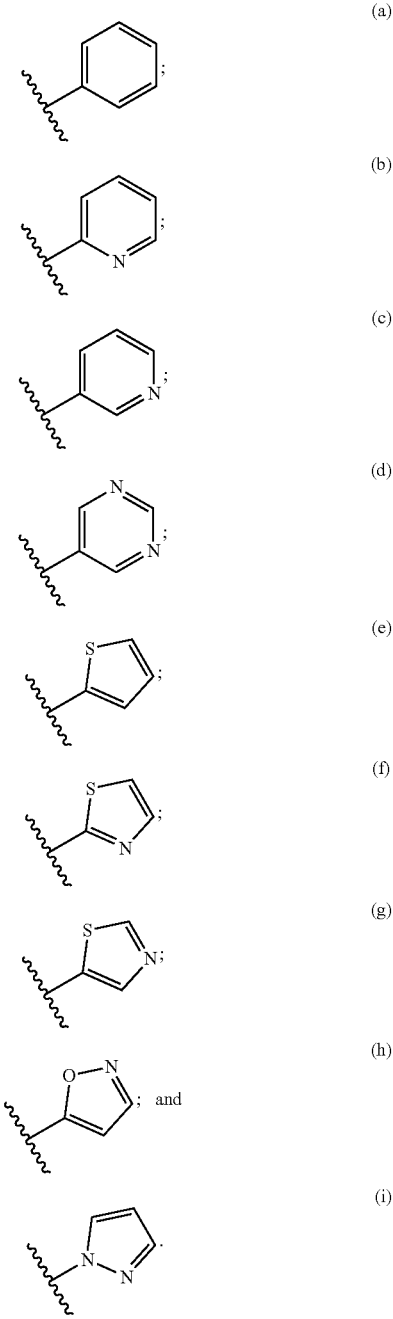

9. The compound of claim 5, or a pharmaceutically acceptable salt thereof, wherein m is 0 or 1.

10. The compound of claim 5, or a pharmaceutically acceptable salt thereof, wherein m is 0.

11. The compound of claim 5, or a pharmaceutically acceptable salt thereof, wherein Ring Z is

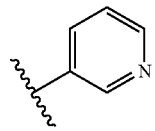 [SMILES: *c1cccnc1]

5

12. The compound of claim 5, or a pharmaceutically acceptable salt thereof, wherein n is 1.

13. The compound of claim 5, or a pharmaceutically acceptable salt thereof, wherein each $R^4$ is independently F, Cl, Br, I, CN, $NO_2$, methyl, ethyl, $CF_3$, $CHF_2$, $OCF_3$, or $OCHF_2$.

14. The compound of claim 13, or a pharmaceutically acceptable salt thereof, wherein each $R^4$ is independently F or Cl.

15. The compound of claim 5, or a pharmaceutically acceptable salt thereof, wherein each $R^4$ is F.

16. The compound of claim 5, or a pharmaceutically acceptable salt thereof, wherein $R^8$ and $R^9$ are each independently selected from H and methyl.

17. The compound of claim 5, or a pharmaceutically acceptable salt thereof, wherein $R^3$ and $R^5$, together with the atoms to which they are attached and together with any intervening atoms, form an unsubstituted 5-7 membered heterocycloalkyl ring.

18. The compound of claim 16, or a pharmaceutically acceptable salt thereof, wherein $R^8$ and $R^9$ are each H.

* * * * *